(12) United States Patent
Nomura et al.

(10) Patent No.: US 8,202,984 B2
(45) Date of Patent: Jun. 19, 2012

(54) GLUCOPYRANOSIDE COMPOUND

(75) Inventors: Sumihiro Nomura, Kawaguchi (JP); Eiji Kawanishi, Kitamoto (JP); Kiichiro Ueta, Wako (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 13/005,757

(22) Filed: Jan. 13, 2011

(65) Prior Publication Data

US 2011/0105424 A1 May 5, 2011

Related U.S. Application Data

(60) Division of application No. 11/045,446, filed on Jan. 31, 2005, now Pat. No. 7,943,788, which is a continuation-in-part of application No. PCT/JP2004/011312, filed on Jul. 30, 2004.

(60) Provisional application No. 60/491,534, filed on Aug. 1, 2003.

(51) Int. Cl.
*C07H 19/00* (2006.01)
*C07H 19/22* (2006.01)
*C07H 19/048* (2006.01)
*C07H 19/056* (2006.01)
*A01N 43/04* (2006.01)
*A61K 31/70* (2006.01)
*C07H 19/06* (2006.01)

(52) U.S. Cl. ............... 536/27.1; 536/28.1; 536/28.6; 514/43

(58) Field of Classification Search .................. None
See application file for complete search history.

(56) References Cited

U.S. PATENT DOCUMENTS

| | | | |
|---|---|---|---|
| 4,160,861 A | 7/1979 | Cole et al. |
| 4,584,369 A | 4/1986 | Klein et al. |
| 5,149,838 A | 9/1992 | Humphrey et al. |
| 5,424,406 A | 6/1995 | Tsujihara et al. |
| 5,731,292 A | 3/1998 | Tsujihara et al. |
| 5,767,094 A | 6/1998 | Tsujihara et al. |
| 5,780,483 A | 7/1998 | Widdowson et al. |
| 5,830,873 A | 11/1998 | Tsujihara et al. |
| 6,048,842 A | 4/2000 | Tsujihara et al. |
| 6,153,632 A | 11/2000 | Rieveley |
| 6,297,363 B1 | 10/2001 | Kubo et al. |
| 6,414,126 B1 | 7/2002 | Ellsworth et al. |
| 6,515,117 B2 | 2/2003 | Ellsworth et al. |
| 6,562,791 B1 | 5/2003 | Maurya et al. |
| 6,617,313 B1 | 9/2003 | Maurya et al. |
| 6,627,611 B2 | 9/2003 | Tomiyama et al. |
| 7,375,213 B2 | 5/2008 | Deshpande |
| 7,511,022 B2 | 3/2009 | Beavers et al. |
| 2001/0041674 A1 | 11/2001 | Tomiyama et al. |
| 2002/0032164 A1 | 3/2002 | Dale et al. |
| 2002/0052326 A1 | 5/2002 | Washburn |
| 2002/0111315 A1 | 8/2002 | Washburn et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |

(Continued)

FOREIGN PATENT DOCUMENTS

CA 2494177 A1 2/2004

(Continued)

OTHER PUBLICATIONS

Mansour et al. Nucleosides, Nucleotides & Nucleic Acids vol. 22, No. 1, pp. 21-44, Jan. 2003.*

Ahmad, R. et al, "Synthesis and Structure Determination of Some Oxadiazole-2-Thione and Triazole-3-Thione Galctosides," Nucleosides, Nucleotides & Nucleic Acids, 2001, vol. 20, No. 9, pp. 1671-1682.

(Continued)

*Primary Examiner* — Layla Bland
(74) *Attorney, Agent, or Firm* — Birch, Stewart, Kolasch & Birch, LLP

(57) ABSTRACT

A compound of the formula:

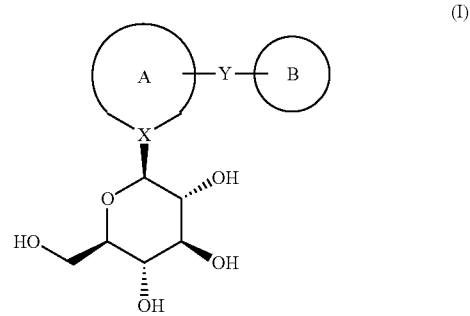

wherein Ring A and Ring B are: (1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring, (2) Ring A is an optionally substituted benzene ring, and Ring B is an optionally substituted unsaturated monocyclic heterocyclic ring or an optionally substituted unsaturated fused heterobicyclic ring, or (3) Ring A is an optionally substituted unsaturated fused heterobicyclic ring, and Ring B are independently an optionally substituted unsaturated monocyclic heterocyclic ring, an optionally substituted unsaturated fused heterobicyclic ring, or an optionally substituted benzene ring; X is a carbon atom or a nitrogen atom; Y is —$(CH_2)_n$— (n is 1 or 2); or a pharmaceutically acceptable salt thereof, or a prodrug thereof.

16 Claims, No Drawings

U.S. PATENT DOCUMENTS

| | | | |
|---|---|---|---|
| 2005/0014704 | A1 | 1/2005 | Frick et al. |
| 2005/0032711 | A1 | 2/2005 | Patel et al. |
| 2005/0032712 | A1 | 2/2005 | Urbanski |
| 2005/0037980 | A1 | 2/2005 | Rybczynski et al. |
| 2005/0037981 | A1 | 2/2005 | Beavers et al. |
| 2005/0124556 | A1 | 6/2005 | Burton |
| 2006/0217323 | A1 | 9/2006 | Patel et al. |
| 2006/0229260 | A1 | 10/2006 | Rybczynski et al. |
| 2006/0234954 | A1 | 10/2006 | Urbanski |
| 2006/0293251 | A1 | 12/2006 | Urbanski et al. |
| 2007/0060545 | A1 | 3/2007 | Nomura et al. |

FOREIGN PATENT DOCUMENTS

| | | | |
|---|---|---|---|
| EP | 0355750 A1 | 2/1990 | |
| EP | 0579204 A2 | 1/1994 | |
| EP | 0579204 A3 | 1/1994 | |
| EP | 1338603 A1 | 8/2003 | |
| EP | 1528066 A1 | 5/2005 | |
| FR | 1.476.537 A | 4/1967 | |
| GB | 2359554 A | 8/2001 | |
| JP | 63-233975 A | 9/1988 | |
| JP | 4-253974 A | 9/1992 | |
| JP | 9-263549 A | 10/1997 | |
| JP | 10-324632 A | 12/1998 | |
| JP | 2000-34230 A | 2/2000 | |
| JP | 2000-34239 A | 2/2000 | |
| JP | 2001-288178 A | 10/2001 | |
| JP | 2003-12686 A | 1/2003 | |
| WO | WO 90/04600 A1 | 5/1990 | |
| WO | WO 93/21178 A1 | 10/1993 | |
| WO | WO 97/25033 A1 | 7/1997 | |
| WO | WO 00/74681 A1 | 12/2000 | |
| WO | WO 01/27128 A1 | 4/2001 | |
| WO | WO 01/64669 A1 | 9/2001 | |
| WO | WO 01/68660 A1 | 9/2001 | |
| WO | WO 01/74834 A1 | 10/2001 | |
| WO | WO 01/74835 A1 | 10/2001 | |
| WO | WO 02/053573 A1 | 7/2002 | |
| WO | WO 02/068439 A1 | 9/2002 | |
| WO | WO 02/068440 A1 | 9/2002 | |
| WO | WO 02/070020 A2 | 9/2002 | |
| WO | WO 02/083066 A2 | 10/2002 | |
| WO | WO 02/088157 A1 | 11/2002 | |
| WO | WO 02/094262 A1 | 11/2002 | |
| WO | WO 03/000712 A1 | 1/2003 | |
| WO | WO 03/011880 A1 | 2/2003 | |
| WO | WO 03/020737 A1 | 3/2003 | |
| WO | WO 03/043621 A1 | 5/2003 | |
| WO | WO 03/087104 A1 | 10/2003 | |
| WO | WO 03/099836 A1 | 12/2003 | |
| WO | WO 2004/007517 A1 | 1/2004 | |
| WO | WO 2004/013118 A1 | 2/2004 | |
| WO | WO 2004/014931 A1 | 2/2004 | |
| WO | WO 2004/019958 A1 | 3/2004 | |
| WO | WO 2004/052902 A1 | 6/2004 | |
| WO | WO 2004/052903 A1 | 6/2004 | |
| WO | WO 2004/063209 A2 | 7/2004 | |
| WO | WO 2004/063209 A3 | 7/2004 | |
| WO | WO 2004/080990 A1 | 9/2004 | |
| WO | WO 2004/087727 A1 | 10/2004 | |
| WO | WO 2004/099230 A1 | 11/2004 | |
| WO | WO 2004/113359 A1 | 12/2004 | |

OTHER PUBLICATIONS

Amishiro, N. et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, vol. 47, No. 10, pp. 1393-1403.

Appleton, J.E. et al, "A Mild and Selective C-3 Reductive Alkylation of Indoles", Tetrahedron Letters, 1993, vol. 34, No. 9, pp. 1529-1532.

Arakawa, K. et al, "Improved diabetic syndrome in C57BL/KsJ-db/db mice by oral administration of the Na+-glucose cotransporter inhibitor T-1095," British Journal of Pharmacology, 2001, vol. 132, pp. 578-586.

Banker, G.S., "Modern Pharmaceutics," Third Edition, Marcel Dekker, Inc., published 1996, p. 596.

Benhaddou, R. et al., "Tetra-n-propylammonium tetra-oxoruthenate(VII): a reagent of choice for the oxidation of diversely protected glycopyranoses and glycofuranoses to lactones", Carbohydrate Research, 1994, vol. 260, pp. 243-250.

Bertolini, G. et al., "A New Simple One-Pot Regioselective Preparatiion of Mixed Diesters of Carbonic Acid.", Journal of Organic Chemistry, 1998, vol. 63, No. 17, pp. 6031-6034.

Blair, J.B. et al., "Effect of Ring Fluorination on the Pharmacology of Hallucinogenic Tryptamines", J. Med. Chem., 2000, vol. 43, pp. 4701-4710.

Boehm, H-J et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., 2000, vol. 43, No. 14, pp. 2664-2674.

Bookser, B.C., "2-Benzyloxymethyl-5-(tributylstannyl)tetrazole. A reagent for the preparation of 5-aryl- and 5-heteroaryl-1H-tetrazoles via the Stille reaction," Tetrahedron Letters, 2000, vol. 41, pp. 2805-2809.

Bouillon, A. et al, "Synthesis of novel halopyridinylboronic acids and esters. Part 2: 2,4, or 5-Halopyridin-3-yl-boronic acids and esters," Tetrahedron, 2002, vol. 58, pp. 3323-3328.

Bouillon, A. et al, "Synthesis of novel halopyridinylboronic acids and esters. Part 3: 2, or 3-Halopyridin-4-yl-boronic acids and esters," Tetrahedron, 2002, vol. 58, pp. 4369-4373.

Bouillon, A. et al, "Synthesis of novel halopyridinylboronic acids and esters. Part 4: Halopyridin-2-yl-boronic acids and esters are stable, crystalline partners for classical Suzuki cross-coupling," Tetrahedron, 2003, vol. 59, pp. 10043-10049.

Brooks, P.R. et al., "Boron Trichloride/Tetra-n-Butylammonium Iodide: A Mild, Selective Combination Reagent for the Cleavage of Primary Alkyl Aryl Ethers", J. Org. Chem., 1999, vol. 64, pp. 9719-9721.

CAS Reg. No. 487001-40-1, IPOrganisers, Entered STN Feb. 7, 2003, pp. 1-2.

Cicchillo, R.M. et al, "A convenient synthesis of glycosyl chlorides from sugar hemiacetals using triphosgene as the chlorine source," Carbohydrate Research, 2000, vol. 328, pp. 431-434.

Clayden, J. et al, "Dearomatizing Cyclization of Arylsulfonylalkoxymethyl Lithiums: A Route to the Podophyllotoxin Skeleton," Organic Letters, 2003, vol. 5, No. 6, pp. 831-834.

Comins, D.L. et al., "Synthesis of 3-Substituted Indoles Via N-Acylindolium Ions", Tetrahedron Letters, 1986, vol. 27, No. 17, pp. 1869-1872.

Cottet, F. et al, "Recommendable Routes to Trifluoromethyl-Substituted Pyridine- and Quinolinecarboxylic Acids," Eur. J. Org. Chem., 2003, pp. 1559-1568.

Czernecki, S. et al., "C-Glycosides. 7. Steriospecific C-Glycosylation of Aromatic and Heterocyclic Rings", J. Org. Chem., 1989, vol. 54, pp. 610-612.

Data and Appendices A-C submitted in parent U.S. Appl. No. 11/045,446 on Sep. 1, 2009.

De Las Heras, F. G. et al, "Alkylating Nucleosides 1. Synthesis and Cytostatic Activity of N-Glycosyl(halomethyl)-1,2,3-triazoles. A New Type of Alkylating Agent," Journal of Medicinal Chemistry, 1979, vol. 22, No. 5, pp. 496-501.

Deeg, M. A. et al., "Pioglitazone and Rosiglitazone Have Different Effects on Serum Lipoprotein Particle Concentrations and Sizes in Patients With Type 2 Diabetes and Dyslipidemia.", Diabetes Care, Oct. 2007, vol. 30, No. 10, pp. 2458-2464.

Deetjen, P. et al., "Renal Handling of D-Glucose and Other Sugars", Textbook of Nephrology, 1995, vol. 1, 3rd Edition, pp. 90-94.

Devivar, R. V. et al., "Benzimidazole Ribonucleosides: Design, Synthesis, and Antiviral Activity of Certain 2-(Alkylthio)- and 2-(Benzylthio)-5,6-dichloro-1-(β-D-ribofuranosyl)benzimidazoles1.", J.Med.Chem., 1994, vol. 37, pp. 2942-2949.

Dewynter, G. et al, "Sythesis of Pseudomucleosides containing Chiral Sulfahydantoins as Aglycone (II)", Tetrahedron, 1996, vol. 52, No. 3, pp. 993-1004.

Dillard, R.D. et al., "Indole Inhibitors of Human Nonpancreatic Secretory Phospholipase A2. 1. Indole-3-acetamides", J. Med. Chem., 1996, vol. 39, pp. 5119-5136.

Dondoni, A. et al., "Stereoselective synthesis of C-glycosylphosphonates from their ketols. Reconsideration of an abandoned route", Tetrahedron: Asymmetry, 2000, vol. 11, pp. 305-317.

Dondoni, A. et al., "Thiazole-Based Synthesis of Formyl C-Glycosides", J. Org. Chem., 1994, vol. 59, pp. 6404-6412.

Dudash, J. Jr. et al, "Glycosylated dihydrochalcones as potent and selective sodium glucose co-transporter 2 (SGLT2) inhibitors," Bioorganic & Medicinal Chemistry Letters, 2004, vol. 14, pp. 5121-5125.

Dunn, J. P. et al., "Analgetic and antiinflammatory 7-Aroylbenzofuran-5-ylacetic acids and 7-Aroylbenzothiophene-5-ylacetic Acids.", Journal of Med. Chem., 1986, vol. 29, No. 1, pp. 2326-2329.

Eid, M. M. et al., "Reaction of Some 1,2,4-Triazines with Acetobromoglucose", Arch. Pharm (Weinheim), 1990, vol. 323, pp. 243-245.

Ellsworth, B. A. et al, "Aglycone exploration of C-arylglucoside inhibitors of renal sodium-dependent glucose transporter SGLT2," Bioorganic & Medicinal Chemistry Letters, 2008, vol. 18, pp. 4770-4773.

Ellsworth, B.A. et al., "C-Arylglucoside synthesis: triisopropylsilane as a selective reagent for the reduction of an anomeric C-phenyl ketal," Tetrahedron: Asymmetry, 2003, vol. 14, pp. 3243-3247.

EPO International Search Report, Appl. No. PCT/JP2004/011312, Nov. 25, 2004, pp. 1-4.

Frahn, J. et al, "Functionalized AB-Type Monomers for Suzuki Polycondensation," Synthesis, Nov. 1997, pp. 1301-1304.

Fresneda, P.M. et al., "Synthesis of the indole alkaloids meridianins from the tunicate Aplidium meridianum" Tetrahedron, 2001, vol. 57, pp. 2355-2363.

Fuller, L.S. et al, "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.

Ganesh, T. et al, "Synthesis and biological evaluation of fluorescently labeled epothilone analogs for tubulin binding studies," Tetrahedron, 2003, vol. 59, pp. 9979-9984.

Gershell, L., "Type 2 diabetes market", Nature Reviews Drug Discovery, May 2005, vol. 4, pp. 367-368.

Gohier, F. et al, "ortho-Metalation of Unprotected 3-Bromo and 3-Chlorobenzoic Acids with Hindered Lithium Dialkylamides," J. Org. Chem., 2003, vol. 68, pp. 2030-2033.

Goodman & Gilman's The Pharmacological Basis of Therapeutics, 10th Edition, McGraw-Hill Medical Publishing Division, 2001, pp. 54-57.

Gronowitz, S. et al, "Some Substitution Reactions of 1-(2-Thienyl)pyrazole and 1-(3'-Thienyl)pyrazole," Chemica Scripta., 1979, vol. 13, pp. 157-161.

Gros, P. et al, "Efficient and Regioselective Access to Bis-heterocycles via Palladium-Catalysed Coupling of Organostannanes and Organozincates Derived from C-6 Lithiated 2-Methoxypyridine," Synthesis, 1999, No. 5, pp. 754-756.

Han, S. et al., "Dapagliflozin, a Selective SGLT2 Inhibitor, Improves Glucose Homeostasis in Normal and Diabetic Rats", Diabetes, Jun. 2008, vol. 57, pp. 1723-1729.

Handlon, A. L., "Sodium glucose co-transporter 2 (SGLT2) inhibitors as potential antidiabetic agents," Expert Opin. Ther. Patents, 2005, vol. 15, No. 11, pp. 1531-1540.

Hofslokken, N. U. et al., "Convenient Method for the ortho-Formylation of Phenols.", Acta Chemica Scandinavica, 1999, vol. 53, pp. 258-262.

Hongu, M. et al, "Na+-Glucose Cotransporter Inhibitors as Antidiabetic Agents. II.1) Synthesis and Structure-Activity Relationships of 4'-Dehydroxyphlorizin Derivatives," Chem. Pharm. Bull., 1998, vol. 46, No. 1, pp. 22-33.

Horton, D. et al., "Synthetic Routes to Higher-Carbon Sugars. Reaction of Lactones with 2-Lithio-1,3-Dithiane", Carbohydrate Research, 1981, vol. 94, pp. 27-41.

Hu, T.Q. et al., "A New Approach Towards the Yellowing Inhibition of Mechanical Pulps. Part I: Selective Removal of alpha-Hydroxyl and alpha-Carbonyl Groups in Lignin Model Compounds", Holzforschung, 1999, vol. 53, No. 1, pp. 43-48.

Huang-Minlon, "Reduction of Steroid Ketones and other Carbonyl Compounds by Modified Wolff-Kishner Method", J. Am. Chem. Soc., Oct. 1949, vol. 71, pp. 3301-3303.

Ibrahim, Y.A. et al, "Facile Approach for the Selective Glycodisation of Cyclic Asymmetric Amides and Thioamides", Carbohydrate Letters, 1996, vol. 1, pp. 425-432.

Ibrahim, Y.A. et al, "Selective Synthesis and Structure of 2-N- and 3-S-Glucosyl-1,2,4-Triazoles of Potential Biological Interest", Carbohydrate Letters, 1999, vol. 3, No. 5, pp. 331-338.

Isaji, M., "Sodium-glucose cotransporter inhibitor for diabetes," Current Opinion in Investigational Drugs, 2007, vol. 8, No. 4, pp. 285-292.

Kahn, B. B. et al, "Normalization of Blood Glucose in Diabetic Rats with Phlorizin Treatment Reverses Insulin-resistant Glucose Transport in Adipose Cells without Restoring Glucose Transporter Gene Expression," J. Clin. Invest., Feb. 1991, vol. 87, pp. 561-570.

Kanai, Y. et al., "The Human Kidney Low Affinity Na+/Glucose Cotransporter SGLT2: Delineation of the Major Renal Reabsorptive Mechanism for D-Glucose", J. Clin. Invest., Jan. 1994, vol. 93, pp. 397-404.

Kasahara, M. et al., "A missense mutation in the Na+/glucose cotransporter gene SGLT1 in a patient with congenital glucose-galactose malabsorption: normal trafficking but inactivation of the mutant protein," Biochimica et Biophysica Acta, 2001, vol. 1536, pp. 141-147.

Katz, A. et al., "Quantitative Insulin Sensitivity Check Index: A Simple, Accurate Method for Assessing Insulin Sensitivity In Humans.", J. of Clin. Endocrinology & Metabolism, 2000, vol. 85, No. 7, pp. 2402-2410.

Ketcha, D. M. et al., "Synthesis of Alyl-Substituted N-Protected Indoles via Acylation and Reductive Deoxygenation1" J. Org. Chem., 1989, vol. 54, pp. 4350-4356.

Khan, M. A. et al, "Reactions of Phenyl-Substituted Heterocyclic Compounds—II. Nitrations and Brominations of 1-Phenylpyrazole Derivatives," Canadian Journal of Chemistry, 1963, vol. 41, pp. 1540-1547.

Lee, J. S. et al, "Synthesis and In Vitro Activity of Novel Isoxazolyl Tetrahydropyridinyl Oxazolidinone Antibacterial Agents," Bioorganic & Medicinal Chemistry Letters, 2003, vol. 13, pp. 4117-4120.

Liang, Y. et al., "JNJ-28431754/TA-7284, an Inhibitor of Sodium-Glucose Cotransporter 2, Ameliorates Diabetic Syndrome in the Zucker Diabetic Fatty Rat," Oct. 2009, Poster presented at International Diabetes Federation 20th World Diabetes Congress, Montreal, Canada.

Liang, Y. et al., "JNJ-28431754/TA-7284, an Inhibitor of Sodium-Glucose Cotransporter 2, Reduces Body Weight Gain in Zucker Fatty Rats," Oct. 2009, Poster presented at International Diabetes Federation 20th World Diabetes Congress, Montreal, Canada.

Liang, Y. et al., "JNJ-28431754/TA-7284, an SGLT Inhibitor, Lowers Blood Glucose and Reduces Body Weight in Obese and type 2 Diabetic Animal Models," Jun. 2009.

Lin, P. et al., "Syntheses of Guanidinoglycosides with the Inventive use of Mitsunobu Conditions and 1,8-Diazabicyclo[5.4.0]undec-7-ene.", Synthesis, 2003, No. 2, pp. 255-261.

Link, J.T. et al., "A method for preparing C-gycosides related to phlorizin" Tetrahedron Letters, 2000, vol. 41, pp. 9213-9217.

Lipscombe, L.L. et al., "Trends in diabetes prevalence, incidence, and mortality in Ontario, Canada 1995-2005: a population-based study", Lancet, 2007, vol. 369, pp. 750-756.

Maatooq, G. T. et al, "C-p-Hydrozybenzoylglycoflavones From Citrullus Colocynthis," Phytochemistry, 1997, vol. 44, No. 1, pp. 187-190.

Mackenzie, B. et al., "Biophysical Characteristics of the Pig Kidney Na+/Glucose Cotransporter SGLT2 Reveal a Common Mechanism for SGLT1 and SGLT2", J. Biol. Chem., 1996, vol. 271, No. 5, pp. 32678-32683.

Manis, M. O. et al., "Metabolism of 4,4'-Methylenebis(2-chloroaniline) By Canine Liver and Kidney Slices.", Drug Metabolism and Disposition, 1986, vol. 14, No. 2, pp. 166-174.

Marsenic, O. MD, "Glucose Control by the Kidney: An Emerging Target in Diabetes.", Am. J. of Kidney Diseases, May 2009, vol. 53, No. 5, pp. 875-883.

Matsuda, M. et al., "Insulin Sensitivity Indices Obtained From Oral Glucose Tolerance Testing: Comparison with the euglycemic insulin clamp," Diabetes Care, Sep. 1999, vol. 22, No. 9, pp. 1462-1470.

Matthews, D.R. et al., "Homeostasis model assessment: insulin resistance and •-cell function from fasting plasma glucose and insulin concentrations in man," Diabetolgia, 1985, vol. 28, pp. 412-419.

Meanwell, N. A. et al., "Regiospecific Functionalization of 1,3-Dihydro-2H-benzimidazol-2-one and Structurally Related Cyclic Urea Derivates.", J. Org. Chemistry, 1995, vol. 60, No. 6, pp. 1565-1582.

Meng, W. et al., "Discovery of Dapagliflozin: A Potent, Selective Renal Sodium-Dependent Glucose Cotransporter 2 (SGLT2) Inhibitor for the Treatment of Type 2 Diabetes", J. Med. Chem., 2008, vol. 51, No. 5, pp. 1145-1149.

Messaoudi, S. et al, "Synthesis and biological evaluation of oxindoles and benzimidazolinones derivatives," European Journal of Medicinal Chemistry, 2004, vol. 39, pp. 453-458.

Mewshaw, R.E. et al., "New Generation Dopaminergic Agents. 7. Heterocyclic Bioisosteres that Exploit the 3-OH-Phenoxyethylamine D2 Template", Bioorganic & Medicinal Chemistry Letters, 1999, vol. 9, pp. 2593-2598.

Miyaura, N. et al., "Palladium-Catalyzed Cross-Coupling Reactions of Organoboron Compounds.", Chem. Rev., 1995, vol. 95, No. 7, pp. 2457-2483.

Nishimura, M. et al, "Tissue-specific mRNA Expression Profiles of Human ATP-binding Cassette and Solute Carrier Transporter Superfamilies," Drug Metab. Pharmacokinet., 2005, vol. 20, No. 6, pp. 452-477.

Nomura, S. et al., "Discovery of Novel C-glucosides with Thiophene Ring as Sodium-dependent Glucose Cotransporter 2 Inhibitors for the Treatment of Type 2 Diabetes Mellitus", MEDI 151, Abstract, The 238th ACS National Meeting, Washington, DC, Aug. 16-20, 2009; American Chemical Society: Washington, DC.

Nomura, S. et al., "Discovery of Novel C-glucosides with Thiophene Ring as Sodium-dependent Glucose Cotransporter 2 Inhibitors for the Treatment of Type 2 Diabetes Mellitus," ACS Poster Presentation 2009.

Nomura, S., "Renal Sodium-Dependent Glucose Cotransporter 2 (SGLT2) Inhibitors for New Anti-Diabetic Agent," Current Topics in Medicinal Chemistry, 2010, vol. 10, No. 4, pp. 411-418.

Ohsumi, K. et al. "Pyrazole-O-Glucosides as Novel Na+-Glucose Cotransporter (SGLT) Inhibitors" Bioorganic & Medicinal Chemistry Letters, 2003, vol. 13, pp. 2269-2272.

Oku, A. et al., "T-1095, an Inhibitor of Renal Na+-Glucose Cotransporters, May Provide a Novel Approach to Treating Diabetes", Diabetes, Sep. 1999, vol. 48, pp. 1794-1800.

Opposition to an Invention Patent (and English translation thereof) from counterpart Costa Rica application 11.263.

Orjales, A. et al. "New 2-Piperazinylbenzimidazole Derivatives as 5-HT-3 Antagonists. Synthesis and Pharmacological Evaluation," J. Med. Chem., 1997, vol. 40, pp. 586-593.

Parker, K. A. et al, "Reductive Aromatization of Quinols: Synthesis of the C-Arylglycoside Nucleus of the Paulacandins and Chaetiacandin," Organic Letters, 2000, vol. 2, No. 4, pp. 497-499.

Patani, G. A. et al, "Bioisosterism: A Rational Approach in Drug Design," Chem. Rev., American Chemical Society, 1996, vol. 96, pp. 3147-3176.

Peng, H. et al., "Post-transcriptional Regulation of Na+/Glucose Cotransporter (SGTL1) Gene Expression in LLC-PK1 Cells.", Journal of Biological Chemistry, 1995, vol. 270, No. 35, pp. 20536-20542.

Polidori, D. et al., "Frequently Used Insulin Sensitivity Measures May Be Inappropriate for Subjects Treated With SGLT2 Inhibitors," Jun. 2009, Poster presented at the American Diabetes Assoc. 69th Scientific Sessions, Jun. 5-9, 2009, New Orleans, LA.

Raynaud, E. et al., "Revised Concept for the Estimation of Insulin Sensitivity From a Single Sample.", Diabetes Care, Jun. 1999, vol. 22, No. 6, pp. 1003-1004.

Rossetti, L. et al, "Correction of Hyperglycemia with Phlorizin Normalizes Tissue Sensitivity to Insulin in Diabetic Rats," J. Clin. Invest., May 1987, vol. 79, pp. 1510-1515.

Rossetti, L. et al, "Effect of Chronic Hyperglycemia on in Vivo Insulin Secretion in Partially Pancreatectomized Rats," J. Clin. Invest., Oct. 1987, vol. 80, pp. 1037-1044.

Rosetti, L. et al., "Glucose Toxicity," Diabetes Cares, 1990, vol. 13, Issue 6, pp. 610-630, Abstract only.

Schmidt, R. R. et al., "Synthese von Pyrazol-, Pyrazolo[3,4-d]pyrimidin-und 1H-1,2,4-Triazolgluconucleosiden aus Glucosehydrazonen," Liebigs Ann. Chem., 1981, pp. 2309-2317.

Silverman, R. B., "The Organic Chemistry of Drug Design and Drug Action," Academic Press, 1992, pp. 19-23.

Somei, M. et al., "The First and Simple Total Synthesis of Cappariloside A1," Heterocycles, 2000, vol. 53, No. 7, pp. 1573-1578.

Srogl, J. et al., "Sulfonium Salts. Participants par Excellence in Metal-Catalyzed Carbon• Carbon Bond-Forming Reactions", J. Am. Chem. Soc., 1997, vol. 119, No. 50, pp. 12376-12377.

Stoner, E. J. et al, "Benzylation via Tandem Grignard Reaction—Iodotrimethylsilane (TMSI) Mediated Reduction," Tetrahedron, 1995, vol. 51, No. 41, pp. 11043-11062.

Stumvoll, M. et al., "Use of the Oral Glucose Tolerance Test to Assess Insulin Release and Insulin Sensitivity.", Diabetes Care, Mar. 2000, vol. 23, No. 3, pp. 295-301.

Tanaka, H. et al. "Solid-Phase Synthesis of •-Mono-Substituted Ketones and an Application to the Synthesis of a Library of Phlorizin Derivatives", Synlett, 2002, No. 9, pp. 1427-1430.

The State Intellectual Property Office of P.R. China Office Action, Appl. No. 2004800220078, Dec. 26, 2008, pp. 1-6, Second Office Action, English translation.

The State Intellectual Property Office of P.R. China Office Action, Appl. No. 2004800220078, Oct. 19, 2007, pp. 1-6, First Office Action, English translation.

The State Intellectual Property Office of P.R. China The Decision of Rejection (PCT) Action, Appl. No. 2004800220078, Nov. 2009, pp. 1-7.

The State Intellectual Property Office of P.R. China, Observations (1st), Appl. No. 2004800220078, May 2008, pp. 1-3, English translation.

The State Intellectual Property Office of P.R. China, Observations (2nd), Appl. No. 2004800220078, May 2009, pp. 1-4, English translation.

The State Intellectual Property Office of P.R. China, Record of Interview, Appl. No. 2004800220078, Sep. 2009, pp. 1-7, English translation.

The State Intellectual Property Office of P.R. China, Response to The Decision of Rejection (PCT), Appl. No. 2004800220078, Feb. 2010, pp. 1-27, English translation.

Thornber, C. T., "Isosterism and Molecular Modification in Drug Design," Chemical Society Reviews, 1979, vol. 8, pp. 563-580.

Tilak, B.D. et al, "Carcinogenesis by Thiophene Isosters of Polycyclic Hydrocarbons," Tetrahedron, 1960, vol. 9, pp. 76-95.

Tsujihara, K. et al, "Na+-Glucose Cotransporter (SGLT) Inhibitors as Antidiabetic Agents. 4. Synthesis and Pharmacological Properties of 4'-Dehydroxyphlorizin Derivatives Substituted on the B Ring," J. Med. Chem., 1999, vol. 42, No. 26, pp. 5311-5324.

Tsujihara, K. et al., "Na+ -Glucose Inhibitors as Antidiabetic.I. Synthesis and Pharmacological Properties of 4'-Dehydroxyphlorizin Derivatives Based on a New Concept," Chem. Pharm. Bull., 1996, vol. 44, No. 6, pp. 1174-1180.

Tsujihara, K. et al., Bio Clinica, 1998, vol. 13, No. 4, pp. 324-328, English language Abstract.

Turk, E. et al., "Glucose/galactose malabsorption caused by a defect in the Na+/glucose cotransporter," Nature, Mar. 1991, vol. 350, pp. 354-356.

Ueta, K. et al, "Anti-diabetic and Anti-obesity effects of TA-7284, a Novel SGLT2 Inhibitor," Partial English translation, JDS Poster Presentation, 2009.

Ueta, K. et al, "Long-term treatment with the Na+-glucose cotransporter inhibitor T-1095 causes sustained improvement in hyperglycemia and prevents diabetic neuropathy in Goto-Kakizaki Rats," Life Sciences, 2005, vol. 76, pp. 2655-2668.

Unger, R. H. et al., "Hyperglycaemia as an inducer as well as a consequence of impaired islet cell function and insulin resistance: implications for the management of diabetes.", Diabetologia, 1985, vol. 28, pp. 119-121.

Wallace, T. M. et al., "Use and Abuse of HOMA Modelling.", Diabetes Care, Jun. 2004, vol. 27, No. 6, pp. 1487-1495.

Wang, X. et al, "Selective monolithiation of 2,5-dibromopyridine with butyllithium," Tetrahedron Letters, 2000, vol. 41, pp. 4335-4338.

Wareham, N.J. et al., "Is There Really an epidemic of diabetes?", Diabetologia, 2005, vol. 48, pp. 1454-1455.

Washburn, W. N., "Evolution of sodium glucose co-transporter 2 inhibitors as anti-diabetic agents," Expert Opin. Ther. Patents, 2009, vol. 19, No. 11, pp. 1485-1499.

Wild, S. et al., "Global Prevalence of Diabetes: Estimates for the year 2000 and projections for 2030," Diabetes Care, May 2004, vol. 27, No. 5, pp. 1047-1053.

Wolff, M. E., vol. 1: Principles and Practice, Burger's Medicinal Chemistry and Drug Discovery, 5th Edition, 1995, pp. 975-977.

Wright, E.M., "Renal Na+-glucose cotransporters," Am J Physiol Renal Physiol, 2001;vol. 280, pp. F10-F18.

Yang, G. et al., "Convergent C-Glycolipid Synthesis via the Ramberg-Bäcklund Reaction: Active Antiproliferative Glycolipids", Org. Lett. 1999, vol. 1, No. 13, pp. 2149-2151.

Yoshimura, H. et al, "Discovery of Novel and Potent Retinoic Acid Receptor alpha- Agonists: Synthesis and Evaluation of Benzofuranyl-pyrrole and Benzothiophenyl-pyrrole Derivatives," J. Med. Chem., 2000, vol. 43, pp. 2929-2937.

Zamani, K. et al, "Synthesis and Structures of Some New N-Glycosides of 4,5-Disubstituted-1,2,4-triazole-3-thiones," Journal of the Chinese Chemical Society, 2002, vol. 49, pp. 1041-1044.

Zhou, F. Y., "The Synthesis and Characterization of 1-Benzyl-3-N-(Beta-D-glucosie-1-yl)-4-fluorouracil", Hecheng Huaxue, 2001, vol. 9, No. 3, pp. 272-274.

Huaxue Shiji, vol. 24, No. 1, 2002, pp. 31-32.

Japanese Office Action for Application No. 2008-100074 dated Aug. 23, 2011 (with English translation).

* cited by examiner

GLUCOPYRANOSIDE COMPOUND

TECHNICAL FIELD

This application is a Divisional of U.S. application Ser. No. 11/045,446 filed Jan. 31, 2005 now U.S. Pat. No. 7,943,788. U.S. application Ser. No. 11/045,446 is a Continuation-In-Part of PCT International Application No. PCT/JP2004/011312 filed on Jul. 30, 2004, which designated the United States and on which priority is claimed under 35 U.S.C. §120, which claims priority of Provisional Application No. 60/491,534 filed on Aug. 1, 2003, the entire contents of which are hereby incorporated by reference.

BACKGROUND ART

Diet therapy and exercise therapy are essential in the treatment of diabetes mellitus. When these therapies do not sufficiently control the conditions of patients, insulin or an oral antidiabetic agent is additionally used for the treatment of diabetes. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. Namely, chronic hyperglycemia leads to decrease of insulin secretion and further to decrease of insulin sensitivity, and as a result, the blood glucose concentration is increased so that diabetes mellitus is self-exacerbated [cf., Diabetologia, vol. 28, p. 119 (1985); Diabetes Care, vol. 13, p. 610 (1990), etc.]. Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved [cf., Journal of Clinical Investigation, vol. 79, p. 1510 (1987); ibid., vol. 80, p. 1037 (1987); ibid., vol. 87, p. 561 (1991), etc.].

In addition, by treating diabetic animal models with SGLT inhibitory agents for along time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001), Ueta, Ishihara, Matsumoto, Oku, Nawano, Fujita, Saito, Arakawa, Life Sci., in press (2005), etc.].

From the above, SGLT inhibitors may be expected to improve insulin secretion and insulin resistance by decreasing the blood glucose level in diabetic patients and further prevent the onset and progress of diabetes mellitus and diabetic complications.

WO 01/27128 discloses an aryl C-glycoside compound having the following structure.

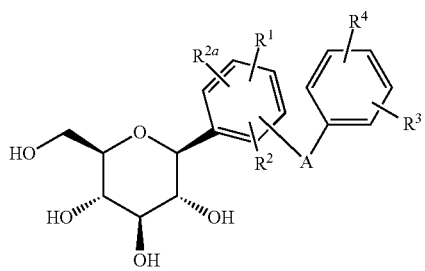

This compound is disclosed to be useful in the prophylaxis or treatment of diabetes mellitus, etc., as an SGLT inhibitor.

DISCLOSURE OF INVENTION

The present invention relates to a compound of the following formula I, or a pharmaceutically acceptable salt thereof, or a prodrug thereof:

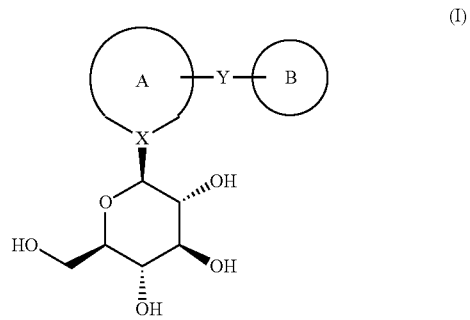

wherein Ring A and Ring B are one of the followings: (1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring, (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring, or (3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom or a nitrogen atom; and

Y is —$(CH_2)_n$— (wherein n is 1 or 2).

The compound of the formula I exhibits an inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, obesity, and delayed wound healing.

BEST MODE FOR CARRYING OUT THE INVENTION

Hereinafter, the present compound (I) is illustrated in more detail.

The definitions for each term used in the description of the present invention are listed below.

The term "halogen atom" or "halo" means chlorine, bromine, fluorine and iodine, and chlorine and fluorine are preferable.

The term "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by 1 to 4 substituents as listed below, if necessary.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group".

Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary.

Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl group" means a formyl group and ones formed by binding an "alkyl group" to a carbonyl group.

The term "alkoxy group" means ones formed by binding an "alkyl group" to an oxygen atom.

The substituent for the above each group includes, for example, a halogen atom (e.g., fluorine, chlorine, bromine, iodine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylakyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a β-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric centers at a carbon atom containing any one of substituents. Therefore, the compound of the formula I may exist in the form of enantiomer or diastereomer, or a mixture thereof. When the present compound (I) contains a double bond, the present compound may exist in the form of geometric isomerism (cis-compound, trans-compound), and when the present compound (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound (I) includes an intramolecular salt, hydrate, solvate or polymorphism thereof.

Examples of the optionally substituted unsaturated monocyclic heterocyclic ring of the present invention include an unsaturated monocyclic heterocyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

Examples of the optionally substituted unsaturated fused heterobicyclic ring of the present invention include an unsaturated fused heterobicyclic ring which may optionally be substituted by 1-5 substituents selected from the group consisting of a halogen atom, a nitro group, a cyano group, an oxo group, a hydroxy group, a mercapto group, a carboxyl group, a sulfo group, an alkyl group, an alkenyl group, an alkynyl group, a cycloalkyl group, a cycloalkylidene-methyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenyl-carbonyl group, a cycloalkynyl-carbonyl group, an arylcarbonyl group, a heterocyclylcarbonyl group, an alkoxycarbonyl group, an alkenyloxycarbonyl group, an alkynyloxy-carbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cyclo-alkynylcarbonyloxy group, an arylcarbonyloxy group, a heterocyclyl-carbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoyl-amino group, a mono- or di-alkoxycarbonylamino group, a mono- or di-arylcarbonylamino group, an alkylsulfinylamino group, an alkyl-sulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cyclo-alkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group, wherein each substituent may optionally be further substituted by these substituents.

Examples of the optionally substituted benzene ring of the present invention include a benzene ring which may optionally be substituted by 1-5 substituents selected from the group consisting of a halogen atom, a nitro group, a cyano group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group wherein each substituent may optionally be further substituted by these substituents. Moreover, examples of the optionally substituted benzene ring include a benzene ring substituted with an alkylene group to form an annelated carbocycle together with the carbon atoms to which they are attached, and also includes a benzene ring substituted with an alkenylene group to form an annelated carbocycle such as a fused benzene ring together with the carbon atoms to which they are attached.

Preferable examples of the optionally substituted unsaturated monocyclic heterocyclic ring include an unsaturated monocyclic heterocyclic ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted unsaturated fused heterobicyclic ring include an unsaturated fused heterobicyclic ring which may optionally be substituted by 1-3 substituents independently selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted benzene ring include a benzene ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, an alkylene group, an alkyleneoxy group, an alkylenedioxy group, and an alkenylene group.

In another preferable embodiment of the present invention, the optionally substituted unsaturated monocyclic heterocyclic ring is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group;

the optionally substituted unsaturated fused heterobicyclic ring is an unsaturated fused heterobicyclic ring which may optionally be substituted by 1-3 substituents selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkanoyl group, an alkylsulfonylamino group, a phenyl group, a phenoxy group, a phenylsulfonylamino group, phenylsulfonyl group, a heterocyclyl group, and an oxo group; and the optionally substituted benzene ring is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxy group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, an oxo group, a carbamoyl group, and a mono- or di-alkylcarbamoyl group.

In a preferable embodiment, the optionally substituted unsaturated monocyclic heterocyclic ring is an unsaturated monocyclic heterocyclic ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is an unsaturated fused heterobicyclic ring which may optionally be substituted by 1-3 substituents independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxy group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In another preferable embodiment, (1) Ring A is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

(2) Ring A is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group, and Ring B is an unsaturated monocyclic heterocyclic ring or an unsaturated fused heterobicyclic ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group; or (3) Ring A is an unsaturated fused heterobicyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In a more preferable embodiment of the present invention, Ring A and Ring B are (1) Ring A is an unsaturated monocyclic heterocyclic ring which may optionally be substituted by a halogen atom, a lower alkyl group, a halo-lower alkyl group, a lower alkoxy group, or an oxo group, and Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mono- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group;

(2) Ring A is a benzene ring which may optionally be substituted by a halogen atom, a lower alkyl group, a halo-lower alkyl group, a lower alkoxy group, a phenyl group, or a lower alkenylene group, and Ring B is (a) an unsaturated monocyclic heterocyclic ring which may optionally be substituted by a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, a mono- or di-lower alkylamino group, or a carbamoyl group; or a heterocyclyl group optionally substituted by a halogen atom, a cyano group, a lower alkyl group, a halo-lower alkyl group, a lower alkoxy group, a mono- or di-lower alkylamino group or a carbamoyl group; (b) an unsaturated fused heterobicyclic ring which may optionally be substituted by a group selected from a halogen atom, cyano group, a lower alkyl group, a halo-lower alkyl group, a phenyl-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (3) Ring A is an unsaturated fused heterobicyclic ring which may optionally be substituted by a halogen atom, a lower alkyl group, a halo-lower alkyl group, a lower alkoxy group, or an oxo group, and Ring B is (a) a benzene ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; (b) an unsaturated monocyclic heterocyclic ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group.

In another more preferable embodiment, Y is —CH$_2$— and is linked at the 3-position of Ring A, with respect to X being the 1-position, Ring A is a benzene ring which is substituted by 1-3 substituents selected from the group consisting of a lower alkyl group, a halo-lower alkyl group, a halogen atom, a lower alkoxy group, a phenyl group, and a lower alkenylene group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxy phenyl group, a lower alkylenedioxyphenyl group, a lower alkyleneoxy phenyl group, a mono- or di-lower alkylaminophenyl group, a carbamoyl phenyl group, a mono- or di-lower alkylcarbamoylphenyl group, a heterocyclyl group, a haloheterocyclyl group, a cyanoheterocyclyl group, a lower alkylheterocyclyl group, a lower alkoxyheterocyclyl group, a mono- or di-lower alkylaminoheterocycyclyl group, a carbamoylheterocyclyl group, and a mono- or di-lower alkylcarbamoyl group.

In another more preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is a benzene ring which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, a cyanoheterocyclyl group, a lower alkylheterocyclyl group, and a lower alkoxyheterocyclyl group.

Further, in another preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxyphenyl group, a heterocyclyl group, a haloheterocyclyl group, a cyanoheterocyclyl group, a lower alkylheterocyclyl group, and a lower alkoxyheterocyclyl group.

In a more preferable embodiment of the present invention, X is a carbon atom and Y is —CH$_2$—.

Further, in another preferable embodiment, Ring A and Ring B are
(1) Ring A is a benzene ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, a phenyl group, and a lower alkenylene group, and
Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group, a halo-lower alkoxy group, or a carbamoyl group; a heterocyclyl group optionally substituted by a halogen atom, a cyano group, a lower alkyl group, a halo-lower alkyl group, a lower alkoxy group, a halo-lower alkoxy group or a carbamoyl group; and an oxo group,
(2) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, and
Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; a lower alkylene group, (3) Ring A is an unsaturated monocyclic heterocyclic ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group;

(4) Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group, or (5) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group.

In another preferable embodiment of the present invention, Y is linked at the 3-position of Ring A, with respect to X being the 1-position, Ring A is a benzene ring which may optionally be substituted by a halogen atom, a lower alkyl group optionally substituted by a halogen atom, a lower alkoxy group, or a phenyl group, and Ring B is an unsaturated monocyclic heterocyclic ring or an unsaturated fused heterobicyclic ring which may optionally be substituted by 1-3 substituents, independently selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and an oxo group.

In another more preferable embodiment of the present invention, Y is linked at the 3-position of Ring A, with respect to X being the 1-position, Ring A is an unsaturated monocyclic heterocyclic ring which may optionally be substituted by a substituent selected from a halogen atom, a lower alkyl group, and an oxo group, and Ring B is a benzene ring which may optionally be substituted by a substituent selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and a lower alkylene group.

Preferable examples of unsaturated monocyclic heterocyclic ring include a 5- or 6-membered unsaturated heterocyclic ring containing 1 or 2 hetero atoms independently selected from a nitrogen atom, an oxygen atom, and a sulfur atom. More specifically, preferred are furan, thiophene, oxazole, isoxazole, triazole, tetrazole, pyrazole, pyridine, pyrimidine, pyrazine, dihydroisoxazole, dihydropyridine, and triazole. Preferable unsaturated fused heterobicyclic ring includes a 9- or 10-membered unsaturated fused heterocyclic ring containing 1 to 4 hetero atoms independently selected from a nitrogen atom, an oxygen atom, and a sulfur atom. More specifically, preferred are indoline, isoindoline, benzothiazole, benzoxazole, indole, indazole, quinoline, isoquinoline, benzothiophene, benzofuran, thienothiophene, and dihydroisoquinoline.

In a more preferred embodiment of the present invention, Ring A is a benzene ring which may optionally be substituted by a substituent selected from the group consisting of a halogen atom, a lower alkyl group, a halo-lower alkyl group, a lower alkoxy group, and a phenyl group, and Ring B is a heterocyclic ring selected from the group consisting of thiophene, furan, benzofuran, benzothiophene, and benzothiazole, wherein the heterocyclic ring may optionally be substituted by a substituent selected from the following group: a halogen atom, a cyano group, a lower alkyl group, a halo-lower alkyl group, a phenyl-lower alkyl group, a lower alkoxy group, a halo-lower alkoxy group, a phenyl group, a halophenyl group, a lower alkylphenyl group, a lower alkoxyphenyl group, a thienyl group, a halothienyl group, a pyridyl group, a halopyridyl group, and a thiazolyl group.

In yet another preferred embodiment, Y is —$CH_2$—, Ring A is an unsaturated monocyclic heterocyclic ring or an unsaturated fused heterobicyclic ring selected from the group consisting of thiophene, dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic ring may optionally substituted by a substituent selected from the following group: a halogen atom, a lower alkyl group, and an oxo group, and Ring B is a benzene ring which may optionally be substituted by a substituent selected from the following group: a halogen atom, a lower alkyl group, a halo-lower alkyl group, a lower alkoxy group, and a halo-lower alkoxy group.

In a further preferred embodiment of the present invention, Ring A is a benzene ring which is substituted by a halogen atom or a lower alkyl group, and Ring B is thienyl group which is substituted by phenyl group or a heterocyclyl group in which said phenyl group and heterocyclyl group is substituted by 1-3 substituents selected from a halogen atom, a cyano group, a lower alkyl group, a halo-lower alkyl group, a lower alkoxy group, and a halo-lower alkoxy group.

Further, in another aspect of the present invention, preferable examples of the compound of the formula I include a compound wherein Ring A is

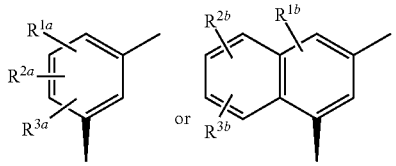

wherein $R^{1a}$, $R^{2a}$, $R^{3a}$, $R^{1b}$, $R^{2b}$, and $R^{3b}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group, or a phenylsulfonyl group, and
Ring B is

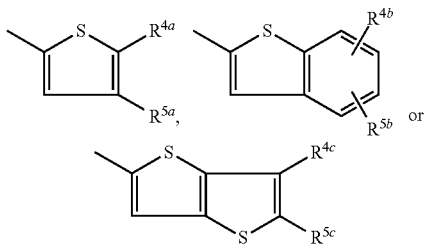

wherein $R^{4a}$ and $R^{5a}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, a mono- or di-alkylamino group, a carbamoyl group, or a mono- or di-alkylcarbamoyl group; or a heterocyclyl group optionally substituted by a halogen atom, a cyano group, an alkyl group, a haloalkyl group, an alkoxy group, a haloalkoxy group, a carbamoyl group, or a mono- or di-alkylcarbamoyl group, or $R^{4a}$ and $R^{5a}$ are bonded to each other at the terminals thereof to form an alkylene group; and
$R^{4b}$, $R^{5b}$, $R^{4c}$ and $R^{5c}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, a methylenedioxy group, an ethyleneoxy group, or a mono- or di-alkylamino group; or a heterocyclyl group optionally substituted by a halogen atom, a cyano group, an alkyl group, a haloalkyl group, an alkoxy group or a haloalkoxy group.

More preferred is a compound wherein $R^{1a}$, $R^{2a}$, $R^{3a}$, $R^{1b}$, $R^{2b}$, and $R^{3b}$ are each independently a hydrogen atom, a halogen atom, a lower alkyl group, a halo-lower alkyl group, a lower alkoxy group, or a phenyl group;
$R^{4a}$ and $R^{5a}$ are each independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, or $R^{4a}$ and $R^{5a}$ are bonded to each other at the terminals thereof to form a lower alkylene group; and
$R^{4b}$, $R^{5b}$, $R^{4c}$, and $R^{5c}$ are each independently a hydrogen atom, a halogen atom, a lower alkyl group, a halo-lower alkyl group, a lower alkoxy group, or a halo-lower alkoxy group.

Further preferred is a compound in which Ring B is

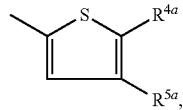

wherein $R^{4a}$ is a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, or $R^{4a}$ and $R^{5a}$ are bonded to each other at the terminals thereof to form a lower alkylene group.

Further more preferred is a compound in which Ring A is

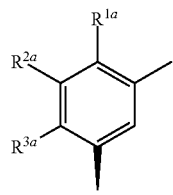

wherein $R^{1a}$ is a halogen atom, a lower alkyl group, or a lower alkoxy group, and $R^{2a}$ and $R^{3a}$ are hydrogen atoms; and Ring B is

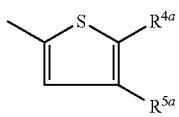

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, and Y is —CH$_2$—.

In more preferable embodiment, $R^{4a}$ is a phenyl group optionally substituted by a halogen atom, a cyano group, a lower alkyl group, a halo-lower alkyl group, a lower alkoxy group, or a halo-lower alkoxy group; or a heterocyclyl group optionally substituted by a halogen atom, a cyano group, a lower alkyl group, or a lower alkoxy group.

In another preferable embodiment of the present invention, a preferable compound can be represented by the following formula IA:

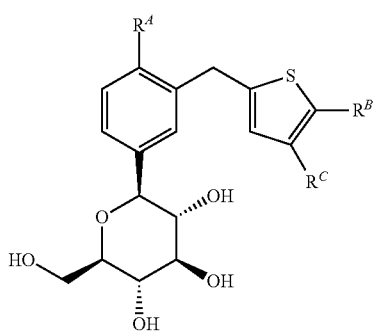

(IA)

wherein $R^A$ is a halogen atom, a lower alkyl group or a lower alkoxy group; $R^B$ is a phenyl group optionally substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group optionally substituted by 1-3 substituents selected from a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; and $R^C$ is hydrogen atom; or $R^B$ and $R^C$ taken together are a fused benzene ring which may be substituted by a halogen atom, a lower alkyl group, a halo-lower alkyl group, a lower alkoxy group or a halo-lower alkoxy group.

In a preferable embodiment, $R^A$ is a halogen atom or a lower alkyl group, $R^C$ is hydrogen atom, and $R^B$ is phenyl group substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group. The chemical structure of such compounds are represented by the following formula (IA'):

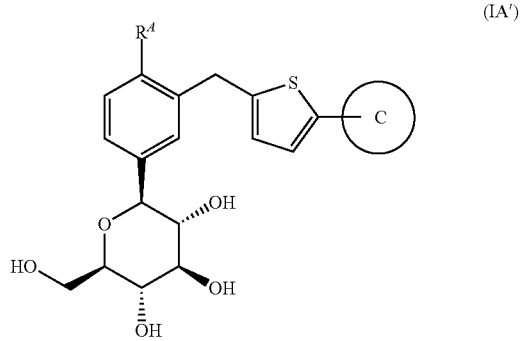

(IA')

wherein $R^A$ is a halogen atom, or a lower alkyl group, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

In a more preferable embodiment, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

Among them, a compound in which Ring C is a phenyl group substituted by a halogen atom, a cyano group, a lower alkyl group, a halo-lower alkyl group, a lower alkoxy group or a halo-lower alkyl group; or a heterocyclyl group substituted by a halogen atom, a cyano group, a lower alkyl group, or a lower alkoxy group is preferred.

A preferred heterocyclyl group includes a 5- or 6-membered heterocyclyl group containing 1 or 2 hetero atoms independently selected from the group consisting of a nitrogen atom, an oxygen atom, and a sulfur atom, or a 9- or 10-membered heterocyclyl group containing 1 to 4 hetero atoms independently selected from the group consisting of a nitrogen atom, an oxygen atom, and a sulfur atom. Specifically, a thienyl group, a pyridyl group, a pyrimidyl group, a pyrazinyl group, pyrazolyl group, a thiazolyl group, a quinolyl group, a tetrazolyl group and an oxazolyl group are preferred.

In a further preferable embodiment, Ring C is a phenyl group substituted by a halogen atom or a cyano group, or a pyridyl group substituted by a halogen atom.

In another preferable embodiment of the present invention, preferred is a compound in which Ring A is

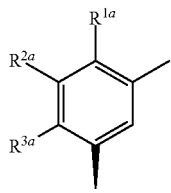

wherein $R^{1a}$ is a halogen atom, a lower alkyl group, or a lower alkoxy group, and $R^{2a}$ and $R^{3a}$ are hydrogen atoms; and Ring B is

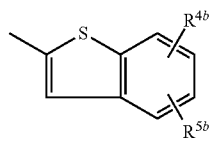

wherein $R^{4b}$ and $R^{5b}$ are each independently a hydrogen atom, a halogen atom, a lower alkyl group, a halo-lower alkyl group, a lower alkoxy group, or a halo-lower alkoxy group.

In another aspect of the present invention, preferable examples of the compound I include a compound represented by the following formula IB:

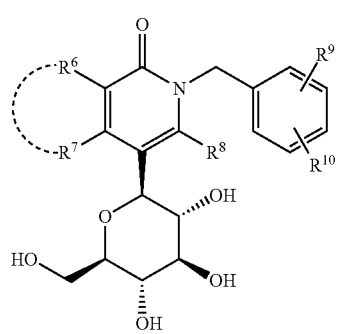

(IB)

wherein $R^8$, $R^9$ and $R^{10}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group; and a group represented by:

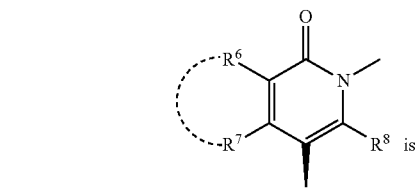 is

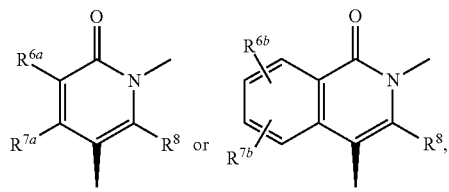

wherein $R^{6a}$ and $R^{7a}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group and $R^{6b}$ and $R^{7b}$ are each independently a hydrogen atom, a halogen atom, an alkyl group, a haloalkyl group, or an alkoxy group.

Among the compounds represented by the formula IB, more preferred is a compound in which $R^8$, $R^9$ and $R^{10}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, and a group represented by:

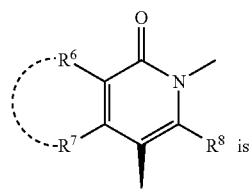 is

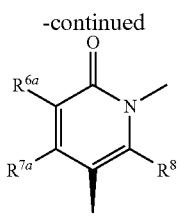

wherein $R^{6a}$, $R^{7a}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, or a group represented by:

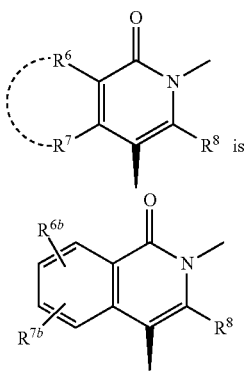

wherein $R^{6b}$ and $R^{7b}$ are each independently a hydrogen atom, a halogen atom, a lower alkyl group, a halo-lower alkyl group, or a lower alkoxy group.

In another aspect of the present invention, preferable examples of the compound I include a compound represented by the following formula IC:

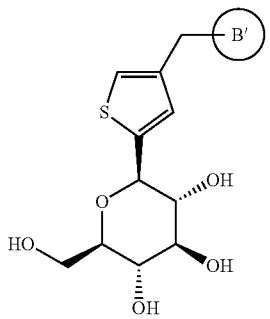

(IC)

wherein Ring B' is an optionally substituted benzene ring, an optionally substituted unsaturated monocyclic heterocyclic ring, or an optionally substituted unsaturated fused heterobicyclic ring.

Preferable examples of Ring B' include a benzene ring and a heterocyclic ring, both of which may have a substituent(s) selected from the group consisting of a halogen atom; a cyano group; a lower alkyl group optionally substituted by a halogen atom; a lower alkoxy group optionally substituted by a halogen atom; a lower alkanoyl group; a mono- or di-lower alkylamino group; a lower alkoxycarbonyl group; a carbamoyl group; a mono- or di-lower alkylcarbamoyl group; a phenyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; a heterocyclyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; an alkylene group; and an oxo group.

More preferable examples of Ring B' include a benzene ring which may be substituted by a substituent selected from the group consisting of a halogen atom; a cyano group; a lower alkyl group optionally substituted by a halogen atom; a lower alkoxy group optionally substituted by a halogen atom; a mono- or di-lower alkylamino group; a phenyl group optionally substituted by a halogen atom, a cyano group, a lower alkyl group optionally substituted by a halogen atom, a lower alkoxy group optionally substituted by a halogen atom; a heterocyclyl group optionally substituted by a halogen atom, a cyano group, a lower alkyl group optionally substituted by a halogen atom, a lower alkoxy group optionally substituted by a halogen atom.

Preferred compound of the present invention may be selected from the following group:

1-(β-D-glucopyranosyl)-4-chloro-3-(6-ethylbenzo[b]thiophen-2-ylmethyl)benzene;
1-(β-D-glucopyranosyl)-4-chloro-3-[5-(5-thiazolyl)-2-thienylmethyl]benzene;
1-(β-D-glucopyranosyl)-4-chloro-3-(5-phenyl-2-thienylmethyl)benzene;
1-(β-D-glucopyranosyl)-4-methyl-3-[5-(4-fluorophenyl)-2-thienylmethyl]benzene;
1-(β-D-glucopyranosyl)-4-chloro-3-[5-(2-pyrimidinyl)-2-thienylmethyl]benzene;
1-(β-D-glucopyranosyl)-4-methyl-3-[5-(2-pyrimidinyl)-2-thienylmethyl]benzene;
1-(β-D-glucopyranosyl)-4-chloro-3-[5-(3-cyanophenyl)-2-thienylmethyl]benzene;
1-(β-D-glucopyranosyl)-4-chloro-3-[5-(4-cyanophenyl)-2-thienylmethyl]benzene;
1-(β-D-glucopyranosyl)-4-methyl-3-[5-(6-fluoro-2-pyridyl)-2-thienylmethyl]benzene;
1-(β-D-glucopyranosyl)-4-chloro-3-[5-(6-fluoro-2-pyridyl)-2-thienylmethyl]benzene;
1-(β-D-glucopyranosyl)-4-methyl-3-[5-(3-difluoromethylphenyl)-2-thienylmethyl]benzene;
1-(β-D-glucopyranosyl)-4-methyl-3-[5-(3-cyanophenyl)-2-thienylmethyl]benzene;
1-(β-D-glucopyranosyl)-4-methyl-3-[5-(4-cyanophenyl)-2-thienylmethyl]benzene;
1-(β-D-glucopyranosyl)-4-chloro-3-[5-(6-fluoro-3-pyridyl)-2-thienylmethyl]benzene;
1-(β-D-glucopyranosyl)-4-fluoro-3-(5-(3-cyanophenyl)-2-thienylmethyl)benzene;
the pharmaceutically acceptable salt thereof; and
the prodrug thereof.

Particularly Preferred compounds of the present invention include:
1-(β-D-glucopyranosyl)-4-methyl-3-[5-(3-cyanophenyl)-2-thienylmethyl]benzene, or a pharmaceutically acceptable salt thereof, or a prodrug thereof;

1-(β-D-glucopyranosyl)-4-methyl-3-[5-(4-cyanophenyl)-2-thienylmethyl]benzene, or a pharmaceutically acceptable salt thereof, or a prodrug thereof;

1-(β-D-glucopyranosyl)-4-methyl-3-[5-(4-fluorophenyl)-2-thienylmethyl]benzene, or a pharmaceutically acceptable salt thereof, or a prodrug thereof;

1-(β-D-glucopyranosyl)-4-chloro-3-[5-(3-cyanophenyl)-2-thienylmethyl]benzene, or a pharmaceutically acceptable salt thereof, or a prodrug thereof;

1-(β-D-glucopyranosyl)-4-methyl-3-[5-(6-fluoro-2-pyridyl)-2-thienylmethyl]benzene, or a pharmaceutically acceptable salt thereof, or a prodrug thereof;

1-(β-D-glucopyranosyl)-4-chloro-3-[5-(6-fluoro-2-pyridyl)-2-thienylmethyl]benzene, or a pharmaceutically acceptable salt thereof, or a prodrug thereof;

1-(β-D-glucopyranosyl)-4-chloro-3-[5-(6-fluoro-3-pyridyl)-2-thienylmethyl]benzene, or a pharmaceutically acceptable salt thereof, or a prodrug thereof; and 1-(β-D-glucopyranosyl)-4-fluoro-3-(5-(3-cyanophenyl)-2-thienylmethyl)benzene, or a pharmaceutically acceptable salt thereof, or a prodrug thereof.

The compound (I) of the present invention exhibits an excellent inhibitory activity against sodium-dependent glucose transporter, and an excellent blood glucose lowering effect. Therefore, the compound of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the compound of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

The compound (I) of the present invention or a pharmaceutically acceptable salt thereof may be administered either orally or parenterally, and can be used in the form of a suitable pharmaceutical preparation. Suitable pharmaceutical preparation for oral administration includes, for example, solid preparation such as tablets, granules, capsules, powders, etc., or solution preparations, suspension preparations, or emulsion preparations, etc. Suitable pharmaceutical preparation for parenteral administration includes, for example, suppositories; injection preparations and intravenous drip preparations using distilled water for injection, physiological saline solution or aqueous glucose solution; or inhalant preparations.

The dosage of the present compound (I) or a pharmaceutically acceptable salt thereof may vary according to the administration routes, ages, body weight, conditions of a patient, or kinds and severity of a disease to be treated, and it is usually in the range of about 0.1 to 50 mg/kg/day, preferably in the range of about 0.1 to 30 mg/kg/day.

The compound of the formula I may be used, if necessary, in combination with one or more of other antidiabetic agents, one or more agents for treating diabetic complications, and/or one or more agents for treatment of other diseases. The present compound and these other agents may be administered in the same dosage form, or in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Concrete examples thereof are biguanide compounds, sulfonylurea compounds, α-glucosidase inhibitors, PPARγ agonists (e.g., thiazolidinedione compounds), PPARα/γ dual agonists, dipeptidyl peptidase IV (DPP4) inhibitors, mitiglinide compounds, and/or nateglinide compounds, and insulin, glucagon-like peptide-1 (GLP-1), PTP1B inhibitors, glycogen phosphorylase inhibitors, RXR modulators, and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula I may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

The present compound of the formula I may be prepared by the following Processes.

Process 1

The compound of the formula I may be prepared by a method as shown in the following scheme:

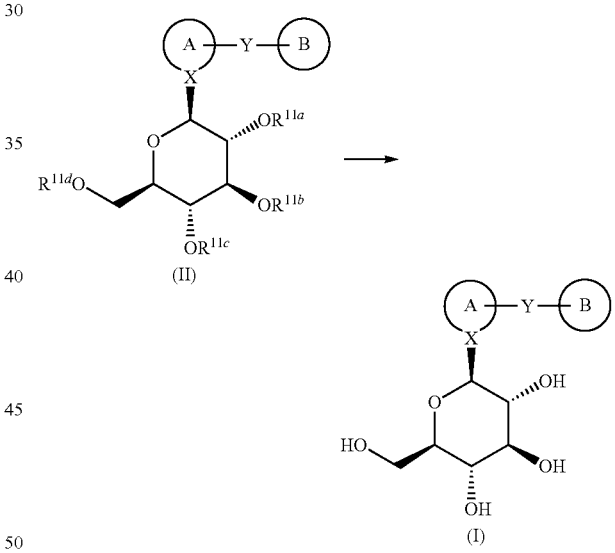

wherein $R^{11a}$ is a hydrogen atom or a protecting group for a hydroxy group, and $R^{11b}$, $R^{11c}$ and $R^{11d}$ are each independently a protecting group for a hydroxy group, and other symbols are as defined above.

The compound of the formula I may be prepared by deprotecting the compound of the formula II.

In the compound of the formula II, the protecting group for hydroxy group may be any conventional protecting groups, and a benzyl group, an acetyl group, and an alkylsilyl group such as a trimethylsilyl group may be used. Further, the protecting group for hydroxy group may form acetal or silylacetal together with adjacent hydroxy groups. Examples of such protecting group include an alkylidene group such as an isopropylidene group, a sec-butylidene group, etc., a benzylidene group, or a dialkylsilylene group such as di-tert-butylsilylene group, etc., which can be formed, for example, by combining $R^{11c}$ and $R^{11d}$ at the terminal thereof.

The deprotection can be carried out according to the kinds of protecting group to be removed, for example, by conventional processes such as reduction, hydrolysis, acid treatment, fluoride treatment, etc.

For example, when a benzyl group is to be removed, the deprotection can be carried out by (1) catalytic reduction using a palladium catalyst (e.g., palladium-carbon, palladium hydroxide) under hydrogen atmosphere in a suitable solvent (e.g., methanol, ethanol, ethyl acetate); (2) treatment with an dealkylating agent such as boron tribromide, boron trichloride, boron trichloride•dimethylsulfide complex, or iodotrimethylsilane in a suitable solvent (e.g., dichloromethane); or (3) treatment with a lower alkylthiol such as ethanethiol in the presence of a Lewis acid (e.g., boron trifluoride•diethyl ether complex) in a suitable solvent (e.g., dichloromethane).

When a protecting group is removed by hydrolysis, the hydrolysis can be carried out by treating the compound of formula II with a base (e.g., sodium hydroxide, potassium hydroxide, lithium hydroxide, sodium methoxide, sodium ethoxide, etc.) in a suitable solvent (e.g., tetrahydrofuran, dioxane, methanol, ethanol, water, etc.).

Acid treatment can be carried out by treating the compound of formula II with an acid (e.g., hydrochloric acid, p-toluenesulfonic acid, methanesulfonic acid, trifluoroacetic acid, etc.) in a suitable solvent (e.g., methanol, ethanol, etc.).

In case of the fluoride treatment, it can be carried out by treating the compound of formula II with a fluoride (e.g., hydrogen fluoride, hydrogen fluoride-pyridine, tetrabutylammonium fluoride, etc.) in a suitable solvent (e.g., acetic acid, a lower alcohol (methanol, ethanol, etc.), acetonitrile, tetrahydrofuran, etc.).

The deprotection reaction can be preferably carried out under cooling or with heating, for example, at a temperature of from 0° C. to 50° C., more preferably at a temperature of from 0° C. to room temperature.

Accordingly, a compound of formula (IA'):

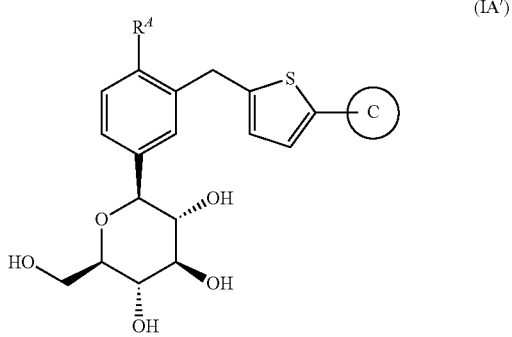

wherein the symbols are the same as defined above, can be prepared by deprotecting a compound of formula (II-A):

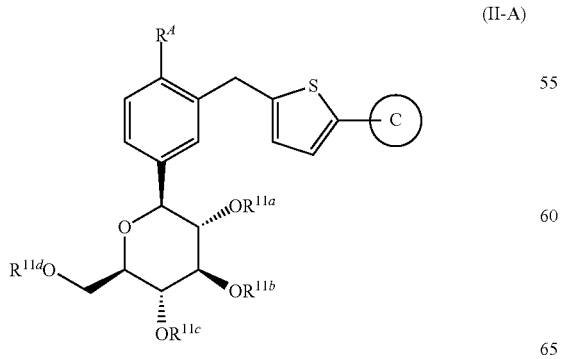

wherein the symbols are the same as defined above, as described above.

Process 2

The compound of the formula I wherein X is a carbon atom may be prepared by a method as shown in the following scheme:

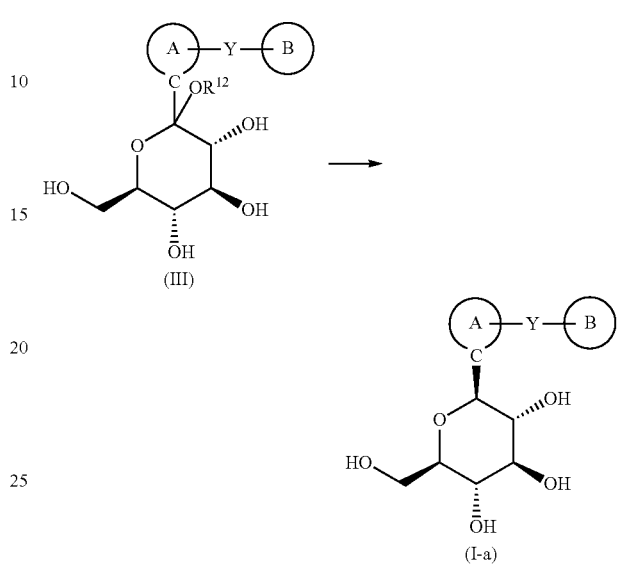

wherein $R^{12}$ is a lower alkyl group, and other symbols are as defined above.

The compound of the formula I-a may be prepared by reducing the compound of the formula III.

The reduction can be carried out by treatment with a silane reagent, in the presence of an acid, in a suitable solvent or in the absence of a solvent.

As the acid, for example, a Lewis acid such as boron trifluoride•diethyl ether complex, titanium tetrachloride, etc., and a strong organic acid such as trifluoroacetic acid, methanesulfonic acid, etc., may preferably be used.

As the silane reagent, for example, a trialkylsilane such as triethylsilane, triisopropylsilane, etc. may preferably be used.

As the solvent, any kinds of solvent may be used as long as it does not affect the reaction, and for example, acetonitrile, dichloromethane, or an acetonitrile/dichloromethane mixture may preferably be used.

Accordingly, the compound of the formula (IA'):

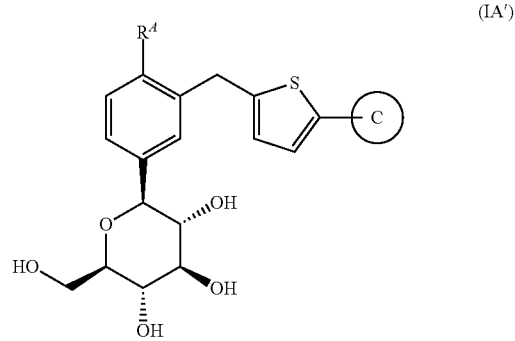

wherein the symbols are the same as defined above, can be prepared by reducing a compound of formula (III-A):

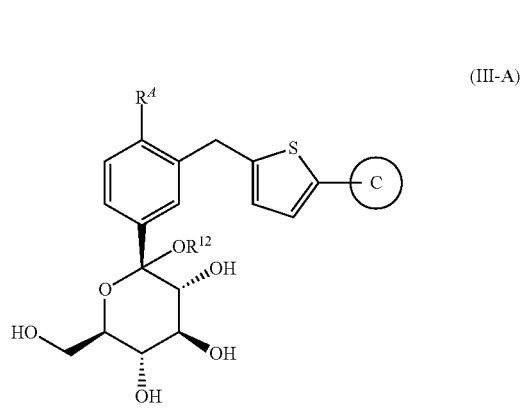

wherein the symbols are the same as defined above, as described above.

Process 3

The compound of the formula I wherein X is a carbon atom may be prepared by a method as shown in the following scheme:

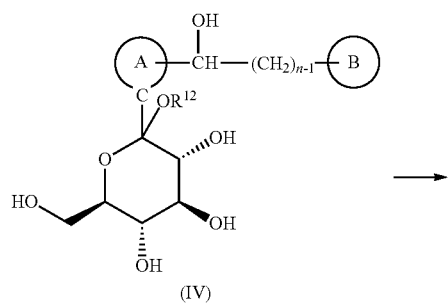

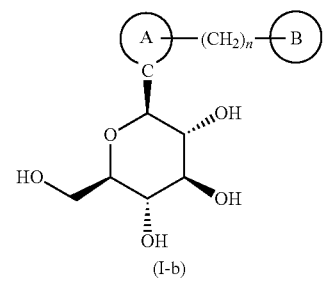

wherein the symbols are as defined above.

Namely, the compound of the formula I-b may be prepared by reducing the compound of the formula IV.

The reduction can be carried out in a manner similar to Process 2. In other words, it can be carried out by treatment with a silane reagent (e.g., triethylsilane, etc.), in the presence of a Lewis acid (e.g., boron trifluoride•diethyl ether complex, etc.), in a suitable solvent (e.g., acetonitrile, dichloromethane, etc.).

The compound of the present invention thus obtained may be isolated and purified by a conventional method well known in the organic synthetic chemistry such as recrystallization, column chromatography, etc.

The starting compound represented by the formula (II), (III) or (IV) may be prepared by either one of the following steps (a)-(l).

Steps (a) and (b):

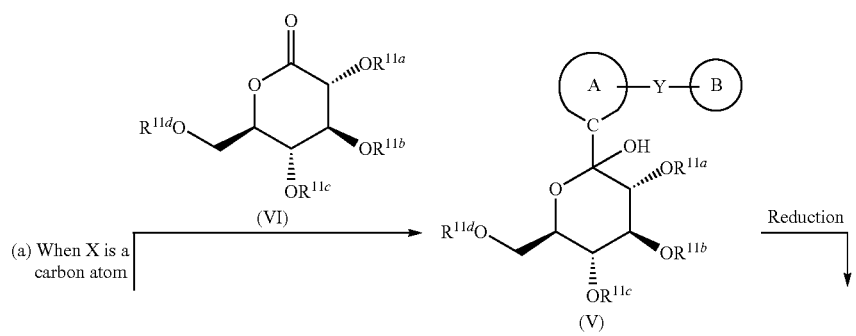

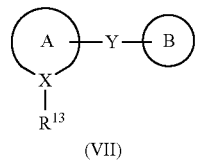

(VII)

(b) When X is a nitrogen atom | Silylation

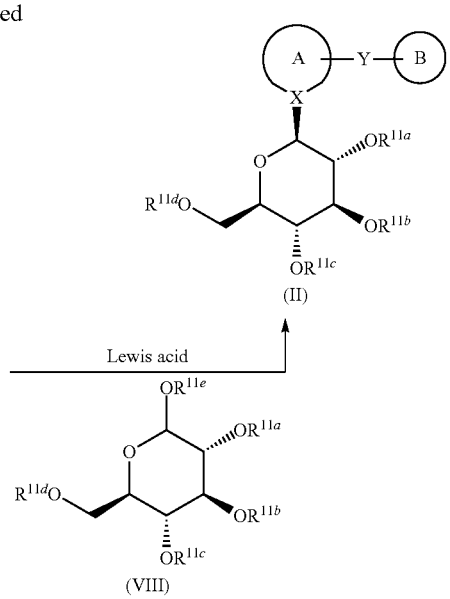

In the above scheme, $R^{13}$ is (1) a bromine atom or an iodine atom when X is a carbon atom; or (2) a hydrogen atom when X is a nitrogen atom, $R^{11e}$ is a protecting group for hydroxy group, and the other symbols are as defined above.

Step (a):

Among the compounds of the formula II, the compound wherein X is a carbon atom may be prepared by coupling the compound of the formula VII with the compound of the formula VI to give the compound of formula V, followed by reduction of the compound of the formula V.

The coupling reaction can be carried out by lithiating the compound of the formula VII, followed by reacting the resultant with the compound of the formula VI.

In particular, the compound of the formula VII can be treated with an alkyllithium, followed by reacting the resultant with the compound of the formula VI. As the alkyllithium, methyl lithium, n-butyl lithium, t-butyl lithium, etc. are preferably used. The solvent may be any solvent which does not disturb the reaction, and ethers such as tetrahydrofuran, diethyl ether, etc., are preferably used. This reaction can be carried out from under cooling (e.g., at −78° C.) to room temperature.

The reduction can be carried out in a manner similar to Process 2. Namely, it can be carried out by treating the compound of formula V with a silane reagent (e.g., triethylsilane, etc.) in the presence of a Lewis acid (e.g., boron trifluoride•diethyl ether complex, etc.) in a suitable solvent (e.g., acetonitrile, dichloromethane, etc.).

Step (b)

Among the compounds of the formula II, the compound wherein X is a nitrogen atom may be prepared by silylating the compound of the formula VII in a solvent, followed by reacting the resultant with the compound of the formula VIII (e.g., an α- or β-D-glucose pentaacetate, etc.) in the presence of a Lewis acid.

The silylation reaction can be carried out by treating the compound of formula VII with a silylating agent in a solvent. The silylating agent includes, for example, N,O-bis(trimethylsilyl)acetamide, 1,1,1,3,3,3-hexamethyldisilazane, etc.

The solvent may be, for example, halogenated hydrocarbons such as dichloromethane, dichloroethane, chloroform, etc., ethers such as diethyl ether, tetrahydrofuran, 1,2-dimethoxyethane, etc., acetonitrile, etc.

This reaction is preferably carried out under cooling or with heating, for example, at a temperature of from 0° C. to 60° C., preferably at a temperature of from room temperature to 60° C.

The reaction with the compound of the formula VIII can be carried out in a solvent in the presence of a Lewis acid.

The Lewis acid includes, for example, trimethylsilyl trifluoromethanesulfonate, titanium tetrachloride, tin tetrachloride, boron trifluoride•diethyl ether complex.

The solvent may be, for example, halogenated hydrocarbons such as dichloromethane, dichloroethane, chloroform, etc., acetonitrile, etc.

This reaction can be carried out under cooling or with heating, for example, at a temperature of from 0° C. to 100° C., preferably at a temperature of from room temperature to 60° C.

Step (c):

Among the compounds of the formula II, the compound wherein X is a carbon atom and $R^{11a}$ is a hydrogen atom may be prepared by a method as shown in the following scheme:

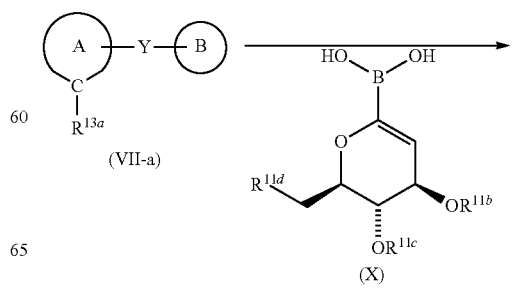

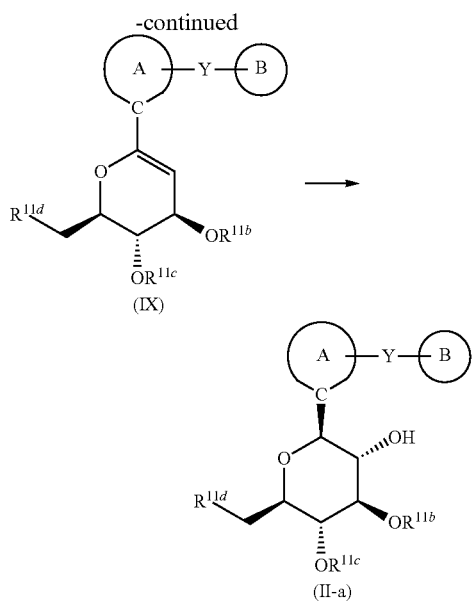

wherein $R^{13a}$ is a bromine atom or an iodine atom, and the other symbols are as defined above.

Namely, the compounds of the formula II-a may be prepared by coupling the compound of the formula VII-a with the compound of the formula X or an ester thereof to give the compound of the formula IX, followed by hydrating the compound of the formula IX.

The ester of the compound of the formula X includes, for example, a lower alkyl ester thereof, and a compound represented by the formula XI:

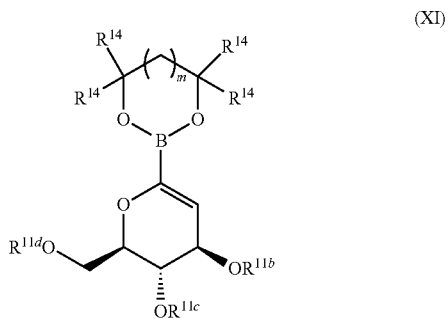

wherein $R^{14}$ is a lower alkyl group, m is 0 or 1, and the other symbols are as defined above.

The coupling reaction of the compound of the formula VII-a with the compound of the formula X or an ester thereof can be carried out in the presence of a base and a palladium catalyst in a suitable solvent.

The base includes an inorganic base such as an alkali metal carbonate (e.g., sodium carbonate, potassium carbonate, etc.), an alkali metal hydrogen carbonate (e.g., sodium hydrogen carbonate, potassium hydrogen carbonate, etc.), an alkali metal hydroxide (e.g., sodium hydroxide, potassium hydroxide, etc.), potassium fluoride, potassium phosphate, etc., and an organic base such as a tri-lower alkylamine (e.g., triethylamine, diisopropylethylamine, etc.), a cyclic tertiary amine (e.g., 1,4-diazabicyclo[2.2.2]octane, 1,5-diazabicyclo[4.3.0]-nona-5-ene, 1,8-diazabicyclo[5.4.0]undeca-7-ene, etc.).

The palladium catalyst may be a conventional catalyst such as tetrakis(triphenyl)phosphinepalladium(0), palladium(II) acetate, palladium(II) chloride, bis(triphenyl)phosphine palladium(II) chloride, palladium(II) chloride•1,1-bis(diphenylphosphino)ferrocene complex, etc.

The solvent may be any inert solvent which does not disturb the reaction, for example, ethers such as tetrahydrofuran, dioxane, 1,2-dimethoxyethane, etc., amide solvents such as N,N-dimethylformamide, 1,3-dimethyl-2-imidazolidinone, etc., aromatic hydrocarbons such as toluene, xylene, etc., dimethylsulfoxide, water, and if desired, a mixture of two or more of these solvents.

This reaction is preferably carried out with heating, for example, at a temperature of from 50° C. to a boiling point of the reaction mixture, and more preferably at a temperature of from 50° C. to 100° C.

The hydration reaction of the compound of the formula IX can be carried out, for example, by hydroboration, more specifically, by reacting with diborane, borane•tetrahydrofuran complex, or 9-borabicyclononane, etc. in a suitable solvent, followed by treating with hydrogen peroxide solution in the presence of a base (e.g., an alkali metal hydroxide such as sodium hydroxide, etc.), or by treating with an oxidizing reagent such as sodium perborate, and oxodiperoxymolybdenum (pyridine) (hexamethylphosphoric triamide) in a suitable solvent.

The solvent may be any inert solvent which does not disturb the reaction, for example, ethers such as diethyl ether, diisopropyl ether, tetrahydrofuran, dioxane, 1,2-dimethoxyethane, etc., aromatic hydrocarbons such as benzene, toluene, xylene, etc., water, and if desired, a mixture of two or more of these solvents. This reaction can be carried out at a temperature of a broad range such as under cooling or with heating, and preferably carried out at a temperature of from −10° C. to a boiling point of the reaction mixture.

Step (d):

Among the compound of the formula II, the compound wherein Ring A is a benzene ring may be prepared in a method as shown in the following scheme:

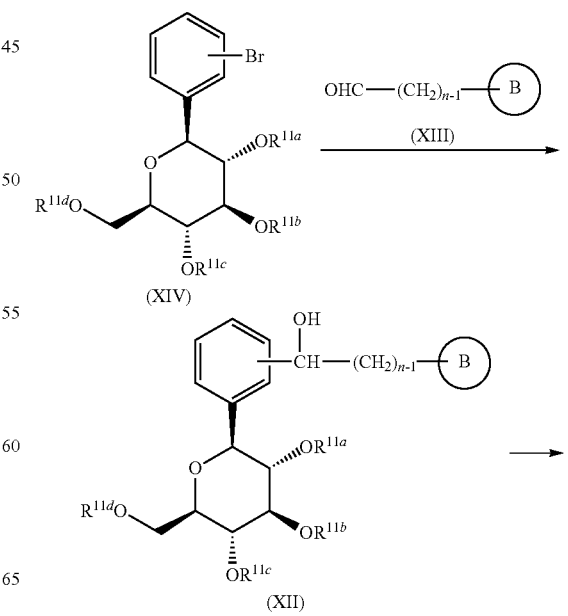

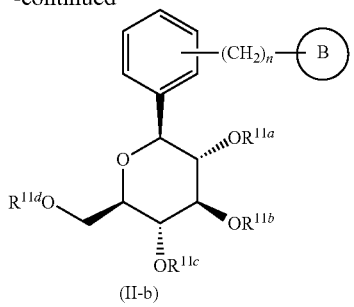

(II-b)

wherein the symbols are as defined above.

Namely, the compounds of the formula II-b may be prepared by coupling the compound of the formula XIV with the compound of the formula XIII, to give the compound of the formula XII, followed by reduction of the compound of the formula XII.

The coupling reaction can be carried out in a manner similar to Step (a). Namely, it can be carried out by lithiating the compound of formula XIV with an alkyl lithium (e.g., n-butyl lithium, tert-butyl lithium, etc.) in a suitable solvent (e.g., diethyl ether, tetrahydrofuran, etc.), followed by reacting the resultant with the compound (XIII).

The reduction reaction can be carried out by (1) treatment with a silane reagent (e.g., trialkyl silane such as triethyl silane, etc.) in a suitable solvent (e.g., acetonitrile, dichloromethane, etc.), at −30° C. to 60° C., in the presence of a Lewis acid such as boron trifluoride•diethyl ether complex or trifluoroacetic acid, (2) treatment with iodotrimethylsilane, or (3) treatment with a reducing agent (e.g., borohydrides such as sodium boron hydride, sodium triacetoxyborohydride, etc., aluminum hydrides such as lithium aluminum hydride, etc.) in the presence of an acid (e.g., a strong acid such as trifluoroacetic acid, etc., and a Lewis acid such as aluminum chloride, etc.).

Step (e):

The compound of the formula III may be prepared by a method as shown in the following scheme:

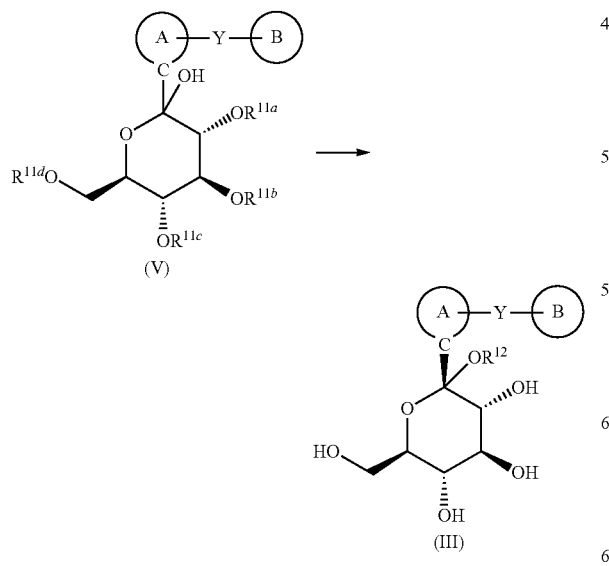

wherein the symbols are as defined above.

Namely, the compound of the formula III may be prepared by deprotecting the compound of the formula V which is a synthetic intermediate of Step (a), followed by treating the resultant compound with an acid in an alcohol solvent.

The deprotection reaction can be carried out in a manner similar to Process 1. Namely, it can be carried out by subjecting the compound V to an acid treatment, reduction, or a fluoride treatment, etc.

Following the deprotection reaction, the resultant compound is treated with an acid in a suitable alcohol. The acid includes, for example, an inorganic acid such as hydrochloric acid, nitric acid, sulfuric acid, etc., an organic acid such as p-toluenesulfonic acid, methanesulfonic acid, trifluoroacetic acid, etc. The alcohol includes a conventional alkyl alcohol which does not disturb the reaction, for example, methanol, ethanol, n-propanol, i-propanol, n-butanol, etc.

Additionally, the deprotection reaction and acid treatment may be carried out in the same step, depending on the kind of the protecting group.

Step (f):

The compound of the formula IV may be prepared by a method as shown in the following scheme:

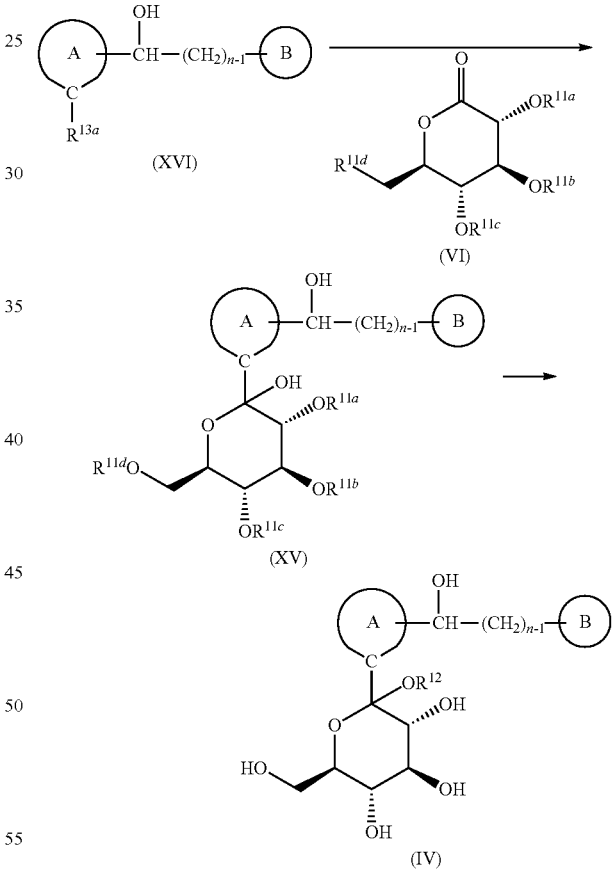

wherein the symbols are as defined as above.

First, the compound of the formula XVI is coupled with the compound of the formula VI to give the compound of the formula XV. Then, after protecting groups are removed from the compound of the formula XV, the resultant is treated with an acid in an alcohol to give the compound of the formula IV.

The coupling reaction can be carried out in a manner similar to Step (a). Namely, the compound XVI is treated with an alkyl lithium (e.g., n-butyl lithium, tert-butyl lithium, etc) in a suitable solvent (e.g., diethyl ether, tetrahydrofuran, etc.), followed by reacting the resultant with the compound VI.

The removal of protecting groups and the acid treatment are carried out in a manner similar to Step (e). Namely, it can be carried out by subjecting the compound XV to reduction, acid treatment or fluoride treatment, depending on the kind of the protecting group to be removed, followed by treating the resultant with an acid (e.g., hydrochloric acid, p-toluenesulfonic acid, methanesulfonic acid, trifluoroacetic acid, etc.) in a suitable solvent (e.g., methanol, ethanol, etc.).

Step (g):

The compound of the formula II may be prepared by a method as shown in the following scheme:

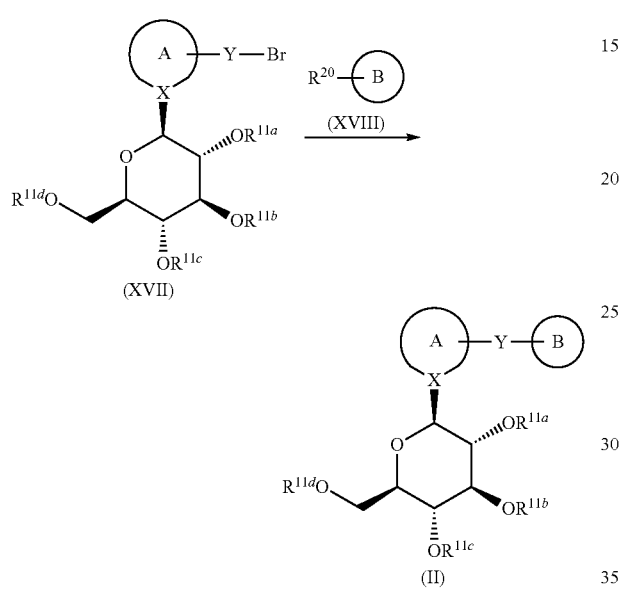

wherein $R^{20}$ is a trialkylstannyl group, or a dihydroxyboryl group or an ester thereof, and the other symbols are as defined above. Examples of esters of dihydroxyboryl group include an ester with a lower alkyl alcohol such as methanol and ethanol and an ester with a lower alkylene diol such as pinacol.

Namely, the compound of the formula II may be prepared by coupling the compound XVII with the compound XVIII in a suitable solvent, in the presence of a palladium catalyst, and in the presence or in the absence of a base.

The coupling reaction can be carried out in a manner similar to Step (c).

Step (h):

Among the compound of the formula II, the compound wherein n is 1 and X is a carbon atom may be prepared in a method as shown in the following scheme:

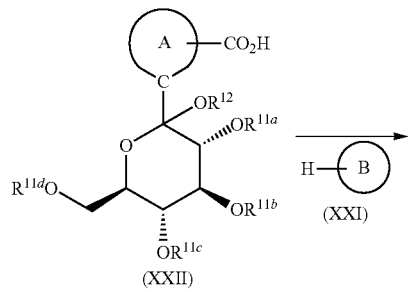

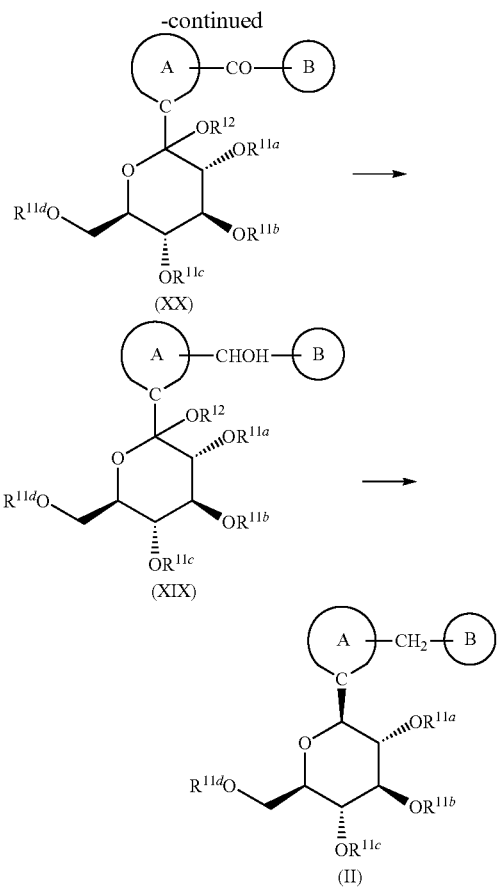

wherein the symbols are as defined above.

Namely, the compound of the formula II may be prepared by the following steps: (1) treating the compound of the formula XXII with a halogenating agent in a suitable solvent or in the absence of a solvent, followed by condensation of the resultant with the compound of the formula XXI in the presence of a Lewis acid to give the compound of formula XX, (2) reducing the compound of formula XX, and (3) further reducing the compound of formula XIX.

The halogenating agent includes a conventional halogenating agent such as thionyl chloride, phosphorus oxychloride, oxalyl chloride, etc.

The solvent may be any solvent which does not disturb the reaction, and for example, dichloromethane, carbon tetrachloride, tetrahydrofuran, toluene, etc. may be mentioned.

Further, in the present reaction, the reaction suitably proceeds by adding a catalyst such as dimethylformamide, etc.

The condensation reaction of the compound (XXII) and the compound (XXI) can be carried out according to a conventional method as known as Friedel-Crafts reaction, in the presence of a Lewis acid and in a suitable solvent.

The Lewis acid includes aluminum chloride, boron trifluoride•diethyl ether complex, tin(IV) chloride, titanium tetrachloride, etc. which are conventionally used in Friedel-Crafts reaction.

The solvent includes halogenated hydrocarbons such as dichloromethane, carbon tetrachloride, dichloroethane, etc.

The reduction of the compound of formula XX can be carried out by treating the compound (XX) with borohydrides (e.g., sodium borohydride, sodium triacetoxyborohydride, etc.) in a suitable solvent (e.g., tetrahydrofuran, etc.).

The present reaction can be carried out under cooling or with heating, for example, at a temperature of from −30° C. to 60° C.

The subsequent reduction reaction can be carried out by treating the compound of formula XIX with a silane reagent (e.g., trialkyl silane, etc.) in a suitable solvent (e.g., acetonitrile, dichloromethane, etc.), in the presence of an acid (e.g., a Lewis acid such as boron trifluoride•diethyl ether complex, etc., and a strong organic acid such as trifluoroacetic acid, methanesulfonic acid, etc.), or by treating with a hydrazine in a suitable solvent (e.g., ethylene glycol, etc.) in the presence of a base (e.g., potassium hydroxide, etc.).

The present reaction can be carried out under cooling or with heating, for example, at a temperature of from −30° C. to 60° C.

Step (i):

Among the compounds of the formula II, the compound wherein X is a nitrogen atom may be prepared by a method as shown in the following scheme:

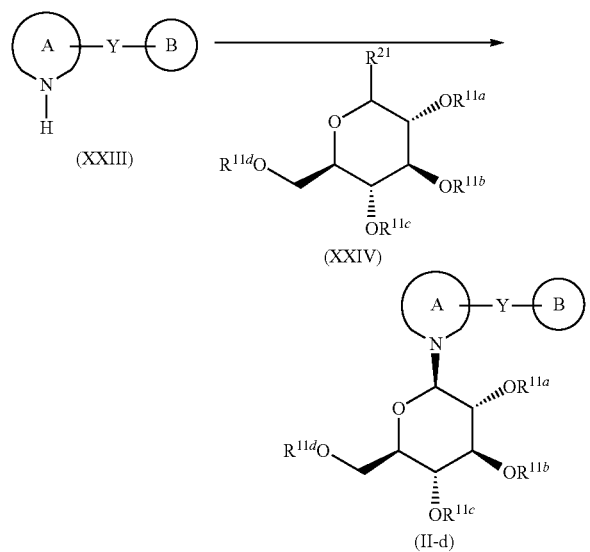

wherein $R^{21}$ is a leaving group, and the other symbols are as defined above.

Examples of the leaving group include a halogen atom such as chlorine atom and bromine atom.

Namely, the compound of the formula II-d may be prepared by condensation of the compound of the formula XXIII with the compound of the formula XXIV.

The condensation reaction can be carried out in a suitable solvent such as acetonitrile, etc., in the presence of a base (e.g., an alkali metal hydroxide, such as potassium hydroxide, etc.).

Step (j):

Among the compound of the formula II, the compound wherein Ring A is a pyrazole substituted by a lower alkyl group, X is a nitrogen atom and Y is —CH$_2$— may be prepared by a method as shown in the following scheme:

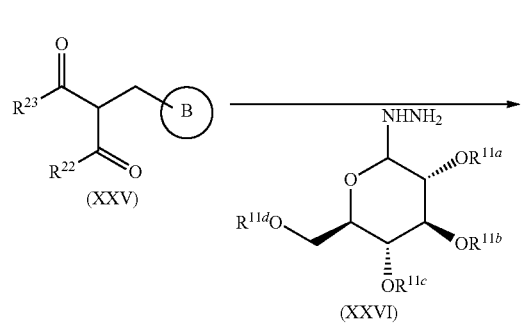

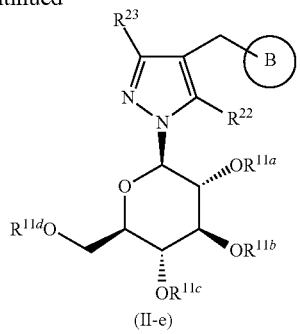

wherein $R^{22}$ and $R^{23}$ are each independently a lower alkyl group, and the other symbols are as defined above.

Namely, the compound II-e may be prepared by condensation of the compound of the formula XXV with the compound of the formula XXVI in a suitable solvent (e.g., ethers such as tetrahydrofuran, etc., an aromatic hydrocarbons such as toluene, etc.).

Step (k):

Among the compounds represented by formula (II), a compound wherein Y is —CH$_2$— group can be prepared by a method as shown in the following scheme:

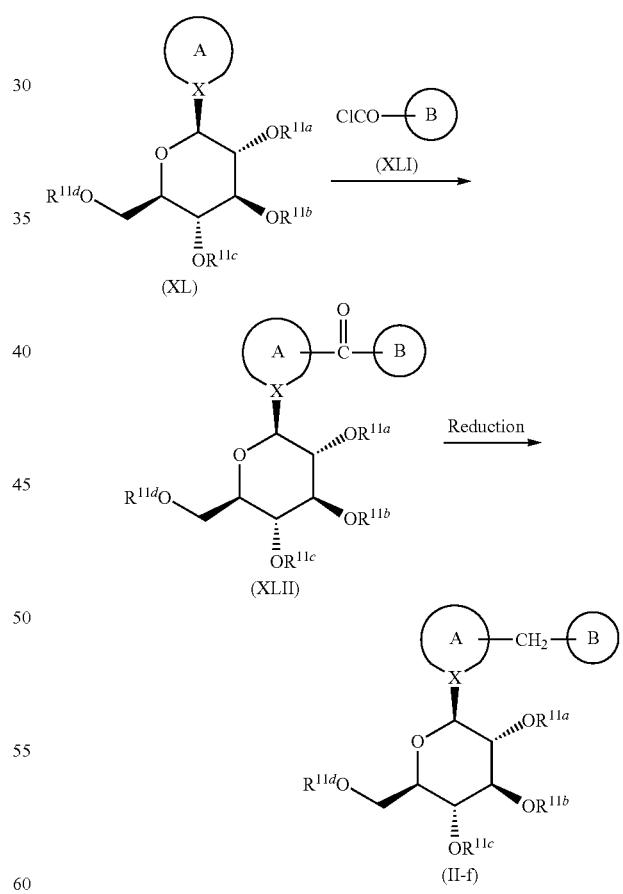

wherein the symbols are the same as defined above.

The compound (II-f) can be prepared by condensing a compound of formula (XL) with a compound of formula (XLI), and reducing a compound of formula (XLII).

The condensation reaction can be carried out in a similar manner as described in Step (h). Namely, the condensation reaction can be carried out in a suitable solvent (e.g., dichloromethane, carbon tetrachloride, dichloroethane, etc.) in the presence of a Lewis acid (e.g., aluminum chloride, zinc chloride, titanium tetrachloride, etc.).

The reduction reaction can be carried out in a similar manner as described in Step (h).

Step (l)

Among the compounds represented by the formula (II), a compound wherein Ring B is an isoindolinyl or dihydroisoquinolinyl group can be prepared by a method as shown in the following scheme:

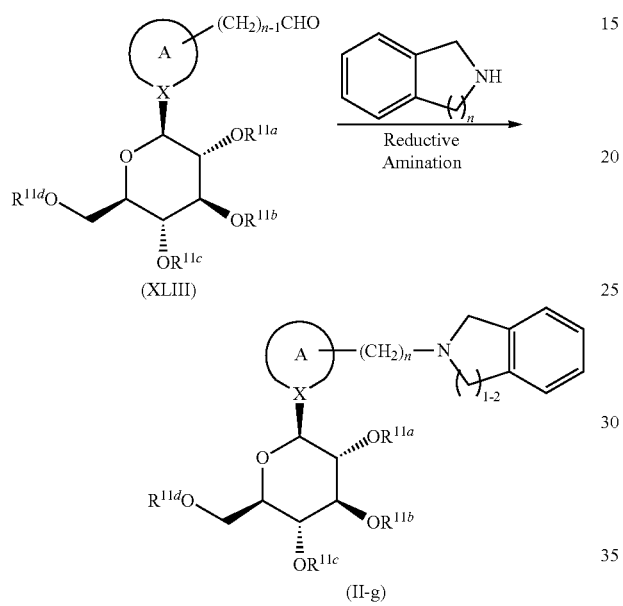

wherein the symbols are the same as defined above.

A compound of formula (II-g) can be prepared by reductive amination of a compound of formula (XLIII) with isoindoline or dihydroisoquinoline. Reductive amination can be carried out in a suitable solvent (e.g., tetrahydrofuran, acetic acid, dichloroethane, etc.) in the presence of a reducing agent such as borohydrides (e.g., sodium borohydride, sodium triacetoxyborohydride) and aluminum hydrides (e.g., lithium aluminum hydride).

Further, the compound of the present invention may be converted to each other within the objective compounds of the present invention. Such conversion reaction may be carried out according to a conventional method, depending on the kind of the objective substituents. It may be preferable that functional groups in the compound would be protected before the conversion. The protective groups for the functional groups can be selected from conventional ones which can be removed by usual methods.

For example, a compound having as a substituent of Ring B an aryl group such as phenyl group or a heterocyclyl group may be prepared by coupling the compound in which substituents of the Ring B is a halogen atom such as a bromine atom, with a suitable phenylboronic acid, phenyltin, heterocyclylboronic acid, or heterocyclyltin.

The coupling reaction may be carried out in a manner similar to Step (c) or Step (g), or in a method as described in the following Examples.

Accordingly, the compound of formula (IA'):

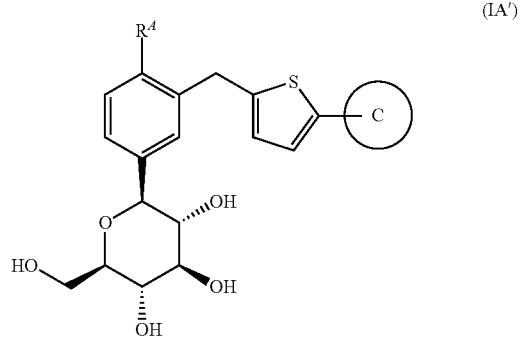

wherein the symbols are the same as defined above, can be prepared by (1) protecting a compound of formula (I-c):

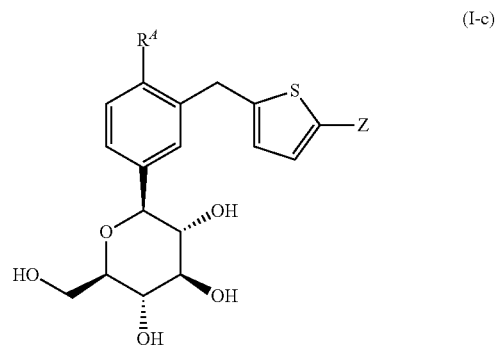

wherein Z is a halogen atom such as chlorine, bromine and iodine atom and $R^A$ is the same as defined above, to afford a compound of formula (II-h):

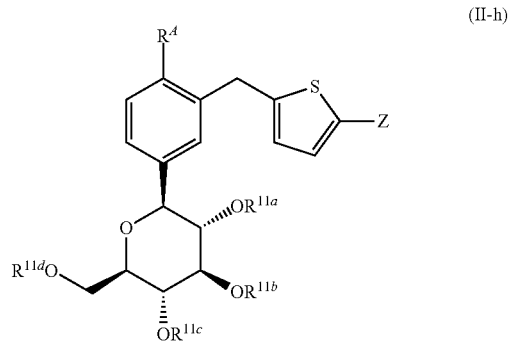

wherein the symbols are the same as defined above, (2) coupling the compound (II-h) with a compound of formula (XLIV):

wherein $R^X$ is $B(OH)_2$ or an ester thereof, or $Sn(\text{lower alkyl})_3$, and Ring C is the same as defined above, to afford a compound of formula (II-A):

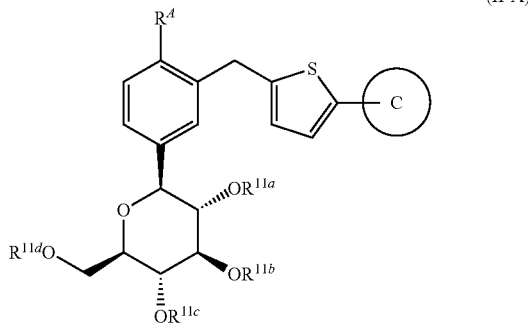
(II-A)

wherein the symbols are the same as defined above, and (3) removing the protecting groups. Examples of esters of $B(OH)_2$ include an ester with a lower alkyl alcohol such as methanol and ethanol and an ester with a lower alkylene diol such as pinacol. Protection of hydroxyl groups can be carried out by conventional methods. Coupling reaction and deprotection can be carried out as described in Step (c) or (g) and Process 1, respectively.

Additionally, the compound of formula (IA'):

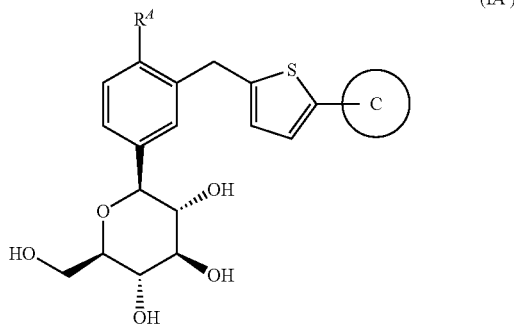
(IA')

wherein the symbols are the same as defined above, can be prepared by (1) converting Z group of a compound of formula (II-h) to $B(OH)_2$ or an ester thereof, (2) coupling said compound with a compound of formula (XLV):

(XLV)

wherein $R^{x1}$ is a halogen atom such as chlorine, bromine and iodine atom and Ring C is the same as defined above, and (3) removing the protecting groups.

Examples of esters of $B(OH)_2$ include an ester with a lower alkyl alcohol such as methanol and ethanol and an ester with a lower alkylene diol such as pinacol.

Conversion of a halogen atom to $B(OH)_2$ or an ester thereof can be carried out in a conventional method. For example, conversion of a halogen atom to $B(OH)_2$ can be carried out by treating the compound (II-h) with an alkyl lithium such as tert-butyl lithium in a suitable solvent (e.g., tetrahydrofuran), reacting the resulting compound with a tri-alkoxyborane in a suitable solvent (e.g., tetrahydrofuran), and hydrolyzing the resulting compound with an acid (such as acetic acid). And conversion of a halogen atom to an ester of $B(OH)_2$ can be carried out by treating the compound (II-h) with an alkyl lithium (such as tert-butyl lithium) in a suitable solvent (e.g., tetrahydrofuran), reacting the resulting compound with a tri-alkoxyborane in a suitable solvent (e.g., tetrahydrofuran), and reacting the resulting compound with an appropriate alcohol in a suitable solvent (e.g., tetrahydrofuran) or without solvent. Coupling reaction and deprotection can be carried out as described in Step (c) or (g) and Process 1, respectively.

In the present compound, the compound wherein heteroatom is oxidized (e.g., S-oxide, S,S-oxide, or N-oxide compounds) may be prepared by oxidizing a corresponding S-form or N-form.

The oxidation reaction can be carried out by a conventional method, for example, by treatment with an oxidizing agent (e.g., peracids such as hydrogen peroxide, m-chloroperbenzoic acid, peracetic acid, etc.) in a suitable solvent (e.g., halogenated hydrocarbons such as dichloromethane, etc.).

The starting compounds of the respective steps described above may be prepared by the methods as disclosed in Reference Examples or a process as mentioned below.

(1) Among the compounds of the formula VII, the compound wherein Y is $-CH_2-$ may be prepared by a method as shown in the following scheme:

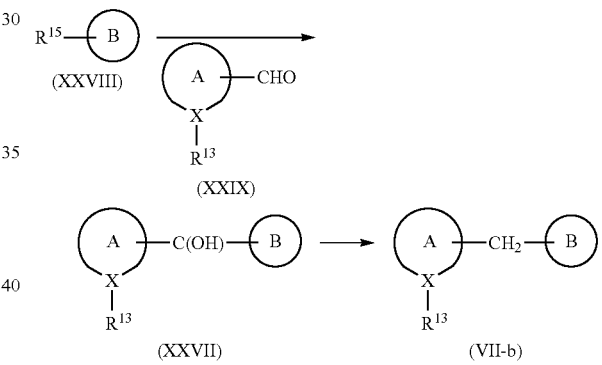

wherein $R^{15}$ is a hydrogen atom or a halogen atom, and the other symbols are as defined above.

Namely, the compound of the formula VII-b may be prepared by coupling the compound of the formula XXVIII with the compound of the formula XXIX to give the compound of the formula XXVII, followed by reducing the obtained compound of the formula XXVII.

The coupling reaction of the present step may be carried out in a manner similar to Step (a). Namely, the compound of the formula XXVIII is treated with an alkyl lithium (e.g., n-butyl lithium, tert-butyl lithium, etc.) in a suitable solvent (e.g., diethyl ether, tetrahydrofuran, etc.), followed by reacting the resultant with the compound of the formula XXIX.

The reduction reaction may be carried out in a manner similar to Step (d), more specifically, by (1) treatment with a silane reagent such as triethylsilane, etc., in a suitable solvent (e.g., acetonitrile, dichloromethane, etc.), at −30° C. to 60° C., in the presence of a Lewis acid such as boron trifluoride•diethyl ether complex or trifluoroacetic acid, (2) treatment with iodotrimethylsilane, or (3) treatment with a reducing agent (e.g., borohydrides such as sodium boron hydride, sodium triacetoxyborohydride, etc., aluminum hydrides such as lithium aluminum hydride, etc.) in the presence of an acid (e.g., a strong acid such as trifluoroacetic acid, etc., a Lewis acid such as aluminum chloride, etc.).

(2) Among the compound of the formula VII, the compound wherein X is a carbon atom and Y is —$CH_2$— may be prepared by a method as shown in the following scheme:

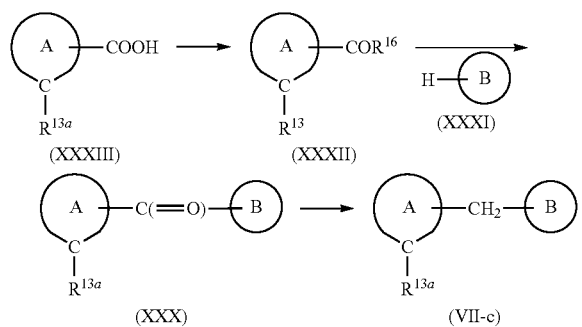

wherein $R^{16}$ is a halogen atom, and the other symbols are as defined above.

The present process may be carried out in a manner similar to Step (h) as mentioned above.

Namely, the compound of the formula VII-c may be prepared by treating the compound of the formula XXXIII with a halogenating reagent (e.g., thionyl chloride, phosphorus oxychloride, oxalyl chloride, etc.) in a suitable solvent (e.g., dichloromethane, carbon tetrachloride, tetrahydrofuran, toluene, etc.) or in the absence of a solvent, to give the compound of the formula XXXII, subsequently by condensing this compound with the compound of the formula XXXI in a suitable solvent (e.g., dichloromethane, carbon tetrachloride, dichloroethane, etc.) in the presence of a Lewis acid (e.g., aluminum chloride, zinc chloride, titanium tetrachloride, etc.), to give the compound of the formula XXX, and further by reducing the obtained compound.

The reduction reaction can be carried out by treating with a silane reagent (e.g., triethylsilane, etc.) in a suitable solvent (e.g., acetonitrile, dichloromethane, etc.), in the presence of an acid (e.g., a Lewis acid such as boron trifluoride•diethyl ether complex, etc., and a strong organic acid such as trifluoroacetic acid, methanesulfonic acid, etc.), or by treating with a hydrazine in a suitable solvent (e.g., ethylene glycol, etc.) in the presence of a base (e.g., potassium hydroxide, etc.).

(3) Among the compounds of the formula VII, the compound wherein X is a carbon atom and Y is —$CH_2$— may be prepared by a method as shown in the following scheme:

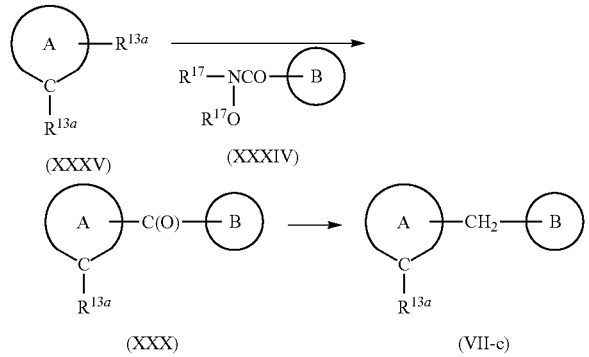

wherein $R^{17}$ is a lower alkyl group, and the other symbols are as defined above.

The compound of the formula VII-c may be prepared by coupling the compound of the formula XXXV with the compound of the formula XXXIV to give the compound of the formula XXX, and subsequently by reducing the obtained compound.

The coupling reaction may be carried out in a manner similar to Step (a). Namely, the compound of the formula (XXV) is lithiated with an alkyllithium (e.g., tert-butyl lithium, n-butyl lithium, etc.) in a suitable solvent (e.g., diethyl ether, tetrahydrofuran, etc.), and subsequently, by reacting the resultant with the compound (XXIV).

The reduction reaction may be carried out in a manner similar to Step (a). Namely, it can be carried out by treating the compound of formula XXX with a silane reagent (e.g., triethylsilane, etc.) in a suitable solvent (e.g., acetonitrile, dichloromethane, etc.), in the presence of an acid (e.g., boron trifluoride•diethyl ether complex, etc).

(4) Among the compound of the formula VII, the compound wherein X is a carbon atom and Y is —$CH_2$— may be prepared by a method as shown in the following scheme:

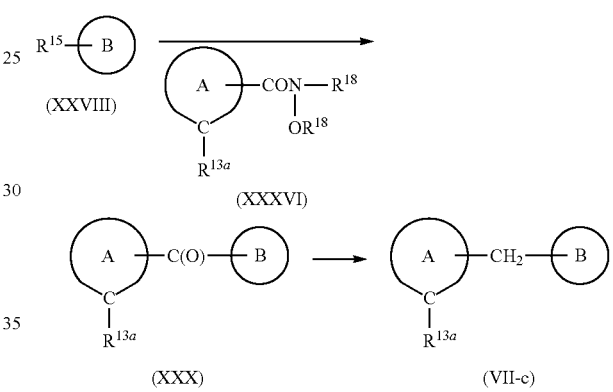

wherein $R^{18}$ is a lower alkyl group, and the other symbols are as defined above.

Namely, the compound of the formula VII-c may be prepared by coupling the compound of the formula XXVIII with the compound of the formula XXXVI to give the compound of the formula XXX, and subsequently by reducing the compound.

The present process may be carried out in a manner similar to Step (3). Namely, the compound of the formula (XXVIII) is lithiated with an alkyllithium (e.g., tert-butyl lithium, n-butyl lithium, etc.) in a suitable solvent (e.g., diethyl ether, tetrahydrofuran, etc.), and subsequently, by reacting the resultant with the compound (XXXVI) to give the compound of the formula (XXX). Subsequently, the compound of the formula XXX is treated with a silane reagent (e.g., triethylsilane, etc.) in a suitable solvent (e.g., acetonitrile, dichloromethane, etc.) in the presence of an acid (e.g., boron trifluoride•diethyl ether complex, etc), to give the compound of the formula (VII-c).

The compound of the formula XIV wherein Ring A is a benzene ring is disclosed in WO 01/27128 pamphlet.

The compound of the formula VI is disclosed in WO 01/27128 or Benhaddu, S. Czernecki et al., Carbohydr. Res., vol. 260, p. 243-250, 1994.

The compound of the formula VIII may be prepared from D-(+)-glucono-1,5-lactone according to the method disclosed in U.S. Pat. No. 6,515,117.

The compound of the formula X and the compound of the formula XI may be prepared by the following Reaction Scheme:

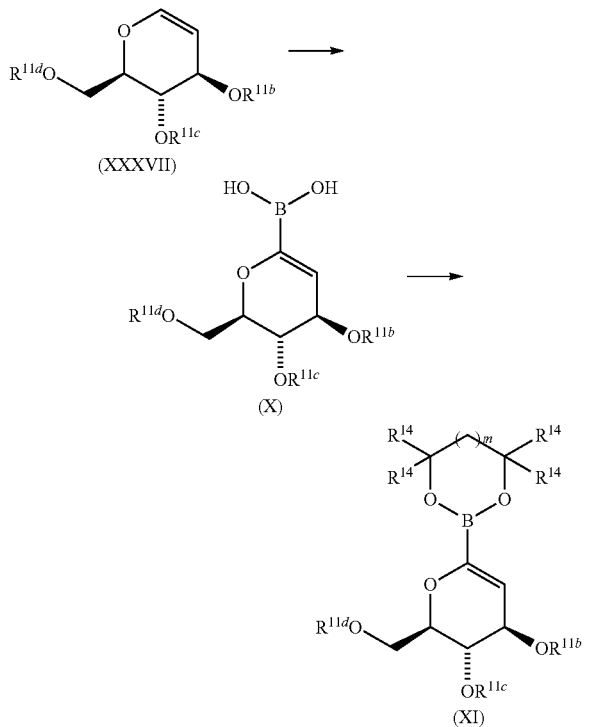

wherein the symbols are as defined above.

First, the compound of the formula XXXVII is lithiated with t-butyl lithium in a suitable solvent (e.g., tetrahydrofuran, etc.) under cooling (e.g., −78° C.), followed by reacting with trimethyl borate to give the compound of the formula X.

Then, the compound of the formula X is reacted with a 1,2-diol (e.g., pinacol, etc.) or 1,3-diol (e.g., 2,4-dimethyl-2, 4-pentanediol, etc.) to give the compound of the formula XI.

The other starting compounds are commercially available or are described in WO 01/27128 or WO 2004/080990, or may easily be prepared by a standard method well known to an ordinary skilled person in this field.

Hereinafter, the present invention will be illustrated by Examples and Reference Examples, but the present invention should not be construed to be limited thereto.

Example 1

1-(β-D-glucopyranosyl)-3-(5-ethyl-2-thienylmethyl)benzene

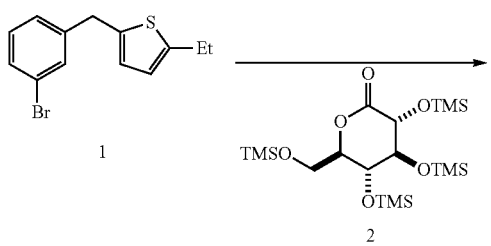

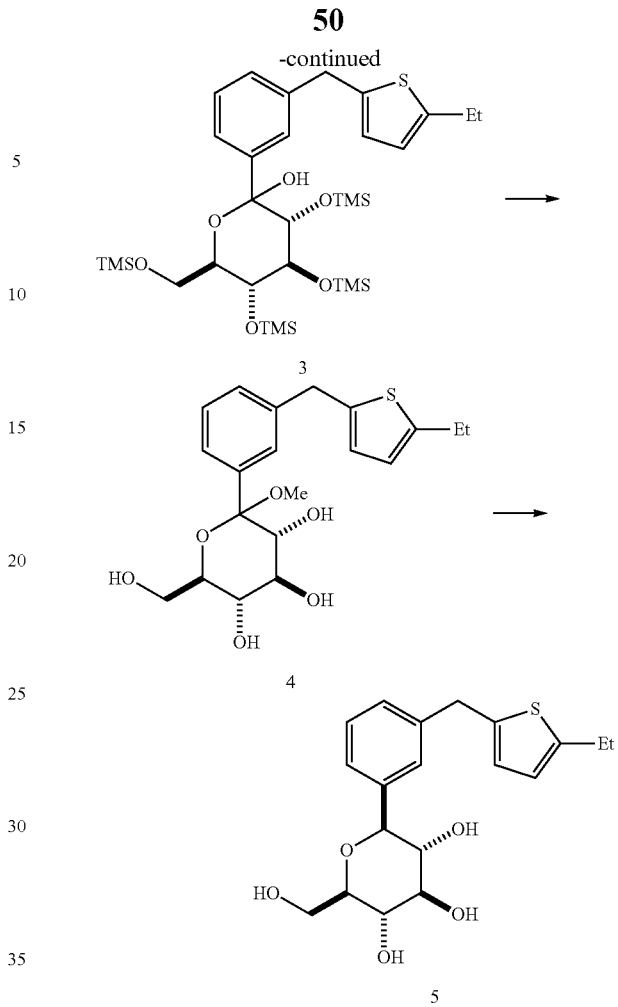

In the above scheme, Me is a methyl group, Et is an ethyl group, TMSO and OTMS are a trimethylsilyloxy group.

(1) 3-Bromo-(5-ethyl-2-thienylmethyl)benzene 1 (211 mg) was dissolved in tetrahydrofuran (2 ml)-toluene (4 ml), and the mixture was cooled to −78° C. under argon atmosphere. To the mixture was added dropwise n-butyl lithium (2.44 M hexane solution, 0.29 ml), and the mixture was stirred at the same temperature for 30 minutes. Then, a solution of 2,3,4, 6-tetrakis-O-trimethylsilyl-D-glucono-1,5-lactone 2 (see U.S. Pat. No. 6,515,117) (233 mg) in toluene (5 ml) was added dropwise, and the mixture was further stirred at the same temperature for one hour to give a lactol compound 3. Without isolating this compound, a solution of methanesulfonic acid (0.1 ml) in methanol (5 ml) was added to the reaction solution, and the mixture was stirred at room temperature overnight. Under ice-cooling, to the mixture was added a saturated aqueous sodium hydrogen carbonate solution, and the mixture was extracted with ethyl acetate. The extract was washed with brine, dried over magnesium sulfate, and the solvent was evaporated under reduced pressure. The residue was purified by silica gel column chromatography (chloroform:methanol=19:1) to give a methyl ether compound 4 (136 mg) of the lactol. APCI-Mass m/Z 412 (M+NH$_4$).

(2) A solution of the above methyl ether compound 4 (100 mg) in dichloromethane (5 ml) was cooled to −78° C. under argon atmosphere, and thereto were added dropwise successively triisopropylsilane (0.16 ml), and boron trifluoride·diethyl ether complex (0.10 ml). The mixture was stirred at the same temperature for 10 minutes, and warmed. The mixture was stirred at 0° C. for 1 hour and 20 minutes, and then further stirred at room temperature for 2 hours. Under ice-cooling, a saturated aqueous sodium hydrogen carbonate solution was added, and the mixture was extracted with ethyl acetate. The extract was washed with brine, dried over magnesium sulfate, and the solvent was evaporated under reduced pressure. The residue was purified by silica gel column chromatography (chloroform:methanol=19:1) to give the desired 1-(β-D-glucopyranosyl)-3-(5-ethyl-2-thienylmethyl)benzene 5 (59 mg). APCI-Mass m/Z 382 (M+NH$_4$).

Example 2
5-(β-D-glucopyranosyl)-1-(4-ethylphenylmethyl)-1H-pyridin-2-one

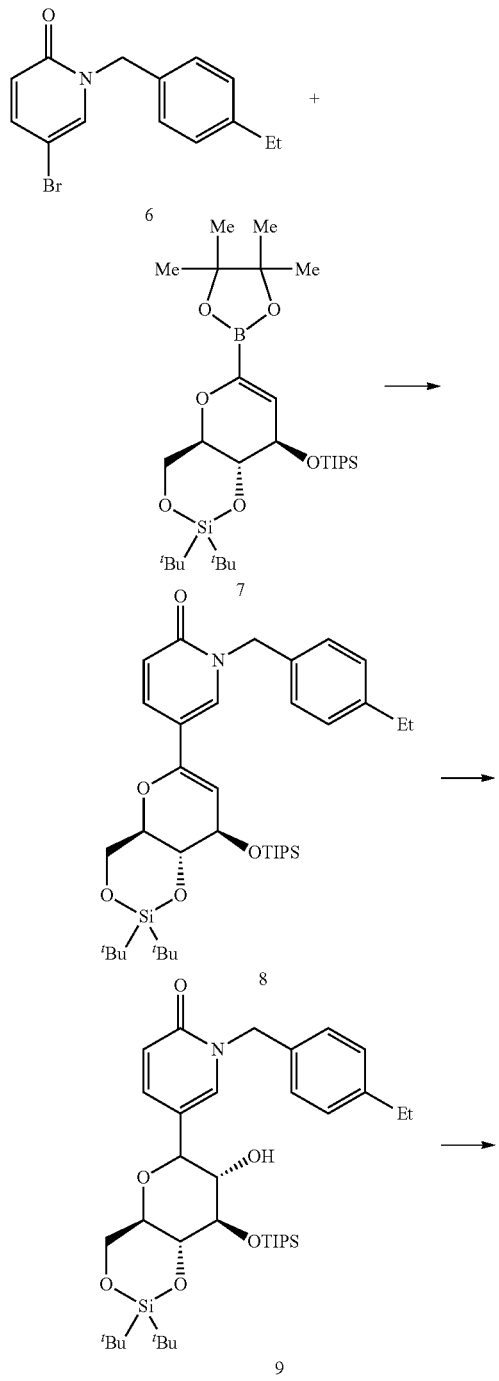

-continued

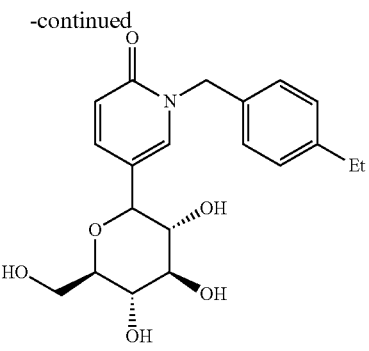

In the above scheme, tBu is a tert-butyl group, OTIPS is a triisopropylsilyloxy group, and the other symbols are as defined above.

(1) 5-Bromo-1-(4-ethylphenylmethyl)-1H-pyridin-2-one 6 (293 mg) and boronic acid ester of glucal 7 (1.0 g) were dissolved in dimethoxyethane (5 ml). To the mixture were added bis(triphenyl)phosphine palladium(II) dichloride (35 mg) and 2M sodium carbonate (2.5 ml), and the mixture was heated with stirring under reflux under argon atmosphere for 5 hours. The mixture was cooled to room temperature, and the reaction solution was diluted with ethyl acetate, and washed with water. The organic layer was collected, dried over magnesium sulfate, and the solvent was evaporated under reduced pressure. The residue was purified by silica gel column chromatography (hexane:ethyl acetate=95:5-70:30) to give glucal derivative 8 (276 mg) as colorless powder. APCI-Mass m/Z 654 (M+H).

(2) A solution of glucal derivative 8 (260 mg) in tetrahydrofuran (5 ml) was cooled to 0° C. under argon atmosphere, and thereto was added dropwise a solution of borane•tetrahydrofuran complex (1.13 M tetrahydrofuran solution, 1.06 ml), and the reaction solution was stirred at the same temperature overnight. A mixture of an aqueous hydrogen peroxide solution (31%, 5.0 ml) and 3N aqueous sodium hydroxide solution (5.0 ml) was added to the reaction solution, and the mixture was warmed to room temperature, and stirred for 30 minutes. To the mixture was added 20% aqueous sodium thiosulfate solution (30 ml), and the mixture was extracted with ether. The extract was washed with brine, dried over magnesium sulfate, and the solvent was evaporated under reduced pressure. The residue was purified by silica gel column chromatography (hexane:ethyl acetate=96:4-66.34) to give C-glucoside compound 9 (59 mg) as colorless powder. APCI-Mass m/Z 672 (M+H).

(3) The above C-glucoside compound 9 (55 mg) was dissolved in tetrahydrofuran (2 ml), and thereto was added tetrabutyl ammonium fluoride (1.0 M tetrahydrofuran solution, 0.41 ml). The mixture was heated with stirring under reflux for 3 hours under argon atmosphere, and the reaction solution was cooled to room temperature. The solvent was evaporated under reduced pressure, and the residue was purified by silica gel column chromatography (chloroform:methanol=100:0-88:12) to give the desired 5-(β-D-glucopyranosyl)-1-(4-ethylphenylmethyl)-1H-pyridin-2-one 10 (10 mg) as colorless powder. APCI-Mass m/Z 376 (M+H).

Example 3

1-(β-D-glucopyranosyl)-3-(benzo[b]thiophen-2-ylmethyl)benzene

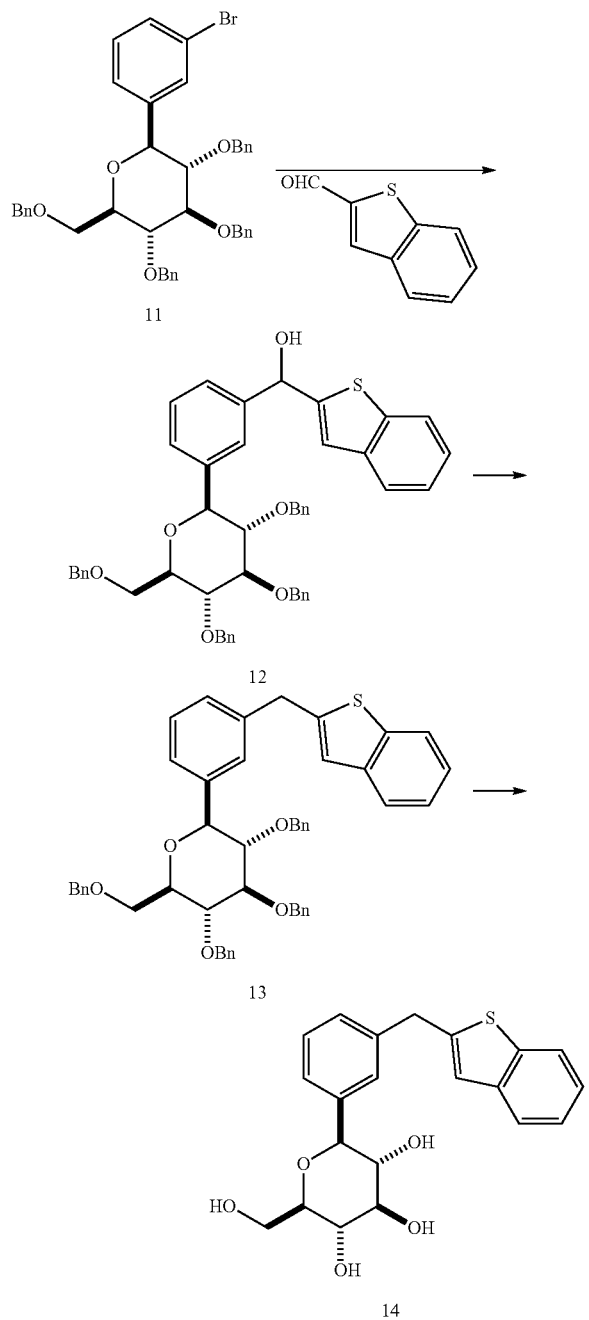

In the above scheme, Bn is a benzyl group.

(1) β-m-Bromophenyl-tetra-O-benzyl-C-glucoside 11 (see WO 01/27128) (1.00 g) was dissolved in diethyl ether (60 ml), and the mixture was cooled to −78° C. under argon atmosphere. To the mixture was added dropwise t-butyl lithium (1.49 M pentane solution, 0.99 ml), and the mixture was stirred at the same temperature for 10 minutes. Then, a solution of 2-formylbenzo[b]thiophene (286 mg) in diethyl ether (2 ml) was added dropwise, and the mixture was further stirred at the same temperature for 30 minutes. To the reaction mixture was added a saturated aqueous ammonium chloride solution, and the mixture was warmed to room temperature. The mixture was extracted with diethyl ether, the extract was dried over magnesium sulfate, and the solvent was evaporated under reduced pressure. The residue was purified by silica gel column chromatography (hexane:ethyl acetate=90:10-50:50) to give an alcohol compound 12 (835 mg). APCI-Mass m/Z 780 (M+NH$_4$).

(2) A solution of the above alcohol compound 12 (820 mg) in dichloromethane (15 ml) was cooled to −78° C. under argon atmosphere, and thereto were added dropwise successively triethylsilane (0.52 ml), and boron trifluoride•diethyl ether complex (0.20 ml). The reaction mixture was warmed to room temperature and stirred at the same temperature for 30 minutes. Added thereto was a saturated aqueous sodium hydrogen carbonate solution, and the mixture was extracted with dichloromethane. The extract was dried over magnesium sulfate, and the solvent was evaporated under reduced pressure. The residue was purified by silica gel column chromatography (hexane:ethyl acetate=94:6-75:25) to give the compound 13 (703 mg). APCI-Mass m/Z 764 (M+NH$_4$).

(3) A solution of the above compound 13 (690 mg) in dichloromethane (20 ml) was cooled to 0° C., and iodotrimethylsilane (0.66 ml) was added thereto and the mixture was stirred at room temperature for one hour. Addition of iodotrimethylsilane and stirring at room temperature were repeated in the same manner for 3 times. Total amount of the iodotrimethylsilane was summed up to 2.64 ml. Under ice-cooling, water was added to the reaction mixture, and the mixture was extracted with diethyl ether twice, and washed with an aqueous sodium thiosulfate solution. The extract was dried over magnesium sulfate, and the solvent was evaporated under reduced pressure. The residue was purified by silica gel column chromatography (chloroform:methanol=100:0-89:11) to give the desired 1-(β-D-glucopyranosyl)-3-(benzo[b]thiophen2-ylmethyl)benzene 14 (180 mg). APCI-Mass m/Z 404 (M+NH$_4$).

Example 4

1-(β-D-glucopyranosyl)-3-(5-chloro-2-thienylmethyl)-4-methylbenzene

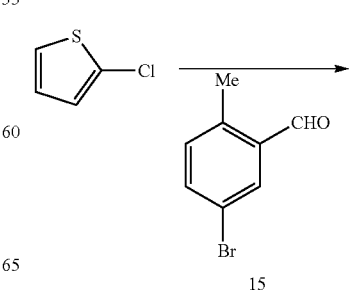

-continued

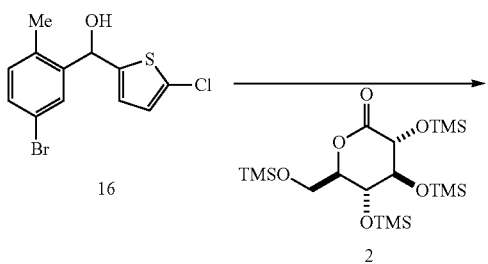

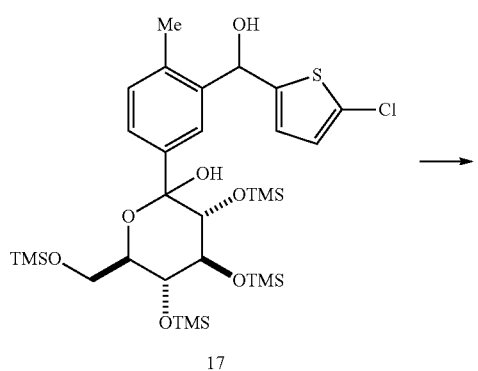

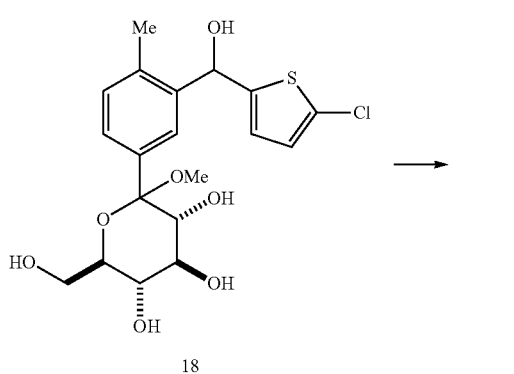

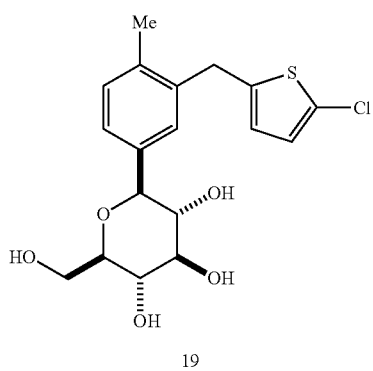

In the above scheme, the symbols are as defined above.

(1) A solution of 2-chlorothiophene (447 mg) in tetrahydrofuran (10 ml) was cooled to −78° C. under argon atmosphere, and thereto was added dropwise n-butyl lithium (1.59 M hexane solution, 2.61 ml). The mixture was stirred at the same temperature for one hour, and added dropwise thereto was a solution of 5-bromo-2-methylbenzaldehyde 15 (750 mg) in tetrahydrofuran (5 ml). The mixture was stirred at the same temperature for 30 minutes to give a compound 16. Toluene (30 ml) was added, and further added dropwise thereto was n-butyl lithium (1.59 M hexane solution, 2.37 ml). The mixture was further stirred at the same temperature for 30 minutes, and a solution of 2,3,4,6-tetrakis-O-trimethylsilyl-D-glucono1,5-lactone 2 (see U.S. Pat. No. 6,515,117) (1.76 g) in toluene (5 ml) was added dropwise, and the mixture was further stirred at the same temperature for one and a half hours to give a lactol compound 17. Subsequently, a solution of methanesulfonic acid (1.22 ml) in methanol (25 ml) was added to the reaction solution, and the mixture was stirred at room temperature overnight. To the mixture was added a saturated aqueous sodium hydrogen carbonate solution, and the mixture was extracted with ethyl acetate. The extract was washed with brine, dried over sodium sulfate, and the solvent was evaporated under reduced pressure to give a crude methyl ether compound 18, which was used in the subsequent step without further purification.

(2) A solution of the above crude methyl ether compound 18 in dichloromethane (25 ml) was cooled to −78° C. under argon atmosphere, and thereto were added dropwise successively triethylsilane (3.01 ml), and boron trifluoride•diethyl ether complex (2.39 ml). The reaction mixture was warmed to 0° C., and stirred at the same temperature for 3 hours. Added thereto was a saturated aqueous sodium hydrogen carbonate solution, and the mixture was extracted with ethyl acetate. The extract was washed with brine, dried over sodium sulfate, and the solvent was evaporated under reduced pressure. The residue was purified by silica gel column chromatography (chloroform:methanol=100:0-92:8) to give the desired 1-(β-D-glucopyranosyl)-3-(5-chloro-2-thienylmethyl)-4-methylbenzene 19 (183 mg). APCI-Mass m/Z 402/404 (M+NH$_4$).

In a manner similar to the method disclosed in any of the above Examples 1 to 4, the compounds shown in Table 1 below were prepared from corresponding starting materials. The numbers shown in a column of "preparation method" in the Table indicates the Example number, according to which the preparation was carried out.

TABLE 1
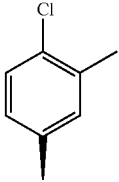
| Examples | Ring A | Ring B | Preparation Method | APCI-Mass (m/Z) |
|---|---|---|---|---|
| 5 | 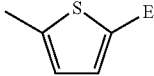 | 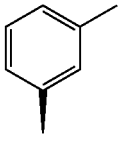 | 1 | 416/418 (M + NH$_4$) |
| 6 | 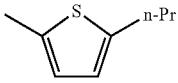 | 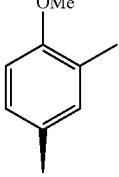 | 1 | 396 (M + NH$_4$) |
| 7 | 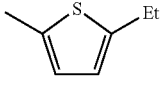 | 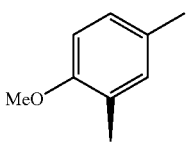 | 1 | 412 (M + NH$_4$) |
| 8 | 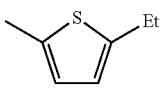 | 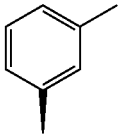 | 1 | 412 (M + NH$_4$) |
| 9 | 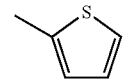 | 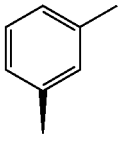 | 3 | 354 (M + NH$_4$) |
| 10 | 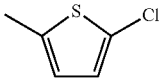 | 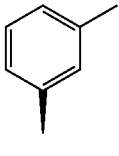 | 3 | 388/390 (M + NH$_4$) |
| 11 | 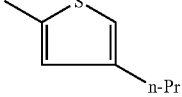 |  | 1 | 396 (M + NH$_4$) |

TABLE 1-continued
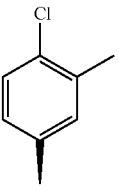
| Examples | Ring A | Ring B | Preparation Method | APCI-Mass (m/Z) |
|---|---|---|---|---|
| 12 | 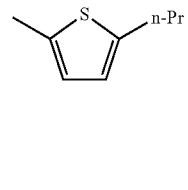 | 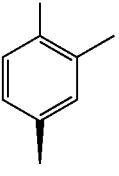 | 1 | 430/432 (M + NH$_4$) |
| 13 | 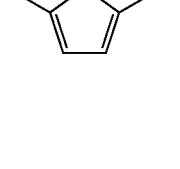 | 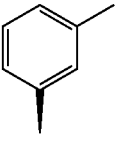 | 1 | 426 (M + NH$_4$) |
| 14 | 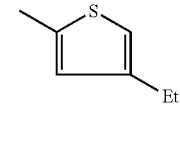 | 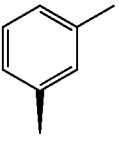 | 1 | 382 (M + NH$_4$) |
| 15 | 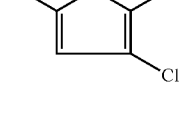 | 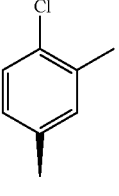 | 1 | 416/418 (M + NH$_4$) |
| 16 | 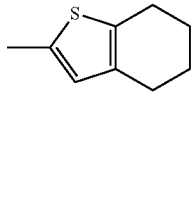 | 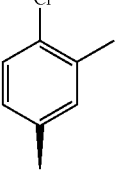 | 1 | 442/444 (M + NH$_4$) |
| 17 | 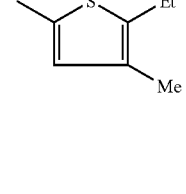 | 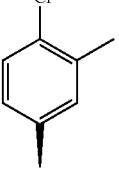 | 1 | 430/432 (M + NH$_4$) |
| 18 | 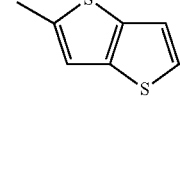 |  | 2 | 444/446 (M + NH$_4$) |

TABLE 1-continued

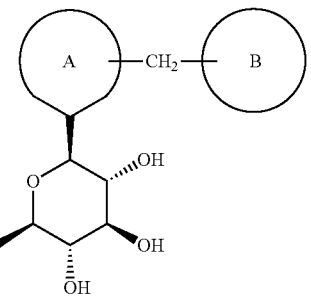

| Examples | Ring A | Ring B | Preparation Method | APCI-Mass (m/Z) |
|---|---|---|---|---|
| 19 | Cl, Me-phenyl | 5-methyl-2-chlorothiophene | 1 | 422/424 (M + NH$_4$) |
| 20 | Cl, Me-phenyl | 5-methyl-2-benzylthiophene | 1 | 478/480 (M + NH$_4$) |
| 21 | Cl, Me-phenyl | 5-methyl-2-(2-thienyl)thiophene | 2 | 470/472 (M + NH$_4$) |
| 22 | Me, Me-phenyl | 5-methyl-5'-chloro-2,2'-bithiophene | 1 | 484/486 (M + NH$_4$) |
| 23 | Cl, Me-phenyl | 5-methyl-2-ethyl-3-chlorothiophene | 1 | 450/452 (M + NH$_4$) |
| 24 | Cl, Me-phenyl | 5-methyl-2-chloro-3-methylthiophene | 4 | 436/438 (M + NH$_4$) |

TABLE 1-continued
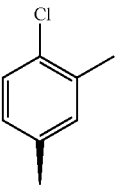
| Examples | Ring A | Ring B | Preparation Method | APCI-Mass (m/Z) |
|---|---|---|---|---|
| 25 | 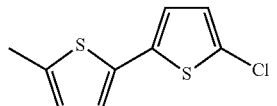 | 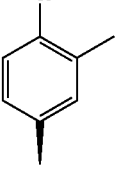 | 1 | 504/506 (M + NH$_4$) |
| 26 | 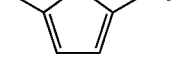 | 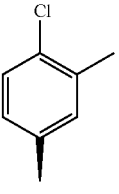 | 2 | 456/458 (M + NH$_4$) |
| 27 | 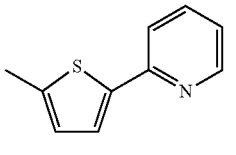 | 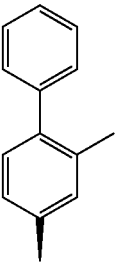 | 1 | 448/450 (M + NH$_4$) |
| 28 | 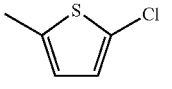 | 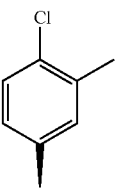 | 1 | 464/466 (M + NH$_4$) |
| 29 | 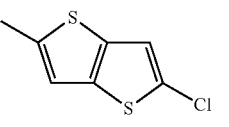 | 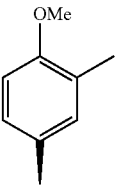 | 4 | 478/480 (M + NH$_4$) |
| 30 | 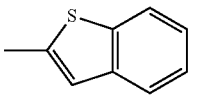 | | 1 | 434 (M + NH$_4$) |

TABLE 1-continued
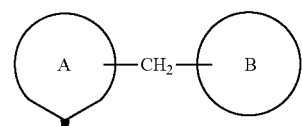
| Examples | Ring A | Ring B | Preparation Method | APCI-Mass (m/Z) |
|---|---|---|---|---|
| 31 | 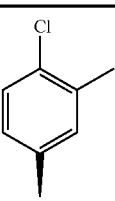 | 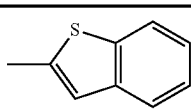 | 1 | 438/440 (M + NH₄) |
| 32 | 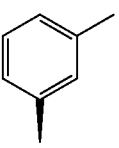 | 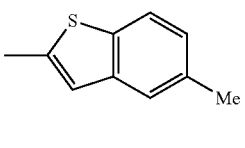 | 1 | 418 (M + NH₄) |
| 33 | 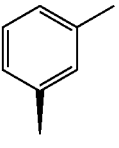 | 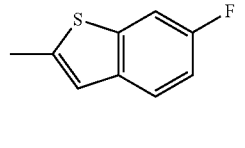 | 1 | 422 (M + NH₄) |
| 34 | 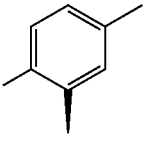 | 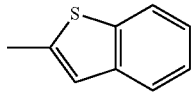 | 1 | 422 (M + NH₄) |
| 35 | 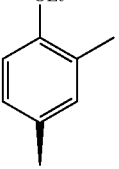 | 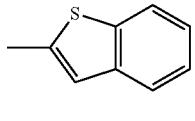 | 1 | 448 (M + NH₄) |
| 36 | 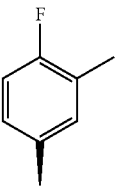 | 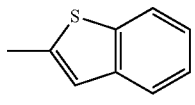 | 1 | 422 (M + NH₄) |
| 37 | 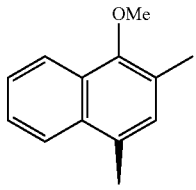 | 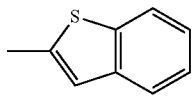 | 1 | 484 (M + NH₄) |

TABLE 1-continued

| Examples | Ring A | Ring B | Preparation Method | APCI-Mass (m/Z) |
|---|---|---|---|---|
| 38 | (3-substituted phenyl) | 2-methyl-5-CF₃-benzothiophene | 1 | 472 (M + NH₄) |
| 39 | (3-substituted phenyl) | 2-methyl-3-Me-benzothiophene | 1 | 418 (M + NH₄) |
| 40 | (3-substituted phenyl) | 2-methyl-5-F-benzothiophene | 1 | 422 (M + NH₄) |
| 41 | (2-Me-5-substituted phenyl) | 2-methyl-benzothiophene | 2 | 418 (M + NH₄) |
| 42 | (3-Me-5-substituted phenyl) | 2-methyl-benzothiophene | 1 | 418 (M + NH₄) |
| 43 | (2-Cl-5-substituted phenyl) | 2-methyl-5-Me-benzothiophene | 1 | 452/454 (M + NH₄) |
| 44 | (2-Cl-5-substituted phenyl) | 2-methyl-7-Me-benzothiophene | 1 | 452/454 (M + NH₄) |

TABLE 1-continued

| Examples | Ring A | Ring B | Preparation Method | APCI-Mass (m/Z) |
|---|---|---|---|---|
| 45 | Cl, Me-phenyl | 5-Cl-2-methylbenzothiophene | 1 | 472/474 (M + NH$_4$) |
| 46 | Cl, Me-phenyl | 5,7-diMe-2-methylbenzothiophene | 1 | 466/468 (M + NH$_4$) |
| 47 | Me, Me-phenyl | 2-methylbenzothiophene | 1 | 418 (M + NH$_4$) |
| 48 | Cl, Me-phenyl | 6-OMe-2-methylbenzothiophene | 1 | 468/470 (M + NH$_4$) |
| 49 | Cl, Me-phenyl | 6-Cl-2-methylbenzothiophene | 1 | 472/474 (M + NH$_4$) |
| 50 | Cl, Me-phenyl | 6-CF$_3$-2-methylbenzothiophene | 2 | 506/508 (M + NH$_4$) |

TABLE 1-continued
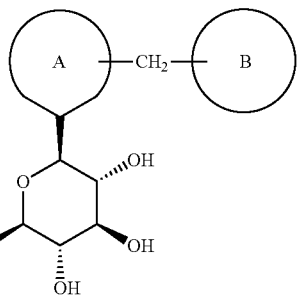
| Examples | Ring A | Ring B | Preparation Method | APCI-Mass (m/Z) |
|---|---|---|---|---|
| 51 | 4-Cl, 3-methylphenyl | 2-benzothiophene | 2 | 438/440 (M + NH$_4$) |
| 52 | 4-Cl, 3-methylphenyl | 6-F-2-benzothiophene | 2 | 456/458 (M + NH$_4$) |
| 53 | 4-F, 3-methylphenyl | 6-F-2-benzothiophene | 2 | 440 (M + NH$_4$) |
| 54 | 3-Cl, 5-methylphenyl | 2-benzothiophene | 2 | 438/440 (M + NH$_4$) |
| 55 | 4-Cl, 3-methylphenyl | 7-OMe-2-benzothiophene | 1 | 468/470 (M + NH$_4$) |
| 56 | 4-Cl, 3-methylphenyl | 5-OMe-2-benzothiophene | 1 | 468/470 (M + NH$_4$) |

TABLE 1-continued

| Examples | Ring A | Ring B | Preparation Method | APCI-Mass (m/Z) |
|---|---|---|---|---|
| 57 | 4-Cl, 3-Me-phenyl | 5-fluoro-2-methylbenzothiophene | 2 | 456/458 (M + NH$_4$) |
| 58 | 4-Cl, 3-Me-phenyl | 7-fluoro-6-methyl-2-methylbenzothiophene | 1 | 470/472 (M + NH$_4$) |
| 59 | 4-Cl, 3-Me-phenyl | 4-fluoro-2-methylbenzothiophene | 2 | 456/458 (M + NH$_4$) |
| 60 | 4-Cl, 3-Me-phenyl | 7-fluoro-2-methylbenzothiophene | 2 | 456/458 (M + NH$_4$) |
| 61 | 4-Cl, 3-Me-phenyl | 4-chloro-2-methylbenzothiophene | 2 | 472/474 (M + NH$_4$) |
| 62 | 4-F, 3-Me-phenyl | 5-fluoro-2-methylbenzothiophene | 2 | 440 (M + NH$_4$) |

TABLE 1-continued

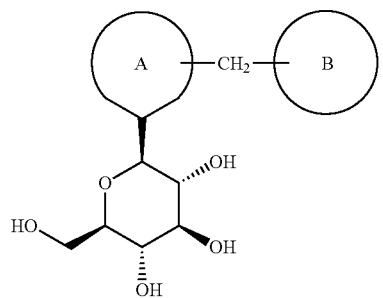

| Examples | Ring A | Ring B | Preparation Method | APCI-Mass (m/Z) |
|---|---|---|---|---|
| 63 | 4-Me, 3-(attachment), phenyl with Me | 2-methyl-5-chloro-benzothiophene | 4 | 452/454 (M + NH₄) |
| 64 | 3-Me, 2-Cl phenyl | 2-methyl-benzothiophene | 2 | 438/440 (M + NH₄) |
| 65 | 4-Et, 3-Me phenyl | 2-methyl-benzothiophene | 1 | 432 (M + NH₄) |
| 66 | 4-CF₃, 3-Me phenyl | 2-methyl-benzothiophene | 2 | 472 (M + NH₄) |
| 67 | 4-Cl, 3-Me phenyl | 2-methyl-5-phenyl-thiophene | 1 | 464/466 (M + NH₄) |
| 68 | 4-Cl, 3-Me phenyl | 2-methyl-5-(4-methylphenyl)-thiophene | 1 | 478/480 (M + NH₄) |

TABLE 1-continued
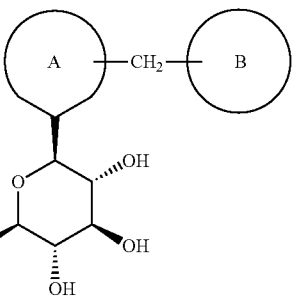
| Examples | Ring A | Ring B | Preparation Method | APCI-Mass (m/Z) |
|---|---|---|---|---|
| 69 | 4-Cl, 3-Me-phenyl | 5-(2-F-phenyl)-thiophen-2-yl | 1 | 482/484 (M + NH$_4$) |
| 70 | 4-Cl, 3-Me-phenyl | 5-(4-F-phenyl)-thiophen-2-yl | 1 | 482/484 (M + NH$_4$) |
| 71 | 4-Cl, 3-Me-phenyl | 5-(4-OEt-phenyl)-thiophen-2-yl | 1 | 508/510 (M + NH$_4$) |
| 72 | 4-Cl, 3-Me-phenyl | 5-(3-OEt-phenyl)-thiophen-2-yl | 1 | 508/510 (M + NH$_4$) |
| 73 | 4-Cl, 3-Me-phenyl | 5-(2-OEt-phenyl)-thiophen-2-yl | 1 | 508/510 (M + NH$_4$) |
| 74 | 4-F, 3-Me-phenyl | 5-phenyl-thiophen-2-yl | 1 | 448 (M + NH$_4$) |

TABLE 1-continued

| Examples | Ring A | Ring B | Preparation Method | APCI-Mass (m/Z) |
|---|---|---|---|---|
| 75 | 2-F, 3-Me phenyl | 5-(4-ethoxyphenyl)thiophen-2-yl | 1 | 492 (M + NH$_4$) |
| 76 | 2-F, 3-Me phenyl | 5-(2-ethoxyphenyl)thiophen-2-yl | 1 | 492 (M + NH$_4$) |
| 77 | 2-F, 3-Me phenyl | 5-(2-fluorophenyl)thiophen-2-yl | 1 | 466 (M + NH$_4$) |
| 78 | 2-Cl, 3-Me phenyl | 5-(3-fluorophenyl)thiophen-2-yl | 1 | 482/484 (M + NH$_4$) |
| 79 | 2-F, 3-Me phenyl | 5-(3-ethoxyphenyl)thiophen-2-yl | 1 | 492 (M + NH$_4$) |
| 80 | 2-F, 3-Me phenyl | 5-(3-fluorophenyl)thiophen-2-yl | 1 | 466 (M + NH$_4$) |

TABLE 1-continued

| Examples | Ring A | Ring B | Preparation Method | APCI-Mass (m/Z) |
|---|---|---|---|---|
| 81 | 4-F, 3-Me phenyl | 5-(4-F-phenyl)thien-2-yl | 1 | 466 (M + NH$_4$) |
| 82 | 4-Me, 3-Me phenyl | 5-phenylthien-2-yl | 1 | 444 (M + NH$_4$) |
| 83 | 4-Me, 3-Me phenyl | 5-(3-F-phenyl)thien-2-yl | 1 | 462 (M + NH$_4$) |
| 84 | 4-Me, 3-Me phenyl | 5-(4-F-phenyl)thien-2-yl | 1 | 462 (M + NH$_4$) |
| 85 | 4-OMe, 3-Me phenyl | 5-phenylthien-2-yl | 2 | 460 (M + NH$_4$) |
| 86 | 4-Me, 3-Me phenyl | 5-(3-Me-phenyl)thien-2-yl | 1 | 458 (M + NH$_4$) |

TABLE 1-continued

| Examples | Ring A | Ring B | Preparation Method | APCI-Mass (m/Z) |
|---|---|---|---|---|
| 87 | 4-Cl, 3-Me-phenyl | 5-(3-Me-phenyl)-thiophen-2-yl | 1 | 478/480 (M + NH$_4$) |
| 88 | 4-Cl, 3-Me-phenyl | 5-(3-Cl-phenyl)-thiophen-2-yl | 1 | 498/500 (M + NH$_4$) |
| 89 | 3,4-diMe-phenyl | 5-(3-Cl-phenyl)-thiophen-2-yl | 1 | 478/480 (M + NH$_4$) |
| 90 | 3,4-diMe-phenyl | 5-(3-OMe-phenyl)-thiophen-2-yl | 1 | 474 (M + NH$_4$) |
| 91 | 2-methyl-1-oxo-1,2-dihydroisoquinolin-4-yl | 4-Et-phenyl | 2 | 426 (M + H) |
| 92 | 2,8-dimethyl-1-oxo-1,2-dihydroisoquinolin-4-yl | 4-Et-phenyl | 2 | 440 (M + H) |

TABLE 1-continued
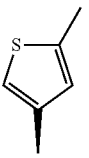
| Examples | Ring A | Ring B | Preparation Method | APCI-Mass (m/Z) |
|---|---|---|---|---|
| 93 | 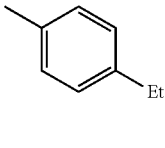 | 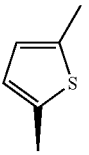 | 2 | 382 (M + NH$_4$) |
| 94 | 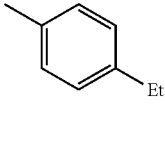 | 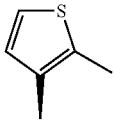 | 2 | 382 (M + NH$_4$) |
| 95 | 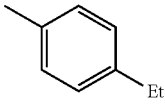 | 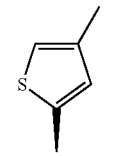 | 2 | 382 (M + NH$_4$) |
| 96 | 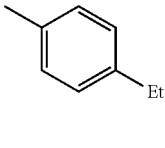 | 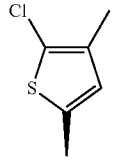 | 2 | 382 (M + NH$_4$) |
| 97 | 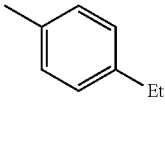 | 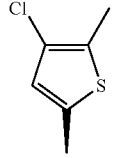 | 2 | 416/418 (M + NH$_4$) |
| 98 | 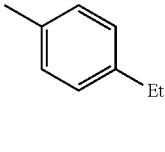 | 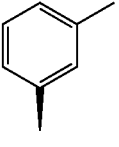 | 2 | 416/418 (M + NH$_4$) |
| 99 | 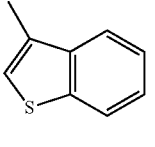 | 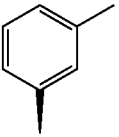 | 1 | 404 (M + NH$_4$) |
| 100 | 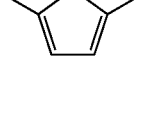 |  | 1 | 366 (M + NH$_4$) |

TABLE 1-continued

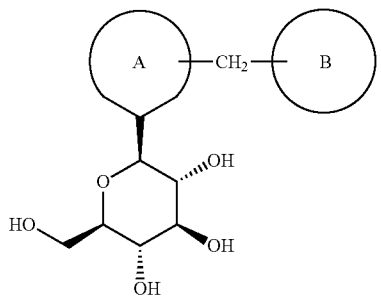

| Examples | Ring A | Ring B | Preparation Method | APCI-Mass (m/Z) |
|---|---|---|---|---|
| 101 | (3-methylphenyl) | (2-methylbenzofuran) | 1 | 388 (M + NH₄) |
| 102 | (4-chloro-3-methylphenyl) | (2-methylbenzofuran) | 1 | 422/424 (M + NH₄) |

Example 103

1-(β-D-glucopyranosyl)-3-(benzothiazol-2-ylmethyl)-4-methylbenzene

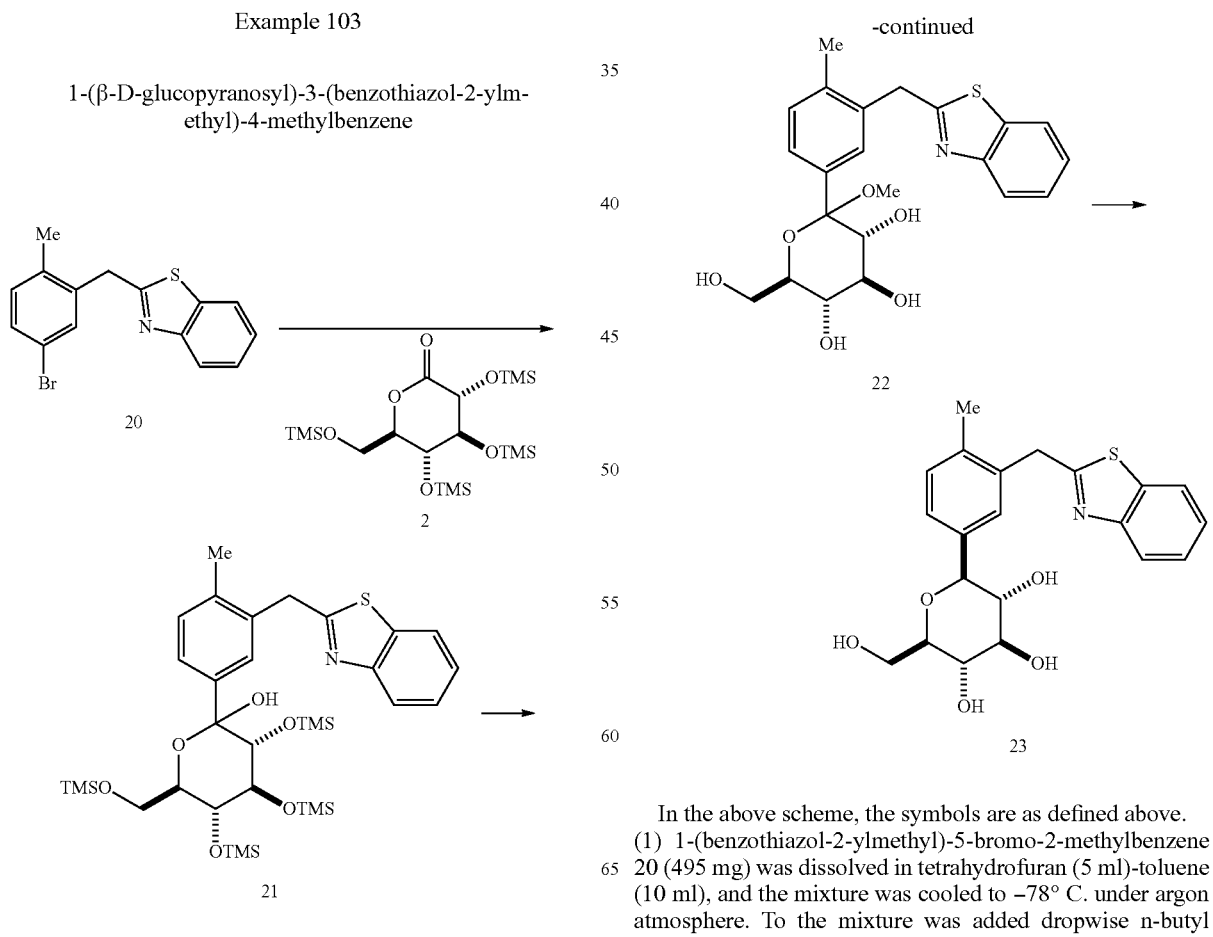

In the above scheme, the symbols are as defined above.
(1) 1-(benzothiazol-2-ylmethyl)-5-bromo-2-methylbenzene 20 (495 mg) was dissolved in tetrahydrofuran (5 ml)-toluene (10 ml), and the mixture was cooled to −78° C. under argon atmosphere. To the mixture was added dropwise n-butyl lithium (2.44 M hexane solution, 0.67 ml), and successively was added dropwise t-butyl lithium (2.44 M pentane solution, 1.57 ml). The mixture was stirred at the same temperature for 10 minutes, and then, a solution of 2,3,4,6-tetrakis-O-trimethylsilyl-D-glucono-1,5-lactone 2 (see U.S. Pat. No. 6,515,117) (2.17 g) in toluene (5 ml) was added dropwise, and the mixture was further stirred at the same temperature for 15 minutes to give a lactol compound 21. Without isolating this compound, a solution of methanesulfonic acid (1.5 ml) in methanol (25 ml) was added to the reaction solution, and the mixture was stirred at room temperature overnight. Under ice-cooling, to the mixture was added a saturated aqueous sodium hydrogen carbonate solution, and the mixture was extracted with ethyl acetate. The extract was washed with brine, dried over magnesium sulfate, and the solvent was evaporated under reduced pressure to give a methyl ether compound 22, which was used in the subsequent step without further purification.

(2) A solution of the above methyl ether compound 22 in dichloromethane (20 ml)-acetonitrile (10 ml) was cooled to −78° C. under argon atmosphere, and thereto were added dropwise successively triethylsilane (1.24 ml), and boron trifluoride diethyl ether complex (0.99 ml). The mixture was warmed to room temperature and stirred at the same temperature for 30 minutes. Under ice-cooling, a saturated aqueous sodium hydrogen carbonate solution was added, and the solvent was evaporated under reduced pressure. The residue was extracted with ethyl acetate. The extract was washed with brine, dried over magnesium sulfate, and the solvent was evaporated under reduced pressure. The residue was purified by silica gel column chromatography (chloroform:methanol=100:0-85:15) to give 1-(β-D-glucopyranosyl)-3-(benzothiazol-2-ylmethyl)-4-methylbenzene 23 (200 mg) as colorless powder. APCI-Mass m/Z 402 (M+H).

In a manner similar to Examples 103, the compounds shown in Table 2 below were prepared from corresponding starting materials.

TABLE 2

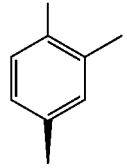

| Examples | Ring A | Ring B | APCI-Mass (m/Z) |
|---|---|---|---|
| 104 | 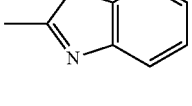 | 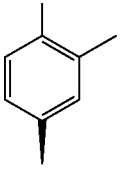 | 422/424 (M + H) |

TABLE 2-continued

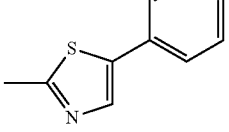

| Examples | Ring A | Ring B | APCI-Mass (m/Z) |
|---|---|---|---|
| 105 | 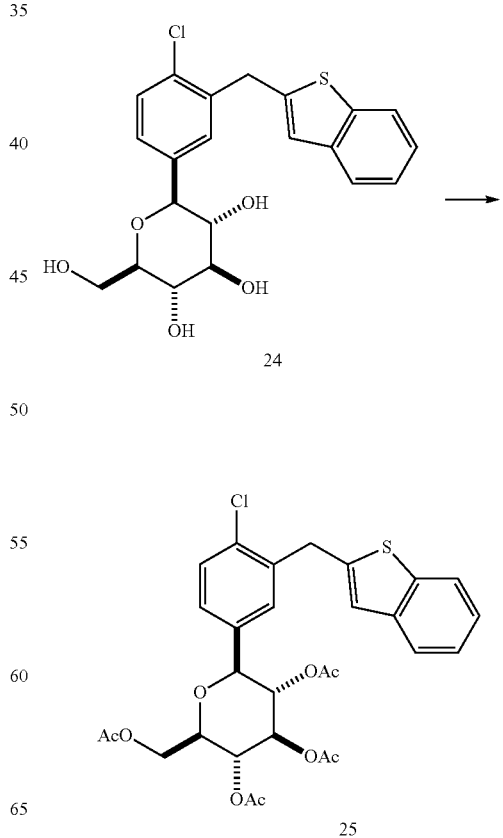 | | 480/482 (M + NH$_4$) |

Example 106

1-(β-D-glucopyranosyl)-4-chloro-3-(1-oxybenzo[b]thiophen-2-ylmethyl)benzene

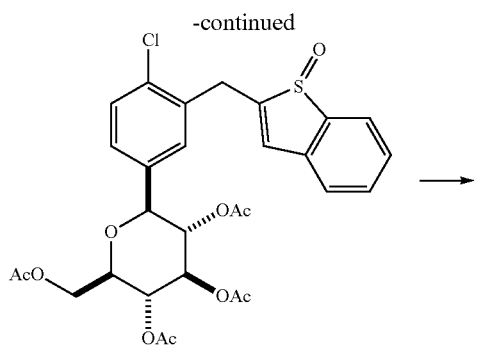

26

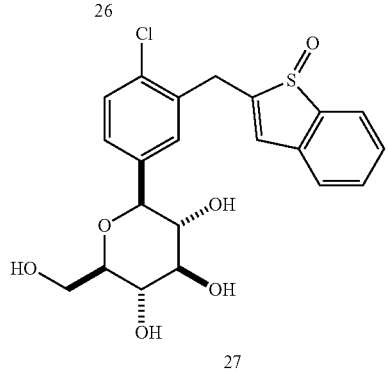

27

In the above scheme, AcO and OAc are an acetyloxy group.

(1) The compound 24 (9.61 g) obtained in Example 31 was dissolved in chloroform (100 ml), and to the mixture were added acetic anhydride (21.6 ml), pyridine (18.5 ml), and 4-dimethylaminopyridine (128 mg), and the mixture was stirred at room temperature for 3.5 days. Then, Chloroform was evaporated under reduced pressure, and the residue was dissolved in ethyl acetate (200 ml). The solution was washed successively with 10% aqueous hydrochloric acid solution, water, a saturated aqueous sodium hydrogen carbonate solution, and brine, dried over magnesium sulfate, and treated with activated carbon. The solvent was evaporated under reduced pressure, and the residue was crystallized from ethanol to give a tetraacetate compound 25 (6.14 g). APCI-Mass m/Z 606/608 (M+NH$_4$).

(2) The above tetraacetate compound 25 (1.00 g) was dissolved in dichloromethane (20 ml), and under ice-cooling, m-chloroperbenzoic acid (439 mg) was added thereto, and the mixture was stirred a room temperature overnight. m-Chloroperbenzoic acid was further added thereto, and the mixture was stirred again at room temperature overnight. The reaction mixture was washed successively with 10% aqueous sodium thiosulfate solution, a saturated aqueous sodium hydrogen carbonate solution, and brine. The mixture was dried over magnesium sulfate, and the solvent was evaporated under reduced pressure. The residue was purified by silica gel column chromatography (hexane:ethyl acetate=2:1-1:2) to give a sulfoxide compound 26 (295 mg). APCI-Mass m/Z 622/624 (M+NH$_4$).

(3) The above sulfoxide compound 26 (293 mg) was dissolved in a mixture of methanol (10 ml)-tetrahydrofuran (5 ml), and sodium methoxide (28% methanol solution, 2 drops) was added thereto, and the mixture was stirred at room temperature for one hour. The solvent was evaporated under reduced pressure, and the residue was purified by silica gel column chromatography (chloroform:methanol=9:1) to give 1-(β-D-glucopyranosyl)-4-chloro-3-(1-oxybenzo[b]thiophen-2-yl methylbenzene as pale yellow powder. APCI-Mass m/Z 454/456 (m+NH$_4$).

Example 107

1-(β-D-glucopyranosyl)-4-chloro-3-(1,1-dioxybenzo[b]thiophen-2-ylmethyl)benzene

The target compound was prepared in a manner similar to Example 106. APCI-Mass m/Z 470/472 (M+NH$_4$).

Example 108

3,5-dimethyl-4-(4-ethylphenylmethyl)-1-(β-D-glucopyranosyl)pyrazole

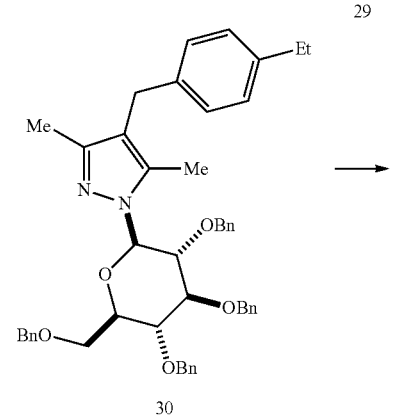

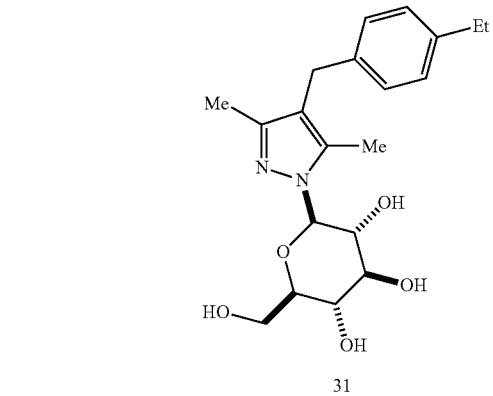

31

In the above scheme, the symbols are as defined above.
(1) 3-(4-ethylphenylmethyl)-2,4-pentanedione 28 (700 mg) and 2,3,4,6-tetra-O-benzyl-α,β-D-glucosehydrazone 29 (1.70 g) (See Schmidt, R. R. et al., *Liebigs Ann. Chem.* 1981, 2309) were dissolved in tetrahydrofuran (20 ml), and the mixture was stirred at room temperature for 18 hours under argon atmosphere. The solvent was evaporated under reduced pressure, and the residue was dissolved in toluene (20 ml), and the mixture was heated with stirring under reflux for 2 hours. The mixture was left alone until it was cooled, and the solvent was evaporated under reduced pressure. The residue was purified by silica gel column chromatography (hexane: ethyl acetate=90:10-65:35) to give 3,5-dimethyl-4-(4-ethylphenylmethyl)-1-(2,3,4,6-tetra-O-benzyl-β-D-glucopyranosyl)pyrazole 30 (299 mg) as a pale yellow semisolid. APCI-Mass m/Z 737 (M+H).

(2) The above tetrabenzyl compound 30 (294 mg) was dissolved in a mixture of ethanol (5 ml) and tetrahydrofuran (4 ml), and added thereto was palladium hydroxide (100 mg), and the mixture was stirred at room temperature for 16 hours under hydrogen atmosphere under normal pressure. Insoluble materials were filtered off, and the solvent was evaporated under reduced pressure. The residue was crystallized from diethyl ether to give the desired 3,5-dimethyl-4-(4-ethylphenylmethyl)-1-(β-D-glucopyranosyl)pyrazole 31 (118 mg) as colorless powder. APCI-Mass m/Z 377 (M+H).

Example 109

4-(4-ethylphenylmethyl)-1-(β-D-glucopyranosyl)-1,2,3-triazole

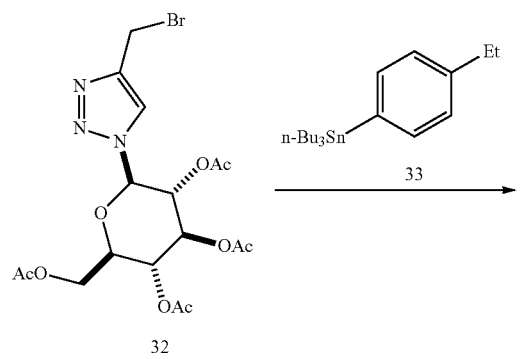

32

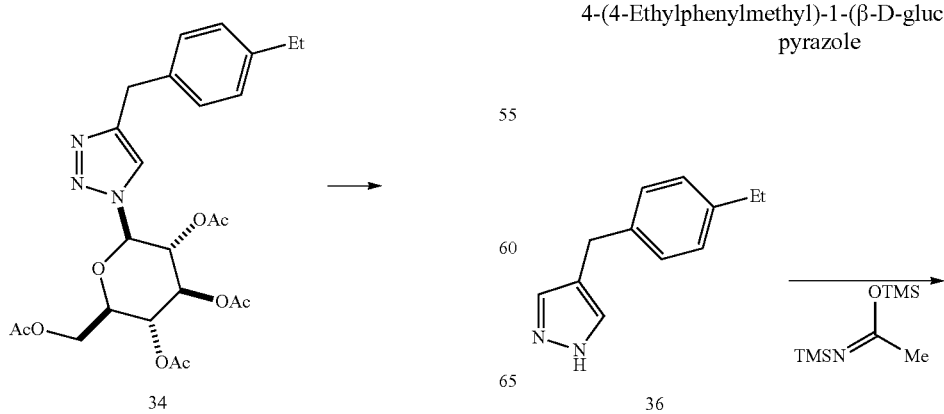

34

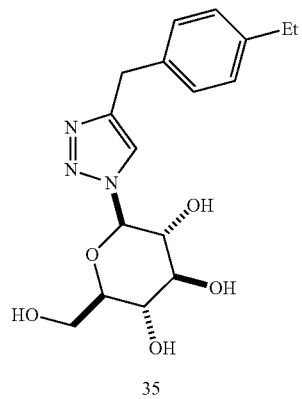

35

In the above scheme, n-Bu is n-butyl group, and other symbols are as defined above.

(1) A solution of 4-(bromomethyl)-1-(2,3,4,6-tetra-O-acetyl-β-D-glucopyranosyl)-1,2,3-triazole 32 (500 mg) (See Federico G. H. et al., *J. Med. Chem.* (1979) 29, 496), tri-n-butyl(4-ethylphenyl)tin 33 (604 mg) and tetrakis(triphenylphosphine)palladium (0) (59 mg) in tetrahydrofuran (10 ml) was stirred under heating at 70° C. for 12 hours under argon atmosphere. The reaction mixture was cooled to room temperature, diluted with ethyl acetate, and then, an aqueous potassium fluoride solution was added thereto and the mixture was stirred at room temperature for one hour. Insoluble materials were filtered off, and the filtrate was washed with water, and dried over magnesium sulfate. The solvent was evaporated under reduced pressure. The residue was purified by silica gel column chromatography (hexane:ethyl acetate=90:10-50:50) to give 4-(4-ethylphenylmethyl)-1-(2,3,4,6-tetra-O-acetyl-β-D-glucopyranosyl)-1,2,3-triazole 34 (90 mg) as a colorless solid. APCI-Mass m/Z 518 (M+H).

(2) From the above tetraacetate compound 34, the desired 4-(4-ethylphenylmethyl)-1-(β-D-glucopyranosyl)1,2,3-triazole 35 was prepared in a manner similar to Example 106-(3) as a colorless solid.

APCI-Mass m/Z 350 (M+H).

Example 110

4-(4-Ethylphenylmethyl)-1-(β-D-glucopyranosyl)pyrazole

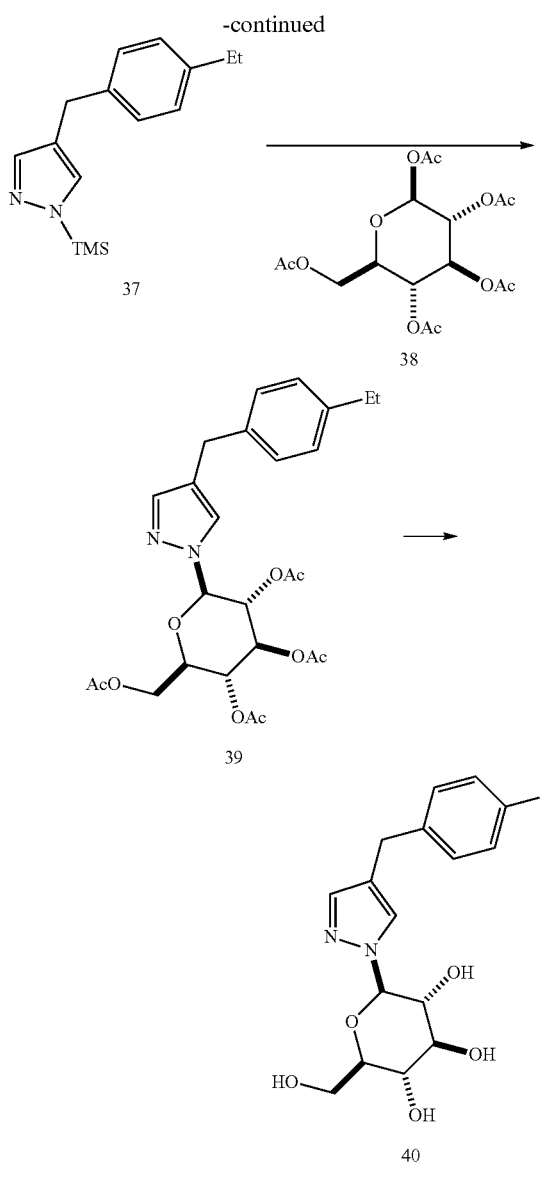

and dried over sodium sulfate. The solvent was evaporated under reduced pressure, and the residue was purified by silica gel column chromatography (hexane:ethyl acetate=80:20-50:50) to give 4-(4-ethylphenylmethyl)-1-(2,3,4,6-tetra-O-acetyl-β-D-glucopyranosyl)pyrazole 39 (610 mg) as a colorless semisolid. APCI-Mass m/Z 517 (M+H).

(3) From the above tetraacetate compound 39, the desired 4-(4-ethylphenylmethyl)-1-(β-D-glucopyranosyl)pyrazole 40 was prepared in a manner similar to Example 106-(3) as colorless oil. APCI-Mass m/Z 349 (M+H).

In a manner similar to Example 110, the compounds shown in Table 3 below were prepared from corresponding starting materials.

TABLE 3

| Examples | Ring A | APCI-Mass (m/Z) |
|---|---|---|
| 111 | CH₃-pyrazole | 363 (M + H) |
| 112 | CH₃-pyrazole | 363 (M + H) |
| 113 | methylpyridinone | 376 (M + H) |
| 114 | methylpyridinone | 393 (M + NH₄) |
| 115 | methylindole | 415 (M + NH₄) |

In the above scheme, TMS is a trimethylsilyl group, and other symbols are as defined above.

(1) To a solution of 4-(4-ethylphenylmethyl)pyrazole 36 (495 mg) in acetonitrile (2.0 ml) was added N,O-bis(trimethylsilyl)acetamide (1.05 ml), and the mixture was stirred under heating at 60° C. for 2.5 hours under argon atmosphere. The reaction mixture was cooled to room temperature, and the solvent was evaporated under reduced pressure to give crude 4-(4-ethylphenylmethyl)-1-trimethylsilylpyrazole 37, which was used in the subsequent reaction without further purification.

(2) The above N-silyl compound 37 was dissolved in dichloroethane (7.0 ml), and added thereto were molecular sieve 4A powder (500 mg), 1,2,3,4,6-penta-O-acetyl-β-D-glucopyranose 38 (1.04 g) and trimethylsilyl trifluoromethanesulfonate (0.51 ml). The mixture was stirred under heating at heating at 80° C. for 3 hours under argon atmosphere. The reaction mixture was cooled to room temperature, and insoluble materials were filtered off. Subsequently, the filtrate was poured into a saturated aqueous sodium hydrogen carbonate solution. The mixture was extracted twice with dichloromethane,

TABLE 3-continued

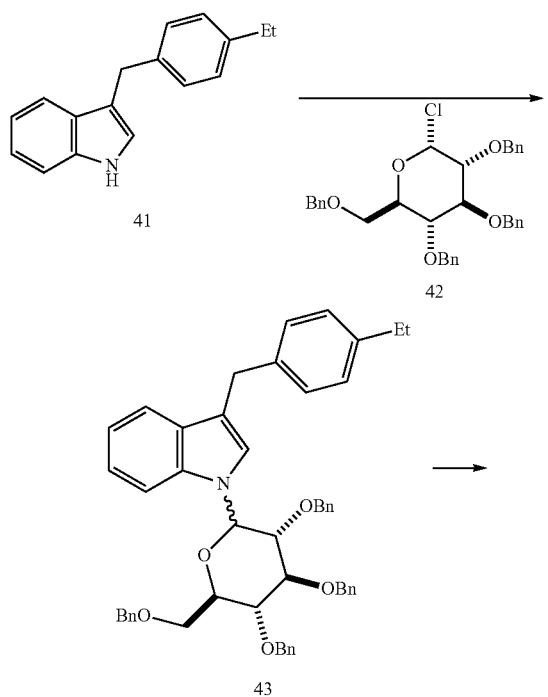

| Examples | Ring A | APCI-Mass (m/Z) |
|---|---|---|
| 116 | (3-methyl-2H-indazol-2-yl) | 399 (M + H) |
| 117 | (1,3-dimethyl-1H-indazol-?) | 399 (M + H) |

Example 118

3-RS-(4-ethylphenylmethyl)-1-(β-D-glucopyranosyl)-2,3-dihydroindole

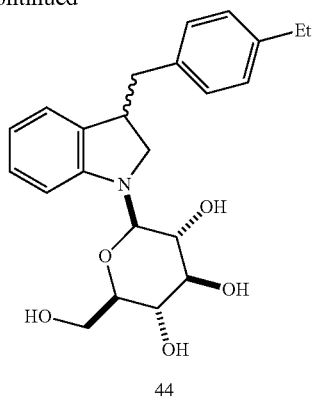

In the above scheme, the symbols are as defined above.

(1) To a suspension of potassium hydroxide power (953 mg) and sodium sulfate (6.0 g) in acetonitrile (50 ml) was added 3-(4-ethylphenylmethyl)-1H-indole 41 (500 mg), and the mixture was stirred at room temperature for one hour under argon atmosphere. To the reaction mixture was added a solution of benzylchloro-α-D-glucose 42 (3.0 g) (see Cicchillo R. M. et al., *Carbohydrate Research* (2000) 328, 431) in acetonitrile (20 ml), and the mixture was stirred at room temperature overnight. The reaction mixture was poured into 2N aqueous hydrochloric acid solution, and the mixture was extracted with diethyl ether. The extract was washed with brine, dried over magnesium sulfate, and the solvent was evaporated under reduced pressure. The residue was purified by silica gel column chromatography (hexane:ethyl acetate=100:0-85:15) to give 3-(4-ethylphenylmethyl)-1-(2,3,4,6-tetra-O-benzyl-αβ-D-glucopyranosyl)-1H-indole 43 (1.04 g) as a pale yellow syrup. APCI-Mass m/Z 758 (M+H).

(3) From the above tetrabenzyl compound 43, the desired 3-RS-(4-ethylphenylmethyl)-1-(β-D-glucopyranosyl)-2,3-dihydroindole 44 was prepared in a manner similar to Example 108-(2) as pale pink powder. APCI-Mass m/Z 400 (M+H).

Example 119

1-(β-D-glucopyranosyl)-4-chloro-3-(5-(2-pyrimidinyl)-2-thienylmethyl)benzene

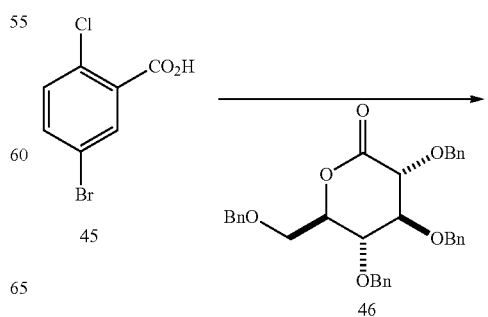

-continued

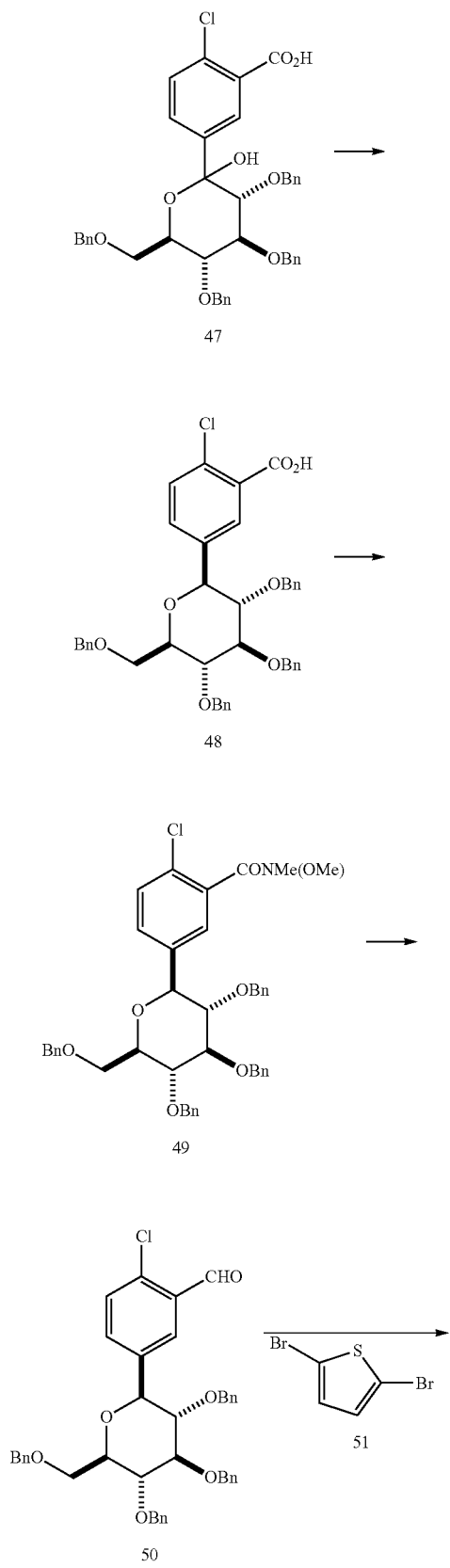

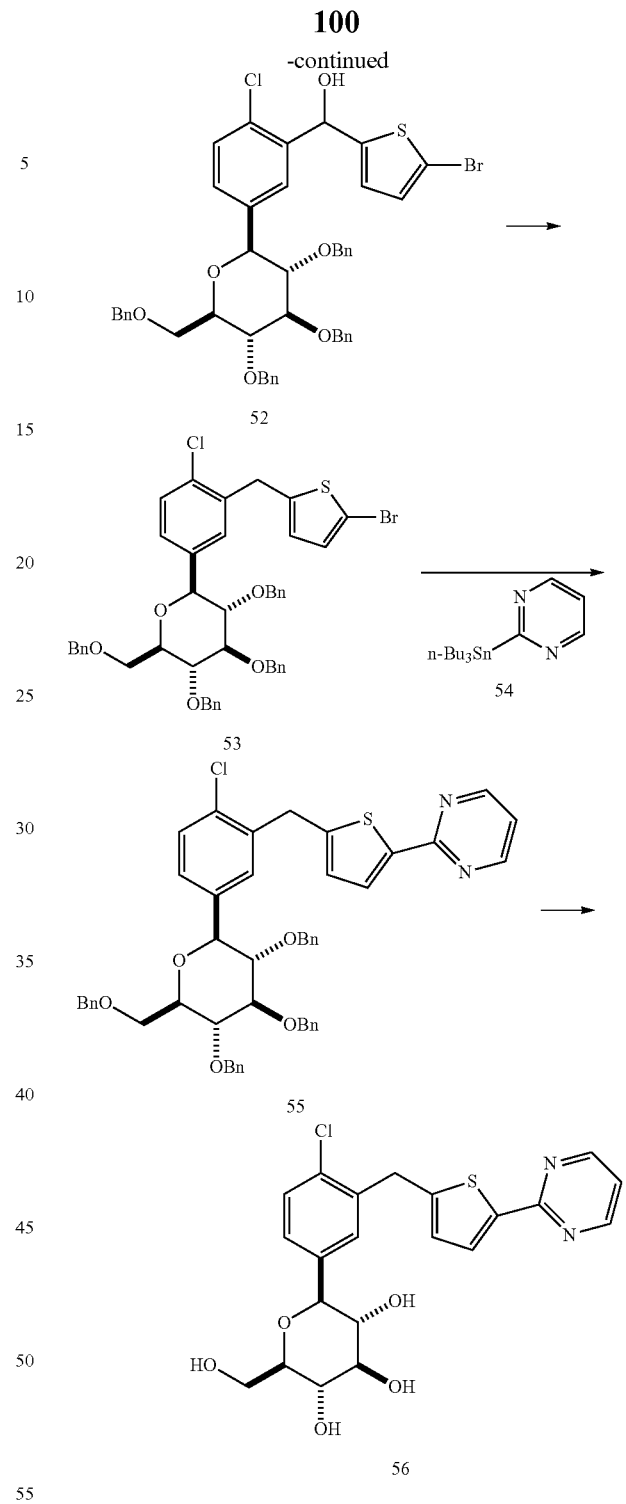

In the above scheme, the symbols are as defined above.

(1) To a solution of 5-bromo-2-chlorobenzoic acid 45 (1.22 g) in a mixture of tetrahydrofuran (20 ml)-toluene (20 ml) was added dropwise n-butyl lithium (2.44 M hexane solution, 4.26 ml) at −78° C. under argon atmosphere. The mixture was stirred at −78° C. for 30 minutes, and added dropwise thereto was a solution of 2,3,4,6-tetra-O-benzyl-β-D-glucolactone 46 (2.16 g) in toluene (10 ml), and the mixture was further stirred at the same temperature for 2 hours. To the mixture was added a saturated aqueous ammonium chloride solution, and the mixture was warmed to room temperature. The reaction mixture was made acidic by addition of 10% aqueous hydrochloric acid solution, and extracted with ethyl acetate. The extract was washed with brine, and dried over magnesium sulfate. The solvent was evaporated under reduced pressure to give a crude compound 47 as oil, which was used in the subsequent step without further purification.

(2) The above crude compound 47 was dissolved in dichloromethane (30 ml), and thereto were added dropwise triisopropylsilane (2.46 ml) and boron trifluoride•diethyl ether complex (1.52 ml) at −78° C. Subsequently, the mixture was stirred at 0° C. for one hour, and added thereto was a saturated aqueous sodium hydrogen carbonate solution, and the mixture was further stirred for 20 minutes. The reaction mixture was made acidic by addition of 10% aqueous hydrochloric acid solution, and extracted with ethyl acetate. The extract was washed with brine, and dried over magnesium sulfate. The solvent was evaporated under reduced pressure, and the residue was purified by silica gel chromatography (chloroform:methanol=100:1-50:1) to give a compound 48 (1.41 g) as oil.

(3) The compound 48 (1.41 g) was dissolved in dichloromethane (10 ml), and added thereto was oxalyl chloride (2 ml). The mixture was stirred at room temperature for 3 hours. The solvent was evaporated under reduced pressure to give a corresponding acid chloride. The compound was dissolved in chloroform (10 ml), and added dropwise to a solution of N,O-dimethylhydroxyamine hydrochloride (390 mg) and triethyl amine (1.12 ml) in chloroform (10 ml) at 0° C. The mixture was stirred at room temperature overnight, and the reaction mixture was washed successively with 10% aqueous hydrochloric acid solution, water, a saturated aqueous sodium hydrogen carbonate solution and brine. The mixture was dried over magnesium sulfate, and the solvent was evaporated under reduced pressure. The residue was purified by silica gel column chromatography (hexane:ethyl acetate=4:1-2:1) to give a compound 49 (784 mg) as pale yellow oil. APCI-Mass m/Z 739/741 (M+NH$_4$).

(4) The compound 49 (1.22 g) was dissolved in tetrahydrofuran (20 ml), and the mixture was cooled to −78° C. under argon atmosphere. To the mixture was added dropwise diisobutylaluminum hydride (1.0 M toluene solution, 4.2 ml), and the mixture was stirred at the same temperature for 3 hours. Added thereto was 10% aqueous hydrochloric acid solution, and the mixture was extracted with ethyl acetate. The extract was washed successively with a saturated aqueous sodium hydrogen carbonate solution and brine. The extract was dried over magnesium sulfate and the solvent was evaporated under reduced pressure. The residue was purified by silica gel column chromatography (hexane:ethyl acetate=9:1) to give a compound 50 (771 mg) as pale yellow oil. APCI-Mass m/Z 680/682 (M+NH$_4$).

(5) 2,5-dibromothiophene 51 (1.31 g) was dissolved in tetrahydrofuran (30 ml) and the mixture was cooled to −78° C. under argon atmosphere. To the mixture was added dropwise n-butyl lithium (2.59 M hexane solution, 2.01 ml), and the mixture was stirred at the same temperature for 30 minutes. Added dropwise thereto was a solution of the above compound 50 (2.40 g) in tetrahydrofuran (15 ml), and the mixture was stirred at −78° C. for 2 hours. Added thereto was a saturated aqueous ammonium chloride solution, and the mixture was extracted with ethyl acetate and washed with brine. The extract was dried over magnesium sulfate and the solvent was evaporated under reduced pressure. The residue was purified by silica gel column chromatography (hexane:ethyl acetate=9:1-4:1) to give a compound 52 (2.62 mg) as pale brown oil. APCI-Mass m/Z 842/844 (M+NH$_4$).

(6) The compound 52 was treated in a manner similar to Example 3-(2) to give 1-(2,3,4,6-tetra-O-benzyl-β-D-glucopyranosyl)-3-(5-bromo-2-thienylmethyl)-4-chlorobenzene 53 as a pale yellow solid. APCI-Mass m/Z 826/828 (M+NH$_4$).

(7) A mixed solution of the above 1-(2,3,4,6-tetra-O-benzyl-β-D-glucopyranosyl)-3-(5-bromo-2-thienylmethyl)-4-chlorobenzene 53 (200 mg), tri-n-butyl(2-pyrimidinyl)tin 54 (137 mg) and bis(triphenylphosphine)palladium (II) dichloride (9 mg) in N-methyl-2-pyrrolidinone (5 ml) was stirred at 100° C. four 7 hours under argon atmosphere. The mixture was cooled to room temperature, and water was added thereto, and the mixture was extracted with ethyl acetate. The extract was washed with water and subsequently with brine, and dried over magnesium sulfate. The solvent was evaporated under reduced pressure. The residue was purified by silica gel column chromatography (hexane:ethyl acetate=4:1-2:1) to give 1-(2,3,4,6-tetra-O-benzyl-β-D-glucopyranosyl)-4-chloro-3-(5-(2-pyrimidinyl)-2-thienylmethyl)benzene 55 (93 mg) as pale brown oil. APCI-Mass m/Z 826/828 (M+NH$_4$).

(8) To a solution of the above 1-(2,3,4,6-tetra-O-benzyl-β-D-glucopyranosyl)-4-chloro-3-(5-(2-pyrimidinyl)-2-thienylmethyl)benzene 55 (90 mg) in ethanethiol (1.5 ml) was added boron trifluoride•ether complex (0.42 ml) at 0° C., and the mixture was stirred at room temperature overnight. The mixture was cooled again to 0° C., and added thereto were a saturated aqueous sodium hydrogen carbonate solution and an aqueous sodium thiosulfate solution. The mixture was extracted with ethyl acetate and tetrahydrofuran, and the extract was dried over magnesium sulfate. The solvent was evaporated under reduced pressure. The residue was purified by silica gel column chromatography (chloroform:methanol=19:1-9:1) to give the desired 1-(β-D-glucopyranosyl)-4-chloro-3-(5-(2-pyrimidinyl)-2-thienylmethyl)benzene 56 (27 mg) as pale yellow powder. APCI-Mass m/Z 449/451 (M+H).

Example 120

1-(β-D-glucopyranosyl)-3-(5-(6-fluoro-3-pyridyl)-2-thienylmethyl)-4-methylbenzene

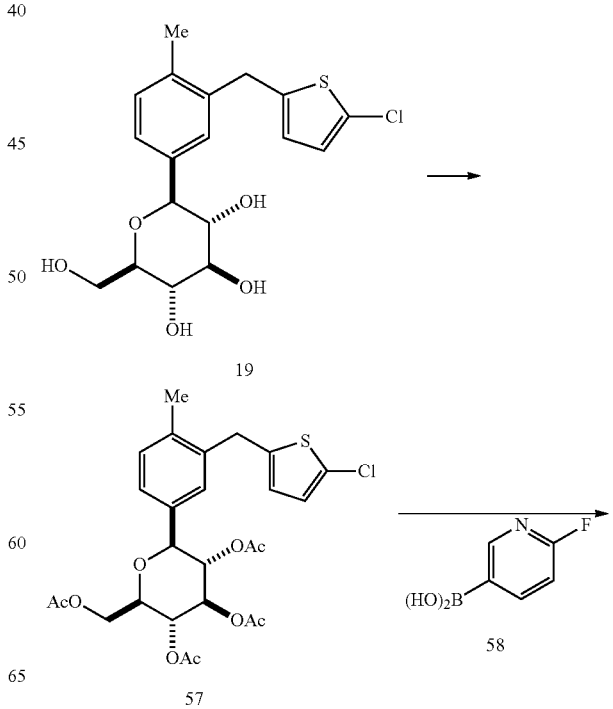

-continued

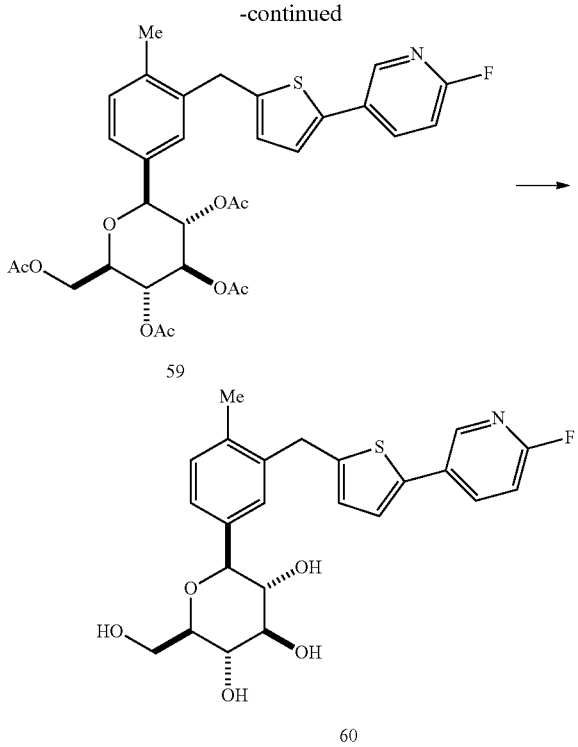

In the above scheme, the symbols are as defined as above.
(1) The compound 19 obtained in Example 4 was treated in a manner similar to Example 106-(1) to give 1-(2,3,4,6-tetra-O-acetyl-β-D-glucopyranosyl)-3-(5-chloro-2-thienylmethyl)-4-methylbenzene 57 as colorless crystals. APCI-Mass m/Z 570/572 (M+NH$_4$).
(2) A solution of the above 1-(2,3,4,6-tetra-O-acetyl-β-D-glucopyranosyl)-3-(5-chloro-2-thienylmethyl)-4-methylbenzene 57 (200 mg), 6-fluoropyridine-3-boronic acid 58 (117 mg), tri-tert-butylphosphine•tetrafluoroboric acid adduct (24 mg), potassium fluoride (80 mg) and tris(dibenzylideneacetone) dipalladium (0) (27 mg) in tetrahydrofuran (8 ml) was stirred at room temperature for 2 days under argon atmosphere. Added thereto was a saturated aqueous ammonium chloride solution and the mixture was extracted with ethyl acetate. The extract was dried over magnesium sulfate. The solvent was evaporated under reduced pressure and the residue was purified by silica gel column chromatography (hexane:ethyl acetate=90:10-70:30) to give 1-(2,3,4,6-tetra-O-acetyl-β-D-glucopyranosyl)-3-(5-(6-fluoro-3-pyridyl)-2-thienylmethyl)-4-methylbenzene 59 (44 mg) as colorless crystals. APCI-Mass m/Z 631 (M+NH$_4$).
(3) The above 1-(2,3,4,6-tetra-O-acetyl-β-D-glucopyranosyl)-3-(5-(6-fluoro-3-pyridyl)-2-thienylmethyl)-4-methylbenzene 59 (39 mg) was dissolved in 1,4-dioxane (4 ml)-tetrahydrofuran (4 ml), and added thereto was 2N sodium hydroxide (2 ml). The mixture was stirred at room temperature for one hour. The mixture was made acidic by addition of an aqueous citric acid solution, and the mixture was extracted with ethyl acetate. The extract was washed successively with a saturated aqueous sodium hydrogen carbonate solution and brine, and then dried over sodium sulfate. The solvent was evaporated under reduced pressure to give the desired 1-(β-D-glucopyranosyl)-3-(5-(6-fluoro-3-pyridyl)-2-thienylmethyl)-4-methylbenzene 60 (34 mg) as colorless powder. APCI-Mass m/Z 463 (M+NH$_4$).

Example 121

1-(β-D-glucopyranosyl)-4-chloro-3-(2-(5-phenyl-2-thienyl)ethyl)benzene

The target compound was obtained in a manner similar to Example 1, from 5-bromo-2-chloro-1-(2-(5-phenyl-2-thienyl)ethyl)benzene. APCI-Mass m/Z 478/480 (M+NH$_4$).

Example 122

1-(β-D-glucopyranosyl)-3-(5-(3-dimethylaminophenyl)-2-thienylmethyl)-4-methylbenzene (1) 1-(2,3,4,6-tetra-O-acetyl-β-D-glucopyranosyl)-3-(5-chloro-2-thienylmethyl)-4-methylbenzene 57 obtained in Example 120 (1) and 3-dimethylaminophenylboronic acid were used and treated in a manner similar to Example 120-(2) to give 1-(2,3,4,6-tetra-O-acetyl-β-D-glucopyranosyl)-3-(5-(3-dimethylaminophenyl)-2-thienylmethyl)-4-methylbenzene. APCI-Mass m/Z 638 (M+H).
(2) the above 1-(2,3,4,6-tetra-O-acetyl-β-D-glucopyranosyl)-3-(5-(3-dimethylaminophenyl)-2-thienylmethyl)-4-methylbenzene was treated in a manner similar to Example 106-(3) to give the target compound. APCI-Mass m/Z 470 (M+H).

Example 123

1-(β-D-glucopyranosyl)-4-chloro-3-(5-(3-cyanophenyl)-2-thienylmethyl)benzene (1) A mixed solution of 1-(2,3,4,6-tetra-O-benzyl-β-D-glucopyranosyl)-3-(5-bromo-2-thienylmethyl)-4-chlorobenzene 53 (1.24 g) obtained in Example 119-(6), 3-cyanophenylboronic acid (270 ml), bis(triphenylphosphine)palladium (II) dichloride (54 mg) and 2M aqueous sodium carbonate solution (2.3 ml) in 1,2-dimethoxyethane (12 ml) was heated under reflux for 4 hours. The mixture was diluted with ethyl acetate and washed successively with a saturated aqueous sodium hydrogen carbonate solution and brine. The mixture was dried over sodium sulfate, and the solvent was evaporated under reduced pressure. The residue was purified by silica gel column chromatography (hexane:ethyl acetate=7:1-5:1) to give 1-(2,3,4,6-tetra-O-benzyl-β-D-glucopyranosyl)-4-chloro-3-(5-(3-cyanophenyl)-2-thienylmethyl)benzene (1.12 g) as colorless oil. APCI-Mass m/Z 849/851 (M+NH$_4$).
(2) The above 1-(2,3,4,6-tetra-O-benzyl-β-D-glucopyranosyl)-4-chloro-3-(5-(3-cyanophenyl)-2-thienylmethyl)benzene was used and treated in a manner similar to Example 3-(3) to give the target compound as colorless powder. APCI-Mass m/Z 489/491 (M+NH$_4$).

Example 124

1-(β-D-glucopyranosyl)-4-methyl-3-(5-(5-pyrimidinyl)-2-thienylmethyl)benzene (1) A mixed solution of 1-(2,3,4,6-tetra-O-acetyl-β-D-glucopyranosyl)-3-(5-chloro-2-thienylmethyl)-4-methylbenzene 57 (600 mg) obtained in Example 120-(1), tri-n-butyl(5- pyrimidinyl)tin (600 mg), tri-tert-butylphosphine•tetrafluoroboric acid adduct (116 mg), cesium fluoride (414 mg), and tris(dibenzylideneacetone)dipalladium (0) (91 mg) in 1,4-dioxane (18 ml) was heated under reflux at 100° C. for 3 hours under argon atmosphere. Insoluble materials were filtered off, and the filtrate was diluted with ethyl acetate and washed with brine. The solvent was evaporated under reduced pressure, and the residue was purified by silica gel column chromatography (hexane:ethyl acetate=75:25-40:60) to give 1-(2,3,4,6-tetra-O-acetyl-β-D-glucopyranosyl)-4-methyl-3-(5-(5-pyrimidinyl)-2-thienylmethyl)benzene (266 mg) as colorless crystals. APCI-Mass m/Z 597 (M+H).

(2) The above 1-(2,3,4,6-tetra-O-acetyl-β-D-glucopyranosyl)-4-methyl-3-(5-(5-pyrimidinyl)-2-thienylmethyl)benzene was used and treated in a manner similar to Example 106-(3) to give the target compound as colorless powder. APCI-Mass m/Z 429 (M+H).

Example 125

1-(β-D-glucopyranosyl)-4-chloro-3-(2-phenyl-5-thiazolylmethylbenzene

The target compound was prepared in a manner similar to Example 1, starting from 5-bromo-2-chloro-1-(2-phenyl-5-thiazolylmethyl)benzene. APCI-Mass m/Z 448/450 (M+H).

Example 126

1-(β-D-glucopyranosyl)-4-chloro-3-(5-(3-pyridyl)-2-thienylmethyl)benzene (1) 1-(β-D-glucopyranosyl)-4-chloro-3-(5-chloro-2-thienylmethyl)benzene obtained in Example 19 was used and treated in a manner similar to Example 106-(1) to give 1-(2,3,4,6-tetra-O-acetyl-β-D-glucopyranosyl)-4-chloro-3-(5-chloro-2-thienylmethyl)benzene as colorless crystals. APCI-Mass m/Z 590/592 (M+NH$_4$).

(2) The above 1-(2,3,4,6-tetra-O-acetyl-β-D-glucopyranosyl)-4-chloro-3-(5-chloro-2-thienylmethyl)benzene and tri-n-butyl(3-pyridyl)tin were used and treated in a manner similar to Example 124 to give the target compound as colorless powder. APCI-Mass m/Z 448/450 (M+H).

Example 127

1-(β-D-glucopyranosyl)-3-(5-(3-cyanophenyl)-2-thienylmethyl)-4-methylbenzene (1) 1-(2,3,4,6-tetra-O-acetyl-β-D-glucopyranosyl)-3-(5-chloro-2-thienylmethyl)-4-methylbenzene 57 obtained in Example 120-(1) and 3-cyanophenylboronic acid were used and treated in a manner similar to Example 120-(2) to give 1-(2,3,4,6-tetra-O-acetyl-β-D-glucopyranosyl)-3-(5-(3-cyanophenyl)-2-thienylmethyl)-4-methylbenzene. APCI-Mass m/Z 637 (M+NH$_4$).

(2) The above 1-(2,3,4,6-tetra-O-acetyl-β-D-glucopyranosyl)-3-(5-(3-cyanophenyl)-2-thienylmethyl)-4-methylbenzene was used and treated in a manner similar to Example 106-(3) to give the target compound as colorless powder. APCI-Mass m/Z 469 (M+NH$_4$).

Example 128

1-(β-D-glucopyranosyl)-4-chloro-3-(5-pyrazinyl-2-thienylmethyl)benzene

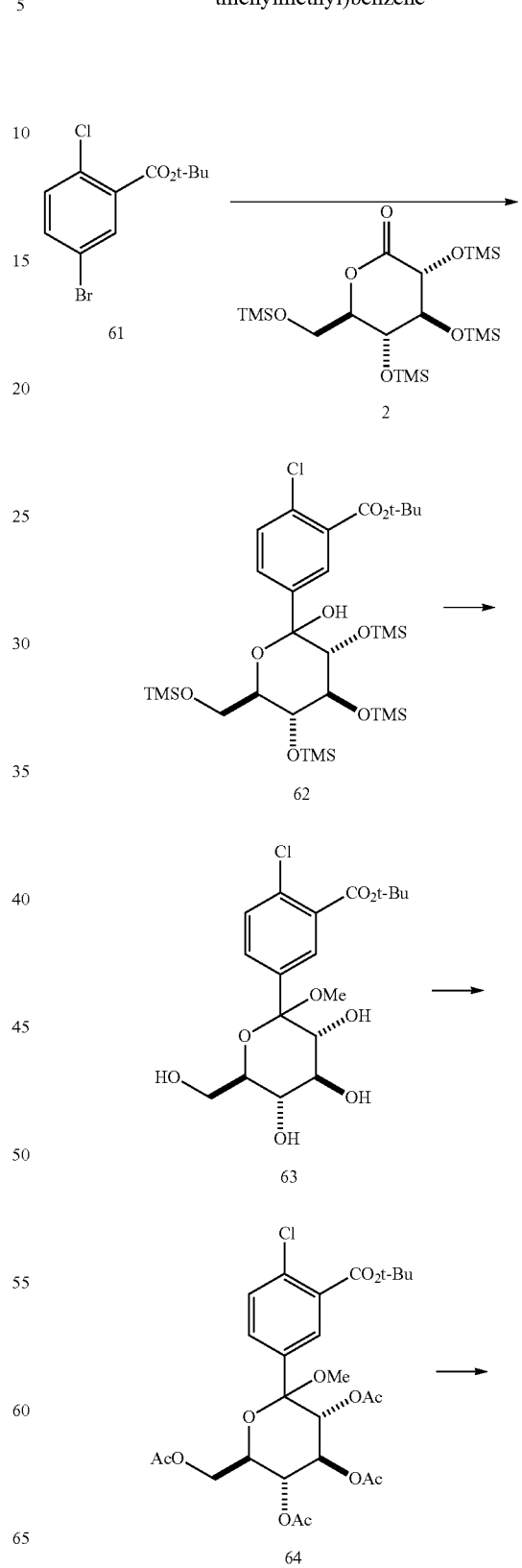

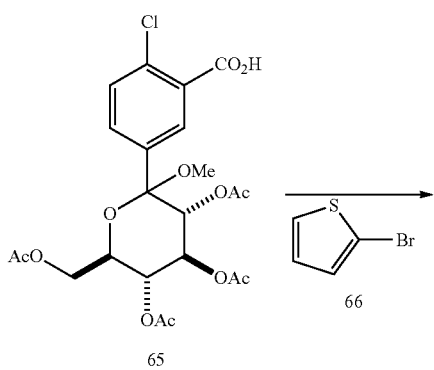

65

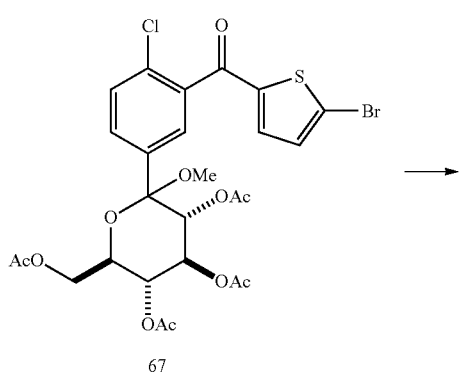

67

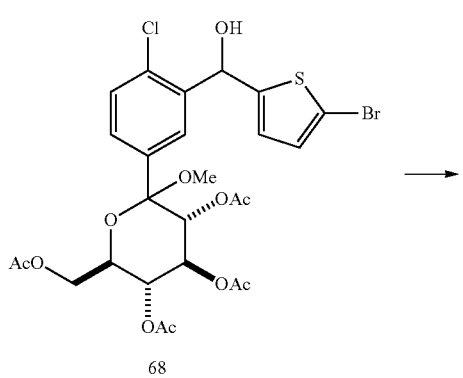

68

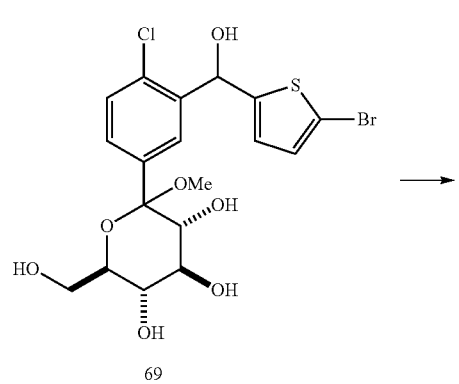

69

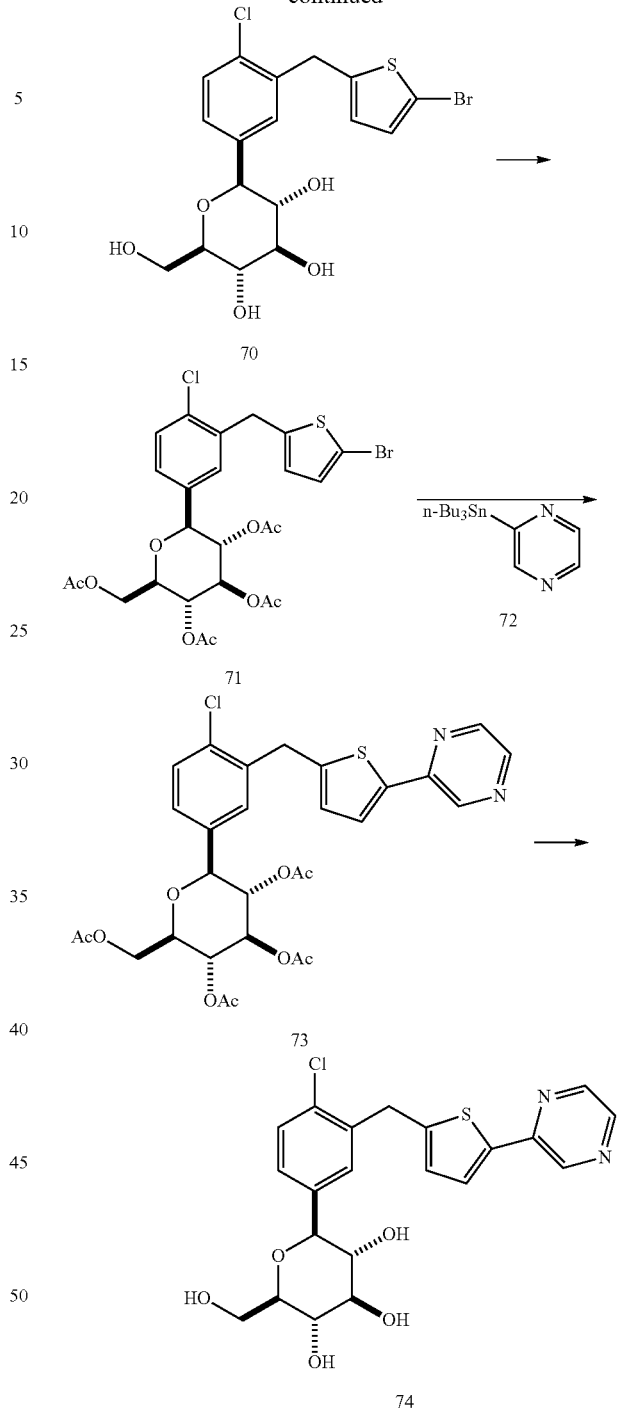

In the above scheme, the symbols are as defined above.

(1) A solution of mesityl bromide (4.74 g) in tetrahydrofuran (100 ml) was cooled to −78° C. under argon atmosphere, and thereto was added dropwise t-butyl lithium (1.43 M pentane solution, 33 ml). The mixture was stirred at −30 to −20° C. for one hour, and then, a mixed solution of t-butyl 5-bromo-2-chlorobenzoate 61 (4.94 g) and 2,3,4,6-tetrakis-O-trimethylsilyl-D-glucono-1,5-lactone 2 (see U.S. Pat. No. 6,515,117) (11.10 g) in tetrahydrofuran (70 ml) was added dropwise thereto at −78° C. The mixture was stirred at the same temperature for one hour to give a compound 62. Without isolating this compound, a solution of methanesulfonic acid (3.75 ml) in methanol (50 ml) was added to the reaction solution, and the mixture was stirred at room temperature for 18 hours. To the mixture was added a saturated aqueous sodium hydrogen carbonate solution at 0° C., and the mixture was extracted with ethyl acetate twice. The extract was washed with brine, dried over magnesium sulfate, and the solvent was evaporated under reduced pressure. The residue was purified by silica gel column chromatography (chloroform:methanol=19:1) to give a methyl ether compound 63 (4.55 g) of the lactol as pale yellow powder. APCI-Mass m/Z 422/424 (M+NH$_4$).

(2) The compound 63 was treated in a manner similar to Example 106-(1) to give the compound 64. APCI-Mass m/Z 590/592 (M+NH$_4$).

(3) A solution of the above compound 64 (7.10 g) in formic acid (50 ml) was stirred at 50° C. for 30 minutes. The solvent was evaporated under reduced pressure, and the residue was subjected to azeotropic distillation with toluene, twice, to give a compound 65 as colorless powder. Without further purification, this compound was dissolved in dichloromethane (50 ml). Added thereto were oxalyl chloride (1.3 ml) and N,N-dimethylformamide (one drop), and the mixture was stirred at room temperature overnight. The solvent was evaporated under reduced pressure to give a corresponding acid chloride, which was dissolved in dichloroethane (50 ml), without further purification. To the solution was added 2-bromothiophene 66 (2.63 g) and the mixture was cooled to 0° C. Added gradually thereto was aluminum chloride (8.26 g), and subsequently, the mixture was stirred at the same temperature for 30 minutes. The reaction mixture was poured into ice-cold water, and the mixture was extracted with ethyl acetate. The extract was washed successively with water, a saturated aqueous sodium hydrogen carbonate solution and brine, dried over sodium sulfate, and the solvent was evaporated under reduced pressure. The residue was purified by silica gel column chromatography (hexane:ethyl acetate=10:1-5:1) to give a compound 67 (7.01 g) as pale yellowish powder. APCI-Mass m/Z 678/680 (M+NH$_4$).

(4) The above ketone compound 67 (7.01 g) was dissolved in ethanol (50 ml), and thereto was added sodium borohydride (401 mg), and the mixture was stirred at room temperature for 30 minutes. The solvent was evaporated under reduced pressure, and the residue was dissolved in ethyl acetate. The solution was washed with successively with water, 2N aqueous hydrochloride acid solution, a saturated aqueous sodium hydrogen carbonate solution and brine, and dried over sodium sulfate. The solvent was evaporated under reduced pressure to give a compound 68 as pale yellow powder, which was dissolved in methanol (50 ml) without further purification. To the solution, sodium methoxide (28% methanol solution, 5 drops) was added, and then the mixture was stirred at room temperature for 2.5 hours. The solvent was evaporated under reduced pressure to give a deacetylated compound 69 as pale yellow powder. Without further purification, it was dissolved in dichloromethane (170 ml)-acetonitrile (70 ml), and added thereto was triethylsilane (10.2 ml), and the mixture was cooled to 0° C. Added dropwise thereto was boron trifluoride•diethyl ether complex (8.1 ml), and the mixture was stirred at room temperature for 5 hours. To the mixture was added a saturated aqueous sodium hydrogen carbonate solution, and the mixture was extracted with ethyl acetate, and the extract was dried over magnesium sulfate. The solvent was evaporated under reduced pressure to give a crude 1-(β-D-glucopyranosyl)-3-(5-bromo-2-thienylmethyl)-4-chlorobenzene 70 as pale brown powder. Without further purification, this was dissolved in dichloromethane (30 ml), and added thereto were acetic anhydride (10.0 ml), pyridine (8.57 ml) and 4-dimethylaminopyridine (258 mg), and the mixture was stirred at room temperature for one hour. The solvent was evaporated under reduced pressure, and the residue was dissolved in ethyl acetate, and the solution was washed successively with water, 1N aqueous hydrochloric acid solution, a saturated aqueous sodium hydrogen carbonate solution and brine. The solution was dried over sodium sulfate, and the solvent was evaporated under reduced pressure. The residue was crystallized from methanol to give 1-(2,3,4,6-tetra-O-acetyl-β-D-glucopyranosyl)-3-(5-bromo-2-thienylmethyl)-4-chlorobenzene 71 (3.17 g) as colorless crystals. APCI-Mass m/Z 634/636 (M+NH$_4$).

(5) The above 1-(2,3,4,6-tetra-O-acetyl-β-D-glucopyranosyl)-3-(5-bromo-2-thienylmethyl)-4-chlorobenzene 71 (600 mg) was dissolved in 1,4-dioxane (11 ml). Added thereto were tri-n-butyl(pyrazinyl)tin 72 (720 mg), tetrakis(triphenylphosphine)palladium (0) (206 mg) and copper (I) iodide (51 mg), and the mixture was stirred under heating at 100° C. for 1.5 hours, under irradiation by a microwave (500 W). The mixture was diluted with ethyl acetate, the insoluble materials were filtered off, and the filtrate was washed with water. The solvent was evaporated under reduced pressure. The residue was purified by silica gel column chromatography (hexane:ethyl acetate=75:25-30:70), and crystallized from hexane-diethyl ether to give 1-(2,3,4,6-tetra-O-acetyl-β-D-glucopyranosyl)-4-chloro-3-(5-pyrazinyl-2-thienylmethyl)benzene 73 (263 mg) as pale yellow crystals. APCI-Mass m/Z 617/619 (M+H).

(6) The above 1-(2,3,4,6-tetra-O-acetyl-β-D-glucopyranosyl)-4-chloro-3-(5-pyrazinyl-2-thienylmethyl)benzene 73 was used and treated in a manner similar to Example 106-(3) to give the desired 1-(β-D-glucopyranosyl)-4-chloro-3-(5-pyrazinyl-2-thienyl methyl)benzene 74 as colorless powder. APCI-Mass m/Z 449/451 (M+H).

Example 129

1-(β-D-glucopyranosyl)-4-chloro-3-(6-ethoxybenzo[b]thiophen-2-ylmethyl)benzene

5-Bromo-2-chloro-1-(6-ethoxybenzo[b]thiophen-2-ylmethyl)benzene was used and treated in a manner similar to Example 1 to give the target compound. APCI-Mass m/Z 482/484 (M+NH$_4$).

Example 130

1-(β-D-glucopyranosyl)-3-(5-(3-difluoromethylphenyl)-2-thienylmethyl)-4-methylbenzene (1) 1-(2,3,4,6-tetra-O-acetyl-β-D-glucopyranosyl)-3-(5-chloro-2-thienylmethyl)-4-methylbenzene 57 obtained in Example 120-(1) and 3-formylphenylboronic acid were used and treated in a manner similar to Example 120-(2) to give 1-(2,3,4,6-tetra-O-acetyl-β-D-glucopyranosyl)-3-(5-(3-formylphenyl)-2-thienylmethyl)-4-methylbenzene. APCI-Mass m/Z 640 (M+NH$_4$).

(2) The above 1-(2,3,4,6-tetra-O-acetyl-β-D-glucopyranosyl)-3-(5-(3-formylphenyl)-2-thienylmethyl)-4-methylbenzene (100 mg) was dissolved in dichloromethane (2 ml), and added thereto was (diethylamino) sulfur trifluoride (0.30 ml). The mixture was stirred at room temperature overnight. Water was added to the mixture and the mixture was extracted with chloroform. The extract was washed with brine and dried over magnesium sulfate, and then, the solvent was evaporated under reduced pressure. The residue was purified by silica gel column chromatography (hexane:ethyl acetate=9:1-1:1) to give 1-(2,3,4,6-tetra-O-acetyl-β-D-glucopyranosyl)-3-(5-(3-difluoromethylphenyl)-2-thienylmethyl)-4-methylbenzene (82 mg). APCI-Mass m/Z 662 (M+NH$_4$).

(3) The above obtained 1-(2,3,4,6-tetra-O-acetyl-β-D-glucopyranosyl)-3-(5-(3-difluoromethylphenyl)-2-thienylmethyl)-4-methylbenzene was used and treated in a manner similar to Example 120-(3) to give the desired 1-(β-D-glucopyranosyl)-3-(5-(3-difluoromethylphenyl)-2-thienylmethyl)-4-methylbenzene as colorless powder. APCI-Mass m/Z 494 (M+NH$_4$).

Example 131

1-(β-D-glucopyranosyl)-4-chloro-3-(6-phenyl-3-pyridylmethyl)benzene

5-Bromo-2-chloro-1-(6-phenyl-3-pyridylmethyl)benzene was used and treated in a manner similar to Example 1 to give the target compound. APCI-Mass m/Z 442/444 (M+H).

In a manner similar to the method disclosed in any of the above Examples, the compounds shown in Table 4 below were prepared from corresponding starting materials. The numbers shown in a column of "preparation method" in the Table indicates the Example number, according to which the preparation was carried out in the similar manner.

TABLE 4

| Examples | Ring A | R$^{4a}$ | Preparation Method | APCI-Mass (m/Z) |
|---|---|---|---|---|
| 132 | 2-CH$_3$-phenyl | 4-CF$_3$-phenyl | 1 | 512 (M + NH$_4$) |
| 133 | 2-CH$_3$-phenyl | 3-CF$_3$-phenyl | 1 | 512 (M + NH$_4$) |
| 134 | 2-CH$_3$-phenyl | 4-CH$_2$CH$_3$-phenyl | 4 | 472 (M + NH$_4$) |
| 135 | 2-CH$_3$-phenyl | 4-CH$_3$-phenyl | 4 | 458 (M + NH$_4$) |

TABLE 4-continued
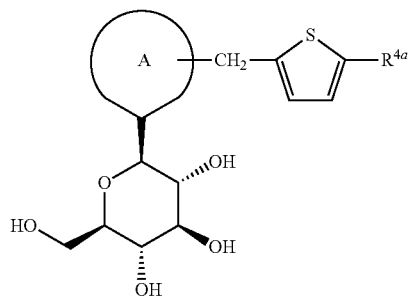
| Examples | Ring A | R$^{4a}$ | Preparation Method | APCI-Mass (m/Z) |
|---|---|---|---|---|
| 136 | 2,4-disubstituted CH$_3$-phenyl | 5-methyl-2,3-dihydrobenzofuran | 4 | 486 (M + NH$_4$) |
| 137 | 1-F, 2,4-disubstituted naphthyl | Cl | 1 | 456/458 (M + NH$_4$) |
| 138 | 2,4,5-tri(CH$_3$) phenyl | phenyl | 2 | 458 (M + NH$_4$) |
| 139 | 2-CF$_3$, 4-substituted phenyl | phenyl | 2 | 498 (M + NH$_4$) |
| 140 | 2,4-disubstituted CH$_3$-phenyl | 3-CH$_2$CH$_3$-phenyl | 1 | 472 (M + NH$_4$) |
| 141 | 2,4-disubstituted CH$_3$-phenyl | 2-pyridyl | 1 | 428 (M + H) |

TABLE 4-continued
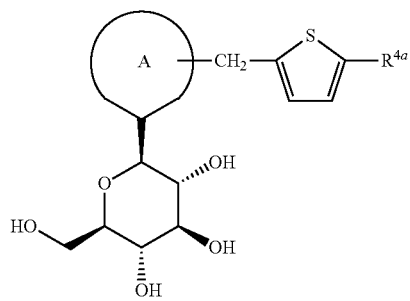
| Examples | Ring A | R$^{4a}$ | Preparation Method | APCI-Mass (m/Z) |
|---|---|---|---|---|
| 142 | 4-Cl, 3-Me-phenyl | 5-F-thiophen-2-yl (via methyl) | 4 | 488/490 (M + NH$_4$) |
| 143 | 3-Me-phenyl | pyridin-3-yl | 1 | 428 (M + H) |
| 144 | 3-Me-phenyl | 4-OCH$_3$-phenyl | 1 | 474 (M + NH$_4$) |
| 145 | 3-Me-phenyl | benzo[1,3]dioxol-5-yl | 1 | 488 (M + NH$_4$) |
| 146 | 3-Me-phenyl | 6-F-pyridin-2-yl | 1 | 463 (M + NH$_4$) |
| 147 | 3-Me-phenyl | CF$_3$ | 1 | 436 (M + NH$_4$) |

TABLE 4-continued
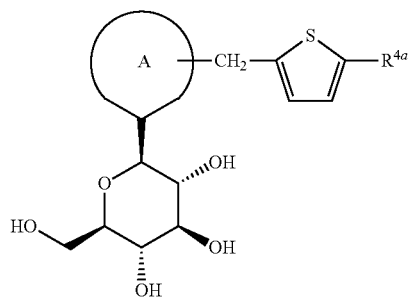
| Examples | Ring A | $R^{4a}$ | Preparation Method | APCI-Mass (m/Z) |
|---|---|---|---|---|
| 148 | 2,4-dimethylphenyl (CH₃) | 5-fluoro-2-thienyl | 1 | 468 (M + NH₄) |
| 149 | 3-fluoro-2-methyl-4-methylphenyl | phenyl | 1 | 462 (M + NH₄) |
| 150 | 2,4-dimethylphenyl | 6-(2-methylpropan-2-yl)pyridin-3-yl | 103 | 484 (M + H) |
| 151 | 2,4-dimethylphenyl | 4-cyanophenyl | 124 | 469 (M + NH₄) |
| 152 | 2-chloro-4-methylphenyl | quinolin-3-yl | 122 | 494/500 (M + H) |
| 153 | 2-chloro-4-methylphenyl | 2-thiazolyl | 128 | 454/456 (M + H) |

TABLE 4-continued

| Examples | Ring A | $R^{4a}$ | Preparation Method | APCI-Mass (m/Z) |
|---|---|---|---|---|
| 154 | 2-Cl, 3-methyl-thiophen-5-yl | phenyl | 2 | 470/472 (M + NH$_4$) |
| 155 | 4-Cl, 3-methyl-phenyl | 4-CN-phenyl | 122 | 489/491 (M + NH$_4$) |
| 156 | 4-Cl, 3-methyl-phenyl | 6-fluoropyridin-2-yl | 122 | 466/468 (M + H) |

Example 157

1-(β-D-glucopyranosyl)-4-chloro-3-(6-isopropyloxy-benzo[b]thiophen-2-ylmethyl)benzene 5-Bromo-2-chloro-1-(6-isopropyloxybenzo[b]thiophen-2-ylmethyl)benzene was treated in a manner similar to Example 1 to give the target compound. APCI-Mass m/Z 496/498 (M+NH$_4$).

Example 158

1-(β-D-glucopyranosyl)-4-methyl-3-(2-thienylmethyl)benzene (1) 1-(2,3,4,6-tetra-O-acetyl-β-D-glucopyranosyl)-3-(5-chloro-2-thienylmethyl)-4-methylbenzene 57 (12.0 g) obtained in Example 120-(1) was dissolved in tetrahydrofuran (120 ml) and methanol (360 ml), and added thereto were triethylamine (24.2 ml) and 10% palladium carbon catalyst (wet, 3.6 g), and the mixture was stirred at room temperature for 18 hours under hydrogen atmosphere under normal pressure. The insoluble materials were filtered off, washed with tetrahydrofuran, and the filtrate was evaporated under reduced pressure. The residue was dissolved in chloroform, washed successively with a 5% aqueous citric acid solution, a saturated aqueous sodium hydrogen carbonate solution and water, and dried over sodium sulfate. The solvent was evaporated under reduced pressure, and the residue was recrystallized from ethanol to give 1-(2,3,4,6-tetra-O-acetyl-β-D-glucopyranosyl)-4-methyl-3-(2-thienylmethyl)benzene (7.79 g) as colorless crystals. APCI-Mass m/Z 536 (M+NH$_4$).

(2) The above 1-(2,3,4,6-tetra-O-acetyl-β-Dglucopyranosyl)-4-methyl3-(2-thienylmethyl)benzene was treated in a manner similar to Example 106-(3) to give the desired 1-(β-D-glucopyranosyl)-4-methyl-3-(2-thienylmethyl)benzene as colorless powder. APCI-Mass m/Z 368 (M+NH$_4$).

Example 159

1-(β-D-glucopyranosyl)-3-(5-bromo-2-thienylmethyl)-4-methylbenzene (1) 1-(2,3,4,6-tetra-O-acetyl-β-D-glucopyranosyl)-4-methyl-3-(2-thienylmethyl)benzene (11.08 g) obtained in Example 158-(1) was dissolved in chloroform (100 ml), and added dropwise thereto at 0° C. was a solution of bromine (3.71 g) in chloroform (13 ml). The mixture was stirred at 0° C. for 1.5 hours, and then, at room temperature for 1 hour, and the mixture was poured into a 10% aqueous sodium thiosulfate solution and a saturated aqueous sodium hydrogen carbonate solution. The mixture was extracted twice with chloroform, washed with brine, and dried over magnesium sulfate. The solvent was evaporated under reduced pressure, and the residue was purified by silica gel column chromatography (hexane:ethyl acetate=80:20-67:33) to give 1-(2,3,4,6-tetra-O-acetyl-β-D-glucopyranosyl)-3-(5-bromo-2-thienylmethyl)-4-methylbenzene (7.13 g) as a colorless solid. APCI-Mass m/Z 614/616 (M+NH$_4$).

(2) The above 1-(2,3,4,6-tetra-O-acetyl-β-Dglucopyranosyl)-3-(5-bromo-2-thienylmethyl)-4-methylbenzene was treated in a manner similar to Example 106-(3) to give the desired 1-(β-D-glucopyranosyl)-3-(5-bromo-2-thienylmethyl)-4-methylbenzene as colorless powder. APCI-Mass m/Z 446/448 (m+NH$_4$).

Example 160

1-(β-D-glucopyranosyl)-3-(5-phenyl-2-thienylmethyl)benzene

2-Phenylthiophene and 3-bromobenzaldehyde was treated in a manner similar to Example 4 to give the target compound. APCI-Mass m/Z 430 (M+NH$_4$).

Example 161

1-(β-D-glucopyranosyl)-3-(5-cyano-2-thienylmethyl)-4-methylbenzene (1) 1-(2,3,4,6-tetra-O-acetyl-β-D-glucopyranosyl)-3-(5-bromo-2-thienylmethyl)-4-methylbenzene (500 mg) obtained in Example 159-(1) was dissolved in N,N-dimethylacetamide (10 ml), and added thereto were zinc cyanide (98 mg), tris(dibenzylideneacetone)dipalladium(0) (77 mg), 1,1'-bis(diphenylphosphino)ferrocene (47 mg) and zinc power (14 mg). The mixture was heated under stirring at 120° C. overnight. The reaction solution was cooled, diluted with ethyl acetate and water, and the insoluble materials were filtered off. The organic layer of the filtrate was washed twice with water and successively washed with brine. After drying the same over sodium sulfate, the solvent was evaporated under reduced pressure, and the residue was purified by silica gel column chromatography (hexane:ethyl acetate=100:0-50:50) to give 1-(2,3,4,6-tetra-O-acetyl-β-Dglucopyranosyl)-3-(5-cyano-2-thienylmethyl)-4-methylbenzene (207 mg) as colorless crystals. APCI-Mass m/Z 561 (M+NH$_4$).

(2) The above 1-(2,3,4,6-tetra-O-acetyl-β-Dglucopyranosyl)-3-(5-cyano-2-thienylmethyl)-4-methylbenzene was treated in a manner similar to Example 106-(3) to give the desired 1-(β-D-glucopyranosyl)-3-(5-cyano-2-thienylmethyl)-4-methylbenzene as colorless powder. APCI-Mass m/Z 393 (M+NH$_4$).

Example 162

1-(β-D-glucopyranosyl)-4-fluoro-3-(5-(2-pyridyl)-2-thienylmethyl)naphthalene

4-Bromo-1-fluoro-2-(5-(2-pyridyl)-2-thienylmethyl) naphthalene was treated in a manner similar to Example 1 to give the target compound. APCI-Mass m/Z 482 (M+H).

Example 163

1-(β-D-glucopyranosyl)-3-(5-bromo-2-thienylmethyl)-4-chlorobenzene 1-(2,3,4,6-tetra-O-acetyl-β-D-glucopyranosyl)-3-(5-bromo-2-thienylmethyl)-4-chlorobenzene 71 obtained in Example 128-(4) was treated in a manner similar to Example 106-(3) to give the target compound. APCI-Mass m/Z 466/468 (M+NH$_4$).

Example 164

1-(β-D-glucopyranosyl)-4-methyl-3-(5-(2-pyrimidinyl)-2-thienylmethyl)benzene 1-(2,3,4,6-tetra-O-acetyl-β-D-glucopyranosyl)-3-(5-bromo-2-thienylmethyl)-4-methylbenzene obtained in Example 159-(1) and tri-n-butyl (2-pyrimidinyl)tin 54 were treated in a manner similar to Example 128-(5) and (6) to give the target compound. APCI-Mass m/Z 429 (M+H).

Example 165

1-(β-D-glucopyranosyl)-4-methyl-3-(5-(2-thiazolyl)-2-thienylmethyl)benzene 1-(2,3,4,6-tetra-O-acetyl-β-D-glucopyranosyl)-3-(5-bromo-2-thienylmethyl)-4-methylbenzene obtained in Example 159-(1) and tri-n-butyl(2-thiazolyl)tin were treated in a manner similar to Example 128-(5) and (6) to give the target compound. APCI-Mass m/Z 434 (M+H).

Example 166

1-(β-D-glucopyranosyl)-4-chloro-3-(6-ethyl-3-pyridylmethyl)benzene

5-Bromo-2-chloro-1-(6-ethyl-3-pyridylmethyl)benzene was treated in a manner similar to Example 1 to give the target compound. APCI-Mass m/Z 394/396 (M+H).

Example 167

1-(β-D-glucopyranosyl)-4-chloro-3-(6-ethylbenzo[b]thiophen-2-ylmethyl)benzene

6-Ethylbenzo[b]thiophene and 5-bromo-2-chlorobenzaldehyde obtained in Reference Example 16-(1) were treated in a manner similar to Example 4 to give the target compound. APCI-Mass m/Z 466/468 (M+H).

Example 168

1-(β-D-glucopyranosyl)-4-chloro-3-(5-(6-fluoro-3-pyridyl)-2-thienylmethyl)benzene (1) 1-(2,3,4,6-tetra-O-acetyl-β-D-glucopyranosyl)-3-(5-bromo-2-thienylmethyl)-4-chlorobenzene 71 (500 mg) obtained in Example 128-(4) was dissolved in 1,2-dimethoxyethane (15 ml), and added thereto were 6-fluoropyridine-3-boronic acid 58 (228 mg), tetrakis(triphenylphosphine)palladium(0) (94 mg) and cesium fluoride (738 mg). The mixture was heated under reflux for 30 minutes. The reaction solution was poured into a saturated aqueous sodium hydrogen carbonate solution and the mixture was extracted with ethyl acetate. The extract was washed with brine and dried over magnesium sulfate, and the solvent was evaporated under reduced pressure. The residue was purified by silica gel column chromatography (hexane:ethyl acetate=75:25-60:40) to give 1-(2,3,4,6-tetra-O-acetyl-β-D-glucopyranosyl)-4-chloro-3-(5-(6-fluoro-3-pyridyl)-2-thienylmethyl)benzene (454 mg) as a colorless solid. APCI-Mass m/Z 634/636 (M+H).

(2) The above 1-(2,3,4,6-tetra-O-acetyl-β-Dglucopyranosyl)-4-chloro-3-(5-(6-fluoro-3-pyridyl)-2-thienylmethyl) benzene was treated in a manner similar to Example 106-(3) to give the desired 1-(β-D-glucopyranosyl)-4-chloro-3-(5-(6-fluoro-3-pyridyl)-2-thienylmethyl)benzene as colorless powder. APCI-Mass m/Z 483 (M+NH$_4$), 466 (M+H).

Example 169

1-(β-D-glucopyranosyl)-4-chloro-3-(5-(6-methoxy-3-pyridyl)-2-thienylmethyl)benzene 1-(2,3,4,6-tetra-O-acetyl-β-D-glucopyranosyl)-3-(5-bromo-2-thienylmethyl)-4-chlorobenzene 71 obtained in Example 128-(4) and 6-methoxypyridine-3-boronic acid were treated in a manner similar to Example 168 to give the target compound. APCI-Mass m/Z 478/480 (M+H).

Example 170

1-(β-D-glucopyranosyl)-4-chloro-3-(5-(6-methoxy-2-pyridyl)-2-thienylmethyl)benzene 1-(2,3,4,6-tetra-O-acetyl-β-D-glucopyranosyl)-3-(5-bromo-2-thienylmethyl)-4-chlorobenzene 71 obtained in Example 128-(4) and tri-n-butyl(6-methoxy-2-pyridyl)tin (see Gros, Philippe; Fort, Yves. Synthesis (1999), 754-756) were treated in a manner similar to Example 128-(5) and (6) to give the target compound. APCI-Mass m/Z 478/480 (M+H).

Example 171

1-(β-D-glucopyranosyl)-4-chloro-3-(1-oxo-2-isoindolinylmethyl)benzene

5-Bromo-2-chloro-1-(1-oxo-2-isoindolynilmethyl)benzene was treated in a manner similar to Example 2 to give the target compound. APCI-Mass m/Z 437/439 (M+NH$_4$).

Example 172

1-(β-D-glucopyranosyl)-4-chloro-3-(1-phenyl-4-pyrazolylmethyl)benzene

5-Bromo-2-chloro-1-(1-phenyl-4-pyrazolylmethyl)benzene was treated in a manner similar to Example 1 to give the target compound. APCI-Mass m/Z 431/433 (M+H).

Example 173

1-(β-D-glucopyranosyl)-4-chloro-3-(5-(6-ethoxy-2-pyridyl)-2-thienylmethyl)benzene (1) 1-(2,3,4,6-tetra-O-acetyl-β-D-glucopyranosyl)-3-(5-bromo-2-thienylmethyl)-4-chlorobenzene 71 obtained in Example 128-(4) and tri-n-butyl (6-ethoxy-2-pyridyl)tin (see WO 00/74681) were treated in a manner similar to Example 128-(5) to give 1-(2,3,4,6-tetra-O-acetyl-β-Dglucopyranosyl)-4-chloro-3-(5-(6-ethoxy-2-pyridyl)-2-thienylmethyl) benzene as colorless crystals. APCI-Mass m/Z 660/662 (M+H).
(2) The above 1-(2,3,4,6-tetra-O-acetyl-β-Dglucopyranosyl)-4-chloro-3-(5-(6-ethoxy-2-pyridyl)-2-thienylmethyl) benzene (245 mg) was dissolved in tetrahydrofuran (5 ml), added thereto was a solution of sodium hydride (oil, 9 mg) in ethanol (5 ml), and the mixture was stirred at room temperature for 2 hours. The solvent was evaporated under reduced pressure and the residue was purified by silica gel column chromatography (chloroform:methanol=100:0-90:10) to give the desired 1-(β-D-glucopyranosyl)-4-chloro-3-(5-(6-ethoxy-2-pyridyl)-2-thienylmethyl)benzene (145 mg) as colorless powder. APCI-Mass m/Z 492/494 (M+H).

Example 174

1-(β-D-glucopyranosyl)-4-chloro-3-(6-n-propyloxy-benzo[b]thiophen-2-ylmethyl)benzene 5-Bromo-2-chloro-1-(6-n-propyloxybenzo[b]thiophen-2-yl methyl)benzene was treated in a manner similar to Example 1 to give the target compound. APCI-Mass m/Z 496/498 (M+NH$_4$).

Example 175

1-(β-D-glucopyranosyl)-4-chloro-3-(6-(2-fluoroethyloxy)benzo[b]thiophen-2-ylmethyl)benzene 5-Bromo-2-chloro-1-(6-(2-fluoroethyloxy)benzo[b]thiophen-2-yl methylbenzene was treated in a manner similar to Example 1 to give the target compound. APCI-Mass m/Z 500/502 (M+NH$_4$).

Example 176

1-(β-D-glucopyranosyl)-3-(5-(4-difluoromethylphenyl)-2-thienylmethyl)-4-methylbenzene (1) 1-(2,3,4,6-tetra-O-acetyl-β-D-glucopyranosyl)-3-(5-bromo-2-thienylmethyl)-4-methylbenzene from Example 159-(1) and 4-formylphenylboronic acid were treated in a manner similar to Example 168-(1) to give 1-(2,3,4,6-tetra-O-acetyl-β-D-glucopyranosyl)-3-(5-(4-formylphenyl)-2-thienylmethyl)-4-methylbenzene as a colorless solid. APCI-Mass m/Z 640 (M+NH$_4$).
(2) The above 1-(2,3,4,6-tetra-O-acetyl-β-Dglucopyranosyl)-3-(5-(4-formylphenyl)-2-thienylmethyl)-4-methylbenzene was treated in a manner similar to Example 130-(2) to give the desired 1-(2,3,4,6-tetra-O-acetyl-β-Dglucopyranosyl)-3-(5-(4-difluoromethylphenyl)-2-thienylmethyl)-4-methylbenzene as colorless crystals. APCI-Mass m/Z 662 (M+NH$_4$).
(3) The above 1-(2,3,4,6-tetra-O-acetyl-β-Dglucopyranosyl)-3-(5-(4-difluoromethylphenyl)-2-thienylmethyl)-4-methylbenzene was treated in a manner similar to Example 106-(3) to give the desired 1-(β-D-glucopyranosyl)-3-(5-(4-difluoromethylphenyl)-2-thienylmethyl)-4-methylbenzene as colorless powder. APCI-Mass m/Z 494 (M+NH$_4$).

Example 177

1-(β-D-glucopyranosyl)-3-(5-(3,4-difluorophenyl)-2-thienylmethyl)-4-methylbenzene (1) 1-(2,3,4,6-tetra-O-acetyl-β-D-glucopyranosyl)-3-(5-bromo-2-thienylmethyl)-4-methylbenzene obtained in Example 159-(1) and 3,4-difluorophenylboronic acid were treated in a manner similar to Example 168-(1) to give 1-(2,3,4,6-tetra-Oacetyl-β-D-glucopyranosyl)-3-(5-(3,4-difluorophenyl)-2-thienylmethyl)-4-methylbenzene as colorless crystals. APCI-Mass m/Z 648 (M+NH$_4$).
(2) The above 1-(2,3,4,6-tetra-O-acetyl-β-Dglucopyranosyl)-3-(5-(3,4-difluorophenyl)-2-thienylmethyl)-4-methylbenzene was treated in a manner similar to Example 106-(3) to give the desired 1-(β-D-glucopyranosyl)-3-(5-(3,4-difluorophenyl)-2-thienylmethyl)-4-methylbenzene as colorless powder. APCI-Mass m/Z 480 (M+NH$_4$).

Example 178

1-(β-D-glucopyranosyl)-4-chloro-3-(5-(3-difluoromethylphenyl)-2-thienylmethyl)benzene (1) 1-(2,3,4,6-tetra-O-acetyl-β-D-glucopyranosyl)-3-(5-bromo-2-thienylmethyl)-4-chlorobenzene 71 obtained in Example 128-(4) and 3-formylphenylboronic acid were treated in a manner similar to Example 168-(1) to give 1-(2,3,4,6-tetra-O-acetyl-β-D-glucopyranosyl)-4-chloro-3-(5-(3-formylphenyl)-2-thienylmethyl)benzene as a colorless solid. APCI-Mass m/Z 660/662 (M+NH$_4$).
(2) The above 1-(2,3,4,6-tetra-O-acetyl-β-Dglucopyranosyl)-4-chloro-3-(5-(3-formylphenyl)-2-thienylmethyl)benzene was treated in a manner similar to Example 130-(2) to give 1-(2,3,4,6-tetra-O-acetyl-β-Dglucopyranosyl)-4-chloro-3-(5-(3-difluoromethylphenyl)-2-thienylmethyl)benzene as colorless crystals. APCI-Mass m/Z 682/684 (M+NH$_4$).
(3) The above 1-(2,3,4,6-tetra-O-acetyl-β-Dglucopyranosyl)-4-chloro-3-(5-(3-difluoromethylphenyl)-2-thienylmethyl)benzene was treated in a manner similar to Example 120-(3) to give the desired 1-(β-D-glucopyranosyl)-4-chloro-3-(5-(3-difluoromethylphenyl)-2-thienylmethyl)benzene as colorless powder. APCI-Mass m/Z 514/516 (M+NH$_4$).

Example 179

1-(β-D-glucopyranosyl)-4-chloro-3-(5-(4-difluoromethylphenyl)-2-thienylmethyl)benzene (1) 1-(2,3,4,6-tetra-O-acetyl-β-D-glucopyranosyl)-3-(5-bromo-2-thienylmethyl)-4-chlorobenzene 71 obtained in Example 128-(4) and 4-formylphenylboronic acid were treated in a manner similar to Example 168-(1) to give 1-(2,3,4,6-tetra-Oacetyl-β-D-glucopyranosyl)-4-chloro-3-(5-(4-formylphenyl)-2-thienylmethyl)benzene as a colorless solid. APCI-Mass m/Z 660/662 (M+NH$_4$).
(2) The above 1-(2,3,4,6-tetra-O-acetyl-β-Dglucopyranosyl)-4-chloro-3-(5-(4-formylphenyl)-2-thienylmethyl)benzene was treated in a manner similar to Example 130-(2) to give 1-(2,3,4,6-tetra-O-acetyl-β-D-glucopyranosyl)-4-chloro-3-(5-(4-difluoromethylphenyl)-2-thienylmethyl)benzene as colorless crystals. APCI-Mass m/Z 682/684 (M+NH$_4$).
(3) The above 1-(2,3,4,6-tetra-O-acetyl-β-Dglucopyranosyl)-4-chloro-3-(5-(4-difluoromethylphenyl)-2-thienylmethyl)benzene was treated in a manner similar to Example 120-(3) to give the desired 1-(β-D-glucopyranosyl)-4-chloro-3-(5-(4-difluoromethylphenyl)-2-thienylmethyl)benzene as colorless powder. APCI-Mass m/Z 514/516 (M+NH$_4$).

Example 180

1-(β-D-glucopyranosyl)-4-chloro-3-(5-(4-difluoromethyl-3-fluorophenyl)-2-thienylmethyl)benzene (1) 1-(2,3,4,6-Tetra-O-acetyl-β-D-glucopyranosyl)-3-(5-bromo-2-thienylmethyl)-4-chlorobenzene obtained in Example 128-(4) and 3-fluoro-4-formylphenylboronic acid were treated in a manner similar to Example 168-(1) to give 1-(2,3,4,6-tetra-O-acetyl-β-D-glucopyranosyl)-4-chloro-3-(5-(3-fluoro-4-formylphenyl)-2-thienylmethyl)benzene as colorless foam. APCI-Mass m/Z 678/680 (M+NH$_4$).
(2) 1-(2,3,4,6-Tetra-O-acetyl-β-D-glucopyranosyl)-4-chloro-3-(5-(3-fluoro-4-formylphenyl)-2-thienylmethyl)benzene was treated in a manner similar to Example 178-(2) and
(3) to give the desired 1-(β-D-glucopyranosyl)-4-chloro-3-(5-(4-difluoromethyl-3-fluorophenyl)-2-thienylmethyl)benzene as a colorless foam. APCI-Mass m/Z 532/534 (M+NH$_4$).

Example 181

1-(β-D-glucopyranosyl)-4-chloro-3-(5-(1H-tetrazol-5-yl)-2-thienylmethyl)benzene (1) 1-(2,3,4,6-tetra-O-acetyl-β-D-glucopyranosyl)-3-(5-bromo-2-thienylmethyl)-4-chlorobenzene obtained in Example 128-(4) and (2-benzyloxymethyl-2H-tetrazol-5-yl)trin-butyltin (see *Tetrahedron Lett.* (2000) 2805) were treated in a manner similar to Example 128-(5) to give 1-(2,3,4,6-tetra-O-acetyl-β-D-glucopyranosyl)-3-(5-(2-benzyloxymethyl-2H-tetrazol-5-yl)-2-thienylmethyl)-4-chlorobenzene as colorless solid. APCI-Mass m/Z 727/729 (M+H).
(2) A mixture of 1-(2,3,4,6-tetra-O-acetyl-β-Dglucopyranosyl)-3-(5-(2-benzyloxymethyl-2H-tetrazol-5-yl)-2-thienylmethyl)-4-chlorobenzene (247 mg), 6M aqueous hydrochloric acid solution (2 ml) and methanol (20 ml) was refluxed overnight. The solvent was evaporated under reduced pressure and the residue was triturated with diethyl ether to give the desired 1-(β-D-glucopyranosyl)-4-chloro-3-(5-(1H-tetrazol-5-yl)-2-thienylmethyl)benzene (172 mg) as colorless powder. ESI-Mass m/Z 437/439 (M−H).

Example 182

1-(β-D-glucopyranosyl)-4-chloro-3-(5-(2-methyl-2H-tetrazol-5-yl)-2-thienylmethyl)benzene 1-(β-D-glucopyranosyl)-4-chloro-3-(5-(1H-tetrazol-5-yl)-2-thienylmethyl)benzene (140 mg) obtained in Example 181 was dissolved in dimethylformamide (5 ml) and added thereto were methyl iodide (100 μl) and potassium carbonate (220 mg). The mixture was stirred at room temperature overnight. The reaction solution was poured into water and the mixture was extracted with ethyl acetate. The extract was washed with brine and dried over sodium sulfate, and the solvent was evaporated under reduced pressure to give the desired 1-(β-D-glucopyranosyl)-4-chloro-3-(5-(2-methyl-2H-tetrazol-5-yl)-2-thienylmethyl)benzene as colorless powder. APCI-Mass m/Z 470/472 (M+NH$_4$).

Example 183

1-(β-D-glucopyranosyl)-4-chloro-3-(5-(4-cyano-3-fluorophenyl)-2-thienylmethyl)benzene (1) 1-(2,3,4,6-Tetra-O-acetyl-β-D-glucopyranosyl)-4-chloro-3-(5-(3-fluoro-4-formylphenyl)-2-thienylmethyl)benzene (272 mg) obtained in Example 180-(1) was dissolved in N-methyl-2-pyrrolidone (10 ml) and added thereto was hydroxylamine hydrochloride (34 mg). The mixture was heated under stirring at 117° C. overnight. The reaction solution was cooled and diluted with ethyl acetate and water. The organic layer was washed with water and successively washed with brine. After drying over magnesium sulfate, the solvent was evaporated under reduced pressure. The residue was purified by silica gel column chromatography (hexane: ethyl acetate=3:1-2:1) to give 1-(2,3,4,6-tetra-O-acetyl-β-D-glucopyranosyl)-4-chloro-3-(5-(4-hydroxyimino-3-fluorophenyl)-2-thienylmethyl)benzene (177 mg) as colorless caramel. APCI-Mass m/Z 693/695 (M+NH$_4$).

(2) The above 1-(2,3,4,6-tetra-O-acetyl-β-D-glucopyranosyl)-4-chloro-3-(5-(4-hydroxyimino-3-fluorophenyl)-2-thienylmethyl)benzene (175 mg) was dissolved in chloroform (5 ml) and added thereto was 1,1'-carbonyldiimidazole (46 mg). The mixture was stirred at room temperature overnight. 1,1'-Carbonyldiimidazole (92 mg) was further added thereto, and the mixture was stirred at 40° C. for 6 hours. The reaction solution was cooled and diluted with ethyl acetate and water. The organic layer was separated and successively washed with brine. After drying over magnesium sulfate, the solvent was evaporated under reduced pressure. The residue was purified by silica gel column chromatography (hexane: ethyl acetate=2:1) to give 1-(2,3,4,6-tetra-O-acetyl-β-D-glucopyranosyl)-4-chloro-3-(5-(4-cyano-3-fluorophenyl)-2-thienylmethyl)benzene (158 mg) as colorless caramel. APCI-Mass m/Z 675/677 (M+NH$_4$).

(3) The above 1-(2,3,4,6-tetra-O-acetyl-β-D-glucopyranosyl)-4-chloro-3-(5-(4-cyano-3-fluorophenyl)-2-thienylmethyl)benzene was treated in a manner similar to Example 106-(3) to give desired 1-(β-D-glucopyranosyl)-4-chloro-3-(5-(4-cyano-3-fluorophenyl)-2-thienylmethyl)benzene as pale yellow powder. APCI-Mass m/Z 507/509 (M+NH$_4$).

Example 184

1-(β-D-glucopyranosyl)-4-chloro-3-(1,3-dihydroisoindol-2-ylmethyl)benzene

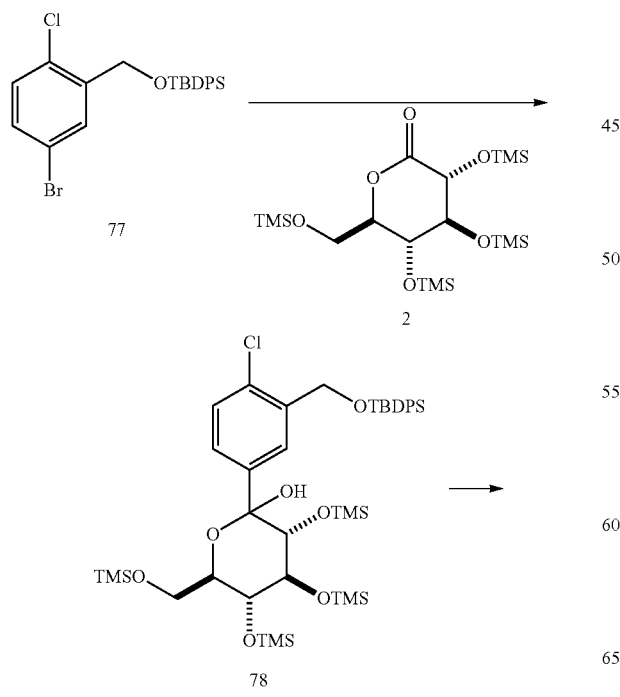

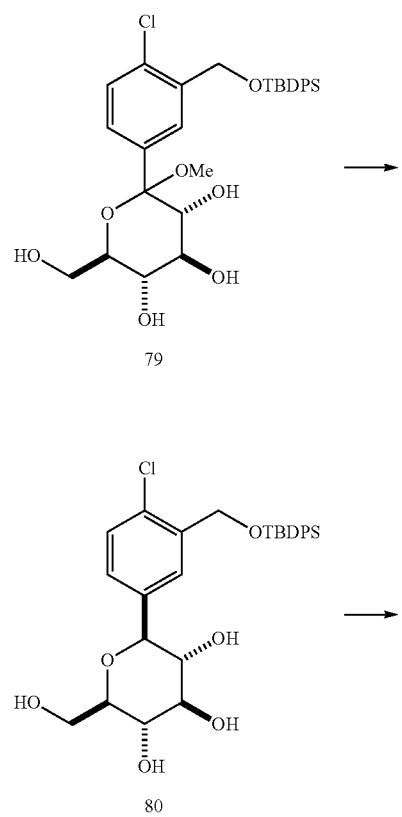

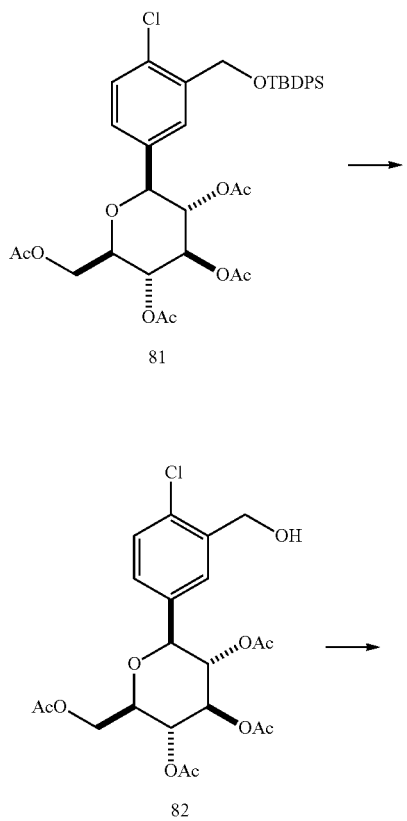

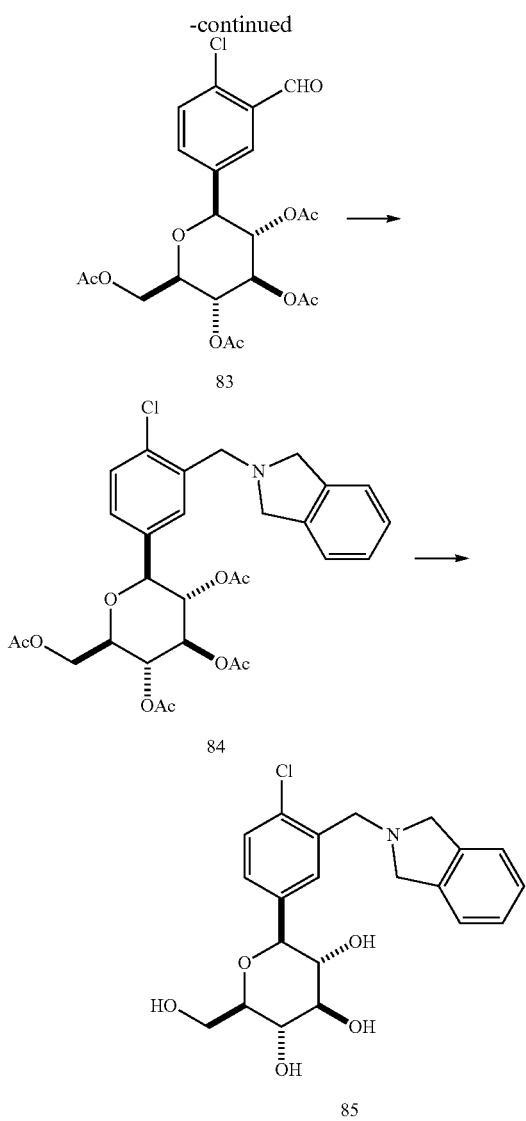

(In the above scheme, OTBDPS is a tert-butyldiphenylsilyloxy group, and the other symbols are the same as defined above.)

(1) A mixed solution of 5-bromo-2-chloro-1-(tert-butyldiphenylsilyloxymethyl)benzene 77 (10.83 g) and 2,3,4,6-tetrakis-O-trimethylsilyl-D-glucono-1,5-lactone 2 (see U.S. Pat. No. 6,515,117) (13.2 g) in tetrahydrofuran (400 ml) was cooled to −78° C. under argon atmosphere, and thereto was added dropwise tert-butyl lithium (1.60 M pentane solution, 30.9 ml), and the mixture was stirred at the same temperature for 30 minutes to give a compound 78. Without isolating this compound, a solution of methanesulfonic acid (6.12 ml) in methanol (200 ml) was added to the reaction solution, and the reaction mixture was warmed to room temperature, and stirred at the same temperature for 15 hours. Under ice-cooling, to the mixture was added a saturated aqueous sodium hydrogen carbonate solution, and the mixture was extracted with ethyl acetate. The extract was washed with brine, and dried over magnesium sulfate. The solvent was evaporated under reduced pressure, and the residue was purified by silica gel column chromatography (chloroform:methanol=93:7) to give a methyl ether compound 79 (9.71 g) as colorless powder. APCI-Mass m/Z 590/592 (m+NH$_4$).

(2) A solution of the above methyl ether compound 79 (3.46 g) in dichloromethane (70 ml) was cooled to 0° C. under argon atmosphere, and thereto were added dropwise successively triethylsilane (2.89 ml) and boron trifluoride•diethyl ether complex (2.28 ml). The mixture was stirred at the same temperature for 1 hour. Under ice-cooling, a saturated aqueous sodium hydrogen carbonate solution was added, and the mixture was extracted with ethyl acetate. The extract was washed with brine and dried over magnesium sulfate, and the solvent was evaporated under reduced pressure. The residue was purified by silica gel column chromatography (chloroform:methanol=100:0-94:4) to give 1-(β-D-glucopyranosyl)-4-chloro-3-(tert-butyldiphenylsilyloxymethyl)benzene 80 (2.52 g) as colorless powder. APCI-Mass m/Z 560/562 (M+NH$_4$).

(3) The above compound 80 (4.12 g) was treated in a manner similar to Example 106-(1) to give the compound 81 (5.44 g). APCI-Mass m/Z 728/730 (M+NH$_4$).

(4) A mixed solution of the above compound 81 (5.44 g), acetic acid (1.29 ml) in tetrahydrofuran (60 ml) was cooled to 0° C. under argon atmosphere, and thereto was added tetrabutyl ammonium fluoride (1.0 M tetrahydrofuran solution, 8.43 ml). The mixture was stirred at the same temperature for 30 minutes, and then further stirred at room temperature for 15 hours. The mixture was diluted with ethyl acetate and washed successively with 0.4 M aqueous hydrochloric acid solution, a saturated aqueous sodium hydrogen carbonate solution and brine. The mixture was dried over magnesium sulfate, and the solvent was evaporated under reduced pressure. The residue was purified by silica gel column chromatography (hexane: ethyl acetate=4:1-1:1) to give the compound 82 (2.97 g) as a colorless solid. APCI-Mass m/Z 490/492 (M+NH$_4$).

(5) A solution of the above compound 82 (1.60 g) in dichloromethane (50 ml) was cooled to 0° C. under argon atmosphere, and thereto was added Dess-Martin periodinane (1.58 g). The mixture was warmed to room temperature and stirred at the same temperature for 3 hours. The mixture was diluted with ethyl acetate, and insoluble materials were filtered off. The filtrate was washed successively with a saturated aqueous sodium hydrogen carbonate solution and brine, and dried over magnesium sulfate. The solvent was evaporated under reduced pressure, and the residue was purified by silica gel column chromatography (hexane:ethyl acetate=3:1-1:1) to give 5-(2,3,4,6-tetra-O-acetyl-β-D-glucopyranosyl)-2-chloro benzaldehyde 83 (1.35 g) as colorless crystals. APCI-Mass m/Z 488/490 (M+NH$_4$).

(6) To a mixed solution of the above 5-(2,3,4,6-tetra-O-acetyl-β-D-glucopyranosyl)-2-chlorobenzaldehyde 83 (325 mg), 2,3-dihydro-1H-isoindole (98 mg), acetic acid (82 mg) in 1,2-dichloroethane (5 ml) was added sodium triacetoxyborohydride (219 mg). The mixture was stirred at room temperature for 3 hours, and cooled to 0° C. A saturated aqueous sodium hydrogen carbonate solution was added thereto to basify the reaction mixture. The mixture was extracted with ethyl acetate, and the extract was washed with brine, and dried over magnesium sulfate. The solvent was evaporated under reduced pressure, and the residue was purified by silica gel column chromatography (hexane:ethyl acetate=1:0-1:1) to give 1-(2,3,4,6-tetra-O-acetyl-β-D-glucopyranosyl)-4-chloro-3-(1,3-dihydro-isoindol-2-ylmethyl)benzene 84 (234 mg) as a colorless solid. APCI-Mass m/Z 574/576 (M+H).

(7) The above 1-(2,3,4,6-tetra-O-acetyl-β-Dglucopyranosyl)-4-chloro-3-(1,3-dihydro-isoindol-2-ylmethyl)benzene 84 was treated in a manner similar to Example 106-(3) to give the desired 1-(β-D-glucopyranosyl)-4-chloro-3-(1,3-dihydro-isoindol-2-ylmethyl)benzene 85 as colorless powder. APCI-Mass m/Z 406/408 (M+H).

Example 185

1-(β-D-glucopyranosyl)-4-methyl-3-(5-(3-cyano-4-fluorophenyl)-2-thienylmethyl)benzene 1-(2,3,4,6-tetra-O-acetyl-β-D-glucopyranosyl)-3-(5-bromo-2-thienylmethyl)-4-methylbenzene obtained in Example 159-(1) and 4-fluoro-3-formylphenylboronic acid were used and treated in a manner similar to Example 177-(1) and Example 183 to give the title compound as colorless powder. APCI-Mass m/z 487 (m+NH$_4$).

Example 186

1-(β-D-glucopyranosyl)-3-(5-(2-cyano-5-pyridyl)-2-thienylmethyl)-4-methylbenzene (1) 1-(2,3,4,6-Tetra-O-acetyl-β-D-glucopyranosyl)-3-(5-bromo-2-thienylmethyl)-4-methylbenzene (597 mg) obtained in Example 159-(1) was dissolved in N-methyl-2-pyrrolidone (10 ml) and added thereto were tri-n-butyl(2-cyano-5-pyridyl)tin (590 mg), dichlorobis(triphenylphosphine)palladium(II) (70 mg) and copper(I)iodide (19 mg). The mixture was heated under stirring at 100° C. for 4 hours. The reaction solution was cooled and diluted with ethyl acetate and water. The organic layer was washed with water and successively washed with brine. After drying over magnesium sulfate, the solvent was evaporated under reduced pressure. The residue was purified by silica gel column chromatography (hexane:ethyl acetate=2:1) to give 1-(2,3,4,6-tetra-O-acetyl-β-D-glucopyranosyl)-3-(5-(2-cyano-5-pyridyl)-2-thienylmethyl)-4-methylbenzene (351 mg) as colorless powder. APCI-Mass m/Z 621 (M+H).

(2) The above 1-(2,3,4,6-tetra-O-acetyl-β-D-glucopyranosyl)-3-(5-(2-cyano-5-pyridyl)-2-thienylmethyl)-4-methylbenzene (62 mg) was dissolved in a mixture of tert-butanol (3 ml)tetrahydrofuran (3 ml) and added thereto was sodium tert-butoxide (48 mg). The mixture was stirred at room temperature for 3.5 hours. Sodium tert-butoxide (19 mg) was further added thereto, and the mixture was stirred at room temperature for 1 hour. To the mixture was added a saturated aqueous ammonium chloride solution at 0° C., and the mixture was extracted with ethyl acetate twice. The extract was washed with brine, dried over magnesium sulfate, and the solvent was evaporated under reduced pressure. The residue was purified by silica gel column chromatography (chloroform:methanol=19:1) to give the desired 1-(β-Dglucopyranosyl)-3-(5-(2cyano-5-pyridyl)-2-thienylmethyl)-4-methylbenzene (23 mg) as colorless powder. APCI-Mass m/Z 470 (M+NH$_4$).

Example 187

1-(β-D-glucopyranosyl)-4-chloro-3-(5-(2-cyano-5-pyridyl)-2-thienylmethyl)benzene (1) 1-(2,3,4,6-Tetra-O-acetyl-β-D-glucopyranosyl)-3-(5-bromo-2-thienylmethyl)-4-chlorobenzene obtained in Example 128-(4) was treated in a manner similar to Example 186-(1) to give 1-(2,3,4,6-tetra-O-acetyl-β-D-glucopyranosyl)-4-chloro-3-(5-(2-cyano-5-pyridyl)-2-thienylmethyl)benzene as colorless powder. APCI-Mass m/Z 641/643 (M+H).

(2) 1-(2,3,4,6-Tetra-O-acetyl-β-D-glucopyranosyl)-4-chloro-3-(5-(2-cyano-5-pyridyl)-2-thienylmethyl)benzene was treated in a manner similar to Example 186-(2) to give the desired 1-(β-D-glucopyranosyl)-4-chloro-3-(5-(2-cyano-5-pyridyl)-2-thienylmethyl)benzene as pale yellow powder. APCI-Mass m/Z 490/492 (M+NH$_4$).

Example 188

1-(β-D-glucopyranosyl)-3-(5-(2-carbamoyl-5-pyridyl)-2-thienylmethyl)-4-chlorobenzene (1) 1-(2,3,4,6-Tetra-O-acetyl-β-D-glucopyranosyl)-4-chloro-3-(5-(2-cyano-5-pyridyl)-2-thienylmethyl)benzene obtained in Example 187-(1) was treated in a manner similar to Example 106-(3) to give the mixture of 1-(β-D-glucopyranosyl)-4-chloro-3-(5-(2-cyano-5-pyridyl)-2-thienylmethyl)benzene and 1-(β-D-glucopyranosyl)-4-chloro-3-(5-(2-methoxyimidoyl-5-pyridyl)-2-thienylmethyl)benzene. This mixture was dissolved in methanol, and sodium methoxide (28% methanol solution, 1 drop) was added thereto, and the mixture was stirred at 60° C. for 6 hours. The reaction solution was cooled and the solvent was evaporated under reduced pressure to give pure 1-(β-D-glucopyranosyl)-4-chloro-3-(5-(2-methoxyimidoyl-5-pyridyl)-2-thienylmethyl)benzene. APCI-Mass m/Z 505/507 (M+H).

(2) The above 1-(β-D-glucopyranosyl)-4-chloro-3-(5-(2-methoxyimidoyl-5-pyridyl)-2-thienylmethyl)benzene was suspended in tetrahydrofuran, and sodium hydride (60% mineral oil suspension, 2 equivalent) was added thereto, and the mixture was stirred under reflux for 3 hours. The reaction solution was cooled and to the mixture was added a saturated aqueous ammonium chloride solution at 0° C., and the mixture was extracted with a mixture of ethyl acetate and tetrahydrofuran. The extract was washed with brine, dried over magnesium sulfate, and the solvent was evaporated under reduced pressure. The residue was purified by silica gel column chromatography (chloroform:methanol=9:1-5:1) to give the desired 1-(β-D-glucopyranosyl)-3-(5-(2-carbamoyl-5-pyridyl)-2-thienylmethyl)-4-chlorobenzene as pale yellow powder. APCI-Mass m/Z 491/493 (M+H).

Example 189

1-(β-D-glucopyranosyl)-4-fluoro-3-(5-(3-cyanophenyl)-2-thienylmethyl)benzene (1) 5-bromo-2-fluorobenzaldehyde and 2-chlorothiophene were used and treated in a manner similar to Example 4 and Example 106-(1) to give 1-(2,3,4,6-tetra-O-acetyl-β-D-glucopyranosyl)-3-(5-chloro-2-thienylmethyl)-4-fluorobenzene as colorless crystals. APCI-Mass m/z 574/576 (M+NH$_4$). mp 130-131° C.

(2) The above compound was treated in a manner similar to Example 158-(1) to give 1-(2,3,4,6-tetra-O-acetyl-β-Dglucopyranosyl)-3-(2-thienylmethyl)-4-fluorobenzene as colorless crystals. APCI-Mass m/z 540 (M+NH$_4$). mp 119-121° C.

(3) The above compound was treated in a manner similar to Example 159-(1) to give 1-(2,3,4,6-tetra-O-acetyl-β-Dglucopyranosyl)-3-(5-bromo-2-thienylmethyl)-4-fluorobenzene as colorless crystals. APCI-Mass m/z 618/620 (M+NH$_4$). mp 127-129° C.

(4) The above compound and 3-cyanophenylboronic acid were used and treated in a manner similar to Example 168 to give the title compound as colorless powder. APCI-Mass m/z 473 (M+NH$_4$).

Example 190

1-(β-D-glucopyranosyl)-4-fluoro-3-(5-(2-thiazolyl)-2-thienylmethyl)benzene 1-(2,3,4,6-tetra-O-acetyl-β-D-glucopyranosyl)-3-(5-bromo-2-thienylmethyl)-4-fluorobenzene obtained in Example 189-(3) and tri-n-butyl(2-thiazolyl)tin were used and treated in a manner similar to Example 128 to give the title compound as colorless crystals. APCI-Mass m/z 438 (M+NH₄). mp 161.5-162° C.

Example 191

1-(β-D-glucopyranosyl)-4-chloro-3-(5-(4-ethoxycarbonylphenyl)-2-thienylmethyl)benzene (1) 1-(2,3,4,6-Tetra-O-acetyl-β-D-glucopyranosyl)-3-(5-bromo-2-thienylmethyl)-4-chlorobenzene obtained in Example 128-(4) and 4-cyanophenylboronic acid were treated in a manner similar to Example 168-(1) to give 1-(2,3,4,6-tetra-O-acetyl-β-D-glucopyranosyl)-4-chloro-3-(5-(4-cyanophenyl)-2-thienylmethyl)benzene as colorless powder. APCI-Mass m/Z 657/659 (M+NH₄).
(2) The above 1-(2,3,4,6-tetra-O-acetyl-β-D-glucopyranosyl)-4-chloro-3-(5-(4-cyanophenyl)-2-thienylmethyl)benzene (128 mg) was suspended in ethanol (2 ml) and added thereto was a concentrated hydrochloric acid aqueous solution (1 ml). The mixture was heated reflux for 8.5 hours. The reaction solution was cooled and diluted with ethyl acetate and water. The organic layer was washed with water and successively washed with brine. After drying over magnesium sulfate, the solvent was evaporated under reduced pressure. The residue was purified by silica gel column chromatography (chloroform:methanol=9:1) to give the desired 1-(β-D-glucopyranosyl)-4-chloro-3-(5-(4-ethoxycarbonylphenyl)-2-thienylmethyl)benzene (39 mg) as pale yellow foam. APCI-Mass m/Z 536/538 (M+NH₄).

Example 192

1-(β-D-glucopyranosyl)-3-(5-(4-carboxyphenyl)-2-thienylmethyl)-4-chlorobenzene 1-(2,3,4,6-Tetra-O-acetyl-β-D-glucopyranosyl)-4-chloro-3-(5-(4-cyanophenyl)-2-thienylmethyl)benzene (128 mg) obtained in Example 191-(1) was dissolved in acetic acid (2 ml) and added thereto was a concentrated hydrochloric acid aqueous solution (2 ml). The mixture was refluxed for 6.5 hours. To the mixture was added a 10% aqueous sodium hydroxide solution at 0° C., and the mixture was washed with ethyl acetate. The aqueous layer was acidified by adding concentrated hydrochloric acid, and extracted with a mixture of ethyl acetate and tetrahydrofuran. The extract was dried over magnesium sulfate, and the solvent was evaporated under reduced pressure. The residue was purified by washing with a mixture of ethyl acetate and diethyl ether to give the desired 1-(β-D-glucopyranosyl)-3-(5-(4-carboxyphenyl)-2-thienylmethyl)-4-chlorobenzene (49 mg) as pale brown powder. ESI-Mass m/Z 489/491 (M–H).

Example 193

1-(β-D-glucopyranosyl)-3-(5-(4-carbamoylphenyl)-2-thienylmethyl)-4-chlorobenzene 1-(2,3,4,6-Tetra-O-acetyl-β-D-glucopyranosyl)-4-chloro-3-(5-(4-cyanophenyl)-2-thienylmethyl)benzene (282 mg) obtained in Example 191-(1) was suspended in ethanol (5 ml) and added thereto was a 6N aqueous sodium hydroxide solution (0.37 ml). The mixture was stirred at room temperature for 10 minutes. To the mixture was added a 30% aqueous hydrogen peroxide solution (0.2 ml), and the mixture was stirred at room temperature for 1.5 hours and at 45° C. for 3 hours. To the mixture was added water (20 ml) and the mixture was cooled. The powder was collected by filtration and washed with diethyl ether and dried to give the desired 1-(β-D-glucopyranosyl)-3-(5-(4-carbamoylphenyl)-2-thienylmethyl)-4-chlorobenzene (176 mg) as colorless powder. APCI-Mass m/Z 507/509 (M+NH₄).

Example 194

1-(β-D-glucopyranosyl)-4-chloro-3-(5-(5-fluoropyridin-2-yl)-2-thienylmethyl)benzene

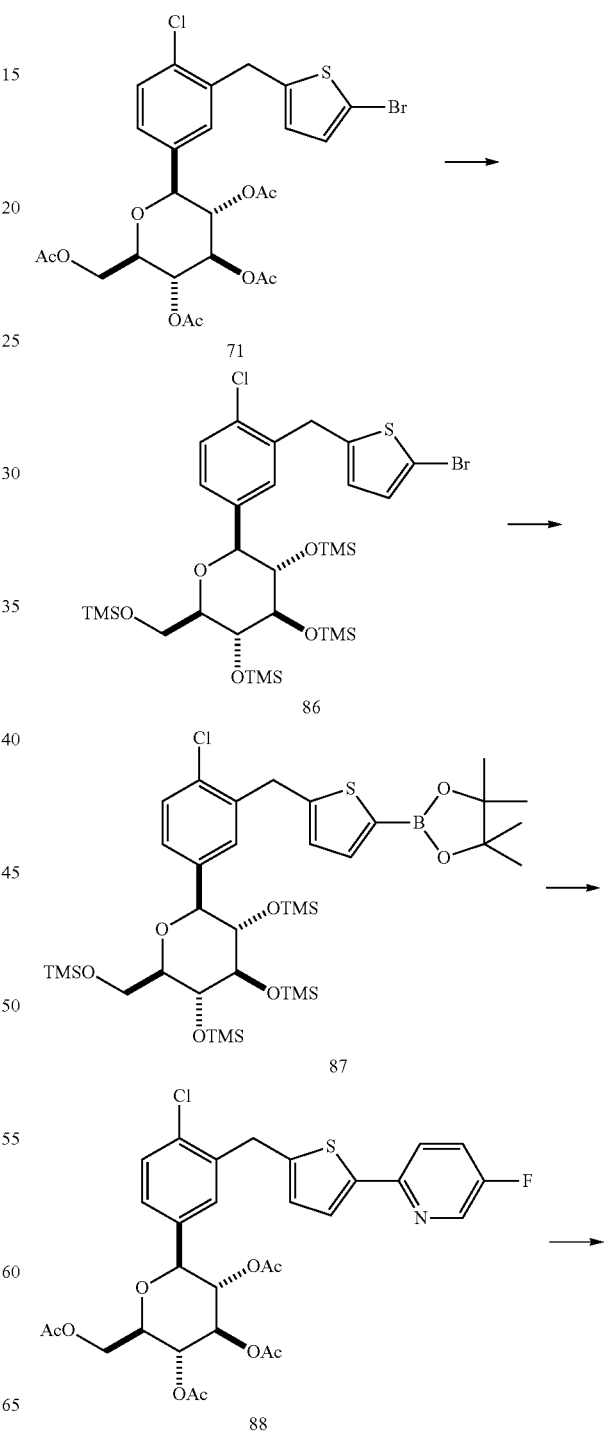

-continued

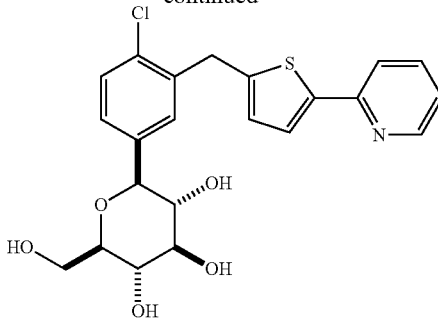

89

In the above scheme, the symbols are defined as above.

(1) The 1-(2,3,4,6-tetra-O-acetyl-β-D-glucopyranosyl)-3-(5-bromo-2-thienylmethyl)-4-chlorobenzene 71 (750 mg) obtained in Example 128-(4) was dissolved in a mixture of methanol (8 ml)tetrahydrofuran (8 ml), and sodium methoxide (28% methanol solution, 1 drop) was added thereto, and the mixture was stirred at room temperature for 2 hours. The solvent was evaporated under reduced pressure. The residue was dissolved in dichloromethane (20 ml), and thereto were added pyridine (0.69 ml) and 4-dimethylaminopyridine (15 mg). The mixture was cooled to 0° C., and thereto was added trimethylsilyl trifluoromethanesulfonate (1.54 ml). The mixture was stirred at room temperature for 3 days. To the mixture was added water, and the mixture was extracted with diethyl ether. The extract was washed with successively with water, a saturated aqueous ammonium chloride solution and brine, and dried over sodium sulfate. The solvent was evaporated under reduced pressure to give the compound 86 (900 mg) as colorless oil.

(2) A mixed solution of the above compound 86 (900 mg), triisopropoxyborane (252 mg) in tetrahydrofuran (22 ml) was cooled to −78° C. under argon atmosphere. Thereto was added dropwise tert-butyl lithium (1.46 M pentane solution, 0.9 ml), and the mixture was stirred at the same temperature for 1 hour. The mixture was warmed to room temperature, and thereto was added pinacol (2.24 g). The mixture was stirred at the same temperature overnight. The mixture was diluted with ethyl acetate, and washed successively with water and brine. The solvent was evaporated under reduced pressure to give the compound 87, which was used in the subsequent reaction without further purification.

(3) The whole amount of the above compound 87 was dissolved in dimethoxyethane (20 ml), and thereto were added 2-bromo-5-fluoropyridine (460 mg), tetrakis(triphenylphosphine)palladium(0) (150 mg) and cesium fluoride (1.4 g). The mixture was stirred at 80° C. for 3 hours. The mixture was cooled to room temperature, acidified with 2 M aqueous hydrochloric acid solution, and stirred at the same temperature overnight. Under ice-cooling, the reaction mixture was poured into a saturated aqueous sodium hydrogen carbonate solution and the mixture was extracted with ethyl acetate. The extract was washed with brine and dried over sodium sulfate, and the solvent was evaporated under reduced pressure. The residue was passed through silica gel column chromatography (chloroform:methanol=100:0-88:12) to give crude oil, which was dissolved in dichloromethane (20 ml). To the mixture were added acetic anhydride (0.71 ml), pyridine (0.61 ml), and 4-dimethylaminopyridine (13 mg), and the mixture was stirred at room temperature for 1 hour. Then, dichloromethane was evaporated under reduced pressure, and the residue was dissolved in ethyl acetate. The mixture was washed successively with 2 M aqueous hydrochloric acid solution, a saturated aqueous sodium hydrogen carbonate solution, and brine, dried over sodium sulfate. The solvent was evaporated under reduced pressure, and the residue was purified by silica gel column chromatography (hexane:ethyl acetate=1:0-3:2) to give 1-(2,3,4,6-tetra-O-acetyl-β-D-glucopyranosyl)-4-chloro-3-(5-(5-fluoropyridin-2-yl)-2-thienylmethyl)benzene 88 (218 mg) as a colorless solid. APCI-Mass m/Z 634/636 (M+H).

(4) The above 1-(2,3,4,6-tetra-O-acetyl-β-D-glucopyranosyl)-4-chloro-3-(5-(5-fluoropyridin-2-yl)-2-thienylmethyl)benzene 88 was treated in a manner similar to Example 106-(3) to give the desired 1-(β-D-glucopyranosyl)-4-chloro-3-(5-(5-fluoropyridin-2-yl)-2-thienylmethyl)benzene 89 as a colorless solid. APCI-Mass m/Z 466/468 (M+H).

Example 195

1-(β-D-glucopyranosyl)-3-(benzo[b]thiophen-2-ylmethyl)indole

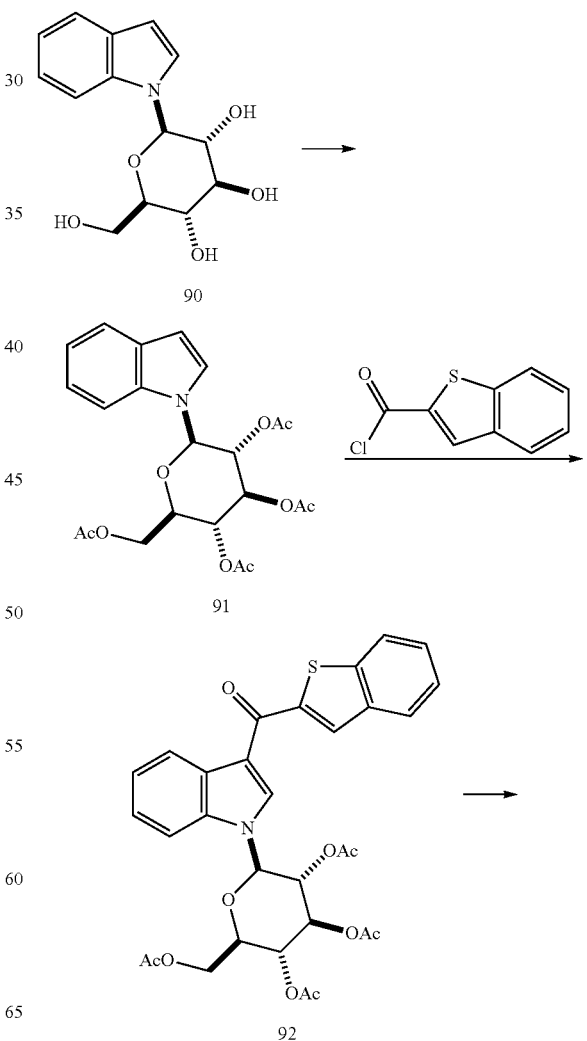

-continued

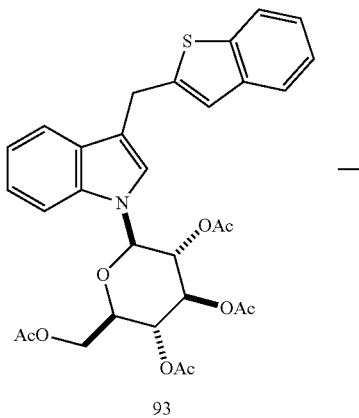

93

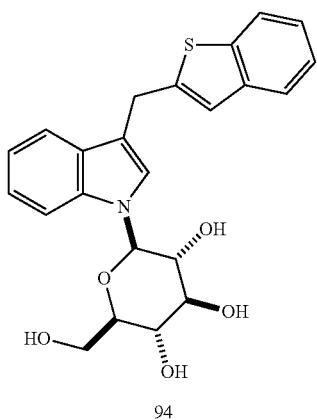

94

In the above scheme, the symbols are defined as above.

(1) 1-(β-D-glucopyranosyl)indole 90 (see *Eur. J. Med. Chem.* (2004) 39, 453-458) was treated in a manner similar to Example 106-(1) to give 1-(2,3,4,6-tetra-O-acetyl-β-D-glucopyranosyl)indole 91 as colorless crystals. APCI-Mass m/Z 465 (M+NH$_4$).

(2) Benzo[b]thiophene-2-carboxylic acid (598 mg) was suspended in dichloromethane (10 ml). Added thereto were oxalyl chloride (0.39 ml) and N,N-dimethylformamide (one drop), and the mixture was stirred at room temperature overnight. The solvent was evaporated under reduced pressure to give a corresponding acid chloride, which was dissolved in dichloroethane (30 ml). To the solution was added 1-(2,3,4,6-tetra-O-acetyl-β-D-glucopyranosyl)indole 91 (1 g) obtained above, and the mixture was cooled to 0° C. Added gradually thereto was aluminum chloride (2.09 g), and subsequently, the mixture was stirred at the same temperature for 30 minutes. The reaction mixture was poured into ice-cold water, and the mixture was extracted with chloroform. The extract was washed successively with water, a saturated aqueous sodium hydrogen carbonate solution and brine, dried over sodium sulfate, and the solvent was evaporated under reduced pressure. The residue was purified by silica gel column chromatography (hexane:ethyl acetate=9:1-5:4) to give Benzo[b]thiophen-2-yl (1-(2,3,4,6-tetra-O-acetyl-β-D-glucopyranosyl)-indol-3-yl) ketone 92 (570 mg) as colorless crystals. APCI-Mass m/Z 608 (M+H).

(3) The above Benzo[b]thiophen-2-yl (1-(2,3,4,6-tetra-Oacetyl-β-D-glucopyranosyl)-indol-3-yl) ketone 92 (440 mg) was dissolved in tetrahydrofuran (6 ml) and ethanol (3 ml). To the solution was added sodium borohydride (137 mg), and the mixture was stirred at room temperature for 60 minutes. The reaction mixture was quenched with cold aqueous HCl solution (0.5 N), and extracted with ethyl acetate. The extract was washed successively with water, a saturated aqueous sodium hydrogen carbonate solution and brine, and dried over sodium sulfate. The solvent was evaporated under reduced pressure. The resultant residue was dissolved in dichloromethane (8 ml) and acetonitrile (4 ml), and the mixture was cooled to 0° C. under argon atmosphere. To the mixture were added triethylsilane (0.58 ml) and boron trifluoride•diethyl ether complex (0.46 ml). After 30 minutes, the mixture was basified with a saturated aqueous sodium hydrogen carbonate solution, and the organic layer was collected, dried over magnesium sulfate, and the solvent was evaporated under reduced pressure. The resultant residue was dissolved in chloroform (20 ml), and to the mixture were added acetic anhydride (0.16 ml), triethylamine (0.2 ml), and 4-dimethylaminopyridine (15 mg), and the mixture was stirred at room temperature for 30 minutes. Then, the solution was washed successively with 10% aqueous hydrochloric acid solution, water, a saturated aqueous sodium hydrogen carbonate solution, and brine, and dried over magnesium sulfate. The solvent was evaporated under reduced pressure, and the resultant residue was purified by silica gel column chromatography (hexane:ethyl acetate=8:2-6:4) to give 1-(2,3,4,6-tetra-O-acetyl-β-D-glucopyranosyl)-3-(benzo-[b]thiophen-2-ylmethyl)indole 93 (290 mg). APCI-Mass m/Z 611 (M+NH$_4$).

(4) The above 1-(2,3,4,6-tetra-O-acetyl-β-D-glucopyranosyl)-3-(benzo[b]thiophen-2-ylmethyl)indole 93 (336 mg) was treated in a manner similar to Example 106-(3) to give the desired 1-(β-D-glucopyranosyl)-3-(benzo[b]thiophen-2-ylmethyl)indole 94 (208 mg) as a colorless powder. APCI-Mass m/Z 443 (M+NH$_4$).

Example 196

1-(β-D-glucopyranosyl)-3-(5-(3-cyanophenyl)-2-thienylmethyl)-4-fluoronaphthalene (1) The 1-(β-D-glucopyranosyl)-3-(5-chloro-2-thienylmethyl)-4-fluoronaphthalene obtained in Example 137 was treated in a manner similar to Example 106-(1) to give 1-(2,3,4,6-tetra-O-acetyl-β-D-glucopyranosyl)-3-(5-chloro-2-thienylmethyl)-4-fluoronaphthalene. APCI-Mass m/Z 624/626 (M+NH$_4$).

(2) The above 1-(2,3,4,6-tetra-O-acetyl-β-D-glucopyranosyl)-3-(5-chloro-2-thienylmethyl)-4-fluoronaphthalene was treated in a manner similar to Example 158-(1) to give 1-(2,3,4,6-tetra-O-acetyl-β-D-glucopyranosyl)-3-(2-thienylmethyl)-4-fluoronaphthalene. APCI-Mass m/Z 590 (M+NH$_4$).

(3) The above 1-(2,3,4,6-tetra-O-acetyl-β-D-glucopyranosyl)-3-(2-thienylmethyl)-4-fluoronaphthalene was treated in a manner similar to Example 159-(1) to give 1-(2,3,4,6-tetra-O-acetyl-β-D-glucopyranosyl)-3-(5-bromo-2-thienylmethyl)-4-fluoronaphthalene. APCI-Mass m/Z 668/670 (M+NH$_4$).

(4) The above 1-(2,3,4,6-tetra-O-acetyl-β-D-glucopyranosyl)-3-(5-bromo-2-thienylmethyl)-4-fluoronaphthalene and 3-cyanophenylboronic acid were treated in a manner similar to Example 168 to give 1-(β-D-glucopyranosyl)-3-(5-(3-cyanophenyl)-2-thienylmethyl)-4-fluoronaphthalene. APCI-Mass m/Z 523 (M+NH$_4$).

Example 197

1-(β-D-glucopyranosyl)-3-(5-(4-aminophenyl)-2-thienylmethyl)-4-chlorobenzene (1) 1-(2,3,4,6-Tetra-O-acetyl-β-D-glucopyranosyl)-3-(5-bromo-2-thienylmethyl)-4-chlorobenzene obtained in Example 128-(4) and 4-(4,4,5,5-tetramethyl-1,3-dioxaborolan-2-yl)aniline were treated in a manner similar to Example 168-(1) to give 1-(2,3,4,6-tetra-O-acetyl-β-D-glucopyranosyl)-3-(5-(4-aminophenyl)-2-thienylmethyl)-4-chlorobenzene as pale yellow powder. APCI-Mass m/Z 630/632 (M+H).

(2) The above 1-(2,3,4,6-tetra-O-acetyl-β-D-glucopyranosyl)-3-(5-(4-aminophenyl)-2-thienylmethyl)-4-chlorobenzene was treated in a manner similar to Example 106-(3) to give the desired 1-(β-D-glucopyranosyl)-3-(5-(4-aminophenyl)-2-thienylmethyl)-4-chlorobenzene as pale yellow foam. APCI-Mass m/Z 479/481 (M+NH$_4$).

Example 198

1-(β-D-glucopyranosyl)-4-chloro-3-(5-(4-methylcarbamoylphenyl)-2-thienylmethyl)benzene (1) 1-(β-D-Glucopyranosyl)-3-(5-(4-carboxyphenyl)-2-thienylmethyl)-4-chlorobenzene (637 mg) obtained in Example 192 was dissolved in a mixture of dichloromethane (10 ml)tetrahydrofuran (5 ml) and added thereto were acetic anhydride (1.22 ml), pyridine (1.05 ml) and 4-dimethylaminopyridine (32 mg). The mixture was stirred at room temperature overnight. The solvents were evaporated under reduced pressure and the residue was dissolved in ethyl acetate. The organic layer was washed with 2N hydrochloric acid aqueous solution and successively washed with brine. After drying over magnesium sulfate, the solvent was evaporated under reduced pressure. The residue was purified by silica gel column chromatography (chloroform:methanol=100:1-50:1) to give 1-(2,3,4,6-tetra-O-acetyl-β-D-glucopyranosyl)-3-(5-(4-carboxyphenyl)-2-thienylmethyl)-4-chlorobenzene (687 mg) as pale yellow powder. ESI-Mass m/Z 657/659 (M−H).

(2) The above 1-(2,3,4,6-tetra-O-acetyl-β-D-glucopyranosyl)-3-(5-(4-carboxyphenyl)-2-thienylmethyl)-4-chlorobenzene (198 mg) was dissolved in dichloromethane (5 ml) and added thereto were oxalyl chloride (1 ml) and N,N-dimethylformamide (one drop), and the mixture was stirred at room temperature for 3.5 hours. The solvent was evaporated under reduced pressure to give a corresponding acid chloride, which was suspended in tetrahydrofuran (4 ml), without further purification. To the suspension was added a 2.0 M solution of methylamine in tetrahydrofuran (1.5 ml), and the mixture was stirred at room temperature for 2 hours. The solvent was evaporated under reduced pressure, and the residue was purified by silica gel column chromatography (chloroform:methanol=100:1) to give 1-(2,3,4,6-tetra-O-acetyl-β-D-glucopyranosyl)-4-chloro-3-(5-(4-methylcarbamoylphenyl)-2-thienylmethyl)benzene (218 mg) as pale yellow powder. APCI-Mass m/Z 689/691 (M+NH$_4$).

(3) The above 1-(2,3,4,6-tetra-O-acetyl-β-D-glucopyranosyl)-4-chloro-3-(5-(4-methylcarbamoylphenyl)-2-thienylmethyl)benzene was treated in a manner similar to Example 106-(3) to give the desired 1-(β-D-glucopyranosyl)-4-chloro-3-(5-(4-methylcarbamoylphenyl)-2-thienylmethyl)benzene as colorless powder. APCI-Mass m/Z 521/523 (M+NH$_4$).

Example 199

1-(β-D-glucopyranosyl)-4-chloro-3-(5-(4-methylsulfonylaminophenyl)-2-thienylmethyl)benzene (1) 1-(2,3,4,6-Tetra-O-acetyl-β-D-glucopyranosyl)-3-(5-(4-aminophenyl)-2-thienylmethyl)-4-chlorobenzene (126 mg) obtained in Example 197-(1) was dissolved in dichloromethane (3 ml) and added thereto were methanesulfonyl chloride (48 mg) and pyridine (48 mg). The mixture was stirred at room temperature for 3.5 hours. To the mixture was added 2N hydrochloric acid aqueous solution at 0° C. and extracted with ethyl acetate. The organic layer was washed with water, aqueous sodium hydrogen carbonate solution and successively washed with brine. After drying over magnesium sulfate, the solvent was evaporated under reduced pressure. The residue was purified by silica gel column chromatography (hexane:ethyl acetate=1:1-1:2) to give 1-(2,3,4,6-tetra-O-acetyl-β-Dglucopyranosyl)-4-chloro-3-(5-(4-methylsulfonylaminophenyl)-2-thienylmethyl)benzene (154 mg) as yellow caramel. ESI-Mass m/Z 706/708 (M−H).

(2) The above 1-(2,3,4,6-tetra-O-acetyl-β-D-glucopyranosyl)-4-chloro-3-(5-(4-methylsulfonylaminophenyl)-2-thienylmethyl)benzene was treated in a manner similar to Example 106-(3) to give the desired 1-(β-D-glucopyranosyl)-4-chloro-3-(5-(4-methylsulfonylaminophenyl)-2-thienylmethyl)benzene as yellow foam. ESI-Mass m/Z 538/540 (M−H).

Example 200

1-(β-D-glucopyranosyl)-3-(5-(4-acetylaminophenyl)-2-thienylmethyl)-4-chlorobenzene 1-(2,3,4,6-Tetra-O-acetyl-β-D-glucopyranosyl)-3-(5-(4-aminophenyl)-2-thienylmethyl)-4-chlorobenzene (126 mg) obtained in Example 197-(1) was treated in a manner similar to Example 106-(1) and (3) to give the target compound as colorless powder. APCI-Mass m/Z 521/523 (M+NH$_4$).

The compounds shown in Table 5 below were prepared in a manner similar to one of the above Examples from the corresponding starting materials. The numbers shown in a column of "preparation method" in the Table indicates the Example number, according to which the preparation was carried out.

TABLE 5
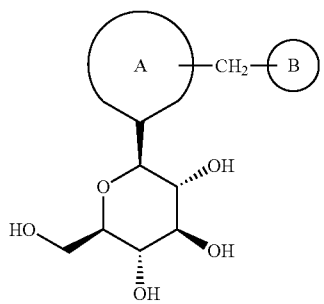
| Examples | A | B | Preparation Method | APCI-Mass (m/Z) |
|---|---|---|---|---|
| 201 | 2-Me, 5- | 5-(3,5-difluorophenyl)thiophen-2-yl | 177 | 480 (M + NH₄) |
| 202 | 2-Cl, 5- | 5-(3,4-difluorophenyl)thiophen-2-yl | 168 | 500/502 (M + NH₄) |
| 203 | 2-Me, 5- | 5-(3-chloro-4-fluorophenyl)thiophen-2-yl | 177 | 496/498 (M + NH₄) |
| 204 | 2-Cl, 5- | 5-(thiazol-5-yl)thiophen-2-yl | 128 | 454/456 (M + H) |
| 205 | 2-Cl, 5- | 5-(3,5-difluorophenyl)thiophen-2-yl | 168 | 500/502 (M + NH₄) |
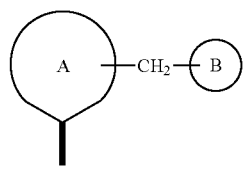
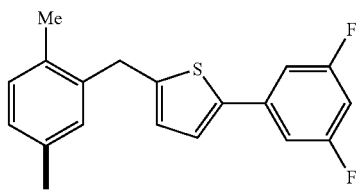
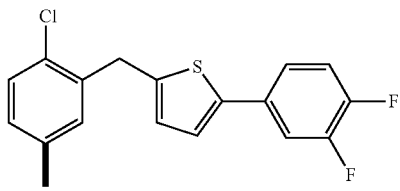
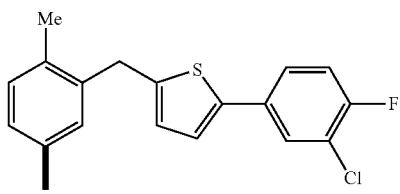
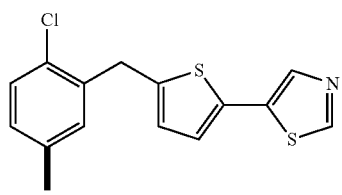
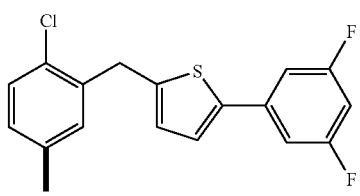

TABLE 5-continued
| Examples | A—CH₂—B | Preparation Method | APCI-Mass (m/Z) |
|---|---|---|---|
| 206 | 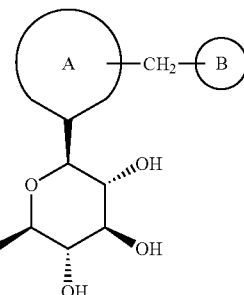 | 168 | 516/518 (M + NH₄) |
| 207 | 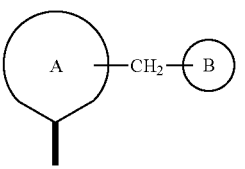 | 128 | 454/456 (M + H) |
| 208 | 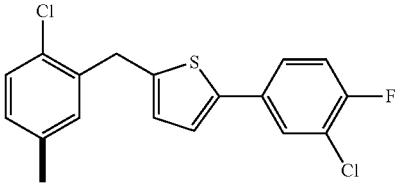 | 164 | 458 (M + H) |
| 209 | 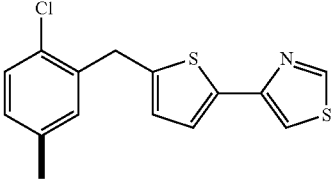 | 177 | 458 (M + H) |
| 210 | 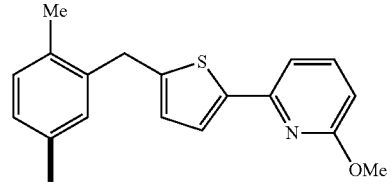 | 164 | 434 (M + H) |

TABLE 5-continued
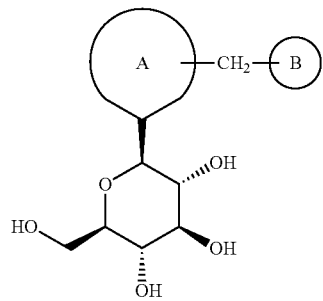
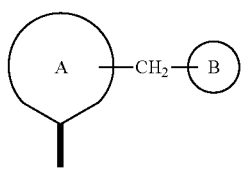
| Examples | | Preparation Method | APCI-Mass (m/Z) |
|---|---|---|---|
| 211 | Me, thiophene-thiophene | 177 | 450 (M + NH$_4$) |
| 212 | Me, thiophene-phenyl-OEt | 177 | 488 (M + NH$_4$) |
| 213 | Cl, benzothiophene-OEt | 1 | 482/484 (M + NH$_4$) |
| 214 | Cl, thiophene-pyrazole | 2 | 437/439 (M + H) |
| 215 | Cl, thiophene-phenyl-F-CN | 183 | 507/509 (M + NH$_4$) |

TABLE 5-continued
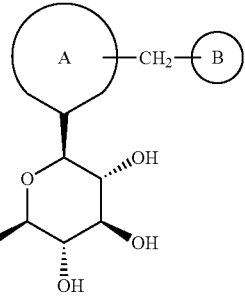
| Examples | A—CH2—B | Preparation Method | APCI-Mass (m/Z) |
|---|---|---|---|
| 216 | 2-Cl, 5-(—) benzyl — thiophene — 2-fluoropyridin-4-yl | 168 | 466/468 (M + H) |
| 217 | 2-Me, 5-(—) benzyl — thiophene — 2-fluoropyridin-4-yl | 177 | 446 (M + H) |
| 218 | 2-Me, 5-(—) benzyl — thiophene — thiazolyl | 164 | 434 (M + H) |
| 219 | 2-Me, 5-(—) benzyl — thiophene — 3-fluoro-4-cyanophenyl | 185 | 487 (M + NH4) |
| 220 | 2-Me, 5-(—) benzyl — thiophene — 4-fluoro-3-(CHF2)phenyl | 176 | 512 (M + NH4) |

TABLE 5-continued
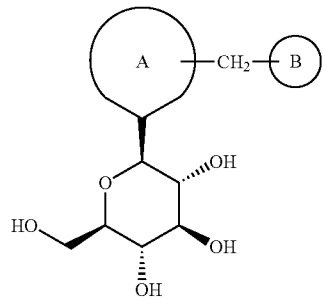
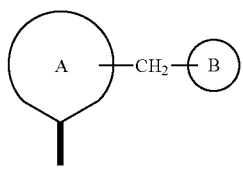
| Examples | A | Preparation Method | APCI-Mass (m/Z) |
|---|---|---|---|
| 221 | (2-Cl, 5-I phenyl)-CH2-[5-(3-OCHF2-phenyl)thiophen-2-yl] | 168 | 530/532 (M + NH4) |
| 222 | (2-Me, 5-I phenyl)-CH2-[5-(3-OCHF2-phenyl)thiophen-2-yl] | 177 | 510 (M + NH4) |
| 223 | (2-Cl, 5-I phenyl)-CH2-[6-OCHF2-benzothiophen-2-yl] | 2 | 504/506 (M + NH4) |
| 224 | (2-Me, 5-I phenyl)-CH2-[6-OCHF2-benzothiophen-2-yl] | 2 | 484 (M + NH4) |
| 225 | (2-Me, 5-I phenyl)-CH2-[5-(6-CN-pyridin-2-yl)thiophen-2-yl] | 186 | 470 (M + NH4) |

TABLE 5-continued
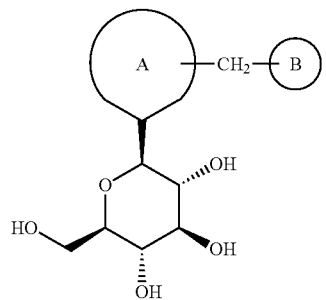
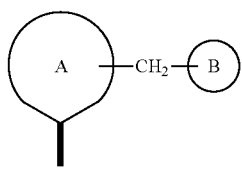
| Examples | | Preparation Method | APCI-Mass (m/Z) |
|---|---|---|---|
| 226 | (2-Cl, 5- benzyl-thiophene-pyridine-CN) | 187 | 490/492 (M + NH₄) |
| 227 | (2-Me, 5- benzyl-thiophene-pyrazole) | 2 | 417 (M + H) |
| 228 | (2-Me, 5- benzyl-benzothiophene-OEt) | 1 | 462 (M + NH₄) |
| 229 | (2-Me, 5- benzyl-benzothiophene-OMe) | 1 | 448 (M + NH₄) |
| 230 | (2-Me, 5- benzyl-benzothiophene-OCH₂CH₂F) | 1 | 480 (M + NH₄) |

TABLE 5-continued
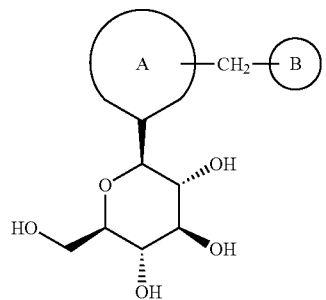
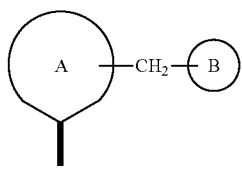
| Examples | | Preparation Method | APCI-Mass (m/Z) |
|---|---|---|---|
| 231 |  | 1 | 462 (M + NH$_4$) |
| 232 | 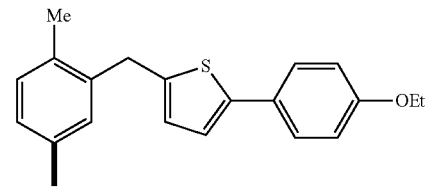 | 177 | 488 (M + NH$_4$) |
| 233 | 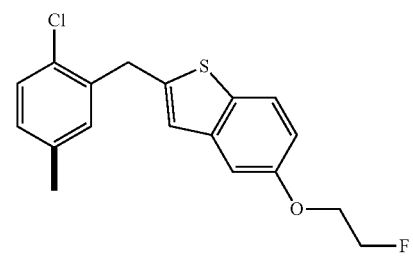 | 1 | 500/502 (M + NH$_4$) |
| 234 | 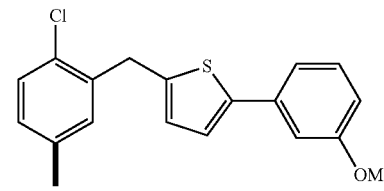 | 168 | 494/496 (M + NH$_4$) |
| 235 | 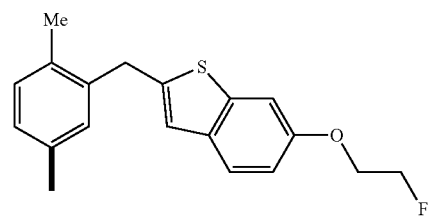 | 1 | 480 (M + NH$_4$) |

TABLE 5-continued
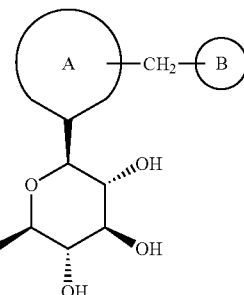
| Examples | A—CH₂—B | Preparation Method | APCI-Mass (m/Z) |
|---|---|---|---|
| 236 | 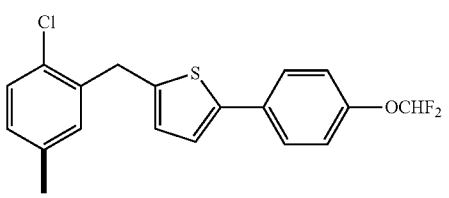 | 168 | 530/532 (M + NH₄) |
| 237 | 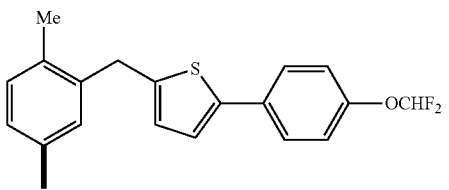 | 177 | 510 (M + NH₄) |
| 238 | 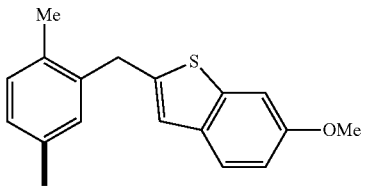 | 1 | 448 (M + NH₄) |
| 239 | 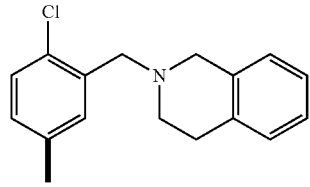 | 184 | 420/422 (M + H) |
| 240 | 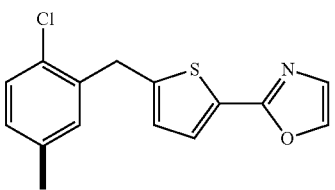 | 128 | 438/440 (M + H) |

TABLE 5-continued
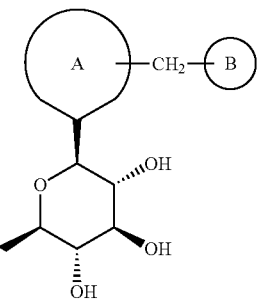
| Examples | A—CH₂—B | Preparation Method | APCI-Mass (m/Z) |
|---|---|---|---|
| 241 | 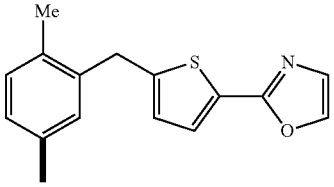 | 164 | 418 (M + H) |
| 242 | 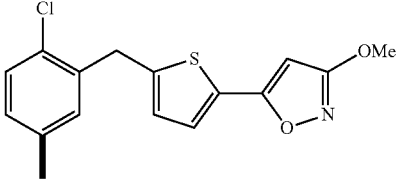 | 128 | 469/471 (M + NH₄) |
| 243 | 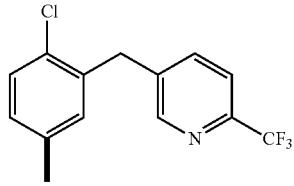 | 1 | 434/436 (M + H) |
| 244 | 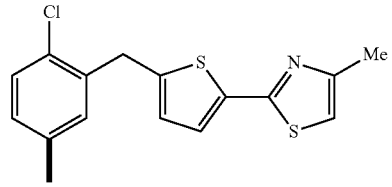 | 128 | 468/470 (M + H) |
| 245 | 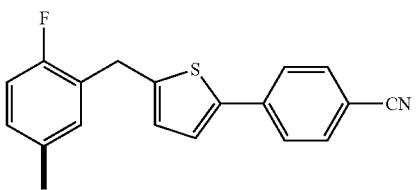 | 189 | 473 (M + NH₄) |

TABLE 5-continued
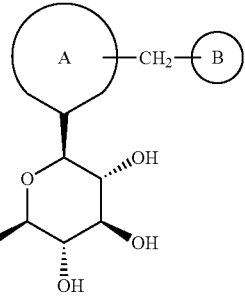
| Examples | | Preparation Method | APCI-Mass (m/Z) |
|---|---|---|---|
| 246 | 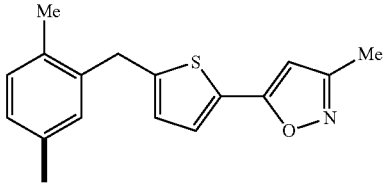 | 164 | 449 (M + NH$_4$) |
| 247 | 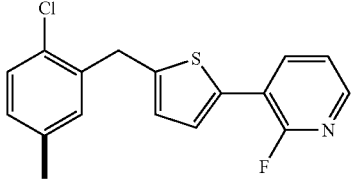 | 168 | 483/485 (M + NH$_4$) |
| 248 | 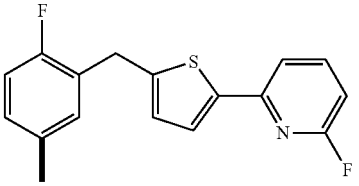 | 189 | 467 (M + NH$_4$) |
| 249 | 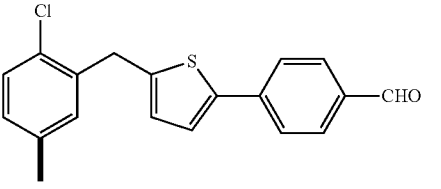 | 168 | 492/494 (M + NH$_4$) |
| 250 | 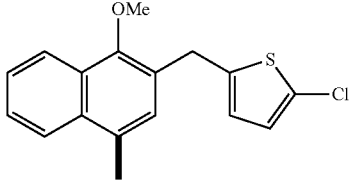 | 1 | 468/470 (M + NH$_4$) |

TABLE 5-continued
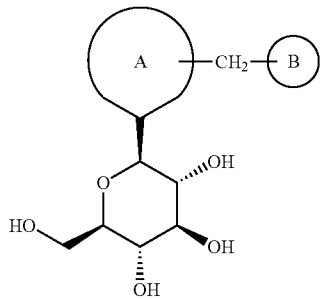
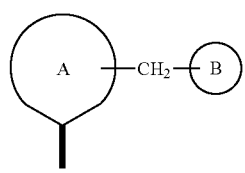
| Examples | | Preparation Method | APCI-Mass (m/Z) |
|---|---|---|---|
| 251 | 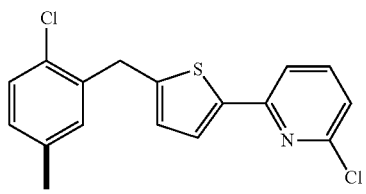 | 168 | 499/501 (M + NH₄) |
| 252 | 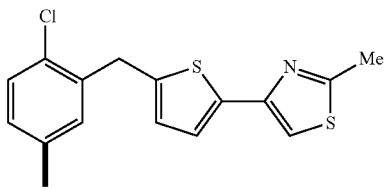 | 128 | 468/470 (M + H) |
| 253 | 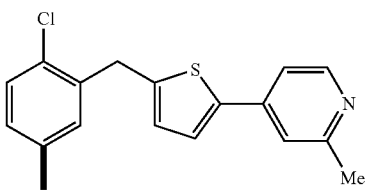 | 168 | 462/464 (M + H) |
| 254 | 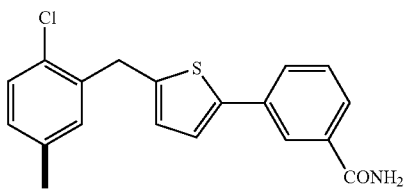 | 193 | 507/509 (M + NH₄) |
| 255 | 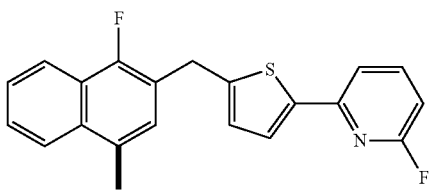 | 196 | 517 (M + NH₄) |

TABLE 5-continued
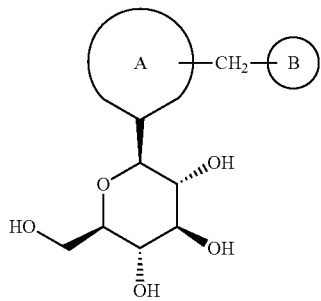
| Examples | | Preparation Method | APCI-Mass (m/Z) |
|---|---|---|---|
| 256 | 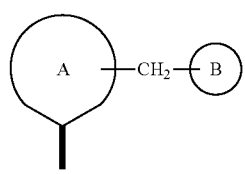 | 1 | 472/474 (M + H) |
| 257 | 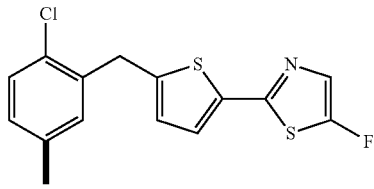 | 168 | 509/511 (M + NH₄) |
| 258 | 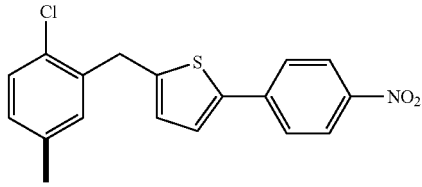 | 168 | 490/492 (M + H) |
| 259 | 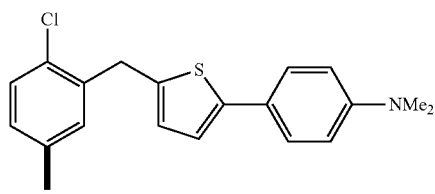 | 198 | 535/537 (M + NH₄) |
| 260 | 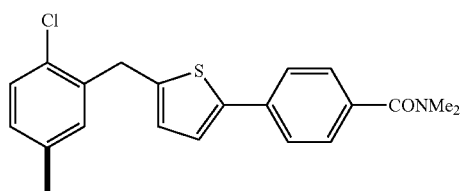 | 198 | 549/551 (M + NH₄) |

The compounds shown in Table 6 below were prepared in a manner similar to Example 195 from the corresponding starting materials.

TABLE 6

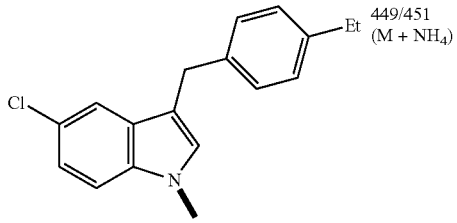

| Examples | | APCI-Mass (m/Z) |
|---|---|---|
| 261 | 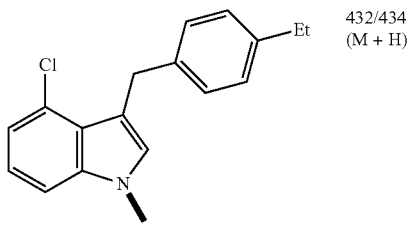 | 449/451 (M + NH₄) |
| 262 | | 432/434 (M + H) |
| 263 | | 449/451 (M + NH₄) |

Example 264

1-(β-D-glucopyranosyl)-4-chloro-3-(5-(4-hydroxymethylphenyl)-2-thienylmethyl)benzene 1-(β-D-Glucopyranosyl)-4-chloro-3-(5-(4-formylphenyl)-2-thienylmethyl)benzene (84 mg) obtained in Example 249 was dissolved in a mixture of ethanol (2 ml)-tetrahydrofuran (2 ml) and added thereto was sodium borohydride (7 mg). The mixture was stirred at room temperature for 1 hour. The mixture was quenched by 2N hydrochloric acid aqueous solution (3 drops) at 0° C., and the solvents were evaporated under reduced pressure. The residue was purified by silica gel column chromatography (chloroform:methanol=9:1) to give the desired 1-(β-D-glucopyranosyl)-4-chloro-3-(5-(4-hydroxymethylphenyl)-2-thienylmethyl)benzene (82 mg) as colorless foam. APCI-Mass m/Z 494/496 (M+NH₄).

Example 265

1-(β-D-glucopyranosyl)-3-(5-phenyl-2-thienylmethyl)-4-methoxynaphthalene (1) 1-(β-D-Glucopyranosyl)-3-(5-chloro-2-thienyl methyl)-4-methoxynaphthalene obtained in Example 250 was treated in a manner similar to Example 106-(1) to give 1-(2,3,4,6-tetra-O-acetyl-β-D-glucopyranosyl)-3-(5-chloro-2-thienylmethyl)-4-methoxynaphthalene. APCI-Mass m/Z 636/638 (M+NH₄).

(2) The above 1-(2,3,4,6-tetra-O-acetyl-β-D-glucopyranosyl)-3-(5-chloro-2-thienylmethyl)-4-methoxynaphthalene was treated in a manner similar to Example 158-(1) to give 1-(2,3,4,6-tetra-O-acetyl-β-D-glucopyranosyl)-3-(2-thienylmethyl)-4-methoxynaphthalene. APCI-Mass m/Z 602 (M+NH₄).

(3) The above 1-(2,3,4,6-tetra-O-acetyl-β-D-glucopyranosyl)-3-(2-thienylmethyl)-4-methoxynaphthalene was treated in a manner similar to Example 159-(1) to give 1-(2,3,4,6-tetra-O-acetyl-β-D-glucopyranosyl)-3-(5-bromo-2-thienylmethyl)-4-methoxynaphthalene. APCI-Mass m/Z 680/682 (M+NH₄).

(4) The above 1-(2,3,4,6-tetra-O-acetyl-β-D-glucopyranosyl)-3-(5-bromo-2-thienylmethyl)-4-methoxynaphthalene and phenylboronic acid were treated in a manner similar to Example 168 to give the desired 1-(β-D-glucopyranosyl)-3-(5-phenyl-2-thienylmethyl)-4-methoxynaphthalene. APCI-Mass m/Z 510 (M+NH₄).

Example 266

1-(β-D-glucopyranosyl)-3-(5-(2-pyrimidinyl)-2-thienylmethyl)-4-methoxynaphthalene 1-(2,3,4,6-tetra-O-acetyl-β-D-glucopyranosyl)-3-(5-bromo-2-thienylmethyl)-4-methoxynaphthalene obtained in Example 265-(3) and 2-tributylstannylpyrimidine were treated in a manner similar to Example 128-(5) and (6) to give 1-(β-D-glucopyranosyl)-3-(5-(2-pyrimidinyl)-2-thienylmethyl)-4-methoxynaphthalene. APCI-Mass m/Z 495 (M+H).

The compounds shown in Table 7 below were prepared in a manner similar to Example 265 from the corresponding starting materials.

TABLE 7

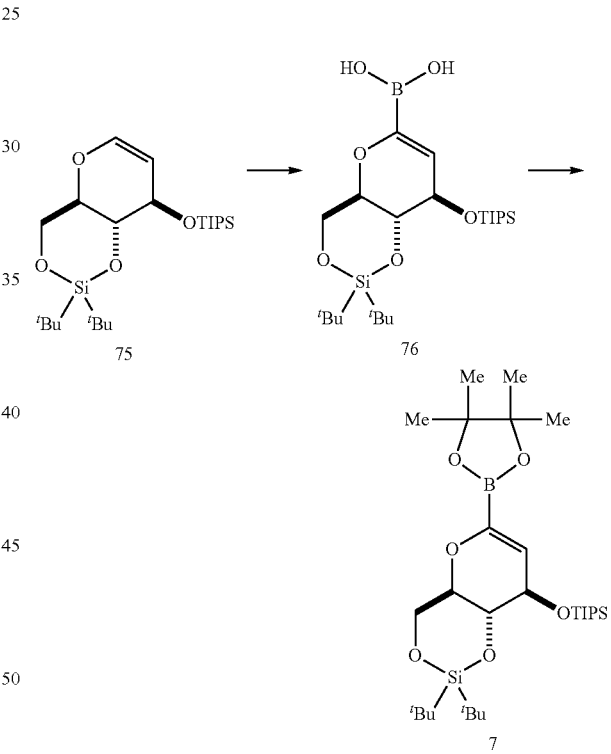

| Examples | A—CH₂—B | APCI-Mass (m/Z) |
|---|---|---|
| 267 | (naphthalene-OMe)—CH₂—(thiophene)—(phenyl-CN) | 535 (M + NH₄) |
| 268 | (naphthalene-OMe)—CH₂—(thiophene)—(pyridine-F) | 529 (M + NH₄) |

Reference Example 1

3-Bromo-1-(5-ethyl-2-thienylmethyl)benzene (1) A solution of 1,3-dibromobenzene (3.7 g) in tetrahydrofuran (25 ml) was cooled to −78° C. under argon atmosphere, and thereto was added dropwise n-butyl lithium (2.44 M hexane solution, 5.55 ml). The reaction mixture was stirred at the same temperature for 10 minutes, and thereto was added dropwise a solution of 5-ethyl-2-thiophenecarboxaldehyde (2.0 g) in tetrahydrofuran (10 ml). The mixture was stirred at the same temperature for 30 minutes, and thereto was added a saturated ammonium chloride solution, and the reaction mixture was warmed to room temperature. The mixture was extracted with ethyl acetate, and the extract was dried over magnesium sulfate, and the solvent was evaporated under reduced pressure. The residue was purified by silica gel column chromatography (hexane:ethyl acetate=97:3-85:15) to give 3-bromophenyl-5-ethyl-2-thienylmethanol (2.97 g) as a pale yellow syrup. APCI-Mass m/Z 279/281 (M+H—H₂O).

(2) The above 3-bromophenyl-5-ethyl-2-thienylmethanol (2.90 g) was dissolved in dichloromethane (38 ml), and the mixture was cooled to −78° C. under argon atmosphere. To the mixture were added triethylsilane (6.18 ml) and boron trifluoride•diethyl ether complex (2.45 ml), and the mixture was gradually warmed to room temperature over a period of one hour. The mixture was basified with a saturated aqueous sodium hydrogen carbonate solution, and the dichloromethane layer was collected, dried over magnesium sulfate, and the solvent was evaporated under reduced pressure. The residue was purified by silica gel column chromatography (hexane) to give the desired 3-bromo-(5-ethyl-2-thienylmethyl)benzene (2.57 g) as a colorless syrup. APCI-Mass m/Z 281/283 (M+H).

Reference Example 2

5-Bromo-1-(4-ethylphenylmethyl)-1H-pyridin-2-one

5-Bromo-1H-pyridin-2-one (1.04 g) and 4-ethylbenzyl bromide (1.43 g) were dissolved in N,N-dimethylformamide (15 ml), and thereto was added potassium carbonate (1.66 g). The mixture was stirred at room temperature overnight, diluted with ethyl acetate, and washed successively with water and brine. The extract was dried over magnesium sulfate, and the solvent was evaporated under reduced pressure. The residue was purified by silica gel column chromatography (hexane:ethyl acetate=10:1-3:1) to give 5-bromo-1-(4-ethylphenylmethyl)-1H-pyridin-2-one (1.58 g) as colorless crystals. APCI-Mass m/Z 292/294 (M+H).

Reference Example 3

In the above scheme, the symbols are as defined above.
(1) A solution of silylated glucal 75 (see Parker et al., Org. Lett. 2000, 2, 497-499) (7.00 g) in tetrahydrofuran (70 ml) was cooled to −78° C. under argon atmosphere. Thereto was added dropwise t-butyl lithium (1.45 M pentane solution, 49.0 ml) over a period of 10 minutes. The mixture was stirred at the same temperature for 15 minutes, and then warmed to room temperature, and further stirred for 30 minutes. The mixture was cooled again to −78° C., and thereto was added trimethyl borate (8.90 ml) in one portion. After 15 minutes, the reaction solution was warmed to room temperature over a period of one hour, and thereto was added water (100 ml) at 0° C. The mixture was stirred for 30 minutes, and extracted twice with diethyl ether. The extract was washed with water, and then washed with brine. The resultant was dried over magnesium sulfate, and the solvent was evaporated under reduced pressure to give the compound 76, which was used in the subsequent reaction without further purification.

(2) The whole amount of the above compound 76 was dissolved in toluene (65 ml), and thereto was added pinacol (2.24 g). The mixture was stirred at room temperature under argon atmosphere for 17 hours. The reaction solution was poured into water, and the mixture was extracted with ethyl acetate, and the extract was washed with brine, dried over magnesium sulfate. The solvent was evaporated under reduced pressure to give the compound 7 (10.4 g) as a yellow semisolid, which was used in the subsequent reaction without further purification. APCI-Mass m/Z 569 (M+H).

Reference Example 4

5-Bromo-2-methylbenzaldehyde (1) Methyl 5-bromo-2-methylbenzoate (see Japanese Unexamined Patent Publication No. 9-263549) (16.12 g) was dissolved in methanol (100 ml), and thereto was added 10% aqueous sodium hydroxide solution (50 ml). The mixture was stirred at 50° C. for 40 minutes. Under ice-cooling, the mixture was adjusted to pH 1 by addition of 10% aqueous hydrochloric acid solution, and diluted with water. Precipitated powder was collected by filtration, and dried to give 5-bromo-2-methylbenzoic acid (14.1 g). ESI-Mass m/Z 213/215 (M−H).

(2) The above 5-bromo-2-methylbenzoic acid (10.0 g) was suspended in dichloromethane (100 ml), and thereto were added oxalyl chloride (8.1 ml) and N,N-dimethylformamide (2 drops). The mixture was stirred at room temperature for 4 hours. The solvent was evaporated under reduced pressure to give 5-bromo-2-methylbenzoyl chloride. This benzoyl chloride was dissolved in dichloromethane (200 ml), and thereto was added N,O-dimethylhydroxylamine hydrochloride (12.3 g). To the mixture was added dropwise triethylamine (20 ml) at 0° C., and the mixture was stirred at room temperature overnight. The solvent was evaporated under reduced pressure, and the residue was extracted with ethyl acetate, and washed successively with water, 10% aqueous hydrochloric acid solution, water, a saturated aqueous sodium hydrogen carbonate solution, and brine. The extract was dried over sodium sulfate, and the solvent was evaporated under reduced pressure to give N-methoxy-N-methyl-5-bromo-2-methylbenzamide (12.25 g) as oil. APCI-Mass m/Z 258/260 (M+H).

(3) A solution of the above N-methoxy-N-methyl-5-bromo-2-methylbenzamide (12.2 g) in tetrahydrofuran (100 ml) was cooled to −78° C. under argon atmosphere. To the mixture was added dropwise diisobutyl aluminum hydride (1.0 M toluene solution, 75 ml), and the mixture was stirred at the same temperature for one hour. 10% aqueous hydrochloric acid solution (50 ml) was added thereto, and the mixture was warmed to room temperature. The mixture was extracted with ethyl acetate twice, and washed successively with a saturated aqueous sodium hydrogen carbonate solution and brine. The extract was dried over magnesium sulfate, and the solvent was evaporated under reduced pressure. The residue was solidified to give 5-bromo-2-methylbenzaldehyde (8.73 g). APCI-Mass m/Z 213/215 (M+H+MeOH—H$_2$O).

Reference Example 5

5-Bromo-2-chloro-1-(5-ethyl-2-thienylmethyl)benzene (1) 5-Bromo-2-chlorobenzoic acid (5.00 g) was suspended in dichloromethane (10 ml), and thereto were added oxalyl chloride (2.2 ml) and N,N-dimethylformamide (2 drops). The mixture was stirred at room temperature for 6 hours. The solvent was evaporated under reduced pressure to give 5-bromo-2-chlorobenzoyl chloride. This compound and 2-ethylthiophene (2.38 g) were dissolved in dichloromethane (20 ml), and thereto was added aluminum chloride (3.11 g) at 0° C. The mixture was stirred at the same temperature for one hour. The reaction mixture was poured into a cold 10% aqueous hydrochloric acid solution, and the mixture was extracted with ethyl acetate. The extract was washed successively with 10% aqueous hydrochloric acid solution, water, a saturated aqueous sodium hydrogen carbonate solution, and brine, and dried over magnesium sulfate. The solvent was evaporated under reduced pressure, the residue was purified by silica gel column chromatography (hexane:ethyl acetate=100:1) to give 5-bromo-2-chlorophenyl 5-ethyl-2-thienyl ketone (5.29 g) as an oil. APCI-Mass m/Z 329/331 (M+H).

(2) A solution of the above 5-bromo-2-chlorophenyl 5-ethyl-2-thienyl ketone (5.29 g) in dichloromethane (50 ml)acetonitrile (50 ml) was cooled under ice-cooling, and thereto were added dropwise triethylsilane (7.69 ml) and boron trifluoride•diethyl ether complex (6.1 ml). Subsequently, the mixture was stirred at room temperature for 3.5 hours, and was cooled again under ice-cooling. To the mixture was added a saturated aqueous sodium hydrogen carbonate solution, and the mixture was extracted with chloroform, washed with brine, and dried over magnesium sulfate. The solvent was evaporated under reduced pressure, and the residue was purified by silica gel column chromatography (hexane) to give 5-bromo-2-chloro-1-(5-ethyl-2-thienylmethyl)benzene (4.52 g) as a colorless liquid.

Reference Example 6

3-Bromo-1-(5-n-propyl-2-thienylmethyl)benzene

3-Bromobenzoic acid and 2-n-propylthiophene were used and treated in a manner similar to Reference Example 5 to give the target compound.

Reference Example 7

5-Bromo-(5-ethyl-2-thienylmethyl)-2-methoxybenzene (1) A solution of 2-ethylthiophene (3.00 g) in tetrahydrofuran (36 ml) was cooled to 0° C. under argon atmosphere, and thereto was added dropwise n-butyl lithium (1.56 M hexane solution, 17.1 ml). The mixture was stirred at the same temperature for 30 minutes, and cooled to −78° C., and thereto was added dropwise a suspension of 5-bromo-2-methoxybenzaldehyde (5.74 g) in tetrahydrofuran (60 ml). The mixture was stirred at the same temperature for 2 hours, warmed to 0° C., and thereto was added a saturated aqueous ammonium chloride solution. The mixture was extracted with ethyl acetate, and the extract was washed with brine, and dried over sodium sulfate. The solvent was evaporated under reduced pressure. The residue was purified by silica gel column chromatography (hexane:ethyl acetate=100:0-85:15) to give 5-bromo-2-methoxyphenyl-5-ethyl-2-thienylmethanol (5.99 g) as a pale yellow syrup. APCI-Mass m/Z 309/311 (M+H—H$_2$O).

(2) The above 5-bromo-2-methoxyphenyl-5-ethyl-2-thienylmethanol was treated in a manner similar to Reference Example 1-(2) to give 5-bromo-(5-ethyl-2-thienylmethyl)-2-methoxybenzene as oil. APCI-Mass m/Z 311/313 (M+H).

Reference Example 8

3-Bromo-1-(5-ethyl-2-thienylmethyl)-4-methoxybenzene

2-Ethylthiophene and 3-bromo-4-methoxybenzaldehyde were used and treated in a manner similar to Reference Example 7 to give the target compound.

Reference Example 9

3-Bromo-1-(4-n-propyl-2-thienylmethyl)benzene (1) 3-n-Propylthiophene and 3-bromobenzaldehyde were used and treated in a manner similar to Reference Example 7-(1) to give 3-bromophenyl-4-n-propyl-2-thienyl methanol. APCI-Mass m/Z 293/295 (M+H—$H_2O$).
(2) A solution of the above 3-bromophenyl-4-n-propyl-2-thienyl methanol (2.4 g) in acetonitrile (10 ml) was added dropwise to a mixed solution of chlorotrimethylsilane (4.54 ml) and sodium iodide (5.36 g) in acetonitrile (10 ml) at 0° C., over a period of 2 hours. The mixture was further stirred at room temperature for 5 minutes, and cooled again to 0° C. An aqueous solution (10 ml) of sodium hydroxide (1.0 g) was added thereto, and the mixture was stirred at 0° C. for 0.5 hours. The mixture was extracted with ethyl acetate, washed successively with an aqueous sodium thiosulfate solution, water and brine, and dried over sodium sulfate. The solvent was evaporated under reduced pressure, and the residue was purified by silica gel column chromatography (hexane) to give 3-bromo-1-(4-n-propyl-2-thienyl)benzene (1.97 g) as colorless oil.

Reference Example 10

5-Bromo-2-chloro-1-(5-n-propyl-2-thienylmethyl)benzene

5-Bromo-2-chlorobenzoic acid and 2-n-propylthiophene were used and treated in a manner similar to Reference Example 5 to give the target compound.

Reference Example 11

5-Bromo-2-methoxy-1-(5-n-propyl-2-thienylmethyl)benzene 2-n-Propylthiophene and 5-bromo-2-methoxybenzaldehyde were used and treated in a manner similar to Reference Example 7 to give the target compound. APCI-Mass m/Z 325/327 (M+H).

Reference Example 12

3-Bromo-1-(4-ethyl-2-thienylmethyl)benzene

3-Ethylthiophene and 3-bromobenzaldehyde were used and treated in a manner similar to Reference Example 9 to give the target compound. APCI-Mass m/Z 281/283 (M+H).

Reference Example 13

3-Bromo-1-(4-chloro-5-ethyl-2-thienylmethyl)benzene (1) To a solution of 5-ethyl-2-thiophenecarboxaldehyde (6.0 g) in N,N-dimethylformamide (60 ml) was added N-chlorosuccinimide (8.57 g), and the mixture was stirred at room temperature for 2 hours, and subsequently stirred under heating at 60° C. for 2 hours. N-chlorosuccinimide (4.00 g) was further added thereto, and the mixture was further stirred under heating at 60° C. for 2 hours. The reaction mixture was poured into water, and the mixture was extracted with ethyl acetate, washed with brine, and dried over sodium sulfate. The solvent was evaporated under reduced pressure, and the residue was purified by silica gel column chromatography (hexane:ethyl acetate=33:1) to give 4-chloro-5-ethyl-2-thiophenecarboxaldehyde (3.1 g) as colorless oil.
(2) The above 4-chloro-5-ethyl-2-thiophenecarboxaldehyde was treated in a manner similar to Reference Example 1 to give 3-bromo-1-(4-chloro-5-ethyl-2-thienylmethyl)benzene as yellow oil. APCI-Mass m/Z 347/349 (M+H+MeOH).

Reference Example 14

5-Bromo-2-chloro-1-(4,5,6,7-tetrahydrobenzo[b]thiophen-2-ylmethyl)benzene (1) To a solution of 4-keto-4,5,6,7-tetrahydrothianaphthene (9.83 g) in ethylene glycol (100 ml) were added hydrazine hydrate (10.4 ml) and potassium hydroxide (13.0 g), and the mixture was stirred under argon atmosphere at 190° C. for 4 hours. The reaction mixture was cooled to room temperature, and poured into water, and the mixture was extracted with ethyl acetate. The extract was washed with water, and dried over sodium sulfate. The solvent was evaporated under reduced pressure, and the residue was purified by silica gel column chromatography (hexane) to give 4,5,6,7-tetrahydrothianaphthene (2.75 g) as colorless oil.
(2) The above 4,5,6,7-tetrahydrothianaphthene was treated in a manner similar to Reference Example 5 to give 5-bromo-2-chloro-1-(4,5,6,7-tetrahydrobenzo[b]thiophen-2-ylmethyl)benzene as a colorless solid. APCI-Mass m/Z 341/343 (M+H).

Reference Example 15

5-Bromo-2-chloro-1-(5-ethyl-4-methyl-2-thienylmethyl)benzene (3) 2-Acetyl-3-methylthiophene was treated in a manner similar to Reference Example 14 to give the target compound. APCI-Mass m/Z 329/331 (M+H).

Reference Example 16

5-Bromo-2-chloro-1-(2-thieno[3,2-b]thienylmethyl)benzene (1) 5-Bromo-2-chlorobenzoic acid was treated in a manner similar to Reference Example 4-(2) and (3) to give 5-bromo-2-chlorobenzaldehyde. APCI-Mass m/Z 233/235 (M+H+MeOH—$H_2O$).
(2) The above 5-bromo-2-chlorobenzaldehyde and thieno[3,2-b]thiophene (see Fuller, L.; Iddon, B.; Smith, K. A. *J. Chem. Soc. Perkin Trans* 1 1997, 3465-3470) were treated in a manner similar to Reference Example 9 to give 5-bromo-2-chloro-1-(2-thieno[3,2-b]thienylmethyl)benzene as colorless oil. APCI-Mass m/Z 343/345 (M+H).

Reference Example 17

5-Bromo-2-chloro-1-(5-chloro-2-thienylmethyl)benzene

2-Chlorothiophene was treated in a manner similar to Reference Example 5 to give the target compound.

Reference Example 18

5-Bromo-2-chloro-1-(5-phenylmethyl-2-thienylmethyl)benzene

2-Benzoylthiophene was treated in a manner similar to Reference Example 14 to give the target compound. APCI-Mass m/Z 377/379 (M+H).

Reference Example 19

5-Bromo-2-chloro-1-(5-(2-thienyl)-2-thienylmethyl)benzene 2,2'-Bithiophene and 5-bromo-2-chlorobenzaldehyde obtained in Reference Example 16-(1) were used and treated in a manner similar to Reference Example 9 to give the target compound. APCI-Mass m/Z 369/371 (M+H).

Reference Example 20

5-Bromo-1-(5-(5-chloro-2-thienyl)-2-thienylmethyl)-2-methylbenzene (1) To a solution of 2-bromo-5-chlorothiophene (4.11 g), thiophene-2-boronic acid (4.00 g), tetrakis(triphenylphosphine)palladium (0) (1.20 g) and 2M aqueous sodium carbonate solution (31.3 ml) in dimethoxyethane (100 ml) was heated under reflux under argon atmosphere for 2.5 hours. The reaction mixture was cooled, and extracted with ethyl acetate. The solvent was evaporated under reduced pressure, and the residue was purified by silica gel column chromatography (hexane) to give 2-(5-chloro-2-thienyl) thiophene (3.37 g) as pale yellow oil.
(2) The above 2-(5-chloro-2-thienyl)thiophene and 5-bromo-2-methylbenzoic acid obtained in Reference Example 4-(1) were used and treated in a manner similar to Reference Example 5 to give 5-bromo-1-(5-(5-chloro-2-thienyl)-2-thienylmethyl)-2-methylbenzene as a colorless solid. APCI-Mass m/Z 383/385 (M+H).

Reference Example 21

5-Bromo-2-chloro-1-(4-chloro-5-ethyl-2-thienylmethyl)benzene

2-Acetyl-3-chlorothiophene (see Japanese Unexamined Patent Publication No. 2000-34230) was treated in a manner similar to Reference Example 14 to give the target compound. APCI-Mass m/Z 347/349 (M+H).

Reference Example 22

5-Chloro-4-methylthiophene

The target compound was prepared according to a method described in Japanese Unexamined Patent Publication No. 10-324632.

Reference Example 23

5-Bromo-2-chloro-1-(5-(5-chloro-2-thienyl)-2-thienylmethyl)benzene 2-(5-Chloro-2-thienyl)thiophene and 5-bromo-2-chlorobenzoic acid were treated in a manner similar to Reference Example 5 to give the target compound.

Reference Example 24

5-Bromo-2-chloro-1-(5-trifluoromethyl-2-thienylmethyl)benzene

2-Trifluoromethylthiophene (see Japanese Unexamined Patent Publication No. 2000-34239) and 5-bromo-2-chlorobenzaldehyde obtained in Reference Example 16-(1) were treated in a manner similar to Reference Example 7 to give the target compound.

Reference Example 25

5-Bromo-2-chloro-1-(5-(2-pyridyl)-2-thienylmethyl)benzene (1) 2-(2-Pyridyl)thiophene and 5-bromo-2-chlorobenzaldehyde obtained in Reference Example 16-(1) were treated in a manner similar to Reference Example 7-(1) to give 5-bromo-2-chlorophenyl-5-(2-pyridyl)-2-thienylmethanol as colorless powder. APCI-Mass m/Z 380/382 (M+H).
(2) A solution of the above 5-bromo-2-chlorophenyl-5-(2-pyridyl)-2-thienylmethanol (3.52 g) in trifluoroacetic acid (45 ml) was added to a solution of sodium borohydride (1.75 g) in trifluoroacetic acid (45 ml), and the mixture was stirred at room temperature for 4 hours. Trifluoroacetic acid was evaporated under reduced pressure. The residue was basified with an aqueous potassium hydroxide solution, and extracted with diethyl ether. The extract was dried over sodium sulfate, and the solvent was evaporated under reduced pressure. The residue was purified by silica gel column chromatography (hexane:ethyl acetate=9:1-4:1) to give 5-bromo-2-chloro-1-(5-(2-pyridyl)-2-thienylmethyl)benzene (2.42 g) as a colorless solid. APCI-Mass m/Z 364/366 (M+H).

Reference Example 26

5-Bromo-1-(5-chloro-2-thienylmethyl)-2-phenylbenzene (1) 5-Bromo-2-iodobenzoic acid (see Jorg Frahn, A.-Dieter Schluter *Synthesis* 1997, 1301-1304) and 2-chlorothiophene were treated in a manner similar to Reference Example 5 to give 5-bromo-1-(5-chloro-2-thienylmethyl)-2-iodobenzene as colorless oil.
(2) To a solution of the above 5-bromo-1-(5-chloro-2-thienylmethyl)-2-iodobenzene (1.0 g) in dimethoxyethane (10 ml) were added phenylboronic acid (310 mg), bis(triphenylphosphine)palladium (II) dichloride (85 mg) and 2M aqueous sodium carbonate solution (3.8 ml), and the mixture was stirred at 50° C. overnight. Added thereto was a saturated aqueous sodium hydrogen carbonate solution and the mixture was extracted with ethyl acetate and dried over sodium sulfate. The solvent was evaporated under reduced pressure, and the residue was purified by silica gel column chromatography (hexane) to give 5-bromo-1-(5-chloro-2-thienylmethyl)-2-phenylbenzene (683 mg) as oil.

Reference Example 27

2-Chlorothieno[3,2-b]thiophene (1) A solution of thieno[3,2-b]thiophene (see Fuller, L.; Iddon, B.; Smith, K. A. *J. Chem. Soc. Perkin Trans* 1 1997, 3465-3470) (1.27 g) in tetrahydrofuran (30 ml) was cooled to −78° C. under argon atmosphere, and thereto was added dropwise n-butyl lithium (1.59 M hexane solution, 5.70 ml). The mixture was stirred at 0° C. for 30 minutes, and cooled again to −78° C. Added thereto was a solution of hexachloroethane (2.14 g) in tetrahydrofuran (5 ml). The mixture was stirred at the same temperature for one hour, and warmed to 0° C. Added thereto was a saturated aqueous ammonium chloride solution, and the mixture was extracted with ethyl acetate. The solvent was evaporated under reduced pressure. The residue was purified by silica gel column chromatography (hexane) to give 2-Chlorothieno[3,2-b]thiophene (1.19 g) as a solid.

Reference Example 28

1-(Benzo[b]thiophen-2-ylmethyl)-5-bromo-2-methoxybenzene

Thianaphthene was treated in a manner similar to Reference Example 7 to give the target compound. ESI-Mass m/Z 331/333(M−H).

Reference Example 29

1-(Benzo[b]thiophen-2-ylmethyl)-5-bromo-2-chlorobenzene

Thianaphthene and 5-bromo-2-chlorobenzaldehyde obtained in Reference Example 16-(1) were treated in a manner similar to Reference Example 7 to give the target compound.

Reference Example 30

3-Bromo-1-(5-methylbenzo[b]thiophen-2-ylmethyl)benzene

5-Methylbenzo[b]thiophene and 3-bromobenzaldehyde were treated in a manner similar to Reference Example 7 to give the target compound.

Reference Example 31

3-Bromo-1-(6-fluorobenzo[b]thiophen-2-ylmethyl)benzene (1) To a solution of 2,4-difluorobenzaldehyde (5.0 g) in dimethylsulfoxide (100 ml) were added methyl thioglycolate (3.45 ml) and triethylamine (10 ml), and the mixture was stirred at 80° C. overnight. The reaction mixture was poured into ice-cold water. The mixture was extracted with ethyl acetate, washed with water and brine, and dried over sodium sulfate. The solvent was evaporated under reduced pressure. The residue was purified by silica gel column chromatography (hexane:ethyl acetate=7:1) to give 6-fluoro-2-methoxycarbonylbenzo[b]thiophene (1.32 g) as colorless powder. GC-EI-Mass m/Z 210 (M).
(2) The above 6-fluoro-2-methoxycarbonylbenzo[b]thiophene was treated in a manner similar to Reference Example 4-(1) to give 6-fluorobenzo[b]thiophen-2-ylcarboxylic acid as colorless powder. ESI-Mass m/Z 195 (M−H).
(3) The above 6-fluorobenzo[b]thiophen-2-ylcarboxylic acid was treated in a manner similar to Reference Example 4-(2) to give 6-fluoro-2-(N-methoxy-N-methylcarbamoyl)benzo[b]thiophene as colorless powder. APCI-Mass m/Z 240 (M+H).
(4) A solution of 1,3-dibromobenzene (493 mg) in tetrahydrofuran (10 ml) was cooled to −78° C. under argon atmosphere, and thereto was added dropwise n-butyl lithium (2.44 M hexane solution, 0.86 ml). The reaction mixture was stirred at the same temperature for 30 minutes, and thereto was added dropwise a solution of the above 6-fluoro-2-(N-methoxy-N-methylcarbamoyl)benzo[b]thiophene (500 mg) in tetrahydrofuran (3 ml). The mixture was warmed to room temperature, and added thereto was a saturated aqueous ammonium chloride solution. The mixture was extracted with ethyl acetate, and dried over magnesium sulfate. The solvent was evaporated under reduced pressure. The residue was purified by silica gel column chromatography (hexane:ethyl acetate=95:5-85:15) to give 3-bromophenyl 6-fluorobenzo[b]thiophen-2-yl ketone (479 mg) as a pale yellow solid. APCI-Mass m/Z 335/337 (M+NH$_4$).
(5) The above 3-bromophenyl 6-fluorobenzo[b]thiophen-2-yl ketone was treated in a manner similar to Reference Example 5-(2) to give 3-bromo-1-(6-fluorobenzo[b]thiophen-2-ylmethyl)benzene as a colorless solid.

Reference Example 32

1-(Benzo[b]thiophen-2-ylmethyl)-3-bromo-4-fluorobenzene

Thianaphthene and 3-bromo-4-fluorobenzaldehyde were treated in a manner similar to Reference Example 7 to give the target compound.

Reference Example 33

1-(Benzo[b]thiophen-2-ylmethyl)-5-bromo-2-ethoxybenzene

Thianaphthene and 5-bromo-2-ethoxybenzaldehyde were treated in a manner similar to Reference Example 7 to give the target compound.

Reference Example 34

1-(Benzo[b]thiophen-2-ylmethyl)-5-bromo-2-fluorobenzene

Thianaphthene and 5-bromo-2-fluorobenzaldehyde were treated in a manner similar to Reference Example 7 to give the target compound.

Reference Example 35

2-(Benzo[b]thiophen-2-ylmethyl)-4-bromo-1-methoxynaphthalene 2,4-Dibromo-1-methoxynaphthalene (see J. Clayden, et al. *Org. Lett.*, 5, (2003) 831) and benzo[b]thiophene-2-carboxaldehyde were treated in a manner similar to Reference Example 1 to give the target compound.

Reference Example 36

3-Bromo-1-(5-trifluoromethylbenzo[b]thiophen-2-ylmethyl)benzene

5-Trifluoromethylbenzo[b]thiophen-2-ylcarboxylic acid was treated in a manner similar to Reference Example 31-(3), (4), and (5) to give the target compound.

Reference Example 37

3-Bromo-1-(3-methylbenzo[b]thiophen-2-ylmethyl)benzene

3-Methylbenzo[b]thiophene-2-carboxaldehyde was treated in a manner similar to Reference Example 1 to give the target compound.

Reference Example 38

3-Bromo-1-(5-fluorobenzo[b]thiophen-2-ylmethyl)benzene 2,5-Difluorobenzaldehyde was treated in a manner similar to Reference Example 31 to give the target compound.

Reference Example 39

1-(Benzo[b]thiophen-2-ylmethyl)-3-bromo-4-methylbenzene (1) 3-Bromo-4-methylbenzoic acid was treated in a manner similar to Reference Example 4-(2) and (3) to give 3-bromo-4-methylbenzaldehyde as colorless crystals. APCI-Mass m/Z 213/215 (M+H+MeOH).
(2) The above 3-bromo-4-methylbenzaldehyde and thianaphthene were treated in a manner similar to Reference Example 7 to give (Benzo[b]thiophen-2-ylmethyl)-3-bromo-4-methylbenzene as a colorless solid.

Reference Example 40

1-(Benzo[b]thiophen-2-ylmethyl)-3-bromo-5-methylbenzene 3,5-Dibromotoluene and benzo[b]thiophene-2-carboxaldehyde were treated in a manner similar to Reference Example 1 to give the target compound.

Reference Example 41

5-Bromo-2-chloro-1-(5-methylbenzo[b]thiophen-2-ylmethyl)benzene

5-Methylbenzo[b]thiophene and 5-bromo-2-chlorobenzaldehyde obtained in Reference Example 16-(1) were treated in a manner similar to Reference Example 7 to give the target compound.

Reference Example 42

5-Bromo-2-chloro-1-(7-methylbenzo[b]thiophen-2-ylmethyl)benzene

7-Methylbenzo[b]thiophene (see Tilak, B. D. *Tetrahedron* 9 (1960) 76-95) and 5-bromo-2-chlorobenzaldehyde obtained in Reference Example 16-(1) were treated in a manner similar to Reference Example 7 to give the target compound.

Reference Example 43

5-Bromo-2-chloro-1-(5-chlorobenzo[b]thiophen-2-ylmethyl)benzene

5-Chlorobenzo[b]thiophene (see Tilak, B. D. *Tetrahedron* 9 (1960) 76-95) and 5-bromo-2-chlorobenzaldehyde obtained in Reference Example 16-(1) were treated in a manner similar to Reference Example 7 to give the target compound.

Reference Example 44

5-Bromo-2-chloro-1-(5,7-dimethylbenzo[b]thiophen-2-ylmethyl)benzene 5,7-Dimethylbenzo[b]thiophene (see Yoshimura, Y. et al., *J. Med. Chem.* 43 (2000) 2929-2937) and 5-bromo-2-chlorobenzaldehyde obtained in Reference Example 16-(1) were treated in a manner similar to Reference Example 7 to give the target compound.

Reference Example 45

1-(Benzo[b]thiophen-2-ylmethyl)-5-bromo-2-methylbenzene (1) A solution of thianaphthene (543 mg) in diethyl ether (20 ml) was cooled to 0° C. under argon atmosphere, and thereto was added dropwise n-butyl lithium (2.44 M hexane solution, 1.74 ml). The reaction mixture was stirred at the same temperature for 3 hours. The reaction mixture was added dropwise to a solution of N-methoxy-N-methyl-5-bromo-2-methylbenzamide (1.15 g) obtained in Reference Example 4-(2) in diethyl ether (10 ml) cooled to −78° C. The mixture was warmed to room temperature and stirred for one hour. Added thereto was a saturated aqueous ammonium chloride solution. The mixture was extracted with ethyl acetate, washed with brine, and dried over sodium sulfate. The solvent was evaporated under reduced pressure. The residue was purified by silica gel column chromatography (hexane:ethyl acetate=100:0-95:5) to give 5-bromo2-methylphenyl benzo[b]thiophen-2-yl ketone (995 mg) as a pale yellow syrup. APCI-Mass m/Z 331/333 (M+H).
(2) The above 5-bromo2-methylphenyl benzo[b]thiophen-2-yl ketone was treated in a manner similar to Reference Example 5-(2) to give 1-(benzo[b]thiophen-2-ylmethyl)-5-bromo-2-methylbenzene as colorless oil.

Reference Example 46

5-Bromo-2-chloro-1-(6-methoxybenzo[b]thiophen-2-ylmethyl)benzene

6-Methoxybenzo[b]thiophene (see WO 97/25033) and 5-bromo-2-chlorobenzaldehyde obtained in Reference Example 16-(1) were treated in a manner similar to Reference Example 7 to give the target compound.

Reference Example 47

5-Bromo-2-chloro-1-(6-chlorobenzo[b]thiophen-2-ylmethyl)benzene (1) 4-Chloro-2-fluorobenzaldehyde was treated in a manner similar to Reference Example 31-(1) and (2) to give 6-chlorobenzo[b]thiophen-2-ylcarboxylic acid as colorless crystals. ESI-Mass m/Z 211/213 (M−H).
(2) A solution of the above 6-chlorobenzo[b]thiophen-2-ylcarboxylic acid (3.0 g) and copper powder (1.2 g) in quinoline (20 ml) was stirred at 210° C. for 40 minutes. The mixture was cooled to room temperature and diluted with diethyl ether, and insoluble materials were filtered off. The filtrate was washed successively with 10% aqueous hydrochloric acid solution and brine, and dried over magnesium sulfate. The solvent was evaporated under reduced pressure, and the residue was purified by silica gel column chromatography (hexane) to give 6-chlorobenzo[b]thiophene (1.79 g) as colorless crystals.
(3) The above 6-chlorobenzo[b]thiophene and 5-bromo-2-chlorobenzaldehyde obtained in Reference Example 16-(1) were treated in a manner similar to Reference Example 7 to give 5-bromo-2-chloro-1-(6-chlorobenzo[b]thiophen-2-ylmethyl)benzene as colorless crystals.

Reference Example 48

5-Bromo-2-chloro-1-(6-trifluoromethylbenzo[b]thiophen-2-ylmethyl)benzene

2-Fluoro-4-trifluoromethylbenzaldehyde was treated in a manner similar to Reference Example 47 to give the target compound.

Reference Example 49

1-Benzo[b]thiophen-2-ylmethyl)-3-bromo-4-chlorobenzene

3-Bromo-4-chlorobenzoic acid was treated in a manner similar to Reference Example 39 to give the target compound.

Reference Example 50

5-Bromo-2-chloro-1-(6-fluorobenzo[b]thiophen-2-ylmethyl)benzene 2,4-Difluorobenzaldehyde was treated in a manner similar to Reference Example 47 to give the target compound.

Reference Example 51

5-Bromo-2-fluoro-1-(6-fluorobenzo[b]thiophen-2-ylmethyl)benzene

6-Fluorobenzo[b]thiophene produced in the preparation process of Reference Example 50 and 5-bromo-2-fluorobenzaldehyde were treated in a manner similar to Reference Example 7 to give the target compound.

Reference Example 52

1-(Benzo[b]thiophen-2-ylmethyl)-3-bromo-5-chlorobenzene

1-Chloro-3,5-dibromobenzene and benzo[b]thiophene-2-carboxaldehyde were treated in a manner similar to Reference Example 1 to give the target compound.

Reference Example 53

5-Bromo-2-chloro-1-(7-methoxybenzo[b]thiophen-2-ylmethyl)benzene

7-Methoxybenzo[b]thiophene (see WO 02/094262) and 5-bromo-2-chlorobenzaldehyde obtained in Reference Example 16-(1) were treated in a manner similar to Reference Example 9 to give the target compound. APCI-Mass m/Z 367/369 (M+H).

Reference Example 54

5-Bromo-2-chloro-1-(5-methoxybenzo[b]thiophen-2-ylmethyl)benzene

5-Methoxybenzo[b]thiophene (see WO 97/25033) and 5-bromo-2-chlorobenzaldehyde obtained in Reference Example 16-(1) were treated in a manner similar to Reference Example 9 to give the target compound. APCI-Mass m/Z 367/369 (M+H).

Reference Example 55

5-Bromo-2-chloro-1-(5-fluorobenzo[b]thiophen-2-ylmethyl)benzene 2,5-Difluorobenzaldehyde was treated in a manner similar to Reference Example 47 to give the target compound.

Reference Example 56

5-Bromo-2-chloro-1-(7-fluoro-6-methylbenzo[b]thiophen-2-ylmethyl)benzene 2,3-Difluoro-4-methylbenzaldehyde was treated in a manner similar to Reference Example 47 to give the target compound. APCI-Mass m/Z 369/371 (M+H).

Reference Example 57

5-Bromo-2-chloro-1-(4-fluorobenzo[b]thiophen-2-ylmethyl)benzene 2,6-Difluorobenzaldehyde was treated in a manner similar to Reference Example 47 to give the target compound.

Reference Example 58

5-Bromo-2-chloro-1-(7-fluorobenzo[b]thiophen-2-ylmethyl)benzene 2,3-difluorobenzaldehyde was treated in a manner similar to Reference Example 47 to give the target compound.

Reference Example 59

5-Bromo-2-chloro-1-(4-chlorobenzo[b]thiophen-2-ylmethyl)benzene

2-Chloro-6-fluorobenzaldehyde was treated in a manner similar to Reference Example 47 to give the target compound.

Reference Example 60

5-Bromo-2-fluoro-1-(5-fluorobenzo[b]thiophen-2-ylmethyl)benzene

5-Fluorobenzo[b]thiophene produced in the preparation process of Reference Example 55 and 5-bromo-2-fluorobenzaldehyde were treated in a manner similar to Reference Example 7 to give the target compound.

Reference Example 61

3-Bromo-2-chloro-1-(benzo[b]thiophen-2-ylmethyl)benzene (1) 3-Bromo-2-chlorobenzoic acid (see Frederic Gohier et al., *J. Org. Chem.* (2003) δ 2030-2033) was treated in a manner similar to Reference Example 4-(2) to give N-methoxy-N-methyl-3-bromo-2-chlorobenzamide as oil. APCI-Mass m/Z 278/280/282 (M+H).
(2) The above N-methoxy-N-methyl-3-bromo-2-chlorobenzamide was treated in a manner similar to Reference Example 45 to give 3-bromo-2-chloro-1-(benzo[b]thiophen-2-ylmethyl)benzene as a colorless solid.

Reference Example 62

1-(Benzo[b]thiophen-2-ylmethyl)-5-bromo-2-ethylbenzene (1) To a solution of 2-ethylbenzoic acid (10.0 g) in dichloromethane (50 ml) were added oxalyl chloride (7.0 ml) and N,N-dimethylformamide (3 drops) and the mixture was stirred at room temperature for 3 hours. The solvent was evaporated under reduced pressure to give a corresponding acid chloride. The acid chloride was dissolved in methanol (60 ml) and the mixture was stirred at room temperature for 3 hours, and then, the solvent was evaporated under reduced pressure. The residue was dissolved in diethyl ether, and washed successively with a saturated aqueous sodium hydrogen carbonate solution and brine, and dried over sodium sulfate. The solvent was evaporated under reduced pressure to give methyl 2-ethylbenzoate, which was used in the subsequent step without further purification.
(2) The above methyl 2-ethylbenzoate was mixed with molecular sieve 13× (powder, 70 g), and while stirring the mixture, bromine (5.2 ml) was added dropwise thereto at 80° C. The mixture was further stirred at the same temperature for 1.5 hours. The mixture was cooled to room temperature, and added thereto were potassium carbonate (7.4 g), water (70 ml) and methanol (350 ml), and the mixture was stirred for 8 hours. Insoluble materials were filtered off, and suspended in a mixed solution of methanol (500 ml)-water (500 ml), and the mixture was stirred at room temperature overnight. Insoluble materials were filtered off and the filtrate was combined with the previously obtained filtrate, and the solvent was evaporated under reduced pressure. The residue was extracted with ethyl acetate, and the extract was washed with brine, and dried over sodium sulfate. The solvent was evaporated under reduced pressure, and the residue was distilled under reduced pressure, to give methyl 5-bromo-2-ethylbenzoate (2.44 g). APCI-Mass m/Z 260/262 (M+NH$_4$).
(3) The above methyl 5-bromo-2-ethylbenzoate was treated in a manner similar to Reference Example 4-(1) and (2) to give N-methoxy-N-methyl-5-bromo-2-ethylbenzamide as colorless oil. APCI-Mass m/Z 272/274 (M+H).
(4) The above N-methoxy-N-methyl-5-bromo-2-ethylbenzamide and thianaphthene were treated in a manner similar to Reference Example 45 to give 1-(Benzo[b]thiophen-2-ylmethyl)-5-bromo-2-ethylbenzene as oil.

Reference Example 63

1-(Benzo[b]thiophen-2-ylmethyl)-5-bromo-2-trifluoromethylbenzene (1) 5-Bromo-2-iodobenzoic acid (see Jorg Frahn, A.-Dieter Schluter *Synthesis* 1997, 1301-1304) was treated in a manner similar to Reference Example 4-(2) to give N-methoxy-N-methyl-5-bromo-2-iodobenzamide as a pale yellow solid. APCI-Mass m/Z 370/372 (M+H).
(2) To a solution of the above N-methoxy-N-methyl-5-bromo-2-iodobenzamide (2.67 g) in N-methyl-2-pyrrolidinone (12 ml) were added copper (I) bromide (124 mg) and methyl fluorosulfonyl(difluoro)acetate (1.34 ml), and the mixture was stirred under heating for 1.5 hours. The reaction mixture was cooled to room temperature, and then, a diluted aqueous ammonia was added thereto, and the mixture was extracted with ethyl acetate. The extract was washed with water and brine, and dried over sodium sulfate. The solvent was evaporated under reduced pressure. The residue was purified by silica gel column chromatography (hexane:ethyl acetate=100:0-85:15) to give N-methoxy-N-methyl-5-bromo-2-trifluoromethylbenzamide (1.59 g) as colorless oil. APCI-Mass m/Z 312/314 (M+H).
(3) The above N-methoxy-N-methyl-5-bromo-2-trifluoromethylbenzamide and thianaphthene were treated in a manner similar to Reference Example 45 to give 1-(Benzo[b]thiophen-2-ylmethyl)-5-bromo-2-trifluoromethylbenzene as a colorless solid. ESI-Mass m/Z 369/371 (M–H).

Reference Example 64

5-Bromo-2-chloro-1-(5-phenyl-2-thienylmethyl)benzene

2-Phenylthiophene was treated in a manner similar to Reference Example 5 to give the target compound. APCI-Mass m/Z 363/365 (M+H).

Reference Example 65

5-Bromo-2-chloro-1-(5-(4-methylphenyl)-2-thienylmethyl)benzene (1) 2-Iodothiophene and 4-methylphenylboronic acid were treated in a manner similar to Reference Example 26-(2) to give 2-(4-methylphenyl)thiophene as colorless crystals. APCI-Mass m/Z 175 (M+H).
(2) The above 2-(4-methylphenyl)thiophene was treated in a manner similar to Reference Example 5 to give 5-bromo-2-chloro-1-(5-(4-methylphenyl)-2-thienylmethyl)benzene as colorless crystals. APCI-Mass m/Z 377/379 (M+H).

Reference Example 66

5-Bromo-2-chloro-1-(5-(2-fluorophenyl)-2-thienylmethyl)benzene (1) 2-Fluorobromobenzene and thiophene-2-boronic acid were treated in a manner similar to Reference Example 26-(2) to give 2-(2-fluorophenyl)thiophene as a colorless liquid.
(2) The above 2-(2-fluorophenyl)thiophene was treated in a manner similar to Reference Example 5 to give 5-bromo-2-chloro-1-(5-(2-fluorophenyl)-2-thienylmethyl)benzene as a colorless solid. APCI-Mass m/Z 381/383 (M+H).

Reference Example 67

5-Bromo-2-chloro-1-(5-(4-fluorophenyl)-2-thienylmethyl)benzene (1) 2-Iodothiophene and 4-fluorophenylboronic acid were treated in a manner similar to Reference Example 26-(2) to give 2-(4-fluorophenyl)thiophene as colorless powder.

(2) The above 2-(4-fluorophenyl)thiophene was treated in a manner similar to Reference Example 5 to give 5-bromo-2-chloro-1-(5-(4-fluorophenyl)-2-thienylmethyl)benzene as colorless powder.

Reference Example 68

5-Bromo-2-chloro-1-(5-(4-ethoxyphenyl)-2-thienyl-methyl)benzene (1) 2-Bromothiophene and 4-ethoxyphenylboronic acid were treated in a manner similar to Reference Example 20-(1) to give 2-(4-ethoxyphenyl)thiophene as a colorless solid. APCI-Mass m/Z 205 (M+H).
(2) The above 2-(4-ethoxyphenyl)thiophene was treated in a manner similar to Reference Example 5 to give 5-bromo-2-chloro-1-(5-(4-ethoxyphenyl)-2-thienylmethyl)benzene as a colorless solid. APCI-Mass m/Z 407/409 (M+H).

Reference Example 69

5-Bromo-2-chloro-1-(5-(3-ethoxyphenyl)-2-thienyl-methyl)benzene (1) 2-Bromothiophene and 3-ethoxyphenylboronic acid were treated in a manner similar to Reference Example 20-(1) to give 2-(3-ethoxyphenyl)thiophene as colorless oil. APCI-Mass m/Z 205 (M+H).
(2) The above 2-(3-ethoxyphenyl)thiophene and 5-bromo-2-chlorobenzaldehyde obtained in Reference Example 16-(1) were treated in a manner similar to Reference Example 9 to give 5-bromo-2-chloro-1-(5-(3-ethoxyphenyl)-2-thienylmethyl)benzene as colorless oil. APCI-Mass m/Z 407/409 (M+H).

Reference Example 70

5-Bromo-2-chloro-1-(5-(2-ethoxyphenyl)-2-thienyl-methyl)benzene (1) 2-Iodothiophene and 2-ethoxyphenylboronic acid were treated in a manner similar to Reference Example 26-(2) to give 2-(2-ethoxyphenyl)thiophene as a pale yellow solid.
(2) The above 2-(2-ethoxyphenyl)thiophene and 5-bromo-2-chlorobenzaldehyde obtained in Reference Example 16-(1) were treated in a manner similar to Reference Example 9 to give 5-bromo-2-chloro-1-(5-(2-ethoxyphenyl)-2-thienylmethyl)benzene as colorless oil. APCI-Mass m/Z 407/409 (M+H).

Reference Example 71

5-Bromo-2-fluoro-1-(5-phenyl-2-thienylmethyl)ben-zene

2-Phenylthiophene and 5-bromo-2-fluorobenzaldehyde were treated in a manner similar to Reference Example 7 to give the target compound. APCI-Mass m/Z 347/349 (M+H).

Reference Example 72

5-Bromo-1-(5-(4-ethoxyphenyl)-2-thienylmethyl)-2-fluorobenzene 2-(4-Ethoxyphenyl)thiophene obtained in Reference Example 68-(1) and 5-bromo-2-fluorobenzaldehyde were treated in a manner similar to Reference Example 7 to give the target compound. APCI-Mass m/Z 391/393 (M+H).

Reference Example 73

5-Bromo-1-(5-(2-ethoxyphenyl)-2-thienylmethyl)-2-fluorobenzene 2-(2-Ethoxyphenyl)thiophene obtained in Reference Example 70-(1) and 5-bromo-2-fluorobenzaldehyde were treated in a manner similar to Reference Example 9 to give the target compound. APCI-Mass m/Z 391/393 (M+H).

Reference Example 74

5-Bromo-2-fluoro-1-(5-(2-fluorophenyl)-2-thienylm-ethyl)benzene 2-(2-Fluorophenyl)thiophene obtained in Reference Example 66-(1) and 5-bromo-2-fluorobenzaldehyde were treated in a manner similar to Reference Example 7 to give the target compound. APCI-Mass m/Z 365/367 (M+H).

Reference Example 75

5-Bromo-2-chloro-1-(5-(3-fluorophenyl)-2-thienyl-methyl)benzene (1) 2-Iodothiophene and 3-fluorophenylboronic acid were treated in a manner similar to Reference Example 26-(2) to give 2-(3-fluorophenyl)thiophene as oil.
(2) The above 2-(3-fluorophenyl)thiophene was treated in a manner similar to Reference Example 5 to give the target compound as powder.

Reference Example 76

5-Bromo-1-(5-(3-ethoxyphenyl)-2-thienylmethyl)-2-fluorobenzene 2-(3-Ethoxyphenyl)thiophene obtained in Reference Example 69-(1) and 5-bromo-2-fluorobenzaldehyde were treated in a manner similar to Reference Example 9 to give the target compound. APCI-Mass m/Z 391/393 (M+H).

Reference Example 77

5-Bromo-2-fluoro-1-(5-(3-fluorophenyl)-2-thienylm-ethyl)benzene 2-(3-Fluorophenyl)thiophene obtained in Reference Example 75-(1) and 5-bromo-2-fluorobenzaldehyde were treated in a manner similar to Reference Example 7 to give the target compound.

Reference Example 78

5-Bromo-2-fluoro-1-(5-(4-fluorophenyl)-2-thienylm-ethyl)benzene 2-(4-Fluorophenyl)thiophene obtained in Reference Example 67-(1) and 5-bromo-2-fluorobenzaldehyde were treated in a manner similar to Reference Example 7 to give the target compound.

Reference Example 79

5-Bromo-2-methyl-1-(5-phenyl-2-thienylmethyl)benzene

2-Phenylthiophene and 5-bromo-2-methylbenzoic acid obtained in Reference Example 4-(1) were treated in a manner similar to Reference Example 5 to give the target compound. APCI-Mass m/Z 343/345 (M+H).

Reference Example 80

5-Bromo-1-(5-(3-fluorophenyl)-2-thienylmethyl)-2-methylbenzene 2-(3-Fluorophenyl)thiophene obtained in Reference Example 75-(1) and 5-bromo-2-methylbenzoic acid obtained in Reference Example 4-(1) were treated in a manner similar to Reference Example 5 to give the target compound.

Reference Example 81

5-Bromo-1-(5-(4-fluorophenyl)-2-thienylmethyl)-2-methylbenzene 2-(4-Fluorophenyl)thiophene obtained in Reference Example 67-(1) and 5-bromo-2-methylbenzoic acid obtained in Reference Example 4-(1) were treated in a manner similar to Reference Example 5 to give the target compound.

Reference Example 82

5-Bromo-2-methoxy-1-(5-phenyl-2-thienylmethyl)benzene

2-Phenylthiophene was treated in a manner similar to Reference Example 7 to give the target compound. APCI-Mass m/Z 359/361 (M+H).

Reference Example 83

5-Bromo-2-methyl-1-(5-(3-methylphenyl)-2-thienylmethyl)benzene (1) 2-Bromothiophene and 3-methylphenylboronic acid were treated in a manner similar to Reference Example 26-(2) to give 2-(3-methylphenyl)thiophene as colorless oil.
(2) The above 2-(3-methylphenyl)thiophene and 5-bromo-2-methylbenzaldehyde obtained in Reference Example 4 were treated in a manner similar to Reference Example 9 to give the target compound. APCI-Mass m/Z 357/359 (M+H).

Reference Example 84

5-Bromo-2-chloro-1-(5-(3-methylphenyl)-2-thienylmethyl)benzene 2-(3-Methylphenyl)thiophene obtained in Reference Example 83-(1) and 5-bromo-2-chlorobenzaldehyde obtained in Reference Example 16-(1) were treated in a manner similar to Reference Example 9 to give the target compound. APCI-Mass m/Z 377/379/381 (M+H).

Reference Example 85

5-Bromo-2-chloro-1-(5-(3-chlorophenyl)-2-thienylmethyl)benzene (1) 2-Bromothiophene and 3-chlorophenylboronic acid were treated in a manner similar to Reference Example 26-(2) to give 2-(3-chlorophenyl)thiophene as colorless oil.
(2) The above 2-(3-chlorophenyl)thiophene was treated in a manner similar to Reference Example 5 to give the target compound as colorless oil.

Reference Example 86

5-Bromo-1-(5-(3-chlorophenyl)-2-thienylmethyl)-2-methylbenzene 2-(3-Chlorophenyl)thiophene obtained in Reference Example 85-(1) and 5-bromo-2-methylbenzoic acid obtained in Reference Example 4-(1) were treated in a manner similar to Reference Example 5 to give the target compound as colorless oil.

Reference Example 87

5-Bromo-1-(5-(3-methoxyphenyl)-2-thienylmethyl)-2-methylbenzene (1) 3-Methoxybromobenzene and thiophene-2-boronic acid were treated in a manner similar to Reference Example 26-(2) to give 2-(3-methoxyphenyl)thiophene as a yellow liquid. APCI-Mass m/Z 191 (M+H).
(2) The above 2-(3-methoxyphenyl)thiophene and 5-bromo-2-methylbenzaldehyde obtained in Reference Example 4 were treated in a manner similar to Reference Example 9 to give the target compound as yellow oil. APCI-Mass m/Z 373/375 (M+H).

Reference Example 88

4-Bromo-2-(4-ethylphenylmethyl)-2H-isoquinolin-1-one

4-Bromo-2H-isoquinolin-1-one (see EP0355750) was treated in a manner similar to Reference Example 2 to give the target compound. APCI-Mass m/Z 342/344 (M+H).

Reference Example 89

4-Bromo-2-(4-ethylphenylmethyl)-8-methyl-2H-isoquinolin-1one (1) To a solution of 8-methyl-2H-isoquinolin-1-one (1.15 g) in dichloromethane (20 ml) was added dropwise a solution of bromine (1.26 g) in dichloromethane (4 ml) at room temperature. The mixture was stirred at the same temperature for one hour, and the solvent was evaporated under reduced pressure. The residue was crystallized from ether to give 4-bromo-8-methyl-2H-isoquinolin-1-one (1.86 g) as colorless crystals. APCI-Mass m/Z 238/240 (M+H).
(2) The above 4-bromo-8-methyl-2H-isoquinolin-1-one was treated in a manner similar to Reference Example 2 to give the target compound as colorless crystals. APCI-Mass m/Z 356/358M+H).

Reference Example 90

4-Bromo-2-(4-ethylphenylmethyl)thiophene (1) A solution of 4-bromo-2-thiophenecarboxaldehyde (4.78 g) in tetrahydrofuran (40 ml) was cooled to 0° C. under argon atmosphere, and thereto was added dropwise 4-ethylphenylmagnesium bromide (0.5 M tetrahydrofuran solution, 50 ml). The mixture was stirred at the same temperature for 30 minutes, and thereto was added a saturated aqueous ammonium chloride solution, and the mixture was extracted with ethyl acetate. The extract was washed with brine and dried over magnesium sulfate, and the solvent was evaporated under reduced pressure. The residue was purified by silica gel column chromatography (hexane:ethyl acetate=97:3-84:16) to give 4-bromo-2-thienyl-4-ethylphenylmethanol (5.37 g) as colorless oil. APCI-Mass m/Z 279/281 (M+H—$H_2O$).
(2) The above 4-bromo-2-thienyl-4-ethylphenylmethanol was treated in a manner similar to Reference Example 1-(2) to give the target compound as colorless oil.

Reference Example 91

5-Bromo-2-(4-ethylphenylmethyl)thiophene

5-Bromo-2-thiophenecarboxaldehyde was treated in a manner similar to Reference Example 90 to give the target compound. ESI-Mass m/Z 279/281 (M−H).

Reference Example 92

3-Bromo-2-(4-ethylphenylmethyl)thiophene (1) 2,3-Dibromothiophene and 4-ethylbenzaldehyde were treated in a manner similar to Reference Example 1-(1) to give 3-bromo-2-thienyl-4-ethylphenylmethanol as yellow oil. APCI-Mass m/Z 279/281 (M+H—$H_2O$).
(2) A solution of the above 3-bromo-2-thienyl-4-ethylphenylmethanol (12.4 g) in diethyl ether (10 ml) was added dropwise into a suspension of lithium aluminum hydride (2.6 g) and aluminum chloride (9.0 g) in diethyl ether (35 ml) at 0° C. Subsequently, the mixture was stirred at room temperature overnight, and then poured onto ice. The mixture was extracted with diethyl ether, washed with a saturated aqueous sodium hydrogen carbonate solution, and dried over magnesium sulfate. The solvent was evaporated under reduced pressure, and the residue was purified by silica gel column chromatography (hexane) to give 3-bromo-2-(4-ethylphenylmethyl)thiophene (8.77 g) as colorless oil. APCI-Mass m/Z 279/281 (M+H).

Reference Example 93

5-Bromo-3-(4-ethylphenylmethyl)thiophene

5-Bromo-3-thiophenecarboxaldehyde (see Amishiro, N. et al., Chem. Pharm. Bull. 47 (1999) 1393-1403) was treated in a manner similar to Reference Example 90 to give the target compound.

Reference Example 94

5-Bromo-2-chloro-3-(4-ethylphenylmethyl)thiophene (1) 5-Bromo-2-chloro-3-thiophenecarboxylic acid (see Japanese Unexamined Patent Publication No. 10-324632) was treated in a manner similar to Reference Example 4-(2) and (3) to give 5-bromo-2-chloro-3-thiophenecarboxaldehyde as pale yellow oil. APCI-Mass m/Z 239/241/243 (M+H+MeOH—$H_2O$).
(2) The above 5-bromo-2-chloro-3-thiophenecarboxaldehyde was treated in a manner similar to Reference Example 90 to give the target compound as colorless oil.

Reference Example 95

5-Bromo-3-chloro-2-(4-ethylphenylmethyl)thiophene (1) A solution of diisopropylamine (6.8 ml) in tetrahydrofuran (75 ml) was cooled to −78° C. under argon atmosphere, and thereto was added dropwise n-butyl lithium (1.59 M hexane solution, 30.5 ml). The reaction mixture was stirred at the same temperature for 30 minutes, and thereto was added dropwise a solution of 3-chloro-2-thiophenecarboxylic acid (3.92 g) in tetrahydrofuran (40 ml). The mixture was stirred at the same temperature for 30 minutes, and thereto was added dropwise 1,2-dibromo-1,1,2,2-tetrafluoroethane (6.0 ml). The mixture was stirred at the same temperature for one hour, and then, warmed to room temperature. The mixture was poured into a diluted aqueous hydrochloric acid solution, and the solution was extracted with ethyl acetate. The extract was washed with brine, and dried over sodium sulfate. The solvent was evaporated under reduced pressure and the residue was crystallized from a mixed solvent of diisopropyl ether and hexane to give 5-bromo-3-chloro-2-thiophenecarboxylic acid (3.79 g) as a yellow solid. ESI-Mass m/Z 239/241 (M−H).
(2) The above 5-bromo-3-chloro-2-thiophenecarboxylic acid was treated in a manner similar to Reference Example 94 to give 5-bromo-3-chloro-2-(4-ethylphenylmethyl)thiophene as colorless oil.

Reference Example 96

3-Bromo-1-(benzo[b]thiophen-3-ylmethyl)benzene

Thianaphthene-3-carboxaldehyde was treated in a manner similar to Reference Example 1 to give the target compound.

Reference Example 97

3-Bromo-1-(5-ethyl-2-furylmethyl)benzene (1) 5-Ethyl-2-furaldehyde was treated in a manner similar to Reference Example 1-(1) to give 3-bromophenyl-5-ethyl-2-furylmethanol as oil. APCI-Mass m/Z 263/265 (M+H—$H_2O$).
(2) The above 3-bromophenyl-5-ethyl-2-furylmethanol was treated in a manner similar to Reference Example 9-(2) to give the target compound as oil.

Reference Example 98

3-Bromo-1-(benzo[b]furan-2-ylmethyl)benzene

2-Benzo[b]furancarboxaldehyde was treated in a manner similar to Reference Example 97 to give the target compound.

Reference Example 99

1-(Benzo[b]furan-2-ylmethyl)-5-bromo-2-chlorobenzene

Benzo[b]furan and 5-bromo-2-chlorobenzaldehyde obtained in Reference Example 16-(1) were treated in a manner similar to Reference Example 7 to give the target compound.

Reference Example 100

1-(Benzothiazol-2-ylmethyl)-5-bromo-2-methylbenzene (1) Benzothiazole and 5-bromo-2-methylbenzaldehyde obtained in Reference Example 4 were treated in a manner similar to Reference Example 7-(1) to give 5-bromo-2-methylphenyl-(benzothiazol-2-yl)methanol as pale yellow crystals. APCI-Mass m/Z 334/336 (M+H).
(2) To a solution of the above 5-bromo-2-methylphenyl-(benzothiazol-2-yl)methanol (2.60 g) in dichloromethane (30 ml)-toluene (10 ml) was added manganese(IV) oxide (3.42 g), and the mixture was stirred at room temperature for 3 hours. Insoluble materials were filtered off, and the filtrate was evaporated under reduced pressure to give 5-bromo-2-methylphenyl benzothiazol-2-yl ketone (2.45 g) as colorless crystals. APCI-Mass m/Z 332/334 (M+H).
(3) The above 5-bromo-2-methylphenyl benzothiazol-2-yl ketone was treated in a manner similar to Reference Example 14-(1) to give 1-(benzothiazol-2-ylmethyl)-5-bromo-2-methylbenzene as oil. APCI-Mass m/Z 318/320 (M+H).

Reference Example 101

1-(Benzothiazol-2-ylmethyl)-5-bromo-2-chlorobenzene

Benzothiazole and 5-bromo-2-chlorobenzaldehyde obtained in Reference Example 16-(1) were treated in a manner similar to Reference Example 100 to give the target compound. APCI-Mass m/Z 338/340 (M+H).

Reference Example 102

5-Bromo-2-chloro-1-(5-phenyl-2-thiazolylmethyl)benzene (1) A solution of thiazole (10.0 g), iodobenzene (2.63 ml), tetrakis(triphenylphosphine)palladium (0) (1.36 g) and potassium acetate (3.46 g) in N,N-dimethylacetamide (100 ml) was stirred under heating at 100° C. overnight. The solvent was evaporated under reduced pressure, and added to the residue was ethyl acetate. The mixture was washed successively with water and brine, and dried over sodium sulfate. The solvent was evaporated under reduced pressure, and the residue was purified by silica gel column chromatography (hexane:ethyl acetate=100:0-90:10) to give 5-phenylthiazole (1.50 g) as a pale yellow solid. APCI-Mass m/Z 162 (M+H).
(2) The above 5-phenylthiazole and 5-bromo-2-chlorobenzaldehyde obtained in Reference Example 16-(1) were treated in a manner similar to Reference Example 100 to give 5-bromo-2-chloro-1-(5-phenyl-2-thiazolylmethyl)benzene as a yellow solid. APCI-Mass m/Z 364/366 (M+H).

Reference Example 103

3-(4-Ethylphenylmethyl)-2,4-pentanedione

A suspension of sodium iodide (15.0 g) in acetonitrile (100 ml) was cooled to 0° C. under argon atmosphere, and thereto were added dropwise chlorotrimethylsilane (12.7 ml), 2,4-pentanedione (2.05 ml) and 4-ethylbenzaldehyde (2.68 g), successively. The reaction mixture was stirred at room temperature for 17 hours, and further stirred at 60° C. for 10 hours. The reaction mixture was cooled to room temperature and poured into an aqueous sodium thiosulfate solution. The mixture was extracted with diethyl ether, and the extract was washed with brine and dried over magnesium sulfate. The solvent was evaporated under reduced pressure and the residue was purified by silica gel column chromatography (hexane:ethyl acetate=9:1) to give 3-(4-ethylphenylmethyl)-2,4-pentanedione (2.72 g) as pale yellow oil. APCI-Mass m/Z 219 (M+H).

Reference Example 104

Tri-n-butyl(4-ethylphenyl)tin

To a solution of magnesium (896 mg) in tetrahydrofuran (20 ml) was added dibromoethan (0.1 ml), and the mixture was stirred at room temperature for 15 minutes. Thereto was added dropwise a solution of 1-bromo-4-ethylbenzene (5.7 g) in tetrahydrofuran (20 ml), and subsequently, the mixture was stirred at room temperature for one hour. The reaction mixture was cooled to −78° C., and thereto was added dropwise tributyltin chloride (9.49 g). The mixture was stirred at the same temperature for 30 minutes, and then at room temperature for one hour. To the reaction mixture were added 10% aqueous potassium fluoride solution and ethyl acetate, and the mixture was stirred at room temperature for 30 minutes. Insoluble materials were filtered off. The organic layer of the filtrate was washed with water and brine successively, and dried over sodium sulfate. The solvent was evaporated under reduced pressure and the residue was purified by alumina column chromatography (hexane) to give the desired tri-n-butyl(4-ethylphenyl)tin (10.7 g) as colorless oil. EI-Mass m/Z 337 (M-Bu).

Reference Example 105

4-(4-Ethylphenylmethyl)pyrazole (1) A mixed solution of 4-ethylbenzyl bromide (10.0 g), malononitrile (6.64 g), potassium carbonate (6.94 g) and tetra-n-butylammonium bromide (648 mg) in toluene (100 ml) was agitated at room temperature for 17 hours. The reaction mixture was poured into water, and the mixture was extracted with ethyl acetate twice. The extract was washed successively with water and brine, and dried over sodium sulfate. The solvent was evaporated under reduced pressure and the residue was purified by silica gel column chromatography (hexane:ethyl acetate=6:1) to give 2-(4-ethylphenylmethyl)malononitrile (3.28 g) as a colorless solid.
(2) A solution of the above 2-(4-ethylphenylmethyl) malononitrile (1.30 g) and hydrazine hydrate (0.86 ml) in ethanol (35 ml) was heated under reflux for 4 hours. Hydrazine hydrate (0.43 ml) was further added thereto and the mixture was further heated under reflux for 4 hours. The reaction mixture was cooled to room temperature and the solvent was evaporated under reduced pressure. The residue was crystallized from ethyl acetate-diethyl ether to give 3,5-diamino-4-(4-ethylphenylmethyl)pyrazole (2.63 g) as pale pink powder. APCI-Mass m/Z 217 (M+H).
(3) The above 3,5-diamino-4-(4-ethylphenylmethyl)pyrazole (1.30 g) was added to 50% aqueous phosphoric acid solution (19 ml), and further added thereto was water (10 ml). The mixture was cooled to 0° C., and thereto was added dropwise an aqueous solution (4 ml) of sodium nitrite (912 mg). The mixture was stirred at the same temperature for 30 minutes, and further stirred at room temperature for 4 hours. The reaction mixture was cooled again to 0° C., 10% aqueous sodium hydroxide solution was added thereto to adjust pH of the reaction mixture to 7. The mixture was extracted with ethyl acetate, washed successively with water and brine, and dried over magnesium sulfate. The solvent was evaporated under reduced pressure, and the residue was purified by silica gel column chromatography (chloroform:methanol=100:0-90:10) to give the desired 4-(4-ethylphenylmethyl)pyrazole (414 mg) as a pale brown semisolid. APCI-Mass m/Z 187 (M+H).

Reference Example 106

3-(4-Ethylphenylmethyl)-5-methyl-1H-pyrazole (1) 4-Ethylphenylacetic acid (3.0 g) (see Japanese Unexamined Patent Publication 63-233975) was dissolved in dichloromethane (15 ml), and thereto were added oxalyl chloride (6.0 ml) and N,N-dimethylformamide (one drop). The mixture was stirred at room temperature for 1.5 hours. The reaction mixture was evaporated under reduced pressure, and the residue was subjected to azeotropic distillation with toluene to give a crude 4-ethylphenylacetyl chloride, which was used in the subsequent step without further purification.
(2) A suspension of magnesium chloride (1.74 g) in dichloromethane (30 ml) was cooled to 0° C., and thereto were added t-butyl acetoacetate (3.03 ml) and pyridine (2.96 ml), and successively was added a solution of the above 4-ethylphenylacetyl chloride in dichloromethane (30 ml). The mixture was stirred at the same temperature for 2.5 hours, and an aqueous citric acid solution was added thereto. The mixture was extracted with chloroform. The extract was washed with brine, and dried over sodium sulfate. The solvent was evaporated under reduced pressure. The residue was purified by silica gel column chromatography (hexane:ethyl acetate=15:1) to give t-butyl 2-acetyl-4-(4-ethylphenyl)-3-oxobutyrate (4.75 g) as pale yellow oil. APCI-Mass m/Z 322 (M+NH$_4$).
(3) A solution of the above t-butyl 2-acetyl-4-(4-ethylphenyl)-3-oxobutyrate in trifluoroacetic acid (60 ml) was stirred at room temperature for 2 hours. The solvent was evaporated under reduced pressure, and the residue was dissolved in ethyl acetate, and the mixture was washed successively with a saturated aqueous sodium hydrogen carbonate solution and brine. The mixture was dried over sodium sulfate, and the solvent was evaporated under reduced pressure to give 1-(4-ethylphenyl)-4-hydroxy-3-penten-2-one (4.00 g) as yellow oil. APCI-Mass m/Z 205 (M+H).
(4) A solution of the above 1-(4-ethylphenyl)-4-hydroxy-3-penten-2-one (3.98 g) and hydrazine hydrate (4.0 ml) in toluene (20 ml) was stirred under heating at 100° C. for 1.5 hours. The reaction mixture was cooled to room temperature, and washed successively with water and brine, and dried over sodium sulfate. The solvent was evaporated under reduced pressure. The residue was purified by silica gel column chromatography (chloroform:ethyl acetate=2:1) to give 3-(4-ethylphenylmethyl)-5-methyl-1H-pyrazole (3.12 g) as yellow oil. APCI-Mass m/Z 201 (M+H).

Reference Example 107

3-(4-Ethylphenylmethyl)-6-hydroxypyridine (1) To a solution of 6-chloronicotinoyl chloride (10.0 g) and N,O-dimethylhydroxyamine hydrochloride (6.65 g) in dichloromethane (200 ml) was added dropwise triethylamine (17.2 g) at 0° C. Subsequently the mixture was stirred at room temperature overnight. The mixture was washed successively with water, 5% aqueous citric acid solution, water and brine, and then, dried over sodium sulfate. The solvent was evaporated under reduced pressure to give N-methoxy-N-methyl-6-chloronicotinamide (11.73 g) as pale yellow oil. APCI-Mass m/Z 201/203 (M+H).
(2) A solution of the N-methoxy-N-methyl-6-chloronicotineamide (4.2 g) in tetrahydrofuran (40 ml) was cooled to 0° C., and thereto was added dropwise 4-ethylphenylmagnesium bromide (0.5 M tetrahydrofuran solution, 55 ml). The mixture was stirred at 0° C. for 4 hours, and then at the room temperature for 10 minutes. The reaction mixture was cooled again to 0° C., and added thereto was 10% aqueous hydrochloric acid solution. The mixture was extracted with ethyl acetate, and washed with brine and dried over sodium sulfate. The solvent was evaporated under reduced pressure, and the residue was purified by silica gel column chromatography (hexane:ethyl acetate=20:1) to give 6-chloro-3-pyridyl 4-ethylphenyl ketone (3.68 g) as colorless crystals. APCI-Mass m/Z 246/248 (M+H).
(3) The above 6-chloro-3-pyridyl 4-ethylphenyl ketone (1.68 g) was dissolved in N-methyl-2-pyrrolidinone (20 ml), and thereto were added benzylalcohol (815 ml) and 60% sodium hydride (275 mg). The mixture was stirred at room temperature for 6 hours, and then at 90° C. for one hour. The reaction mixture was cooled to room temperature, and water was added thereto, and the mixture was extracted with ethyl acetate. The extract was washed with water and subsequently with brine, and dried over sodium sulfate. The solvent was evaporated under reduced pressure, and the residue was purified by silica gel column chromatography (hexane:ethyl acetate=100:0-95:5) to give 6-benzyloxy-3-pyridyl 4-ethylphenyl ketone (1.68 g) as colorless oil. APCI-Mass m/Z 318 (M+H).
(4) The above 6-benzyloxy-3-pyridyl 4-ethylphenyl ketone (865 mg) was dissolved in ethylene glycol (8.5 ml), and thereto were added hydrazine hydrate (0.44 ml) and potassium hydroxide (550 mg). The mixture was stirred under heating at 190° C. for 8 hours. The reaction mixture was cooled to room temperature, and water was added thereto, and the mixture was extracted with ethyl acetate. The extract was washed with water three times, and subsequently with brine, and dried over sodium sulfate. The solvent was evaporated under reduced pressure, and the residue was purified by silica gel column chromatography (hexane:ethyl acetate=100:0-0:100) to give the desired 3-(4-ethylphenylmethyl)-6-hydroxypyridine (256 mg) as colorless powder. APCI-Mass m/Z 214 (M+H).

Reference Example 108

3-(4-Ethylphenylmethyl)-2-hydroxypyridine (1) 2-Chloronicotinoyl chloride was treated in a manner similar to Reference Example 107-(1), (2) and (3) to give 2-benzyloxy-3-pyridyl 4-ethylphenyl ketone as colorless oil. APCI-Mass m/Z 318 (M+H).

(2) The above 2-benzyloxy-3-pyridyl 4-ethylphenyl ketone (1.69 g) was dissolved in ethanol (15 ml), and thereto was added sodium borohydride (403 mg), and the mixture was stirred at room temperature for 3 hours. The solvent was evaporated under reduced pressure, and the residue was dissolved in ethyl acetate. The mixture was washed with water and successively with brine, and dried over sodium sulfate. The solvent was evaporated under reduced pressure to give crude 2-benzyloxy-3-pyridyl-4-ethylphenylmethanol as colorless oil, which was used in the subsequent step without further purification.

(3) The above 2-benzyloxy-3-pyridyl-4-ethylphenylmethanol was dissolved in methanol (10 ml), and thereto were added concentrated hydrochloric acid (1.0 ml) and 10% palladium-carbon (500 mg). The mixture was stirred at room temperature for 15 hours under hydrogen atmosphere under normal pressure. Insoluble materials were filtered off, and the solvent was evaporated under reduced pressure. The residue was dissolved in ethyl acetate, and the solution was washed with water and successively with brine, and dried over sodium sulfate. The solvent was evaporated under reduced pressure, and the residue was purified by silica gel column chromatography (chloroform:methanol=100:0-97:3) to give the desired 3-(4-ethylphenylmethyl)-2-hydroxypyridine (307 mg) as a pale brown solid. APCI-Mass m/Z 214 (M+H).

Reference Example 109

3-(4-Ethylphenylmethyl)-1H-indole (1) To a solution of indole (6.00 g) in methanol (60 ml) were added sodium hydroxide (2.25 g) and 4-ethylbenzaldehyde (7.56 g), and the mixture was stirred at room temperature for 3 days under argon atmosphere. Added thereto was water, and methanol was evaporated under reduced pressure. The residue was extracted with diethyl ether, and the extract was washed with water, and dried over magnesium sulfate. The solvent was evaporated under reduced pressure and the residue was purified by silica gel column chromatography (hexane:ethyl acetate=98:2-70:30) to give 4-ethylphenyl-(1H-indol-3-yl)methanol (2.10 g) as a colorless solid. APCI-Mass m/Z 234 (M+H—H$_2$O).

(2) The above 4-ethylphenyl-(1H-indol-3-yl)methanol was treated in a manner similar to Reference Example 1-(2) to give the desired 3-(4-ethylphenylmethyl)-1H-indole as colorless crystals. APCI-Mass m/Z 236 (M+H).

Reference Example 110

3-(4-Ethylphenylmethyl)-1H-indazole (1) A mixture of zinc powder (712 mg) and dibromoethane (0.04 ml) in N,N-dimethylformamide (2.5 ml) were stirred under heating at 70° C. for 10 minutes under argon atmosphere. The reaction mixture was cooled to room temperature, and chlorotrimethylsilane (0.04 ml) was added thereto, and the mixture was stirred at room temperature for 30 minutes. To the activated zinc solution was added dropwise a solution of 4-ethylbenzyl bromide (1.74 g) in N,N-dimethylformamide (10 ml) at 0° C. over a period of 2 hours. Subsequently, the mixture was stirred at 0° C. for 2 hours, to prepare a solution of 4-ethylbenzylzinc bromide in N,N-dimethylformamide, which was used in the subsequent step without further purification.

(2) A solution of tris(dibenzylideneacetone)dipalladium (0) (167 mg) and tri(2-furyl)phosphine (135 mg) in tetrahydrofuran (20 ml) was stirred at room temperature for 5 minutes under argon atmosphere. Thereto were added 1-t-butoxycarbonyl-3-iodo-1H-indazole (2.0 g) and the above 4-ethylbenzylzinc bromide (N,N-dimethylformamide solution) at 0° C., and the mixture was stirred at room temperature for 5 hours. The reaction mixture was poured into water, and the mixture was extracted with diethyl ether. The extract was washed with water and dried over magnesium sulfate. The solvent was evaporated under reduced pressure, and the residue was purified by silica gel column chromatography (hexane:ethyl acetate=100:0-92:8) to give 1-t-butoxycarbonyl-3-(4-ethylphenylmethyl)-1H-indazole (1.37 g) as colorless oil. APCI-Mass m/Z 337 (M+H).

(3) The above 1-t-butoxycarbonyl-3-(4-ethylphenylmethyl)-1H-indazole (1.35 g) was dissolved in methanol (15 ml), and added thereto was 28% sodium methoxide solution (methanol solution, 1.0 ml), and the mixture was stirred at room temperature for one hour. Added thereto was an aqueous citric acid solution, and the mixture was extracted with ethyl acetate. The extract was washed successively with water and brine, and dried over magnesium sulfate. The solvent was evaporated under reduced pressure, and the residue was crystallized from hexane to give the desired 3-(4-ethylphenylmethyl)-1H-indazole (800 mg) as colorless crystals. APCI-Mass m/Z 237 (M+H).

Reference Example 111

5-Bromo-2-methyl-1-(5-(4-trifluoromethylphenyl)-2-thienylmethyl)benzene (1) 4-Bromobenzotrifluoride and thiophene-2-boronic acid were treated in a manner similar to Reference Example 20-(1) to give 2-(4-trifluoromethylphenyl)thiophene as colorless crystals.

(2) The above 2-(4-trifluoromethylphenyl)thiophene and 5-bromo-2-methylbenzaldehyde obtained in Reference Example 4 were treated in a manner similar to Reference Example 7 to give the desired 5-bromo-2-methyl-1-(5-(4-trifluoromethylphenyl)-2-thienylmethylbenzene as colorless crystals. APCI-Mass m/Z 425/427 (M+H+MeOH).

Reference Example 112

5-Bromo-2-methyl-1-(5-(3-trifluoromethylphenyl)-2-thienylmethyl)benzene (1) 3-Bromobenzotrifluoride and thiophene-2-boronic acid were treated in a manner similar to Reference Example 20-(1) to give 2-(3-trifluoromethylphenyl)thiophene as colorless oil.

(2) The above 2-(3-trifluoromethylphenyl)thiophene and 5-bromo-2-methylbenzaldehyde obtained in Reference Example 4 were treated in a manner similar to Reference Example 7 to give the desired 5-bromo-2-methyl-1-(5-(3-trifluoromethylphenyl)-2-thienylmethyl)benzene as colorless oil.

Reference Example 113

2-(4-Ethylphenyl)thiophene

2-Bromothiophene and 4-ethylphenylboronic acid were treated in a manner similar to Reference Example 20-(1) to give the target compound.

Reference Example 114

2-(4-Methylphenyl)thiophene

2-Bromothiophene and 4-methylphenylboronic acid were treated in a manner similar to Reference Example 20-(1) to give the target compound.

Reference Example 115

2-(2,3-Dihydro-5-benzo[b]furanyl)thiophene (1) 5,7-Dibromo-2,3-dihydrobenzo[b]furan (see WO 02/070020) (3.0 g) in diethyl ether was cooled to −78° C. under argon atmosphere, and thereto was added dropwise n-butyl lithium (2.44 M hexane solution, 5.09 ml). The mixture was stirred at the same temperature for 30 minutes, and poured into a saturated aqueous ammonium chloride solution. The mixture was extracted with diethyl ether, and dried over magnesium sulfate. The solvent was evaporated under reduced pressure to give 5-bromo-2,3-dihydrobenzo[b]furan (2.0 g) as pale yellow crystals, which was used in the subsequent step without further purification.
(2) The above 5-bromo-2,3-dihydrobenzo[b]furan and thiophene-2-boronic acid were treated in a manner similar to Reference Example 20-(1) to give the desired 2-(2,3-dihydro-5-benzo[b]furanyl)thiophene as pale yellow crystals. APCI-Mass m/Z 203 (M+H).

Reference Example 116

4-Bromo-2-(5-chloro-2-thienylmethyl)-1-fluoronaphthalene (1) A solution of 2,2,6,6-tetramethylpiperidine (1.04 g) in tetrahydrofuran (15 ml) was cooled to −78° C. under argon atmosphere, and thereto was added dropwise n-butyl lithium (1.58 M hexane solution, 4.43 ml). The reaction mixture was stirred at the same temperature for 30 minutes, and thereto was added dropwise a solution of 1-bromo-4-fluoronaphthalene (1.50 g) in tetrahydrofuran (12 ml) at −78° C. The mixture was stirred at the same temperature for one hour, and thereto was added dropwise a solution of 5-chloro-2-thiophenecarboxaldehyde (1.07 g) in tetrahydrofuran (11 ml) at −78° C. The mixture was stirred at the same temperature for 30 minutes, and thereto was added a saturated aqueous ammonium chloride solution, and the reaction mixture was extracted with ethyl acetate. The extract was washed with brine, dried over sodium sulfate, and the solvent was evaporated under reduced pressure. The residue was purified by an aminosilane-treated silica gel column chromatography (hexane:ethyl acetate=3:1) to give 4-bromo-1-fluoro-2-naphthyl-5-chloro-2-thienylmethanol (2.00 g) as pale yellow powder. APCI-Mass m/Z 353/355 (M+H—H$_2$O).
(2) The above 4-bromo-1-fluoro-2-naphthyl-5-chloro-2-thienylmethanol was treated in a manner similar to Reference Example 1-(2) to give the desired 4-bromo-2-(5-chloro-2-thienylmethyl)-1-fluoronaphthalene as a yellow solid.

Reference Example 117

5-Bromo-2,4-dimethyl-1-(5-phenyl-2-thienylmethyl)benzene (1) 2,4-dimethylbenzoic acid (20.0 g) was suspended in chloroform (100 ml), and thereto were added oxalyl chloride (6.8 ml) and N,N-dimethylformamide (2 drops). The mixture was stirred at room temperature overnight. The solvent was evaporated under reduced pressure, and the residue was dissolved in methanol (200 ml). The mixture was stirred at room temperature for 3 hours. The solvent was evaporated under reduced pressure, and the residue was dissolved in ethyl acetate. The mixture was washed successively with a saturated aqueous sodium hydrogen carbonate solution and brine, and dried over sodium sulfate. The solvent was evaporated under reduced pressure to give methyl 2,4-dimethylbenzoate as pale yellow oil, which was used in the subsequent step without further purification.
(2) To a mixture of the above methyl 2,4-dimethylbenzoate (19.75 g) and activated aluminum neutral oxide (120 g) was added dropwise bromine (9.25 ml) while stirring at room temperature. The mixture was stirred at room temperature for 8 hours, and diluted with diethyl ether (1000 ml). Insoluble materials were filtered off, and washed with diethyl ether (500 ml). The combined filtrate was washed successively with 10% aqueous sodium thiosulfate solution, a saturated aqueous sodium hydrogen carbonate solution and brine. The filtrate was dried over magnesium sulfate, and the solvent was evaporated under reduced pressure. The residue was crystallized from methanol (40 ml) to give methyl 5-bromo-2,4-dimethylbenzoate (6.34 g) as colorless crystals. APCI-Mass m/Z 243/245 (M+H).
(3) The above methyl 5-bromo-2,4-dimethylbenzoate was treated in a manner similar to Reference Example 4-(1) to give 5-bromo-2,4-dimethylbenzoic acid as colorless crystals. ESI-Mass m/Z 227/229 (M−H)
(4) The above 5-bromo-2,4-dimethylbenzoic acid and 2-phenylthiophene were treated in a manner similar to Reference Example 5 to give 5-bromo-2,4-dimethyl-1-(5-phenyl-2-thienylmethyl)benzene as colorless crystals. APCI-Mass m/Z 357/359 (M+H).

Reference Example 118

5-Bromo-1-(5-phenyl-2-thienylmethyl)-2-trifluoromethylbenzene (1) 5-Bromo-2-iodobenzoic acid (see Jorg Frahn, A.-Dieter Schluter *Synthesis* 1997, 1301-1304) was treated in a manner similar to Reference Example 117-(1) to give methyl 5-bromo-2-iodobenzoate as a brown solid.
(2) To a solution of the above methyl 5-bromo-2-iodobenzoate (4.65 g) in N-methyl-2-pyrrolydinone (20 ml) were added copper (I) bromide (235 mg) and methyl 2,2-difluoro-2-(fluorosulfonyl)acetate (2.6 ml), and the mixture was stirred under heating at 120° C. for 1.5 hours. The reaction mixture was cooled, and added thereto were 10% aqueous hydrochloric acid solution and ethyl acetate. Insoluble materials were filtered off, and an organic layer of the filtrate was washed with water for 4 times, and subsequently washed with a saturated aqueous sodium hydrogen carbonate solution and brine. The filtrate was dried over sodium sulfate, and the solvent was evaporated under reduced pressure. The residue was purified by silica gel column chromatography (hexan:ethyl acetate=80:1) to give methyl 5-bromo-2-trifluoromethylbenzoate (3.55 g) as colorless oil.
(3) The above methyl 5-bromo-2-trifluoromethylbenzoate was treated in a manner similar to Reference Example 4-(1) to give 5-bromo-2-trifluoromethylbenzoic acid as pale brown crystals. ESI-Mass m/Z 267/269 (M−H).
(4) The above 5-bromo-2-trifluoromethylbenzoic acid and 2-phenylthiophene were treated in a manner similar to Reference Example 5-(1) to give 5-bromo-2-trifluoromethylphenyl 5-phenyl-2-thienyl ketone as pale yellow crystals. APCI-Mass m/Z 411/413 (M+H).

(5) To a mixed solution of the above 5-bromo-2-trifluoromethylphenyl 5-phenyl-2-thienyl ketone (670 mg) in methanol (20 ml)-tetrahydrofuran (10 ml) was added sodium borohydride (62 mg), and the mixture was stirred at room temperature for 3 hours. The solvent was evaporated under reduced pressure, and the residue was dissolved in chloroform (10 ml)acetonitrile (20 ml). Thereto was added triethylsilane (0.78 ml), and the mixture was cooled to 0° C. Thereto was added dropwise boron trifluoride•diethyl ether complex (0.52 ml). The mixture was stirred at room temperature for 45 minutes, and added thereto was a saturated aqueous sodium hydrogen carbonate solution, and the mixture was extracted with ethyl acetate. The extract was washed with brine, and dried over sodium sulfate. The solvent was evaporated under reduced pressure, and the residue was purified by silica gel column chromatography (hexane) to give the desired 5-bromo-1-(5-phenyl-2-thienylmethyl)-2-trifluoromethylbenzene (565 mg) as colorless oil.

Reference Example 119

5-Bromo-1-(5-(3-ethylphenyl)-2-thienylmethyl)-2-methylbenzene (1) 1-Bromo-3-ethylbenzene and thiophene-2-boronic acid were treated in a manner similar to Reference Example 20-(1) to give 2-(3-ethylphenyl)thiophene as a pale yellow liquid.
(2) The above 2-(3-ethylphenyl)thiophene and 5-bromo-2-methylbenzaldehyde obtained in Reference Example 4 were treated in a manner similar to Reference Example 9 to give 5-bromo-1-(5-(3-ethylphenyl)-2-thienylmethyl)-2-methylbenzene as pale yellow oil. APCI-Mass m/Z 371/373 (M+H).

Reference Example 120

5-Bromo-2-methyl-1-(5-(2-pyridyl)-2-thienylmethyl)benzene (1) 2-(2-Pyridyl)thiophene and 5-bromo-2-methylbenzaldehyde obtained in Reference Example 4 were treated in a manner similar to Reference Example 7-(1) to give 5-bromo-2-methylphenyl-5-(2-pyridyl)-2-thienylmethanol as colorless oil. APCI-Mass m/Z 360/362 (M+H).
(2) A solution of the above 5-bromo-2-methylphenyl-5-(2-pyridyl)-2-thienylmethanol (1.59 g) in trifluoroacetic acid (40 ml) was cooled to 0° C., and thereto were added gradually sodium triacetoxyborohydride (4.68 g). The mixture was stirred at room temperature for one hour, and cooled again to 0° C. 10% aqueous sodium hydroxide solution was added thereto to basify the reaction mixture. The mixture was extracted with ethyl acetate, and the extract was washed with brine, and dried over sodium sulfate. The solvent was evaporated under reduced pressure and the residue was purified by silica gel column chromatography (hexane:ethyl acetate=3:1) to give the desired 5-bromo-2-methyl-1-(5-(2-pyridyl)-2-thienylmethyl)benzene (1.38 g) as a colorless solid. APCI-Mass m/Z 344/346 (M+H).

Reference Example 121

2-(5-Fluoro-2-thienyl)thiophene 2,2'-Bithiophene (7.40 g) in tetrahydrofuran (90 ml) was cooled to −78° C. under argon atmosphere, and thereto were added dropwise n-butyl lithium (1.59 M hexane solution, 28.0 ml). The mixture was stirred at 0° C. for one 30 minutes, and cooled again to −78° C. Added thereto was N-fluorobenzenesulfonimide (15.5 g), and the mixture was gradually warmed, and stirred at room temperature for 17 hours. The reaction mixture was poured into ice-cold water, and the solution was extracted with hexane twice, and the extract was washed successively with water and brine, and dried over sodium sulfate. The solvent was evaporated under reduced pressure and the residue was purified by silica gel column chromatography (hexane) to give 2-(5-fluoro-2-thienyl)thiophene (5.89 g) as colorless oil.

Reference Example 122

5-Bromo-2-methyl-1-(5-(3-pyridyl)-2-thienylmethyl)benzene 2-(3-Pyridyl)thiophene was treated in a manner similar to Reference Example 120 to give the target compound as colorless crystals. APCI-Mass m/Z 344/346 (M+H).

Reference Example 123

5-Bromo-1-(5-(4-methoxyphenyl)-2-thienylmethyl)-2-methylbenzene (1) p-Bromoanisole and thiophene-2-boronic acid were treated in a manner similar to Reference Example 20-(1) to give 2-(4-methoxyphenyl)thiophene as a pale yellow solid. APCI-Mass m/Z 191 (M+H).
(2) The above 2-(4-methoxyphenyl)thiophene and 4-bromo-2-methylbenzoic acid obtained in Reference Example 4-(1) were treated in a manner similar to Reference Example 5 to give 5-bromo-1-(5-(4-methoxyphenyl)-2-thienylmethyl)-2-methylbenzene as a pale yellow solid. APCI-Mass m/Z 373/375 (M+H).

Reference Example 124

5-bromo-2-methyl-1-(5-(1,2-Methylenedioxybenzen-4-yl)-2-thienylmethyl)benzene

4-Bromo-1,2-(methylenedioxy)benzene was treated in a manner similar to Reference Example 119 to give the target compound as colorless powder.

Reference Example 125

5-Bromo-2-chloro-1-(2-(5-phenyl-2-thienyl)ethyl)benzene (1) To a solution of 5-bromo-2-chlorobenzyl alcohol (10.66 g) in toluene (100 ml) solution were added thionyl chloride (10 ml), and pyridine (2 drops), and the mixture was stirred under heating at 100° C. overnight. The solvent was evaporated under reduced pressure, and the residue was dissolved in ethyl acetate. The solution was washed successively with water, a 10% aqueous hydrochloric acid solution, a saturated aqueous sodium hydrogen carbonate solution and brine, and dried over sodium sulfate. The solvent was evaporated under reduced pressure to give 5-bromo-2-chlorobenzyl chloride as pale yellow crystals, which was used in the subsequent step without further purification.
(2) The above 5-bromo-2-chlorobenzyl chloride was dissolved in acetonitrile (100 ml), and the mixture was cooled to 0° C. Added thereto was tetraethylammonium cyanide (8.8 g), and the mixture was stirred at room temperature for 2 hours. The solvent was evaporated under reduced pressure, and the residue was dissolved in ethyl acetate. The solution was washed successively with water, 10% aqueous hydrochloric acid solution, a saturated aqueous sodium hydrogen carbonate solution and brine, and dried over sodium sulfate. The solvent was evaporated under reduced pressure to give 5-bromo-2-chlorophenylacetonitrile as a pale yellow solid, which was used in the subsequent step without further purification.

(3) The above 5-bromo-2-chlorophenylacetonitrile was added to water (90 ml)-sulfuric acid (75 ml), and the mixture was stirred under heating at 160° C. overnight. The mixture was further diluted with water, and cooled to 0° C. The solvent was removed by decant, and the residue was dissolved in diethyl ether. The solution was washed with water and brine, and extracted with 10% sodium hydroxide. To the extract was added concentrated hydrochloric acid to make the solution acidic. The precipitates were collected by filtration, and purified by silica gel column chromatography (chloroform) to give 5-bromo-2-chlorophenylacetic acid (6.67 g) as colorless crystals. ESI-Mass m/Z 247/249 (M−H).

(4) The above 5-bromo-2-chlorophenylacetic acid was treated in a manner similar to Reference Example 118-(4) and (5) to give the desired 5-bromo-2-chloro-1-(2-(5-phenyl-2-thienyl)ethyl)benzene as a pale yellow solid. APCI-Mass m/Z 377/379 (M+H).

Reference Example 126

5-Bromo-1-(5-(6-fluoro-2-pyridyl)-2-thienylmethyl)-2-methylbenzene (1) 2-Bromo-6-fluoropyridine and thiophene-2-boronic acid were treated in a manner similar to Reference Example 20-(1) to give 2-(6-fluoro-2-pyridyl)thiophene as yellow oil.

APCI-Mass m/Z 180 (M+H).

(2) The above 2-(6-fluoro-2-pyridyl)thiophene was treated in a manner similar to Reference Example 120 to give the desired 5-bromo-1-(5-(6-fluoro-2-pyridyl)-2-thienylmethyl)-2-methylbenzene as a colorless solid. APCI-Mass m/Z 362/364 (M+H).

Reference Example 127

5-Bromo-2-methyl-1-(5-trifluoromethyl-2-thienylmethyl)benzene

2-Trifluoromethylthiophene (see Japanese Unexamined Patent Publication No. 2000-34239) and 5-bromo-2-methylbenzaldehyde obtained in Reference Example 4 were treated in a manner similar to Reference Example 7 to give the target compound as colorless oil.

Reference Example 128

5-Bromo-1-(5-(5-fluoro-2-thienyl)-2-thienylmethyl)-2-methylbenzene

5-Bromo-2-methylbenzoic acid obtained in Reference Example 4-(1) and 2-(5-fluoro-2-thienyl)thiophene obtained in Reference Example 121 were treated in a manner similar to Reference Example 5 to give the target compound as a colorless solid. APCI-Mass m/Z 367/369 (M+H).

Reference Example 129

3-Bromo-2-fluoro-6-methyl-1-(5-phenyl-2-thienylmethyl)benzene

4-Bromo-3-fluorotoluene and 5-phenyl-2-thiophenecarboxaldehyde were treated in a manner similar to Reference Example 116 to give the target compound as pale blue powders. APCI-Mass m/Z 361/363 (M+H).

Reference Example 130

5-Bromo-2-chloro-1-(2-phenyl-5-thiazolylmethyl)benzene (1) 5-Bromo-2-chlorophenylacetic acid (2.0 g) obtained in Reference Example 125-(3) was dissolved in dichloromethane (40 ml), and thereto were added oxalyl chloride (0.77 ml) and N,N-dimethylformamide (one drop) at 0° C. The mixture was stirred at room temperature overnight. The solvent was evaporated under reduced pressure to give 5-bromo-2-chlorophenylacetyl chloride, which was used in the subsequent step without further purification.

(2) A solution of potassium t-butoxide (1.35 g) in tetrahydrofuran (20 ml) was cooled to 0° C., and thereto was added methyl isocyanoacetate (1.33 ml). Then, a solution of the above 5-bromo-2-chlorophenylacetyl chloride in tetrahydrofuran (20 ml) was added thereto, and the mixture was stirred at 0° C. for 2 hours, and then at room temperature overnight. The mixture was cooled again to 0° C. 10% aqueous citric acid solution was added thereto, and the mixture was extracted with ethyl acetate. The extract was washed with water and brine, and dried over sodium sulfate. The solvent was evaporated under reduced pressure and the residue was purified by silica gel column chromatography (hexane:ethyl acetate=3:1) to give 5-bromo-2-chloro-1-(4-methoxycarbonyl-5-oxazolylmethyl)benzene (1.12 g) as a yellow solid. APCI-Mass m/Z 330/332 (M+H).

(3) The above 5-bromo-2-chloro-1-(4-methoxycarbonyl-5-oxazolylmethyl)benzene (1.37 g) was heated under reflux in 6N aqueous hydrochloric acid solution (20 ml) overnight. The solvent was evaporated under reduced pressure, and the residue was dissolved in methanol, and treated with carbon powder. The carbon powder was filtered off, and the filtrate was evaporated under reduced pressure to give crude 1-(3-amino-2-oxopropyl)-5-bromo-2-chlorobenzene•hydrochloride (1.73 g) as a pale brown solid, which was used in the subsequent step without further purification. APCI-Mass m/Z 262/264 (M+H).

(4) A mixed solution of the above 1-(3-amino-2-oxopropyl)-5-bromo-2-chlorobenzene•hydrochloride (1.70 g) in ethyl acetate (30 ml)-water (15 ml) was cooled to 0° C. Added thereto were benzoyl chloride (0.99 ml) and sodium hydrogen carbonate (2.39 g), and the mixture was stirred at the same temperature for 3 hours. The organic layer was washed with brine, and dried over sodium sulfate. The solvent was evaporated under reduced pressure and the residue was purified by silica gel column chromatography (chloroform:ethyl acetate=95:5) to give 1-(3-benzoylamino-2-oxopropyl)-5-bromo-2-chlorobenzene (710 mg) as a colorless solid. APCI-Mass m/Z 366/368 (M+H).

(5) To a solution of the above 1-(3-benzoylamino-2-oxopropyl)-5-bromo-2-chlorobenzene (710 mg) in toluene (20 ml) was added Lawesson reagent (2.35 g), and the mixture was heated under reflux for 2 hours. The reaction mixture was cooled, and the solvent was evaporated under reduced pressure. The residue was purified by silica gel column chromatography (hexane:ethyl acetate=90:10) to give the desired 5-bromo-2-chloro-1-(2-phenyl-5-thiazolylmethyl)benzene (512 mg) as a colorless solid. APCI-Mass m/Z 364/366 (M+H).

Reference Example 131 t-Butyl 5-bromo-2-chlorobenzoic acid

To a solution of 5-bromo-2-chlorobenzoic acid (11.75 g) in N,N-dimethylformamide (50 ml) was added 1,1'-carbonyldiimidazole (8.10 g), and the mixture was stirred under heating at 40° C. for one hour. Thereto were added t-butanol (7.40 g) and 1,8-diazabicyclo[5.4.0]undec-7-ene (7.60 g), and the mixture was further stirred under heating at 40° C. overnight. The mixture was diluted with diethyl ether, and washed successively with water (3 times), 2% aqueous hydrochloric acid solution (twice), a saturated aqueous sodium hydrogen carbonate solution and brine. The mixture was dried over magnesium sulfate, and the solvent was evaporated under reduced pressure to give t-butyl 5-bromo-2-chlorobenzoate (12.53 g) as pale yellow oil.

Reference Example 132

5-Bromo-2-chloro-1-(6-ethoxybenzo[b]thiophen-2-ylmethyl)benzene (1) A solution of 5-bromo-2-chloro-1-(6-methoxybenzo[b]thiophen-2-ylmethyl)benzene (2.70 g) obtained in Reference Example 46 in dichloromethane (27 ml) was cooled to 0° C. under argon atmosphere, and thereto was added dropwise boron tribromide (0.83 ml). The mixture was warmed to room temperature, and stirred for 30 minutes. The mixture was basified with a saturated aqueous sodium hydrogen carbonate solution, and subsequently, the reaction mixture was made acidic with a saturated aqueous citric acid solution. The mixture was extracted with chloroform, and dried over magnesium sulfate. The solvent was evaporated under reduced pressure. The residue was crystallized from chloroform-hexane to give 5-bromo-2-chloro-1-(6-hydroxybenzo[b]thiophen-2-ylmethyl)benzene (2.01 g) as pale green crystals. ESI-Mass m/Z 351/353 (M−H).
(2) The above 5-bromo-2-chloro-1-(6-hydroxybenzo[b]thiophen-2-ylmethyl)benzene (500 mg) was dissolved in N,N-dimethylformamide (5 ml), and thereto were added iodoethane (0.23 ml) and potassium carbonate (390 mg). The mixture was stirred at room temperature for 2 days. Added thereto was water, and the mixture was extracted with ethyl acetate. The extract was washed with water and brine, and dried over magnesium sulfate. The solvent was evaporated under reduced pressure, and the residue was purified by silica gel column chromatography (hexane:ethyl acetate=98:2-80:20) to give the desired 5-bromo-2-chloro-1-(6-ethoxybenzo[b]thiophen-2-ylmethyl)benzene (492 mg) as pale pink oil. APCI-Mass m/Z 381/383 (M+H).

Reference Example 133

5-Bromo-2-chloro-3-(5-phenyl-2-thienylmethyl)thiophene

5-Bromo-2-chloro-3-thiophenecarboxylic acid (see Japanese Unexamined Patent Publication No. 10-324632) and 2-phenylthiophene were treated in a manner similar to Reference Example 5 to give the target compound as a colorless solid. APCI-Mass m/Z 367/369 (M+H).

Reference Example 134

6-Fluoro-2-pyridylboronic acid pinacol ester

A solution of 2-bromo-6-fluoropyridine (1.0 g) in tetrahydrofuran (10 ml) was cooled to −78° C. under argon atmosphere, and thereto was added a solution of n-butyl lithium (2.59 M hexane solution, 2.24 ml) in tetrahydrofuran (10 ml). The mixture was stirred at the same temperature for 45 minutes, and thereto was added dropwise a solution of triisopropoxyborane (1.28 g) in tetrahydrofuran (10 ml). The mixture was stirred at the same temperature for 2 hours, warmed, and further stirred at room temperature for one hour. Subsequently, a solution of pinacol (0.91 g) in tetrahydrofuran (10 ml) was added dropwise thereto, and stirred at room temperature for 20 minutes. Insoluble materials were filtered off. The filtrate was extracted with 2.5% sodium hydroxide, and the extract was cooled to 0° C., and was made weakly acidic with 2N aqueous hydrochloric acid solution. It was extracted with diethyl ether, washed with a small amount of brine, and dried over magnesium sulfate. The solvent was evaporated under reduced pressure and the residue was solidified with hexane to give 6-fluoro-2-pyridylboronic acid pinacol ester (850 mg) as a colorless solid. APCI-Mass m/Z 224 (M+H).

Reference Example 135

5-Bromo-2-chloro-1-(6-phenyl-3-pyridylmethyl)benzene (1) 5-Bromo-2-chlorobenzoic acid was treated in a manner similar to Reference Example 4-(2) to give N-methoxy-N-methyl-5-bromo-2-chlorobenzamide as a colorless solid. APCI-Mass m/Z 278/280 (M+H).
(2) The above N-methoxy-N-methyl-5-bromo-2-chlorobenzamide and 2,5-dibromopyridine were treated in a manner similar to Reference Example 31-(4) to give 5-bromo-2-chlorophenyl 6-bromo-3-pyridyl ketone as a pale yellow solid. APCI-Mass m/Z 374/376 (M+H).
(3) The above 5-bromo-2-chlorophenyl 6-bromo-3-pyridyl ketone and phenylboronic acid were treated in a manner similar to Reference Example 20-(1) to give 5-bromo-2-chlorophenyl 6-phenyl-3-pyridyl ketone as yellow crystals. APCI-Mass m/Z 372/374 (M+H).
(4) The above 5-bromo-2-chlorophenyl 6-phenyl-3-pyridyl ketone was treated in a manner similar to Reference Example 14-(1) to give the desired 5-bromo-2-chloro-1-(6-phenyl-3-pyridylmethyl)benzene as colorless crystals. APCI-Mass m/Z 358/360 (M+H).

Reference Example 136

5-Bromo-2-chloro-1-(6-isopropyloxybenzo[b]thiophen-2-ylmethyl)benzene

5-Bromo-2-chloro-1-(6-hydroxybenzo[b]thiophen-2-ylmethyl)benzene obtained in Reference Example 132-(1) and 2-iodopropane were treated in a manner similar to Reference Example 132-(2) to give the titled compound. APCI-Mass m/Z 395/397 (M+H).

Reference Example 137

4-Bromo-1-fluoro-2-(5-(2-pyridyl)-2-thienylmethyl) naphthalene (1) A solution of 2,2,6,6-tetramethylpiperidine (4.13 ml) in tetrahydrofuran (40 ml) was cooled to −78° C. under argon atmosphere, and added dropwise thereto was n-butyl lithium (2.44 M hexane solution, 10.0 ml). The mixture was stirred at the same temperature for 30 minutes, and added dropwise thereto at −78° C. was a solution of 1-bromo-4-fluoronaphthalene (5.0 g) in tetrahydrofuran (20 ml). The mixture was stirred at the same temperature for 1 hour, and added dropwise thereto at −78° C. was N,N-dimethylformamide (5.16 ml). The mixture was stirred at the same temperature for 1 hour, and added thereto was a saturated aqueous ammonium chloride solution, and the mixture was extracted with ethyl acetate. The extract was washed with water and dried over magnesium sulfate, and the solvent was evaporated under reduced pressure. The residue was crystallized from diisopropyl ether and hexane to give 4-bromo-1-fluoro-2-naphthaldehyde (4.43 g) as pale yellow crystals. APCI-Mass m/Z 267/269 (M+NH$_4$).
(2) The above 4-bromo-1-fluoro-2-naphthaldehyde and 2-(2-pyridyl)thiophene were treated in a manner similar to Reference Example 120 to give the desired 4-bromo-1-fluoro-2-(5-(2-pyridyl)-2-thienylmethyl)naphthalene as colorless powder. APCI-Mass m/Z 398/400 (M+H).

Reference Example 138

5-Bromo-2-chloro-1-(6-ethyl-3-pyridylmethyl)benzene (1) 5-Bromo-2-chlorophenyl 6-bromo-3-pyridyl ketone (3.2 g) from Reference Example 135-(2) was dissolved in tetrahydrofuran (80 ml), and added thereto were triethylaluminium (1.0 M hexane solution, 9.9 ml), tetrakis(triphenylphosphine)palladium(0) (570 mg) and cerium(III) chloride (7.3 g), and the mixture was stirred at 30° C. for 1.5 hours. The reaction mixture was diluted with methanol, and the reaction solution was basified with a saturated aqueous sodium hydrogen carbonate solution. The insoluble materials were filtered off and, the filtrate was extracted with ethyl acetate and dried over magnesium sulfate. The solvent was evaporated under reduced pressure, and the residue was purified by silica gel column chromatography (hexane:ethyl acetate=99:1-85:15) to give 5-bromo-2-chlorophenyl 6-ethyl-3-pyridyl ketone (1.98 g) as a colorless solid. APCI-Mass m/Z 324/326 (M+H).
(2) The above 5-bromo-2-chlorophenyl 6-ethyl-3-pyridyl ketone was treated in a manner similar to Reference Example 14-(1) to give the desired 5-bromo-2-chloro-1-(6-ethyl-3-pyridylmethyl)benzene as a colorless oil. APCI-Mass m/Z 310/312 (M+H).

Reference Example 139

6-Ethylbenzo[b]thiophene (1) 4-Bromo-2-fluorobenzaldehyde and ethyl thioglycolate were treated in a manner similar to Reference Example 31-(1) to give 6-bromo-2-ethoxycarbonylbenzo[b]thiophene as a colorless solid.
(2) The above 6-bromo-2-ethoxycarbonylbenzo[b]thiophene was treated in a manner similar to Reference Example 138-(1) to give 6-ethyl-2-ethoxycarbonylbenzo[b]thiophene as colorless oil. APCI-Mass m/Z 235 (M+H).
(3) The above 6-ethyl-2-ethoxycarbonylbenzo[b]thiophene (1.26 g) was dissolved in tetrahydrofuran (4 ml) and methanol (8 ml), and added thereto was lithium hydroxide monohydrate (677 mg), and the mixture was stirred at room temperature overnight. The solvent was evaporated under reduced pressure, and the residue was dissolved in water and the solution was made acidic with a 10% aqueous hydrochloric acid solution. The precipitates were collected by filtration and washed with water to give 6-ethylbenzo[b]thiophen-2-ylcarboxylic acid (1.15 g) as colorless crystals. ESI-1-Mass m/Z 205 (M−H).
(4) The above 6-ethylbenzo[b]thiophen-2-ylcarboxylic acid was tread in a manner similar to Reference Example 47-(2) to give the desired 6-ethylbenzo[b]thiophene as colorless oil.

Reference Example 140

5-Bromo-2-chloro-1-(1-oxo-2-isoindolinylmethyl) benzene (1) 5-Bromo-2-chlorobenzyl alcohol (3.0 g) was dissolved in toluene (30 ml), and added thereto were thionyl chloride (2.35 ml) and pyridine (two drops), and the mixture was heated under stirring at 100° C. for 2 hours. The mixture was cooled, washed with a saturated aqueous sodium hydrogen carbonate solution and brine, and dried over sodium sulfate. The solvent was evaporated under reduced pressure to give 5-bromo-2-chlorobenzyl chloride (3.34 g) as pale brown oil, which was used in the subsequent step without further purification.
(2) The above 5-bromo-2-chlorobenzyl chloride (3.34 g) was dissolved in N,N-dimethylformamide (30 ml), and added thereto was potassium phthalimide (2.63 g), and the mixture was heated under stirring at 70° C. for 3 hours. The reaction solution was poured into water, and the mixture was extracted with ethyl acetate. The extract was washed with brine, and dried over sodium sulfate. The solvent was evaporated under reduced pressure, and the residue was crystallized from diisopropyl ether to give 5-bromo-2-chloro-1-(phthalimid-2-ylmethyl)benzene (3.33 g) as colorless crystals. APCI-Mass m/Z 350/352 (M+H).
(3) The above 5-bromo-2-chloro-1-(phthalimid-2-ylmethyl)benzene (4.3 g) was dissolved in acetic acid (43 ml), and added thereto was zinc powder (8.02 g), and the mixture was heated at reflux for 3 days. The mixture was cooled and diluted with chloroform and it was basified with an aqueous sodium hydroxide solution. The organic layer was dried over sodium sulfate, and the solvent was evaporated under reduced pressure. The residue was purified by silica gel column chromatography (hexane:ethyl acetate=6:1-4:1) to give the desired 5-bromo-2-chloro-1-(1-oxo-2-isoindolinylmethyl)benzene (1.39 g) as colorless powder. APCI-Mass m/Z 336/338 (M+H).

Reference Example 141

5-Bromo-2-chloro-1-(1-phenyl-4-pyrazolylmethyl) benzene (1) A solution of 1-phenyl-4-bromopyrazole (see M. A. Khan, et al., Can. J. Chem., (1963) 41 1540) (2.23 g) in diethyl ether (30 ml) wad cooled to −78° C. under argon atmosphere, and added dropwise thereto was n-butyl lithium (1.59 M hexane solution, 6.9 ml). The mixture was stirred at −20° C. to −10° C. for 5 hours, and added dropwise thereto at the same temperature was a solution of 5-bromo-2-chlorobenzaldehyde (2.19 g) obtained in Reference Example 16-(1) in diethyl ether (30 ml). The mixture was stirred at the same temperature for 30 minutes, and added thereto was tetrahydrofuran (30 ml), and the mixture was stirred at 0° C. for further 30 minutes. A saturated aqueous ammonium chloride solution was added thereto, and the mixture was extracted with ethyl acetate. The extract was washed with brine and dried over sodium sulfate. The solvent was evaporated under reduced pressure, and the residue was purified by silica gel column chromatography (hexane:ethyl acetate=83:17-80:20) to give 5-bromo-2-chlorophenyl-1-phenyl-4-pyrazolylmethanol (831 mg) as yellow oil. APCI-Mass m/Z 363/365 (M+H).
(2) The above 5-bromo-2-chlorophenyl-1-phenyl-4-pyrazolylmethanol was treated in a manner similar to Reference Example 120-(2) to give the desired 5-bromo-2-chloro-1-(1-phenyl-4-pyrazolylmethyl)benzene as colorless powder. APCI-Mass m/Z 347/349 (M+H).

Reference Example 142

5-Bromo-2-chloro-1-(6-n-propyloxybenzo[b]thiophen-2-ylmethyl)benzene

5-Bromo-2-chloro-1-(6-hydroxybenzo[b]thiophen-2-ylmethyl)benzene obtained in Reference Example 132-(1) and 1-bromopropane were treated in a manner similar to Reference Example 132-(2) to give the target compound. APCI-Mass m/Z 395/397 (M+H).

Reference Example 143

5-Bromo-2-chloro-1-(6-(2-fluoroethyloxy)benzo[b]thiophen-2-yl methylbenzene

5-Bromo-2-chloro-1-(6-hydroxybenzo[b]thiophen-2-ylmethyl)benzene obtained in Reference Example 132-(1) and 1-bromo-2-fluoroethane were treated in a manner similar to Reference Example 132-(2) to give the target compound. APCI-Mass m/Z 399/401 (M+H).

Reference Example 144

5-Tri-n-butylstannanylthiazole

The target compound was prepared according to a method described in WO 03/087104.

Reference Example 145

4-Tri-n-butylstannanylthiazole

The target compound was prepared according to a method described in WO 03/087104.

Reference Example 146

Tri-n-butyl(6-methoxy-2-pyridyl)tin

The target compound was prepared according to a method described in P. Gros, et al., Synthesis (1999) 754.

Reference Example 147

5-Bromo-2-chloro-1-(5-ethoxybenzo[b]thiophen-2-ylmethyl)benzene (1) 5-Bromo-2-chloro-1-(5-methoxybenzo[b]thiophene-2-ylmethyl)benzene obtained in Reference Example 54 was treated in a manner similar to Reference Example 132-(1) to give 5-bromo-2-chloro-1-(5-hydroxybenzo[b]thiophen-2-ylmethyl)benzene. ESI-Mass m/Z 351/353 (M–H).
(2) The above 5-bromo-2-chloro-1-(5-hydroxybenzo[b]thiophen-2-ylmethyl)benzene and iodoethane were treated in a manner similar to Reference Example 132-(2) to give the desired 5-Bromo-2-chloro-1-(5-ethoxybenzo[b]thiophene-2-ylmethyl)-benzene. APCI-Mass m/Z 382/380 (M+H).

Reference Example 148

5-Bromo-2-chloro-1-(5-(1-pyrazolyl)-2-thienylmethyl)benzene 1-(2-thienyl)pyrazole (see: Chemica Scripta (1979) 13, 157-161) and 5-bromo-2-chlorobenzaldehyde obtained in Reference Example 16-(1) were used and treated in a manner similar to Reference Example 7 to give the title compound as colorless solid. APCI-Mass m/z 353/355 (M+H).

Reference Example 149

5-Bromo-2-chloro-1-(tert-butyldiphenylsilyloxymethyl)benzene

To a solution of 5-Bromo-2-chlorobenzylalcohol (5.15 g) in N,N-dimethylformamide (50 ml) was added diisopropylethylamine (19.8 ml) and tert-butyldiphenylchlorosilane (11.9 ml), and the mixture was stirred at room temperature for 2 days. Under ice-cooling, to the mixture was added water, and the mixture was extracted with ethyl acetate. The extract was washed with successively with 0.4 M aqueous hydrochloric acid solution (twice), water, a saturated aqueous sodium hydrogen carbonate solution and brine, and dried over magnesium sulfate. The solvent was evaporated under reduced pressure, and the residue was purified by an aminosilane-treated silica gel column chromatography (hexane) to give 5-bromo-2-chloro-1-(tert-butyldiphenylsiloxymethyl) benzene 77 (10.79 g) as colorless oil. APCI-Mass m/Z 476/478 (M+$NH_4$).

Reference Example 150

2-Fluoropyridin-4-boronic acid

The target compound was prepared according to a method described in *Tetrahedron* (2002) 58, 4369-4373.

Reference Example 151

3-Difluoromethoxybenzeneboronic acid

A solution of 3-(difluoromethoxy)benzene (3.0 g) and triisopropoxyborane (2.78 g) in tetrahydrofuran (15 ml) was cooled to –78° C. under argon atmosphere, and thereto was added a solution of n-butyl lithium (1.59 M hexane solution, 9.3 ml). The mixture was stirred at same temperature for 10 minutes, warmed, and further stirred at room temperature overnight. Thereto was added 3N aqueous hydrochloric acid solution (10 ml), and the mixture was stirred at room temperature for 5 minutes. The mixture was extracted with ethyl acetate. The extract was washed with brine, and dried over sodium sulfate. The solvent was evaporated under reduced pressure. The residue was crystallized from hexane to give 3-difluoromethoxybenzeneboronic acid (1.6 g) as colorless crystals.

Reference Example 152

Tri-n-butyl(2-cyano-5-pyridyl)tin

5-Bromo-2-cyanopyridine was treated in a manner similar to the methods described in European Patent Publication No. 93-00867.

Reference Example 153

5-Bromo-2-chloro-1-(6-difluoromethoxybenzo[b]thiophen-2-ylmethylbenzene

5-Bromo-2-chloro-1-(6-hydroxybenzo[b]thiophen-2-ylmethyl)benzene (1.8 g) obtained in Reference Example 132-(1) was dissolved in dimethylformamide (15 ml), and added thereto were methyl 2-chloro-2,2-difluoroacetate (1.63 ml) and potassium carbonate (2.28 g), and the mixture was stirred at 100° C. for 1.5 hours under argon atmosphere. The reaction mixture was acidified with 2N aqueous HCl solution and extracted with ethyl acetate. The organic layer was washed with brine and dried over magnesium sulfate. The solvent was evaporated under reduced pressure, and the residue was purified by silica gel column chromatography (hexane) to give 5-bromo-2-chloro-1-(6-difluoromethoxybenzo[b]thiophen-2-ylmethyl)benzene (695 mg) as a colorless solid. GC-Mass m/Z 402/404 (M+).

Reference Example 154

5-Bromo-1-(6-difluoromethoxybenzo[b]thiophen-2-ylmethyl)-2-methylbenzene (1) 6-Methoxybenzo[b]thiophene (see WO 97/25033) and 5-bromo-2-methylbenzaldehyde obtained in Reference Example 4 were treated in a manner similar to Reference Example 7 to give 5-Bromo-1-(6-methoxybenzo[b]thiophen-2-ylmethyl)-2-methylbenzene. APCI-Mass m/Z 347/349 (M+NH$_4$).
(2) The above 5-bromo-1-(6-methoxybenzo[b]thiophen-2-ylmethyl)-2-methylbenzene was treated in a manner similar to Reference Example 132-(1) to give 5-Bromo-1-(6-hydroxybenzo[b]thiophen-2-ylmethyl)-2-methylbenzene. ESI-Mass m/Z 331/333 (M–H).
(3) The above 5-bromo-1-(6-hydroxybenzo[b]thiophen-2-ylmethyl)-2-methylbenzene was treated in a manner similar to Reference Example 153 to give the desired 5-bromo-1-(6-difluoromethoxybenzo[b]thiophen-2-ylmethyl)-2-methylbenzene as colorless oil. GC-Mass m/Z 382/384 (M+).

Reference Example 155

(6-Cyanopyridin-2-yl)trimethyltin

2-Bromo-6-cyanopyridine (see Japanese Patent Publication 04-253974) (1.5 g) and hexamethylditin (2.69 g) were dissolved in dimethoxyethane (50 ml) and thereto was added tetrakis(triphenylphosphine)palladium(0) (972 mg). The mixture was refluxed for 5 hours. The solvent was evaporated under reduced pressure, and the residue was purified by silica gel column chromatography (hexane:ethyl acetate=100:1) to give (6-cyanopyridin-2-yl)trimethyltin (980 mg) as colorless oil. APCI-Mass m/Z 265/267/269 (M+H).

Reference Example 156

5-Bromo-2-methyl-1-(5-(1-pyrazolyl)-2-thienylmethyl)benzene 1-(2-thienyl)pyrazole (see Chemica Scripta (1979) 13, 157-161) and 5-bromo-2-methylbenzaldehyde obtained in Reference Example 4 were used and treated in a manner similar to Reference Example 7 to give the title compound as colorless oil. APCI-Mass m/z 333/335 (M+H).

Reference Example 157

5-Bromo-1-(6-ethoxybenzo[b]thiophen-2-ylmethyl)-2-methylbenzene

5-Bromo-1-(6-hydroxybenzo[b]thiophen-2-ylmethyl)-2-methylbenzene obtained in Reference Example 154-(2) and iodoethane were treated in a manner similar to Reference Example 132-(2) to give the desired 5-bromo-1-(6-ethoxybenzo[b]thiophene-2-ylmethyl)-2-methylbenzene as pale yellow wax. APCI-Mass m/Z 361/363 (M+H).

Reference Example 158

5-Bromo-1-(5-methoxybenzo[b]thiophen-2-ylmethyl)-2-methylbenzene

5-Methoxybenzo[b]thiophene (see WO 97/25033) and 5-bromo-2-methylbenzaldehyde obtained in Reference Example 4 were treated in a manner similar to Reference Example 7 to give 5-bromo-1-(5-methoxybenzo[b]thiophen-2-ylmethyl)-2-methyl benzene as colorless wax.

Reference Example 159

5-Bromo-1-(5-(2-fluoroethyloxy)benzo[b]thiophen-2-ylmethyl)-2-methylbenzene (1) 5-Bromo-1-(5-methoxybenzo[b]thiophene-2-yl methyl)-2-methylbenzene obtained in Reference Example 158 was treated in a manner similar to Reference Example 132-(1) to give 5-bromo-1-(5-hydroxybenzo[b]thiophen-2-ylmethyl)-2-methylbenzene as colorless powder. ESI-Mass m/Z 331/333 (M–H).
(2) The above 5-bromo-1-(5-hydroxybenzo[b]thiophen-2-ylmethyl)-2-methylbenzene and 1-bromo-2-fluoroethane were treated in a manner similar to Reference Example 132-(2) to give the desired 5-bromo-1-(5-(2-fluoroethyloxy)benzo[b]thiophene-2-ylmethyl)-2-methylbenzene.

Reference Example 160

5-Bromo-1-(5-ethoxybenzo[b]thiophen-2-ylmethyl)-2-methylbenzene

5-Bromo-1-(5-hydroxybenzo[b]thiophen-2-ylmethyl)-2-methylbenzene obtained in Reference Example 159-(1) and iodoethane were treated in a manner similar to Reference Example 132-(2) to give the desired 5-bromo-1-(5-ethoxybenzo[b]thiophene-2-ylmethyl)-2-methylbenzene as colorless powder.

Reference Example 161

5-Bromo-2-chloro-1-(5-(2-fluoroethyloxy)benzo[b]thiophene-2-ylmethyl)benzene 5-Bromo-2-chloro-1-(5-hydroxybenzo[b]thiophen-2-ylmethyl)benzene obtained in Reference Example 147-(1) and 1-bromo-2-fluoroethane were treated in a manner similar to Example 132-(2) to give the target compound.

Reference Example 162

5-Bromo-1-(6-(2-fluoroethyloxy)benzo[b]thiophen-2-ylmethyl)-2-methylbenzene

5-Bromo-1-(6-hydroxybenzo[b]thiophen-2-ylmethyl)-2-methyl benzene obtained in Reference Example 154-(2) and 1-bromo-2-fluoroethane were treated in a manner similar to Example 132-(2) to give the target compound as colorless wax. APCI-Mass m/Z 379/381 (M+H).

Reference Example 163

4-(Difluoromethoxy)phenylboronic acid

A solution of (4-bromophenoxy)difluoromethane (3 g) and triisopropyl borate (3.42 ml) in tetrahydrofuran (15 ml) was cooled to −78° C. under argon atmosphere, and thereto was added a solution of n-butyl lithium (1.59 M hexane solution, 3.42 ml). The mixture was stirred at room temperature overnight. Added thereto was 6N aqueous hydrochloric acid at 0° C., and the mixture was extracted with ethyl acetate. The extract was washed with brine, and dried over magnesium sulfate. The solvent was evaporated under reduced pressure, and the residue was triturated with cold hexane to give 4-(difluoromethoxy)phenylboronic acid (1.88 g) as colorless solid.

Reference Example 164

Tri-n-butyl(3-methyl-5-isooxazolyl)tin

The target compound was prepared according to a method described in Bioorg. & Med. Chem. Lett. (2003) 13, 4117-4120.

Reference Example 165

5-Bromo-2-chloro-1-(2-trifluoromethyl-5-pyridylmethyl)benzene (1) A solution of 5-Bromo-2-trifluoromethylpyridine (5.3 g) (see Eur. J. Org. Chem. (2003) 1159-1168) in tetrahydrofuran (70 ml) was cooled to 0° C. under argon atmosphere, and thereto was added dropwise isopropylmagnesium chloride (1 mol/l tetrahydrofuran solution, 23.45 ml). The reaction mixture was stirred at the same temperature for 2 hours, and thereto was added dropwise a solution of 5-bromo-2-chlorobenzaldehyde obtained in Reference Example 16-(1) (5.15 g) in tetrahydrofuran (20 ml). The mixture was stirred at the same temperature for 60 minutes, and thereto was added a saturated ammonium chloride solution, and the reaction mixture was warmed to room temperature. The mixture was extracted with ethyl acetate, and the extract was dried over magnesium sulfate, and the solvent was evaporated under reduced pressure. The residue was purified by silica gel column chromatography (hexane:ethyl acetate=98:2-85:15) to give (5-Bromo-2-chloro)phenyl-(2-trifluoromethyl-5-pyridyl)methanol (4.56 g) as a pale brown syrup. APCI-Mass m/Z 366/368 (M+H).
(2) The above (5-Bromo-2-chloro)phenyl-(2-trifluoromethyl-5-pyridyl)methanol (4.55 g) was dissolved in dichloromethane (50 ml) and toluene (50 ml), and added thereto was manganese (IV) oxide (5.39 g), and the mixture was stirred at room temperature overnight. Insoluble materials were filtered off, and the solvent was evaporated under reduced pressure. The resultant residue was purified by silica gel column chromatography (hexane:ethyl acetate=98:2-92:8) to give (5-Bromo-2-chloro)phenyl (2-trifluoromethyl-5-pyridyl) ketone (2.64 g) as a pale yellow syrup. APCI-Mass m/Z 364/366 (M+H).
(3) The above (5-Bromo-2-chloro)phenyl (2-trifluoromethyl-5-pyridyl) ketone was treated in a manner similar to Reference Example 14-(1) to give the desired 5-Bromo-2-chloro-1-(2-trifluoromethyl-5-pyridylmethyl)benzene. APCI-Mass m/Z 350/352 (M+H).

Reference Example 166

4-Methyl-2-tributylstannanylthiazole

A solution of n-butyl lithium (2.71 M hexane solution, 3.9 ml) in tetrahydrofuran (10 ml) was cooled to −78° C. under argon atmosphere, and thereto was added dropwise a solution of 4-methylthiazole (1.0 g) in tetrahydrofuran (10 ml). The mixture was stirred at same temperature for one hour and thereto was added dropwise a solution of tri-n-butyltin chloride (3.6 g) in tetrahydrofuran (10 ml). The mixture was stirred at same temperature for 30 minutes, warmed, and further stirred at room temperature overnight. Thereto was added water, and the mixture was extracted with diethyl ether. The extract was washed with brine, and dried over sodium sulfate. The solvent was evaporated under reduced pressure. The residue was purified by alumina column chromatography (hexane) to give the title compound (1.76 g) as oil. APCI-Mass m/z 386/388 (M+H)

Reference Example 167

2-Fluoropyridine-3-boronic acid

The target compound was prepared according to a method described in Tetrahedron (2002) 58, 3323-3328.

Reference Example 168

4-Bromo-2-(5-chloro-2-thienylmethyl)-1-methoxynaphthalene 2,4-Dibromo-1-methoxynaphthalene (see *Org. Lett.* (2003) 5, 831) and 5-chloro-2-thiophenecarboxaldehyde were treated in a manner similar to Reference Example 1 to give 4-Bromo-2-(5-chloro-2-thienylmethyl)-1-methoxynaphthalene.

Reference Example 169

2-(2-(6-Chloro)pyridine)-4,4,5,5-tetramethyl-1,3-dioxaborolane

The target compound was prepared according to a method described in *Tetrahedron* (2003) 59, 10043-10049.

Reference Example 170

2-Methyl-4-tri-n-butylstannanylthiazole

The target compound was prepared according to a method described in *Tetrahedron* (2003), 9979-9984.

Reference Example 171

2-(4-(2-Methyl)pyridine)-4,4,5,5-tetramethyl-1,3-dioxaborolane

The target compound was prepared according to a method described in United States Patent Publication No. 2003-024914.

Reference Example 172

1-(β-D-glucopyranosyl)-5-chloroindole

5-Chloro-2,3-dihydro-(1H)-indole was treated in a manner similar to the methods described in Eur. J. Med. Chem. (2004) 39, 453-458 to give the title compound. APCI-Mass m/z 314/316 (M+H)

Reference Example 173

5-Bromo-2-chloro-1-(5-(5-fluorothiazol-2-yl)-2-thienylmethyl)benzene (1) 2-Bromothiazole (15.0 g) and 2-thiopheneboronic acid (14.0 g) were dissolved in dimethoxyethane (150 ml). To the mixture was added bis(triphenyl)phosphine palladium(II) dichloride (3.2 g) and 2M sodium carbonate (137 ml), and the mixture was refluxed under argon atmosphere for 2 hours. The mixture was cooled to room temperature, and the reaction solution was diluted with ethyl acetate, and washed with water. The organic layer was collected, dried over sodium sulfate, and the solvent was evaporated under reduced pressure. The residue was purified by silica gel column chromatography (hexane:ethyl acetate=96:4) to give 2-(2-thienyl)thiazole (9.87 g) as oil. APCI-Mass m/z 168 (M+H)
(2) The above compound (3.17 g) was treated in a manner similar to Reference Example 121 to give 5-fluoro-2-(2-thienyl)thiazole (1.58 g) as oil. APCI-Mass m/z 186 (M+H)
(3) The above compound (1.58 g) was dissolved in chloroform (16 ml), cooled to 0° C., and thereto was added dropwise a solution of bromine (1.43 g) in chloroform (15 ml). The mixture was stirred at the same temperature for one hour, warmed, and further stirred at room temperature for one hour. The reaction mixture was poured into saturated aqueous sodium hydrogen carbonate solution, and the mixture was extracted with chloroform. The extract was washed with 10% aqueous sodium thiosulfate solution, brine, and dried over sodium sulfate. The solvent was evaporated under reduced pressure. The residue was purified by silica gel column chromatography (hexane:ethyl acetate=97:3) to give 2-(5-bromo-2-thienyl)-5-fluorothiazole (1.81 g) as a pale yellow solid.
(4) The above compound (300 mg) and 5-bromo-2-chlorobenzaldehyde obtained in Reference Example 16-(1) were used and treated in a manner similar to Reference Example 7 to give the desired 5-bromo-2-chloro-1-(5-(5-fluorothiazol-2-yl)-2-thienylmethyl)benzene (199 mg) as a pale yellow powder.

Reference Example 174

1-(β-D-glucopyranosyl)-4-chloroindole (1) 4-Chloroindole (3.15 g) was dissolved in trifluoroacetic acid (32 ml), thereto was added triethylsilane (8.3 ml) and the mixture was heated at 50° C. with stirring for 30 minutes. The resultant mixture was cooled to room temperature, and trifluoroacetic acid was evaporated under reduced pressure. To the residue was added a saturated aqueous sodium hydrogen carbonate solution, and the mixture was extracted with ethyl acetate twice. The organic layer was dried over magnesium sulfate, and the solvent was evaporated under reduced pressure. The residue was purified by silica gel column chromatography (hexane:ethyl acetate=100:0-80:20) to give 4-chloro-2,3-dihydro-(1H)-indole (2.89 g) as colorless oil. APCI-Mass m/z 154/156 (M+H)
(2) The above 4-chloro-2,3-dihydro-(1H)-indole was treated in a manner similar to described in Eur. J. Med. Chem. (2004) 39, 453-458 to give the title compound. APCI-Mass m/z 314/316 (M+H)

Reference Example 175

1-(β-D-glucopyranosyl)-6-chloroindole

6-Chloroindole was treated in a manner similar to Reference Example 174 to give the title compound. APCI-Mass m/z 314/316 (M+H).

Pharmacological Experiment
1. Assay for SGLT2 Inhibition
Test Compounds:
Compounds described in the above examples were used for the SGLT2 inhibition assay.
Method:
CHOK1 cells expressing human SGLT2 were seeded in 24-well plates at a density of 400,000 cells/well in F-12 nutrient mixture (Ham's F-12) containing 10% fetal bovine serum, 400 µg/ml Geneticin, 50 units/ml sodium penicillin G (Gibco-BRL) and 50 µg/ml streptomycin sulfate. After 2 days of culture at 37° C. in a humidified atmosphere containing 5% $CO_2$, cells were washed once with the assay buffer (137 mM NaCl, 5 mM KCl, 1 mM $CaCl_2$, 1 mM $MgCl_2$, 50 mM Hepes, and 20 mM Tris, pH 7.4) and incubated with 250 µl of the buffer containing test compounds for 10 min at 37° C. Test compounds were dissolved in DMSO. The final concentration of DMSO was 0.5%. The transport reaction was initiated by addition of 50 µl [$^{14}C$]-methyl-α-D-glucopyranoside ($^{14}C$-AMG) solution (final concentration, 0.5 mM). After incubation for 2 hours at 37° C., the uptake was stopped by aspiration of the incubation mixture, the cells were washed three times with ice-cold PBS. Then, cells were solubilized with 0.3 N NaOH and aliquots were taken for determination of radioactivity by a liquid scintillation counter. Nonspecific AMG uptake was defined as that which occurred in the presence of 100 µM of phlorizin, a specific inhibitor of sodium-dependent glucose cotransporter. Specific uptake was normalized for the protein concentrations measured by the method of Bradford. The 50% inhibitory concentration ($IC_{50}$) values were calculated from dose-response curves by least square method.
Results:
Results are shown in the following table:

| Test Compounds (Example No.) | IC50 (nM) |
|---|---|
| 69 | 7.9 |
| 70 | 7.0 |
| 71 | 6.6 |
| 72 | 4.6 |
| 78 | 1.7 |
| 79 | 9.0 |
| 80 | 6.8 |
| 83 | 1.3 |

| Test Compounds (Example No.) | IC50 (nM) |
|---|---|
| 84 | 2.2 |
| 86 | 2.8 |
| 87 | 3.4 |
| 88 | 2.6 |
| 89 | 3.0 |
| 90 | 2.0 |
| 120 | 3.4 |
| 122 | 8.2 |
| 123 | 1.4 |
| 127 | 1.3 |
| 130 | 2.4 |
| 140 | 5.9 |
| 142 | 5.6 |
| 144 | 4.1 |
| 145 | 4.0 |
| 146 | 2.2 |
| 148 | 2.8 |
| 151 | 2.5 |
| 155 | 1.7 |
| 156 | 1.1 |
| 168 | 2.3 |
| 169 | 3.6 |
| 170 | 3.5 |
| 173 | 8.0 |
| 176 | 7.7 |
| 177 | 6.7 |
| 178 | 5.1 |
| 179 | 9.8 |
| 183 | 9.5 |
| 185 | 5.6 |
| 186 | 5.4 |
| 187 | 4.3 |
| 188 | 1.6 |
| 189 | 2.4 |
| 190 | 3.1 |
| 191 | 7.7 |
| 192 | 7.4 |
| 193 | 0.9 |
| 194 | 2.6 |
| 197 | 2.0 |
| 201 | 8.2 |
| 202 | 8.7 |
| 204 | 1.4 |
| 207 | 0.6 |
| 208 | 2.4 |
| 209 | 3.9 |
| 210 | 1.0 |
| 211 | 1.2 |
| 212 | 2.6 |
| 213 | 5.6 |
| 214 | 1.5 |
| 215 | 4.3 |
| 216 | 3.3 |
| 217 | 3.6 |
| 218 | 2.4 |
| 219 | 6.7 |
| 221 | 5.5 |
| 222 | 1.8 |
| 223 | 3.1 |
| 224 | 5.9 |
| 225 | 1.5 |
| 226 | 1.2 |
| 227 | 3.2 |
| 228 | 3.6 |
| 229 | 2.7 |
| 230 | 4.0 |
| 231 | 3.5 |
| 232 | 4.0 |
| 233 | 2.9 |
| 234 | 2.4 |
| 235 | 2.6 |
| 236 | 4.4 |
| 237 | 2.8 |
| 238 | 1.6 |
| 240 | 1.2 |
| 241 | 1.0 |
| 242 | 4.6 |
| 244 | 1.2 |
| 246 | 6.4 |
| 247 | 2.5 |
| 248 | 5.1 |
| 249 | 4.3 |
| 250 | 4.2 |
| 251 | 3.6 |
| 252 | 1.4 |
| 253 | 1.6 |
| 254 | 1.7 |
| 255 | 6.5 |
| 256 | 3.1 |
| 257 | 3.3 |
| 260 | 2.3 |
| 264 | 1.5 |
| 265 | 3.4 |
| 266 | 3.2 |
| 267 | 1.5 |
| 268 | 2.5 |

2. Urinary Glucose Excretion Test in Rats

Test Compounds:

Compounds described in the above examples were used for the urinary glucose excretion test in rats.

Methods:

6-week-old male Sprague-Dawley (SD) rats were housed in individual metabolic cages with free access to food and water from 2 days prior to the experiment. On the morning of the experiment, rats were administered vehicle (0.2% carboxymethyl cellulose solution containing 0.2% Tween80) or test compounds (30 mg/kg) by oral gavage at a volume of 10 ml/kg. Then, urine of the rat was collected for 24 hours, and the urine volume was measured. Subsequently, the glucose concentration in urine was quantified using the enzymatic assay kit and the daily amount of glucose excreted in urine per individual was calculated.

Results:

Urinary glucose amount ranges are depicted by A and B. These ranges are as follows: $A \geq 2000$ mg; $2000$ mg$>B \geq 1000$ mg.

| Test compounds (Example No.) | Urinary glucose |
|---|---|
| 22 | A |
| 25 | B |
| 69 | B |
| 70 | A |
| 81 | B |
| 83 | A |
| 84 | A |
| 88 | B |
| 89 | B |
| 120 | A |
| 123 | A |
| 127 | A |
| 133 | B |
| 140 | B |
| 142 | A |
| 144 | B |
| 146 | A |
| 148 | B |
| 151 | B |
| 155 | A |
| 156 | A |
| 168 | A |
| 169 | B |
| 170 | B |

-continued

| Test compounds (Example No.) | Urinary glucose |
|---|---|
| 177 | A |
| 178 | B |
| 189 | B |
| 194 | A |
| 195 | B |
| 204 | A |
| 207 | A |
| 208 | A |
| 209 | B |
| 210 | B |
| 214 | B |
| 216 | A |
| 217 | B |
| 221 | B |
| 223 | A |
| 226 | B |
| 227 | B |
| 228 | B |
| 229 | B |
| 230 | A |
| 231 | B |
| 232 | B |
| 233 | B |
| 235 | A |
| 236 | B |
| 237 | B |
| 238 | A |
| 247 | A |
| 248 | B |
| 251 | A |
| 252 | B |

What is claimed is:

1. A compound of formula (I):

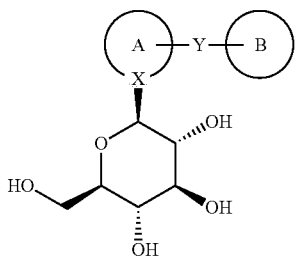

wherein:
Ring A is an unsaturated monocyclic heterocyclic ring, or an unsaturated fused heterobicyclic ring, wherein when Ring A is an unsaturated fused heterobicyclic ring, the sugar moiety X-(sugar) and the moiety —Y-(Ring B) are both on the same heterocyclic ring of the unsaturated fused heterobicyclic ring and the unsaturated fused heterobicyclic ring is selected from the group consisting of indoline, isoindoline, benzothiazole, benzoxazole, indole, indazole, quinoline, isoquinoline and dihydroisoquinoline, and wherein each of the unsaturated monocyclic heterocyclic ring and the unsaturated fused heterobicyclic ring may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, and a heterocyclyl group;

Ring B is a benzene ring, which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or dialkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, and an alkoxycarbonyl group;

X is a nitrogen atom; and
Y is —(CH$_2$)$_n$—, wherein n is 1 or 2;
or a pharmaceutically acceptable salt thereof.

2. The compound according to claim 1 or a pharmaceutically acceptable salt thereof, wherein:
Ring A is an unsaturated monocyclic heterocyclic ring which may optionally be substituted by a halogen atom, a lower alkyl group, a halo-lower alkyl group, or a lower alkoxy group, and
Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, a cyano group, a lower alkyl group, a halo-lower alkyl group, a lower alkoxy group, a halo-lower alkoxy group, a mono- or di-lower alkylamino group, a phenyl group which may be substituted with a halogen atom, a cyano group, a lower alkyl group, a halo-lower alkyl group, a lower alkoxy group, or a mono- or di-lower alkylamino group, and a heterocyclyl group which may optionally be substituted with a group selected from a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, a cyano group, a lower alkyl group, a halo-lower alkyl group, a lower alkoxy group, a halo-lower alkoxy group, a mono- or di-lower alkylamino group, a phenyl group which may be substituted with a halogen atom, a cyano group, a lower alkyl group, a halo-lower alkyl group, a lower alkoxy group, or a mono- or di-lower alkylamino group, and a heterocyclyl group which may optionally be substituted with a group selected from a halogen atom, a cyano group, a lower alkyl group, a halo-lower alkyl group, a lower alkoxy group, or a mono- or di-lower alkylamino group.

3. The compound according to claim 1, or a pharmaceutically acceptable salt thereof, wherein:
Ring A is an unsaturated fused heterobicyclic ring which may optionally be substituted by a halogen atom, a lower alkyl group, a halo-lower alkyl group, or a lower alkoxy group, and
Ring B is (a) a benzene ring which may optionally be substituted by a group selected from a halogen atom, a cyano group, a lower alkyl group, a halo-lower alkyl group, a lower alkoxy group, a halo-lower alkoxy group, a mono- or di-lower alkylamino group, a cycloalkyl group, a cycloalkoxy group, a phenyl group which may be substituted with a halogen atom, a cyano group, a lower alkyl group, a halo-lower alkyl group, a lower alkoxy group, or a mono- or di-lower alkylamino group, and a heterocyclyl group which may optionally be substituted with a group selected from a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group, and a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, a cyano group, a lower alkyl group, a halo-lower alkyl group, a lower alkoxy group, a halo-lower alkoxy group, a mono- or di-lower alkylamino group, a phenyl group which may be substituted with a halogen atom, a cyano group, a lower alkyl group, a halo-lower alkyl group, a lower alkoxy group, or a mono- or di-lower alkylamino group, and a heterocyclyl group which may optionally be substituted with a group selected from a halogen atom, a cyano group, a lower alkyl group, a halo-lower alkyl group, a lower alkoxy group, or a mono- or di-lower alkylamino group.

4. The compound according to claim 1, or a pharmaceutically acceptable salt thereof, wherein:
Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, and a cycloalkoxy group, and an oxo group;
Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group; and
Y is —CH$_2$—.

5. The compound according to claim 1, or a pharmaceutically acceptable salt thereof, wherein:
Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, and a cycloalkoxy group;
Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group; and
Y is —CH$_2$—.

6. The compound according to claim 1, or a pharmaceutically acceptable salt thereof, wherein:
Ring A is an unsaturated monocyclic heterocyclic ring or an unsaturated fused heterobicyclic ring selected from the group consisting of dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic or heterobicyclic ring may be optionally substituted by a substituent selected from a halogen atom, and a lower alkyl group;
Ring B is a benzene ring which may optionally be substituted by a substituent selected from a halogen atom, a lower alkyl group, a halo-lower alkyl group, a lower alkoxy group, and a halo-lower alkoxy group; and
Y is —CH$_2$—.

7. The compound according to claim 6, or a pharmaceutically acceptable salt thereof, wherein:
Ring A is an unsaturated fused heterobicyclic ring selected from dihydroisoquinoline, dihydroindole, indole, indazole, quinoline, and a isoindoline, wherein the heterobicyclic ring may optionally be substituted by a substituent selected from a halogen atom, and a lower alkyl group, and
Ring B is a benzene ring which may optionally be substituted by a substituent selected from a halogen atom, a lower alkyl group, a halo-lower alkyl group, a lower alkoxy group, and a halo-lower alkoxy group.

8. The compound according to claim 7, or a pharmaceutically acceptable salt thereof, wherein the unsaturated fused heterobicyclic ring is dihydroindole, indole or indazole.

9. The compound according to claim 8, or a pharmaceutically acceptable salt thereof, wherein Ring B is a benzene ring substituted by a lower alkyl group.

10. The compound according to claim 1, wherein the compound is selected from:
- 1-(β-D-glucopyranosyl)-3-(4-ethylphenylmethyl)indazole,
- 2-(β-D-glucopyranosyl)-3-(4-ethylphenylmethyl)indazole,
- 1-(β-D-glucopyranosyl)-3-(4-ethylphenylmethyl)indole, and
- 1-(β-D-glucopyranosyl)-3-(RS)-(4-ethylphenylmethyl)-2,3-dihydroindole;

or a pharmaceutically acceptable salt thereof.

11. The compound according to claim 1, wherein the compound is 1-(β-D-glucopyranosyl)-3-(4-ethylphenylmethyl)indole, or a pharmaceutically acceptable salt thereof.

12. A pharmaceutical composition, which comprises the compound as set forth in claim 1, or a pharmaceutically acceptable salt thereof, and a pharmaceutically acceptable carrier or diluent.

13. The pharmaceutical composition according to claim 12, which further comprises another antidiabetic agent.

14. A method for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering to a mammalian species in need of treatment a therapeutically effective amount of the compound as set forth in claim 1, or a pharmaceutically acceptable salt thereof.

15. A method for treatment of type 1 and 2 diabetes mellitus, which comprises administering to a mammalian species in need of treatment a therapeutically effective amount of the compound as set forth in claim 1, or a pharmaceutically acceptable salt thereof, alone, or in combination with another antidiabetic agent, an agent for treating diabetic complications, an anti-obesity agent, an antihypertensive agent, an antiplatelet agent, an anti-atherosclerotic agent and/or a hypolipidemic agent.

16. A process for preparing a compound of formula (I):

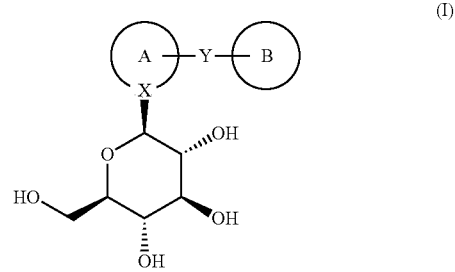

(I)

wherein Ring A, Ring B, X and Y are as defined in claim 1, which comprises deprotecting a compound of formula (II):

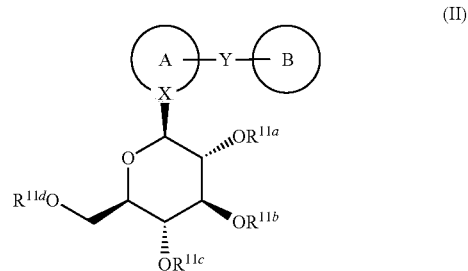

(II)

wherein Ring A, Ring B, X and Y are as defined in claim 1, $R^{11a}$, $R^{11b}$, $R^{11c}$ and $R^{11d}$ are each independently a protecting group for a hydroxy group.

* * * * *